(12) United States Patent
Loiseleur et al.

(10) Patent No.: US 8,598,078 B2
(45) Date of Patent: Dec. 3, 2013

(54) CONDENSED ANTHRAN I LAMI DE DERIVATIVES AS INSECTICIDES

(75) Inventors: Olivier Loiseleur, Stein (CH); Roger Graham Hall, Stein (CH); André Denis Stoller, Stein (CH); Gerald Wayne Craig, Basel (CH); André Jeanguenat, Stein (CH); Andrew Edmunds, Stein (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 271 days.

(21) Appl. No.: 12/674,055

(22) PCT Filed: Aug. 21, 2008

(86) PCT No.: PCT/EP2008/006868
§ 371 (c)(1),
(2), (4) Date: Jul. 21, 2011

(87) PCT Pub. No.: WO2009/024341
PCT Pub. Date: Feb. 26, 2009

(65) Prior Publication Data
US 2011/0271406 A1    Nov. 3, 2011

(30) Foreign Application Priority Data

Aug. 22, 2007  (GB) .................................. 0716414.8

(51) Int. Cl.
| *A01N 25/26* | (2006.01) |
| *A01N 43/647* | (2006.01) |
| *A01N 43/52* | (2006.01) |
| *A01N 43/56* | (2006.01) |
| *A61K 31/41* | (2006.01) |
| *A61K 31/415* | (2006.01) |
| *A61K 31/405* | (2006.01) |
| *C07D 235/12* | (2006.01) |
| *C07D 231/56* | (2006.01) |
| *C07D 249/16* | (2006.01) |
| *C07D 207/00* | (2006.01) |
| *C07D 209/44* | (2006.01) |
| *C07D 409/00* | (2006.01) |

(52) U.S. Cl.
USPC ........... 504/100; 504/261; 504/276; 504/277; 504/281; 504/284; 504/285; 514/259; 514/383; 514/384; 514/394; 514/395; 514/396; 514/398; 514/399; 514/401; 514/403; 514/406; 514/407; 514/415; 514/416; 514/418; 548/257; 548/260; 548/304.4; 548/304.7; 548/310.1; 548/310.4; 548/361.1; 548/361.5; 548/362.5; 548/364.1; 548/365.7; 548/369.4; 548/370.1; 548/370.4; 548/400; 548/452; 548/454; 548/467; 548/469; 548/470; 548/482; 548/490; 548/492; 548/503

(58) Field of Classification Search
USPC ................ 548/257, 260, 304.4, 304.7, 310.1, 548/310.4, 361.1, 361.5, 362.5, 364.1, 548/365.7, 369.4, 370.1, 370.4, 400, 452, 548/454, 467, 469, 470, 482, 490, 492, 548/503; 504/100, 261, 276, 277, 281, 284, 504/285; 514/359, 383, 384, 394, 395, 396, 514/398, 399, 401, 403, 406, 407, 415, 416, 514/418; 564/123, 152, 156; 546/268.4, 546/275.4, 275.7
See application file for complete search history.

(56) References Cited

U.S. PATENT DOCUMENTS

| 6,313,344 | B1 * | 11/2001 | Trah et al. ........................ 564/74 |
| 7,812,170 | B2 * | 10/2010 | Hughes et al. ............. 546/275.4 |
| 8,012,499 | B2 * | 9/2011 | Finkelstein et al. .......... 424/405 |
| 8,399,490 | B2 * | 3/2013 | Hall et al. ...................... 514/338 |
| 2003/0229050 | A1 | 12/2003 | Lahm et al. |

FOREIGN PATENT DOCUMENTS

| WO | 2005085234 | 9/2005 | | |
| WO | 2006111341 | 10/2006 | | |
| WO | WO2006/111341 | * 10/2006 | ........... | C07D 401/04 |
| WO | WO2006/111341 A1 | * 10/2006 | ........... | C07D 401/04 |
| WO | 2007020050 | 2/2007 | | |
| WO | WO2007/020050 A2 | * 2/2007 | ........... | C07D 401/41 |
| WO | WO2007/020050 A2 | * 2/2007 | ........... | C07D 401/14 |
| WO | 2007093402 | 8/2007 | | |

* cited by examiner

*Primary Examiner* — Jane C Oswecki
(74) *Attorney, Agent, or Firm* — R. Kody Jones

(57) ABSTRACT

Compounds of Formula I wherein the substituents are as defined in Claim 1, and the agrochemically acceptable salts and all stereoisomers and tautomeric forms of the compounds of formula I can be used as agrochemical active ingredients and can be prepared in a manner known per se.

(I)

8 Claims, No Drawings

CONDENSED ANTHRANILAMIDE DERIVATIVES AS INSECTICIDES

This application is a 371 of International Application No. PCT/EP2008/006868 filed Aug. 21, 2008, which claims priority to GB 0716414.8 filed Aug. 22, 2007, the contents of which are incorporated herein by reference.

The present invention relates to bicyclic bisamide derivatives, to processes for their preparation, to compositions comprising those compounds, and to their use for controlling insects or representatives of the order Acarina.

Bisamide derivatives with insecticidal action are known and described, for example, in US 2003/0229050, WO 20051085234 and WO 2007/093402.

There have now been found novel bicyclic bisamide derivatives with pesticidal properties.

The present invention accordingly relates to compounds of formula I

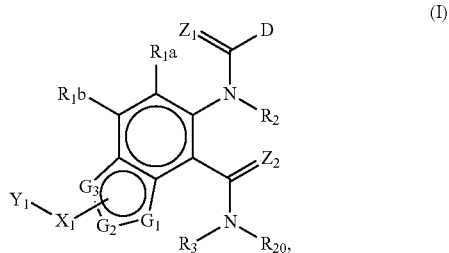

wherein
$G_1$, $G_2$, and $G_3$ form together with the two carbon atoms to which $G_1$ and $G_3$ are attached, a 5-membered aromatic ring system; wherein
$G_1$ is nitrogen or C—$R_{5d}$;
$G_2$ is nitrogen or C—$R_{5b}$;
$G_3$ is nitrogen or C—$R_{5c}$;
with the provisos that;
    a) at least one substituent G represents nitrogen;
    b) the group —$X_1$—$Y_1$ is attached to a nitrogen in the 5-membered ring;
    c) the group —$X_1$—$Y_1$ is different from methyl;
$X_1$ is oxygen, —C(O)—, —(CO)O—, thio, sulphinyl, sulphonyl, —$SO_2NR_{5d}$, —C(S)—, (P(=O)O($R_{5e}$)—, —C(O)S—, —C(S)O—, —C(S)$NR_{5f}$—, —(CO)$NR_{5g}$—, or a direct bond;
$Y_1$ is $C_1$-$C_{30}$alkyl, $C_3$-$C_{30}$alkenyl or $C_3$-$C_{30}$alkynyl which may be interrupted one, two, three, four or five times by atoms or group of atoms independently selected from the group consisting of oxygen, sulphur, suphinyl, sulphonyl, —C(O)—, —OC(O)— and —$NR_{5h}$—, with the proviso that the interrupting atoms are separated from each other by at least one methylene group; and which may be mono- or polysubstituted by substituents selected from the group consisting of halogen, hydroxyl, amino, formyl, nitro, cyano, mercapto, carbamoyl, $C_3$-$C_6$trialkylsilyl, $C_1$-$C_6$alkoxy, $C_1$-$C_6$alkoxycarbonyl, $C_2$-$C_6$alkenyl, $C_2$-$C_5$haloalkenyl, $C_2$-$C_6$alkynyl, $C_2$-$C_6$haloalkynyl, $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkoxy-$C_1$-$C_6$alkoxy-$C_1$-$C_6$alkoxy, $C_1$-$C_6$alkylthio-$C_1$-$C_6$alkoxy, $C_1$-$C_6$alkylsulphinyl-$C_1$-$C_6$alkoxy, $C_1$-$C_6$alkylsulphonyl-$C_1$-$C_6$alkoxy, $C_1$-$C_6$alkoxycarbonyl-$C_1$-$C_6$alkoxy, $C_1$-$C_6$alkoxycarbonyl, $C_1$-$C_6$alkylcarbonyl, —P(O)(O$C_1$-$C_4$alkyl)$_2$, $C_1$-$C_6$alkylthio, $C_1$-$C_6$alkylsulphinyl, $C_1$-$C_6$alkylsulphonyl, $C_1$-$C_6$haloalkylthio, $C_1$-$C_6$haloalkylsulphinyl, $C_1$-$C_6$haloalkylsulphonyl, oxiranyl, which for its part may be substituted by $C_1$-$C_6$alkyl, and by a five- to ten-membered monocyclic or fused bicyclic ring system which may be aromatic, partially saturated or fully saturated and may contain 1 to 4 heteroatoms selected from the group consisting of nitrogen, oxygen and sulphur, and wherein each ring system may not contain more than 2 oxygen atoms and not more than 2 sulphur atoms, and wherein the ring system itself can be substituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphonyl, di($C_1$-$C_4$alkyl)aminosulphonyl, di($C_1$-$C_4$alkyl)amino, halogen, cyano, nitro and phenyl, and wherein the substituents on the nitrogen in the heterocyclic ring are different from halogen;

or $Y_1$ is a five- to ten-membered monocyclic or fused bicyclic ring system which may be aromatic, partially saturated or fully saturated and may contain 1 to 4 heteroatoms selected from the group consisting of nitrogen, oxygen and sulphur, and where each ring system may not contain more than 2 oxygen atoms and not more than 2 sulphur atoms, and where the ring system itself can be mono- or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylsulphonyl, di($C_1$-$C_4$alkyl)aminosulphonyl, di($C_1$-$C_4$alkyl)amino, halogen, cyano, nitro and phenyl, and where the substituents on the nitrogen in the heterocyclic ring are different from halogen;

or the group $X_1$—$Y_1$ together is formyl or cyano;
each of $R_{1a}$, $R_{1b}$, $R_{5a}$, $R_{5b}$, $R_{5c}$, $R_{5d}$, $R_{5e}$, $R_{5f}$, $R_{5g}$, and $R_{5h}$ which may be the same or different, represents hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_5$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulphinyl, $C_1$-$C_4$haloalkylsulphonyl, $C_1$-$C_4$alkylsulphinyl, $C_1$-$C_4$alkylsulphonyl, $C_1$-$C_4$alkylsulphonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, $C_3$-$C_6$trialkylsilyl, phenyl, benzyl or phenoxy; or represents phenyl, benzyl or phenoxy mono-, di- or trisubstituted by substituents selected from the group consisting of halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulphinyl, $C_1$-$C_4$alkylsulphonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy and $C_3$-$C_6$trialkylsilyl;

each of $R_2$ and $R_3$, which may be the same or different, represents hydrogen, $C_1$-$C_6$alkyl, $C_2$-$C_6$alkenyl, $C_2$-$C_6$alkynyl or $C_3$-$C_8$cycloalkyl; or $C_1$-$C_6$alkyl, $C_2$-$C_6$alkenyl, $C_2$-$C_6$alkynyl or $C_3$-$C_8$cycloalkyl mono- or polysubstituted by substituents selected from halogen nitro, cyano, hydroxy, C₁-C₄alkoxy, C₁-C₄haloalkoxy, C₁-C₄alkylthio, C₁-C₄haloalkylthio, C₁-C₄alkylsulphinyl, C₁-C₄alkylsulphonyl, C₁-C₄alkylamino, C₂-C₄dialkylamino, C₃-C₆cycloalkylamino and C₁-C₆alkyl-C₃-C₆cycloalkylamino;

D is 2-pyridyl, 3-pyridyl or 4-pyridyl; or phenyl, 2-pyridyl, 3-pyridyl or 4-pyridyl mono-, di- or trisubstituted by $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulphinyl, $C_1$-$C_4$alkylsulphonyl, $C_1$-$C_4$haloalkylsulphinyl or $C_1$-$C_4$haloalkylsulphonyl;

or D is a group

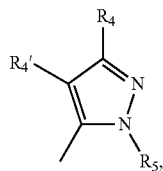  (D₁)

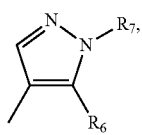  (D₂)

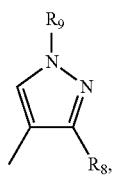  (D₃)

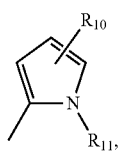  (D₄)

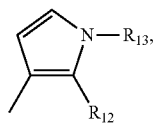  (D₅)

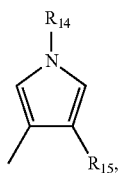  (D₆)

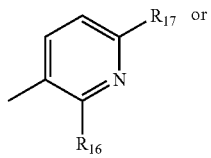  (D₇)

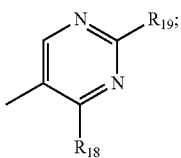  (D₈)

or D is phenyl;

$R_4$, $R_4'$, $R_{10}$, $R_{17}$, and $R_{19}$ independently from each other, are hydrogen, $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_2$-$C_4$alkoxycarbonyl, $C_1$-$C_4$alkylthio, $C_1$-$C_4$haloalkylthio, $C_1$-$C_4$alkylsulphinyl, $C_1$-$C_4$alkylsulphonyl, $C_1$-$C_4$haloalkylsulphinyl or $C_1$-$C_4$haloalkylsulphonyl;

$R_5$, $R_6$, $R_8$, $R_{11}$, $R_{12}$, $R_{15}$, $R_{16}$ and $R_{18}$ independently from each other, are $C_1$-$C_6$alkyl, or $C_1$-$C_6$alkyl mono-, di- or trisubstituted by halogen, cyano, nitro, hydroxy, $C_1$-$C_4$alkoxy, $C_1$-$C_4$alkoxycarbonyl, $C_1$-$C_4$alkylthio, $C_1$-$C_4$alkylsulphinyl, $C_1$-$C_4$alkylsulphonyl, $C_1$-$C_4$alkylamino, $C_2$-$C_4$dialkylamino or $C_3$-$C_6$cycloalkylamino; or are phenyl, 2-pyridyl, 3-pyridyl, 4-pyridyl; or are phenyl, 2-pyridyl, 3-pyridyl or 4-pyridyl mono-, di- or trisubstituted by substituents selected from the group consisting of $C_1$-$C_6$alkyl, $C_3$-$C_6$cycloalkyl, $C_1$-$C_6$haloalkyl, halogen, cyano, $C_1$-$C_4$alkoxy, $C_1$-$C_4$haloalkoxy, $C_1$-$C_4$alkylthio, $C_1$-$C_4$haloalkylthio, $C_1$-$C_4$alkylsulphinyl, $C_1$-$C_4$alkylsulphonyl, $C_1$-$C_4$haloalkylsulphinyl and $C_1$-$C_4$haloalkylsulphonyl;

$R_7$, $R_9$, $R_{13}$ and $R_{14}$ independently from each other, are hydrogen, $C_1$-$C_6$alkyl, $C_1$-$C_6$haloalkyl, $C_2$-$C_6$alkenyl, $C_2$-$C_6$haloalkenyl, $C_3$-$C_6$alkenyl or $C_3$-$C_6$haloalkenyl;

$R_{20}$ is hydrogen, $C_1$-$C_6$alkyl, $C_2$-$C_6$alkenyl, $C_2$-$C_6$alkynyl, or $C_3$-$C_6$cycloalkyl; or is $C_1$-$C_6$alkyl, $C_2$-$C_6$ alkenyl, $C_2$-$C_6$ alkynyl or $C_3$-$C_6$ cycloalkyl substituted with one, two or three substituents selected from the group consisting of halogen, cyano, nitro, hydroxy, $C_1$-$C_4$alkyl, $C_1$-$C_4$alkoxy, $C_1$-$C_4$haloalkoxy, $C_1$-$C_4$alkylthio, $C_1$-$C_4$alkylsulphinyl, $C_1$-$C_4$alkylsulphonyl, $C_1$-$C_4$alkylsulfoximino, $C_2$-$C_6$ alkoxycarbonyl, $C_2$-$C_6$ alkylcarbonyl, $C_2$-$C_6$trialkylsilyl, benzyl, phenoxy and a three- to ten-membered, monocyclic or fused bicyclic ring system which may be aromatic, partially saturated or fully saturated, wherein the three- to ten-membered ring system may contain heteroatoms selected from the group consisting of oxygen, nitrogen and sulphur; it being possible for said benzyl, phenoxy and three- to ten-membered, monocyclic or fused bicyclic ring system in turn to be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_2$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulphinyl, $C_1$-$C_4$alkylsulphonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_2$-$C_8$ dialkylaminocarbonyl and $C_2$-$C_6$ trialkylsilyl;

it being possible for said three- to ten-membered, monocyclic or fused bicyclic ring system to be spiro-bonded to the $C_3$-$C_6$cycloalkyl group;

or $R_{20}$ is $C_1$-$C_4$alkoxy, $C_1$-$C_4$alkylamino, $C_2$-$C_8$dialkylamino, $C_2$-$C_6$ cycloalkylamino, $C_2$-$C_6$alkoxycarbonyl or $C_2$-$C_6$alkylcarbonyl;

or $R_{20}$ is 3-oxetanyl, 3-thietanyl, 1-oxo-3-thietanyl, 1,1-dioxo-3-thietanyl, 1-imino-1-oxo-3-thietanyl or 3-azetdinyl;

or $R_{20}$ is 3-oxetanyl, 3-thietanyl, 1-oxo-3-thietanyl, 1,1-dioxo-3-thietanyl, 1-imino-1-oxo-3-thietanyl, 3-azetdinyl, each of which mono- or polysubstituted by substituents independently selected from the group consisting of $C_1$-$C_4$ alkyl, $C_1$-$C_4$ haloalkyl, halogen, cyano, $C_6$alkoxycarbonyl and $C_2$-$C_6$alkylcarbonyl;

each of $Z_1$ and $Z_2$, which may be the same or different, represents oxygen or sulphur; and agronomically acceptable salts/isomers/enantiomers/tautomers/N-oxides of those compounds.

Compounds of formula I which have at least one basic centre can form, for example, acid addition salts, for example with strong inorganic acids such as mineral acids, for example perchloric acid, sulphuric acid, nitric acid, nitrose acid, a phosphorus acid or a hydrohalic acid, with strong organic carboxylic acids, such as $C_1$-$C_4$alkanecarboxylic acids which are unsubstituted or substituted, for example by halogen, for example acetic acid, such as saturated or unsaturated dicarboxylic acids, for example oxalic acid, malonic acid, succinic acid, maleic acid, fumaric acid or phthalic acid, such as hydroxycarboxylic acids, for example ascorbic acid, lactic acid, malic acid, tartaric acid or citric acid, or such as benzoic acid, or with organic sulfonic acids, such as $C_1$-$C_4$alkane- or arylsulfonic acids which are unsubstituted or substituted, for example by halogen, for example methane- or p-toluenesulfonic acid. Compounds of formula I which have at least one acidic group can form, for example, salts with bases, for example mineral salts such as alkali metal or alkaline earth metal salts, for example sodium, potassium or magnesium salts, or salts with ammonia or an organic amine, such as morpholine, piperidine, pyrrolidine, a mono-, di- or tri-lower-alkylamine, for example ethyl-, diethyl-, triethyl- or dimethylpropylamine, or a mono-, di- or trihydroxy-lower-alkylamine, for example mono-, di- or triethanolamine.

The alkyl groups occurring in the definitions of the substituents can be straight-chain or branched and are, for example, methyl, ethyl, n-propyl, isopropyl, n-butyl, sec-butyl, isobutyl, tert-butyl, pentyl, hexyl, nonyl, decyl and their branched isomers. Alkoxy, alkenyl and alkynyl radicals are derived from the alkyl radicals mentioned. The alkenyl and alkynyl groups can be mono- or polyunsaturated.

$Y_1$ as $C_1$-$C_{30}$alkyl, $C_3$-$C_{30}$alkenyl or $C_3$-$C_{30}$alkynyl which may be interrupted by atoms or group of atoms is understood to be, for example, $-CH_2-$, $-CH_2O-$, $-OCH_2-$, $-CH_2OCH_2-$, $-OCH_2CH_2-$, $-OCH_2CH_2CH_2-$, $-CH_2CH_2OCH_2CH_2-O-(CH_2)_{15}CH_3$, $-(CH_2)_7CH=CH(CH_2)_7CH_3$, $CH_2CH_2O(CH_2)_{26}CH_3$, $-(CH_2)_7C(O)CH_3$, or $-CH_2SCH_2-$.

If $X_1$ designates groups like $-(CO)O-$, $-SO_2NR_{5d}$, $(P(=O)O(R_{5e})-$, $-C(O)S-$, $-C(S)O-$, $-C(S)NR_{5f}-$ or $-(CO)NR_{5g}-$, the left free radical of said groups is attached to the 5-membered aromatic ring system which contains by $G_1$, $G_2$ and $G_3$, and the right radical is attached to the substituent $Y_1$.

Halogen is generally fluorine, chlorine, bromine or iodine. This also applies, correspondingly, to halogen in combination with other meanings, such as haloalkyl or halophenyl.

Haloalkyl groups preferably have a chain length of from 1 to 6 carbon atoms. Haloalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable haloalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl. Among the $C_3$-$C_{20}$alkenyl groups which are mono-, di- or trisubstituted by halogen, preference is given to those having a chain length of from 3 to 5 carbon atoms.

Suitable haloalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl. Among the alkynyl groups which are mono- or polysubstituted by halogen, preference is given to those having a chain length of from 3 to 5 carbon atoms.

Alkoxy groups preferably have a preferred chain length of from 1 to 6 carbon atoms. Alkoxy is, for example, methoxy, ethoxy, propoxy, i-propoxy, n-butoxy, isobutoxy, sec-butoxy and tert-butoxy and also the isomeric pentyloxy and hexyloxy radicals; preferably methoxy and ethoxy.

Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tertbutoxycarbonyl; preferably methoxycarbonyl or ethoxycarbonyl. Haloalkoxy groups preferably have a chain length of from 1 to 6 carbon atoms. Haloalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio groups preferably have a chain length of from 1 to 6 carbon atoms. Alkylthio is, for example, methylthio, ethylthio, propylthio, isopropylthio, n-butylthio, isobutylthio, sec-butylthio or tertbutylthio, preferably methylthio and ethylthio. Alkylsulphinyl is, for example, methylsulphinyl, ethylsulphinyl, propylsulphinyl, isopropylsulphinyl, n-butylsulphinyl, isobutylsulphinyl, secbutylsulphinyl, tert-butylsulphinyl; preferably methylsulphinyl and ethylsulphinyl.

Alkylsulphonyl is, for example, methylsulphonyl, ethylsulphonyl, propylsulphonyl, isopropylsulphonyl, n-butylsulphonyl, isobutylsulphonyl, sec-butylsulphonyl or tertbutylsulphonyl; preferably methylsulphonyl or ethylsulphonyl.

Alkylamino is, for example, methylamino, ethylamino, n-propylamino, isopropylamino or the isomeric butylamines. Dialkylamino is, for example, dimethylamino, methylethylamino, diethylamino, n-propylmethylamino, dibutylamino and diisopropylamino. Preference is given to alkylamino groups having a chain length of from 1 to 4 carbon atoms.

Alkoxyalkyl groups preferably have a chain length of 1 to 6 carbon atoms.

Alkoxyalkyl is, for example, methoxymethyl, methoxyethyl, ethoxymethyl, ethoxyethyl, npropoxymethyl, n-propoxyethyl, isopropoxymethyl or isopropoxyethyl.

Alkylthioalkyl groups preferably have from 1 to 8 carbon atoms. Alkylthioalkyl is, for example, methylthiomethyl, methylthioethyl, ethylthiomethyl, ethylthioethyl, n-propylthiomethyl, npropylthioethyl, isopropylthiomethyl, isopropylthioethyl, butylthiomethyl, butylthioethyl or butylthiobutyl.

The cycloalkyl groups preferably have from 3 to 6 ring carbon atoms, for example cyclopropyl, cyclobutyl, cyclopentyl and cyclohexyl. Phenyl, also as part of a substituent such as phenoxy, benzyl, benzyloxy, benzoyl, phenylthio, phenylalkyl, phenoxyalkyl, may be substituted. In this case, the substituents can be in ortho, meta and/or para position. The preferred substituent positions are the ortho and para positions to the ring attachment point.

In the context of the present invention "mono- to polysubstituted" in the definition of the substituents, means typically, depending on the chemical structure of the substituents, monosubstituted to seven-times substituted, preferably monosubstituted to five-times substituted, more preferably mono-, double- or triple-substituted.

According to the present invention, a three- to ten-membered monocyclic or fused bicyclic ring system which may be aromatic, partially saturated or fully saturated is, depending of the number of ring members, for example, selected from the group consisting of

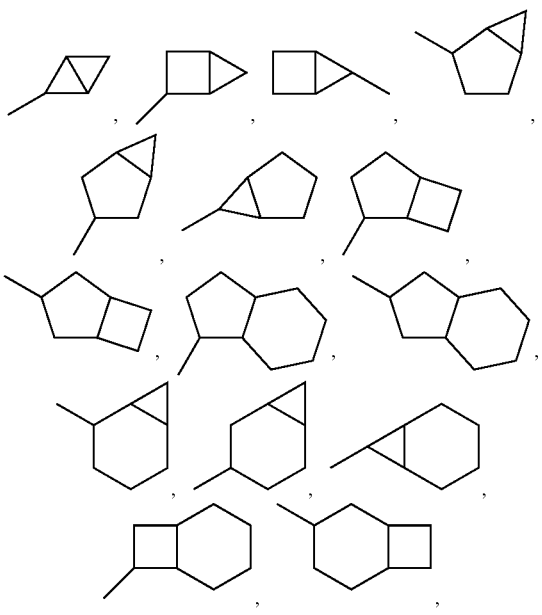

cyclopropyl, cyclobutyl, cyclopentyl, cyclohexyl, where said cycloalkylgroups for their part may be preferably unsubstituted or substituted by $C_1$-$C_6$alkyl or halogen, or is naphthyl or the following heterocyclic groups: pyrrolyl; pyridyl; pyrazolyl; pyrimidyl; pyrazinyl; imidazolyl; thiadiazolyl; quinazolinyl; furyl; oxadiazolyl; indolizinyl; pyranyl; isobenzofuranyl; thienyl; naphthyridinyl; (1-methyl-1H-pyrazol-3-yl)-; (1-ethyl-1H-pyrazol-3-yl)-; (1-propyl-1H-pyrazol-3-yl)-; (1H-pyrazol-3-yl)-; (1,5-dimethyl-1H-pyrazol-3-yl)-; (4-chloro-1-methyl-1H-pyrazol-3-yl)-; (1H-pyrazol-1-yl)-; (3-methyl-1H-pyrazol-1-yl)-; (3,5-dimethyl-1H-pyrazol-1-yl)-; (3-isoxazolyl)-; (5-methyl-3-isoxazolyl)-; (3-methyl-5-isoxazolyl)-; (5-isoxazolyl)-; (1H-pyrrol-2-yl)-; (1-methyl-1H-pyrrol-2-yl)-; (1H-pyrrol-1-yl)-; (1-methyl-1H-pyrrol-3-yl)-; (2-furanyl)-; (5-methyl-2-furanyl)-; (3-furanyl)-; (5-methyl-2-thienyl)-; (2-thienyl)-; (3-thienyl)-; (1-methyl-1H-imidazol-2-yl)-; (1H-imidazol-2-yl)-; (1-methyl-1H-imidazol-4-yl)-; (1-methyl-1H-imidazol-5-yl)-; (4-methyl-2-oxazolyl)-; (5-methyl-2-oxazolyl)-; (2-oxazolyl)-; (2-methyl-5-oxazolyl)-; (2-methyl-4-oxazolyl)-; (4-methyl-2-thiazolyl)-; (5-methyl-2-thiazolyl)-; (2-thiazolyl)-; (2-methyl-5-thiazolyl)-; (2-methyl-4-thiazolyl)-; (3-methyl-4-isothiazolyl)-; (3-methyl-5-isothiazolyl)-; (5-methyl-3-isothiazolyl)-; (1-methyl-1H-1,2,3-triazol-4-yl)-; (2-methyl-2H-1,2,3-triazol-4-yl)-; (4-methyl-2H-1,2,3-triazol-2-yl)-; (1-methyl-1H-1,2,4-triazol-3-yl)-; (1,5-dimethyl-1H-1,2,4-triazol-3-yl)-; (3-methyl-1H-1,2,4-triazol-1-yl)-; (5-methyl-1H-1,2,4-triazol-1-yl)-; (4,5-dimethyl-4H-1,2,4-triazol-3-yl)-; (4-methyl-4H-1,2,4-triazol-3-yl)-; (4H-1,2,4-triazol-4-yl)-; (5-methyl-1,2,3-oxadiazol-4-yl)-; (1,2,3-oxadiazol-4-yl)-; (3-methyl-1,2,4-oxadiazol-5-yl)-; (5-methyl-1,2,4-oxadiazol-3-yl)-; (4-methyl-3-furazanyl)-; (3-furazanyl)-; (5-methyl-1,2,4-oxadiazol-2-yl)-; (5-methyl-1,2,3-thiadiazol-4-yl)-; (1,2,3-thiadiazol-4-yl)-; (3-methyl-1,2,4-thiadiazol-5-yl)-; (5-methyl-1,2,4-thiadiazol-3-yl)-; (4-methyl-1,2,5-thiadiazol-3-yl)-; (5-methyl-1,3,4-thiadiazol-2-yl)-; (1-methyl-1H-tetrazol-5-yl); (1H-tetrazol-5-yl)-; (5-methyl-1H-tetrazol-1-yl)-; (2-methyl-2H-tetrazol-5-yl)-; (2-ethyl-2H-tetrazol-5-yl)-; (5-methyl-2H-tetrazol-2-yl)-; (2H-tetrazol-2-yl)-; (2-pyridyl)-; (6-methyl-2-pyridyl)-; (4-pyridyl)-; (3-pyridyl)-; (6-methyl-3-pyridazinyl)-; (5-methyl-3-pyridazinyl)-; (3-pyridazinyl)-; (4,6-dimethyl-2-pyrimidinyl)-; (4-methyl-2-pyrimidinyl); (2-pyrimidinyl)-; (2-methyl-4-pyrimidinyl)-; (2-chloro-4-pyrimidinyl)-; (2,6-dimethyl-4-pyrimidinyl)-; (4-pyrimidinyl)-; (2-methyl-5-pyrimidinyl)-; (6-methyl-2-pyrazinyl)-; (2-pyrazinyl)-; (4,6-dimethyl-1,3,5-triazin-2-yl)-; (4,6-dichloro-1,3,5-triazin-2-yl)-; (1,3,5-triazin-2-yl)-; (4-methyl-1,3,5-triazin-2-yl)-; (3-methyl-1,2,4-triazin-5-yl)-; (3-methyl-1,2,4-triazin-6-yl)-;

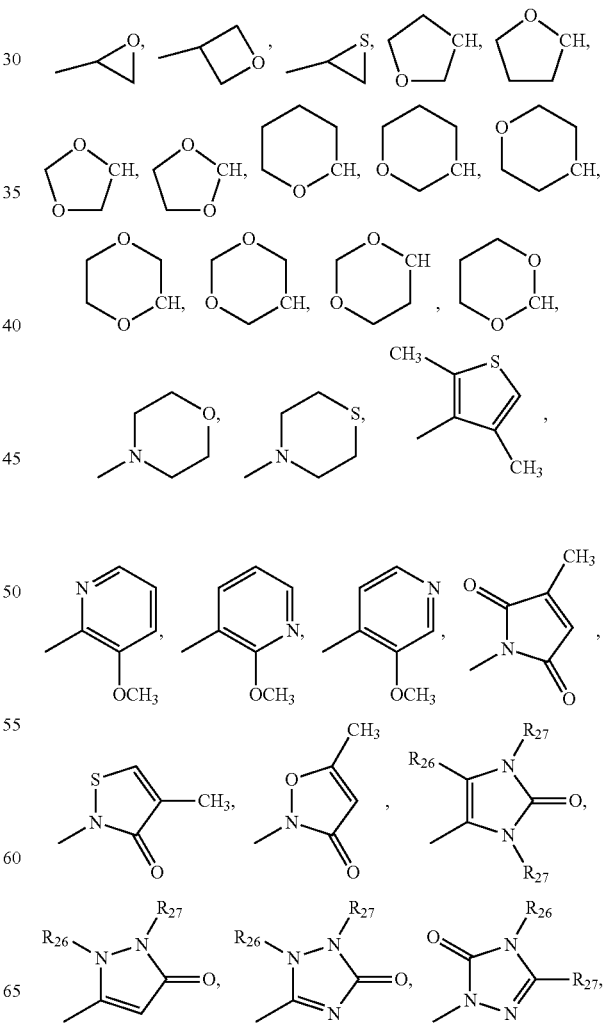

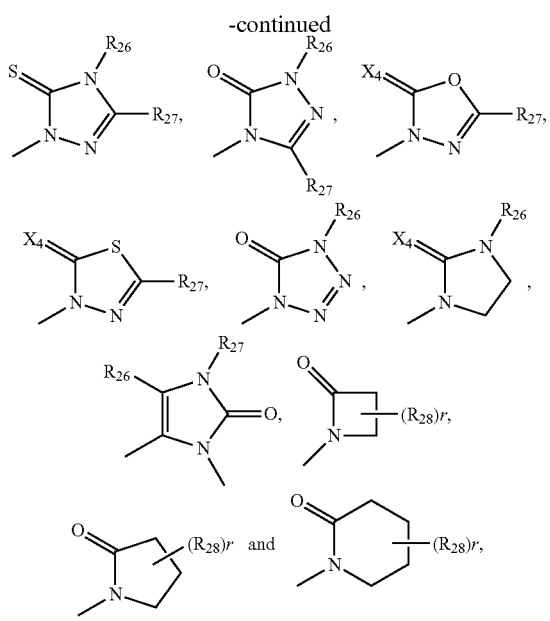

wherein each $R_{26}$ is methyl, each $R_{27}$ and each $R_{28}$ are independently hydrogen, $C_1$-$C_3$alkyl, $C_1$-$C_3$alkoxy, $C_1$-$C_3$alkylthio or trifluoromethyl, $X_4$ is oxygen or sulphur and r is 1, 2, 3 or 4.

Examples for a three- to ten-membered, monocyclic or fused bicyclic ring system which is spiro-bonded to the $C_3$-$C_6$cycloalkyl group of the substituent $R_{20}$ are

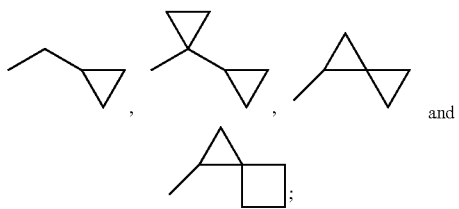

Where no free valency is indicated in those definitions, for example as in

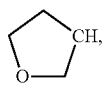

the linkage site is located at the carbon atom labelled "CH" or in a case such as, for example,

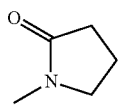

at the bonding site indicated at the bottom left.

Preferably $Z_1$ and/or $Z_2$ is oxygen. Further compounds of formula I are preferred, wherein $R_2$ and/or $R_3$ is hydrogen.

In a preferred group of compounds of formula I, $Y_1$ is $C_1$-$C_{20}$alkyl, $C_3$-$C_{20}$alkenyl or $C_3$-$C_{20}$alkynyl which may be interrupted one, two or three times by oxygen, with the proviso that the interrupting atoms are separated from each other by at least one methylene group; and which $Y_1$ may be mono- or polysubstituted by substituents selected from halogen, cyano, $C_3$-$C_6$cycloalkyl, pyridyl, phenyl and triazinyl, wherein said $C_3$-$C_6$cycloalkyl, pyridyl, phenyl and triazinyl may be substituted by $C_1$-$C_6$alkoxy or halogen.

In a further preferred group of compounds of formula I, $X_1$ is —C(O), —C(O)O—, thio, sulfonyl, —C(O)S—, C(O)NR$_{5g}$, wherein R$_{5g}$ is as defined above, or a direct bond.

In an especially preferred group of compounds of formula I, $X_1$ is preferably a direct bond, sulphonyl, —C(O)S— or —C(O)— and $Y_1$ is preferably $C_1$-$C_{10}$alkyl, $C_3$-$C_{10}$alkenyl or $C_3$-$C_{10}$alkinyl which may be interrupted one, two or three times by atoms or group of atoms independently selected from the group consisting of oxygen, —C(O)— or —OC(O)—; with the proviso that the interrupting atoms are separated from each other by at least one methylene group; and which may be mono- or polysubstituted by substituents selected from the group consisting of $C_3$-$C_6$cycloalkyl, halogen, cyano, $C_1$-$C_4$alkoxy, —P(O)(OC$_1$-$C_4$alkyl)$_2$, benzothiazolyloxy, pyridyl, furyl, thienyl, phenoxy, phenylthio and phenyl;

and pyridyl, phenoxy, phenylthio and phenyl, wherein said pyridyl, phenoxy, phenylthio and phenyl are mono- or disubstituted by substituents selected from the group consisting of $C_1$-$C_4$alkoxy and halogen.

Most preferably $Y_1$ is $C_1$-$C_6$alkyl, $C_3$-$C_6$alkenyl or $C_3$-$C_{16}$alkinyl which may be interrupted one, two or three times by atoms or group of atoms independently selected from the group consisting of oxygen, —C(O)— or —OC(O)—; with the proviso that the interrupting atoms are separated from each other by at least one methylene group; and which may be mono- or polysubstituted by substituents selected from the group consisting of $C_3$-$C_6$cycloalkyl, halogen, cyano, $C_1$-$C_4$alkoxy, —P(O)(OC$_1$-$C_4$alkyl)$_2$, benzothiazolyloxy, pyridyl, furyl, thienyl, phenoxy, phenylthio and phenyl;

and pyridyl, phenoxy, phenylthio and phenyl wherein said pyridyl, phenoxy, phenylthio and phenyl are mono- or disubstituted by substituents selected from the group consisting of $C_1$-$C_4$alkoxy and halogen.

$R_{20}$ is preferably hydrogen, methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)CH_3$, $C(CH_3)_2CH_2S(O)_2CH_3$, $CH_2CN$, $CH(CH_3)CH_3SCH_3$, $CH(CH_3)CH_3S(O)CH_3$ or $CH(CH_3)CH_3S(O)_2CH_3$, 3-methyl-thietan-3-yl, 1-oxo-3-methyl-thietan-3-yl or 1,1-dioxo-3-methyl-thietan-3-yl, in particular hydrogen, methyl, ethyl, i-propyl, tert.-butyl, $CH_2$—$C_3H_5$, $C(CH_2CH_2)$—$C_3H_5$, $C(CH_3)_2CH_2SCH_3$, $C(CH_3)_2CH_2S(O)CH_3$, $C(CH_3)_2CH_2S(O)_2CH_3$, $CH_2CN$, $CH(CH_3)CH_3SCH_3$, $CH(CH_3)CH_3S(O)CH_3$ or $CH(CH_3)CH_3S(O)_2CH_3$.

Special emphasis should also be given to compounds of formula I wherein D is a group $D_1$, wherein $R_5$ is 2-pyridyl which can be substituted by halogen, preferably which is monosubstituted by chloro at the 3-position of the pyridine ring and $R_4$ is halogen preferably chloro or bromo, $C_1$-$C_6$alkoxy, preferably methoxyl, $C_1$-$C_4$haloalkoxy most preferably $OCF_2H$ or 2,2,2-trifluoroethoxy, preferably $C_1$-$C_6$haloalkyl, most preferably trifluoromethyl.

Special mention should be made of compounds of formula I wherein each of $R_{1a}$, $R_{1b}$, $R_{5a}$, $R_{5b}$, $R_{5b}$, and $R_{5d}$ which may be the same or different, represents hydrogen, halogen, cyano, hydroxy, CHO, $C_1$-$C_6$alkyl, $C_3$-$C_6$cycloalkyl, $C_1$-$C_6$haloalkyl, $C_1$-$C_4$alkoxy, $C_1$-$C_4$alkoxy-$C_1$-$C_4$alkoxy- $C_1$-$C_4$alkyl, $C_1$-$C_4$alkylthio, $C_1$-$C_4$alkylsulphinyl, $C_1$-$C_4$alkylsulphonyl, $C_1$-$C_4$alkylsulphonyl-$C_1$-$C_4$alkyl, $C_1$-$C_4$alkylsulfoximino-$C_1$-$C_4$alkyl, $C_2$-$C_4$dialkylamino or $C_1$-$C_4$alkoxyimino-$C_1$-$C_4$alkyl; and $X_1$ is oxygen, —C(O)—, —(CO)O—, thio, sulphinyl, sulphonyl, —$SO_2NR_{5d}$, or a direct bond, preferably —C(O)—, —(CO)O—, sulphonyl, —$SO_2NR_{5d}$, or a direct bond, wherein $R_{5d}$ is defined as described above.

An outstanding group of compounds of formula I is represented by the formula Ic

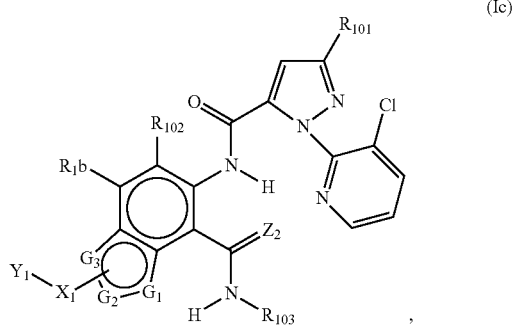

(Ic)

wherein
$G_1$, $G_2$, and $G_3$ have the meaning as given for formula I above;
$R_1b$ has the meaning as given for formula I above; preferably hydrogen or methyl;
—$X_1$—$Y_1$ have the meaning as given for formula I above; preferably
$X_1$ is a direct bond or —C(O)—;
$Y_1$ is $C_1$-$C_{10}$alkyl, $C_3$-$C_{10}$alkenyl or $C_3$-$C_{10}$alkinyl which may be interrupted one, two or three times by atoms or group of atoms independently selected from the group consisting of oxygen, —C(O)— or —OC(O)—; with the proviso that the interrupting atoms are separated from each other by at least one methylene group; and which may be mono- or polysubstituted by substituents selected from the group consisting of $C_3$-$C_6$cycloalkyl, halogen, cyano, $C_1$-$C_4$alkoxy, —P(O)(OC$_1$-$C_4$alkyl)$_2$, benzothiazolyloxy, pyridyl, furyl, thienyl, phenoxy, phenylthio and phenyl;
and pyridyl, phenoxy, phenylthio and phenyl mono- or disubstituted by substituents selected from the group consisting of $C_1$-$C_4$alkoxy and halogen.

In said outstanding group of compounds of formula I, $Y_1$ is most preferably $C_1$-$C_6$alkyl, $C_3$-$C_6$alkenyl or $C_3$-$C_{16}$alkinyl which may be interrupted one, two or three times by atoms or group of atoms independently selected from the group consisting of oxygen, —C(O)— or —OC(O)—; with the proviso that the interrupting atoms are separated from each other by at least one methylene group; and which may be mono- or polysubstituted by substituents selected from the group consisting of $C_3$-$C_6$cycloalkyl, halogen, cyano, $C_1$-$C_4$alkoxy, —P(O)(OC$_1$-$C_4$alkyl)$_2$, benzothiazolyloxy, pyridyl, furyl, thienyl, phenoxy, phenylthio and phenyl;
and pyridyl, phenoxy, phenylthio and phenyl mono- or disubstituted by substituents selected from the group consisting of $C_1$-$C_4$alkoxy and halogen;
$R_{101}$ is halogen, haloalkyl, haloalkoxy or alkoxy, especially difluoromethyl, trifluoromethyl, chlorine, bromine, OCF$_2$H$_2$O—CH$_2$—CF$_3$ or OCH$_3$, in particular halogen, haloalkyl, haloalkoxy, alkoxy especially trifluoromethyl, chlorine, bromine or OCH$_3$;

$R_{102}$ is halogen, $C_1$-$C_6$-alkyl, $C_2$-$C_6$-alkynyl or cyano, especially methyl, ethynyl, chlorine or bromine; in particular halogen, $C_1$-$C_6$-alkyl, especially methyl, chlorine or bromine; and $R_{103}$ is methyl, ethyl, i-propyl, tert.-butyl, CH$_2$—C$_3$H$_5$, C(CH$_2$CH$_2$)—C$_3$H$_5$, C(CH$_3$)$_2$CH$_2$SCH$_3$, C(CH$_3$)$_2$CH$_2$S(O)CH$_3$ or C(CH$_3$)$_2$CH$_2$S(O)$_2$CH$_3$, CH$_2$CN, CH(CH$_3$)CH$_3$SCH$_3$, CH(CH$_3$)CH$_3$S(O)CH$_3$, CH(CH$_3$)CH$_3$S(O)$_2$CH$_3$, 3-methyl-thietan-3-yl, 1-oxo-3-methyl-thietan-3-yl or 1,1-dioxo-3-methyl-thietan-3-yl; in particular methyl, ethyl, i-propyl, tert.-butyl, CH$_2$—C$_3$H$_5$, C(CH$_2$CH$_2$)—C$_3$H$_5$, C(CH$_3$)$_2$CH$_2$SCH$_3$, C(CH$_3$)$_2$CH$_2$S(O)CH$_3$, C(CH$_3$)$_2$CH$_2$S(O)$_2$CH$_3$, CH$_2$CN, CH(CH$_3$)CH$_3$SCH$_3$, CH(CH$_3$)CH$_3$S(O)CH$_3$ or CH(CH$_3$)CH$_3$S(O)$_2$CH$_3$.

Especially preferred compounds of formula I are selected from the group consisting of formulae Ic$_a$ to Ic$_f$:

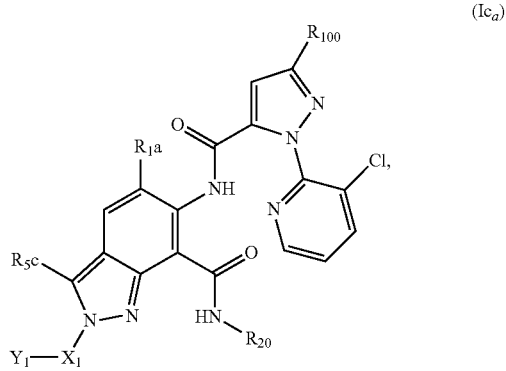

(Ic$_a$)

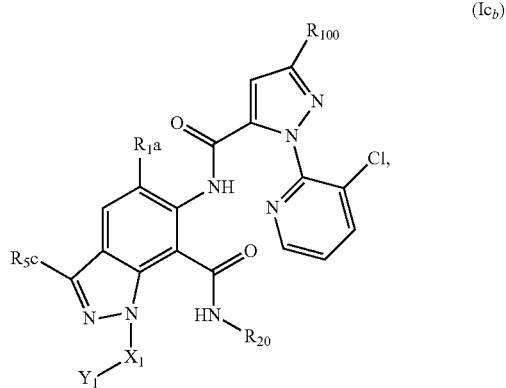

(Ic$_b$)

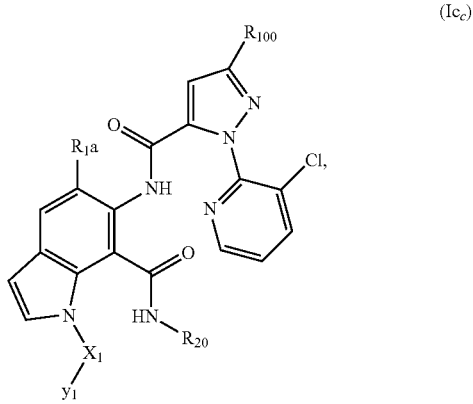

(Ic$_c$)

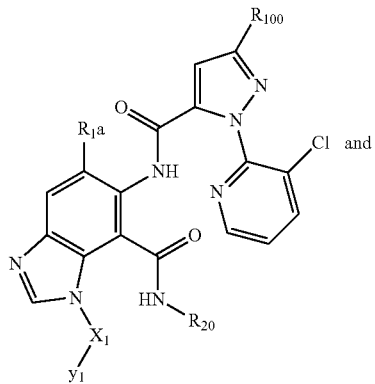
(Ic_e)

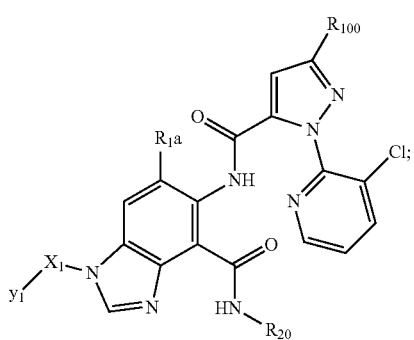
(Ic_f)

in particular formula (Ic_a) and (Ic_b), wherein
R_{5c} is preferably hydrogen, $C_1$-$C_4$alkyl, $C_2$-$C_4$alkynyl, halogen or cyano;
R_{20} is preferably hydrogen, $C_1$-$C_6$alkyl, $C_1$-$C_6$alkylthio-$C_1$-$C_6$alkyl, $C_1$-$C_6$alkylsulphonyl-$C_1$-$C_6$alkyl, $C_1$-$C_6$alkylsulphinyl-$C_1$-$C_6$alkyl, thiethan-3-yl, thiethan-3-yl substituted by $C_1$-$C_4$alkyl, preferably 3-methyl-thiethan-3-yl,

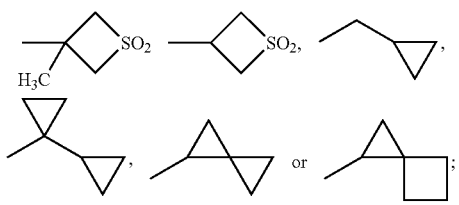

in particular hydrogen, $C_1$-$C_6$alkyl, $C_1$-$C_6$alkylthio-$C_1$-$C_6$alkyl, $C_1$-$C_6$alkylsulphonyl-$C_1$-$C_6$alkyl, $C_1$-$C_6$alkylsulphinyl-$C_1$-$C_6$alkyl,

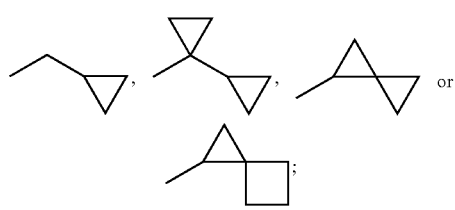

and R_{100} is preferably halogen, $C_1$-$C_6$alkyl, $C_1$-$C_6$haloalkyl, $C_1$-$C_6$alkoxy or $C_1$-$C_6$haloalkoxy; in particular halogen, $C_1$-$C_6$alkoxy, $C_1$-$C_6$haloalkyl or $C_1$-$C_6$haloalkoxy; and
—X_1—Y_1 is as defined under formula I above.

Further preferred embodiments of the present invention are the embodiments E1 to E121, which are defined as compounds of formula I which are represented by one formula selected from the group consisting of formulae T1 to T121 as described below, wherein in formulae T1 to T121
R_{1a} is preferably $C_1$-$C_4$alkyl, halogen or hydrogen;
R_{20} is preferably hydrogen, $C_1$-$C_6$alkyl, $C_1$-$C_6$alkylthio-$C_1$-$C_6$alkyl, $C_1$-$C_6$alkylsulphonyl-$C_1$-$C_6$alkyl, $C_1$-$C_6$alkylsulphinyl-$C_1$-$C_6$alkyl,

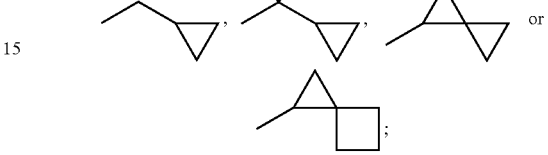

and
R_{100} is preferably $C_1$-$C_6$haloalkyl, $C_1$-$C_6$alkoxy, halogen or $C_1$-$C_6$haloalkoxy, in particular trifluorormethyl, difluoromethyl, methoxy, bromo, chloro or 1,1,1-trifluoroethoxy.
For example, embodiment E1 is represented by the compounds of formula T1

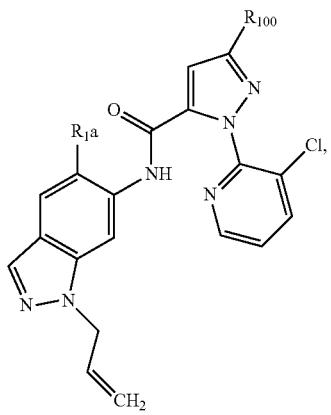
(T1)

wherein
R_{1a} is preferably $C_1$-$C_4$alkyl, halogen or hydrogen;
R_{20} is preferably hydrogen, $C_1$-$C_6$alkyl, $C_1$-$C_6$alkylthio-$C_1$-$C_6$alkyl, $C_1$-$C_6$alkylsulphonyl-$C_1$-$C_6$alkyl, $C_1$-$C_6$alkylsulphinyl-$C_1$-$C_6$alkyl,

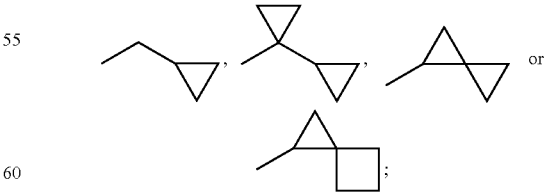

and
R_{100} is preferably $C_1$-$C_6$haloalkyl, halogen or $C_1$-$C_6$haloalkoxy, in particular trifluorormethyl, difluoromethyl, methoxy, bromo, chloro or 1,1,1-trifluoroethoxy.
Embodiments E2 to E121 are defined accordingly.

The method according to the invention for the preparation of compounds of formula I

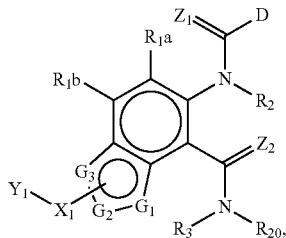 (I)

wherein $G_1$, $G_2$, $G_3$, $R_{1a}$, $R_{1b}$, $R_3$, $R_2$, $R_{20}$, D, $Z_1$, $Z_2$, $X_1$ and $Y_1$ are as defined hereinbefore, comprises reacting a compound of formula IIa (IIa),

 (IIa)

in which $Y_1$ and $X_1$ are as defined under formula I and $Z_3$ is a leaving group, for example halogen or cyano, with a compound of formula IIIa

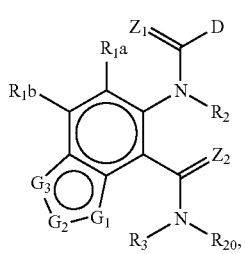 (IIIa)

wherein $G_1$, $G_2$, $G_3$, $R_{1a}$, $R_{1b}$, $R_3$, $R_2$, $R_{20}$, D, $Z_1$, and $Z_2$ are as defined hereinbefore, in an inert organic solvent in the presence of a base, (IIa), or b) reacting a compound of formula II

 (IIa)

in which $Y_1$ and $X_1$ are as defined under formula I and $Z_3$ is a leaving group, for example halogen or cyano, with a compound of formula IIIb

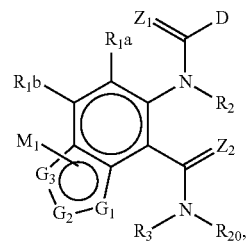 (IIIb)

wherein $G_1$, $G_2$, $G_3$, $R_{1a}$, $R_{1b}$, $R_3$, $R_2$, $R_{20}$, D, $Z_1$, and $Z_2$ are as defined under formula I above and $M_1$ is an alkaline earth metal cation or an alkali metal cation, preferably a lithium, sodium, or potassium cation. In that method, the salt of formula IIIa either may be used as such or, preferably, may be formed in situ in the reaction mixture by addition of an appropriate base. The method according to the invention is illustrated in the following Scheme 1.

Scheme 1

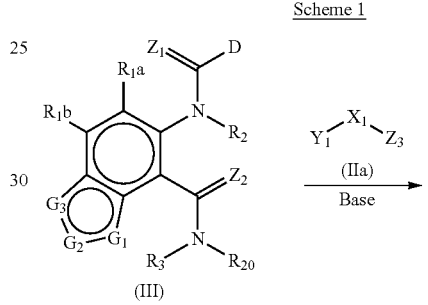

According to reaction scheme 1, the derivatives of formula IIa, in which $Z_3$ is a leaving group such as halogen, for example iodine, bromine, and in particular chlorine, N-oxyphthalimide or N,O-dimethylhydroxylamino or part of an activated ester, for example

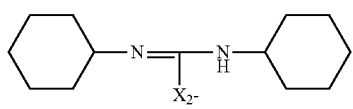

(where $X_2$ is O, S, N, formed from dicyclohexylcarbodiimide (DCC) and the corresponding compound with an acidic hydrogen) or

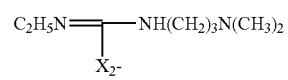

(formed from N-ethyl N'-(3-dimethylaminopropyl)carbodiimide (EDC) and the corresponding compound with an acidic hydrogen) are used as starting material for preparing the compounds of formula I. The starting materials are reacted in an inert organic solvent such as a halogenated hydrocarbon, for example dichloromethane, a nitrile, for example acetonitrile, or an aromatic hydrocarbon, for example toluene, and in the presence of a base such as an alkylamine, for example triethylamine, an aromatic amine, for example pyridine or 4-dimethylaminopyridine (DMAP). This esterification can be carried out at temperatures of from 0° C. to 110° C.

Compounds of formula I, in which $G_1$, $G_2$, $G_3$, $R_{1a}$, $R_{1b}$, $R_3$, $R_2$, $R_{20}$, D, $Z_1$, and $Z_2$ are as defined above, can also be prepared by reacting a compound of formula IIa, in which $Y_1$ and $X_1$ are as defined under formula I and $Z_3$ is a leaving group, for example halogen, by treating with compounds of formula IIIa, in the presence of a base such as sodium hydride or an alkaline earth metal oxide or carbonate in an inert solvent such as dimethylformamide or THF at temperatures between −5 and 160° C., or, to prepare the corresponding sulphinyl or sulphonyl derivatives, by reacting with an oxidizing agent such as m-chloroperbenzoic acid or sodium periodate, or sodium perborate, with, depending on the degree of oxidation, temperature control known to the person skilled in the art (for example −30° C. to +50° C. for sulphinyl compounds and −20° C. to +100° C. for sulphonyl compounds, respectively), in an inert solvent such as dichloromethane.

The preparation of the intermediates of formula III is described, for example, in WO 2007/020050 and WO 2007/093402.

Alternatively, intermediates of formula III wherein $G_1$ and $G_2$ are nitrogen, $G_3$ is methine, $R_{1a}$ is $C_1$-$C_6$alkyl, $R_{1b}$, $R_3$ and $R_2$ are hydrogen, $Z_1$, and $Z_2$ are oxygen, and D is a group $D_1$ or $D_6$, are prepared by converting a compound of formula IV

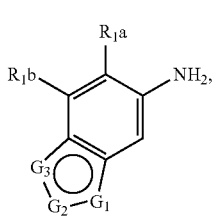
(IV)

in which $G_1$ and $G_2$ are nitrogen, $G_3$ is methine, $R_{1a}$ is $C_1$-$C_6$alkyl, and $R_{1b}$ is hydrogen, in the presence of chloralhydrate, hydroxylamine hydrochlorid, in a protic solvent, such as water, at temperatures between 20-100° C., into a compound of formula V

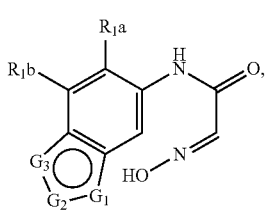
(V)

wherein $G_1$ and $G_2$ are nitrogen, $G_3$ is methine, $R_{1a}$ is $C_1$-$C_6$alkyl, and $R_{1b}$ is hydrogen. The compounds of formula V are treated with a strong acid, such as sulphuric acid, optionally in the presence of a solvent, such as water, at temperatures between 0-100° C., to give the compounds of formula VI;

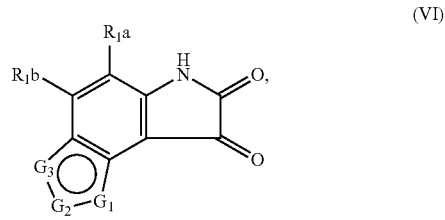
(VI)

wherein $G_1$ and $G_2$ are nitrogen, $G_3$ is methine, $R_{1a}$ is $C_1$-$C_6$alkyl, and $R_{1b}$ is hydrogen. Treatment of the compounds of formula VI with an oxidising agent, such as hydrogen peroxide, in a protic solvent in the presence of a base, such as sodium hydroxide, leads to compounds of formula (VII)

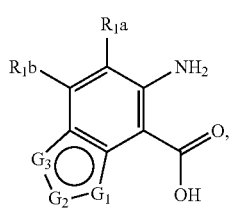
(VII)

wherein $G_1$ and $G_2$ are nitrogen, $G_3$ is CH, $R_{1a}$ is $C_1$-$C_6$alkyl, and $R_{1b}$ is hydrogen. Similar conversions of anilines to anthranillic acids are well known in the literature (for example, *Heterocycles*, 15(2), 1053-9, 1981)). The anthranilic acids of formula VII can be converted to the compounds of formula III by methods described in WO 2007/093402.

Compounds of formula III are converted into compounds of formula I by the methods shown in scheme 1. This complete reaction sequence is summarised in Scheme 2 wherein $G_1$ and $G_2$ are nitrogen, $G_3$ is methine, $R_{1a}$ is $C_1$-$C_6$alkyl, and $R_{1b}$ is hydrogen, and D, $R_{20}$ are as described in formula I.

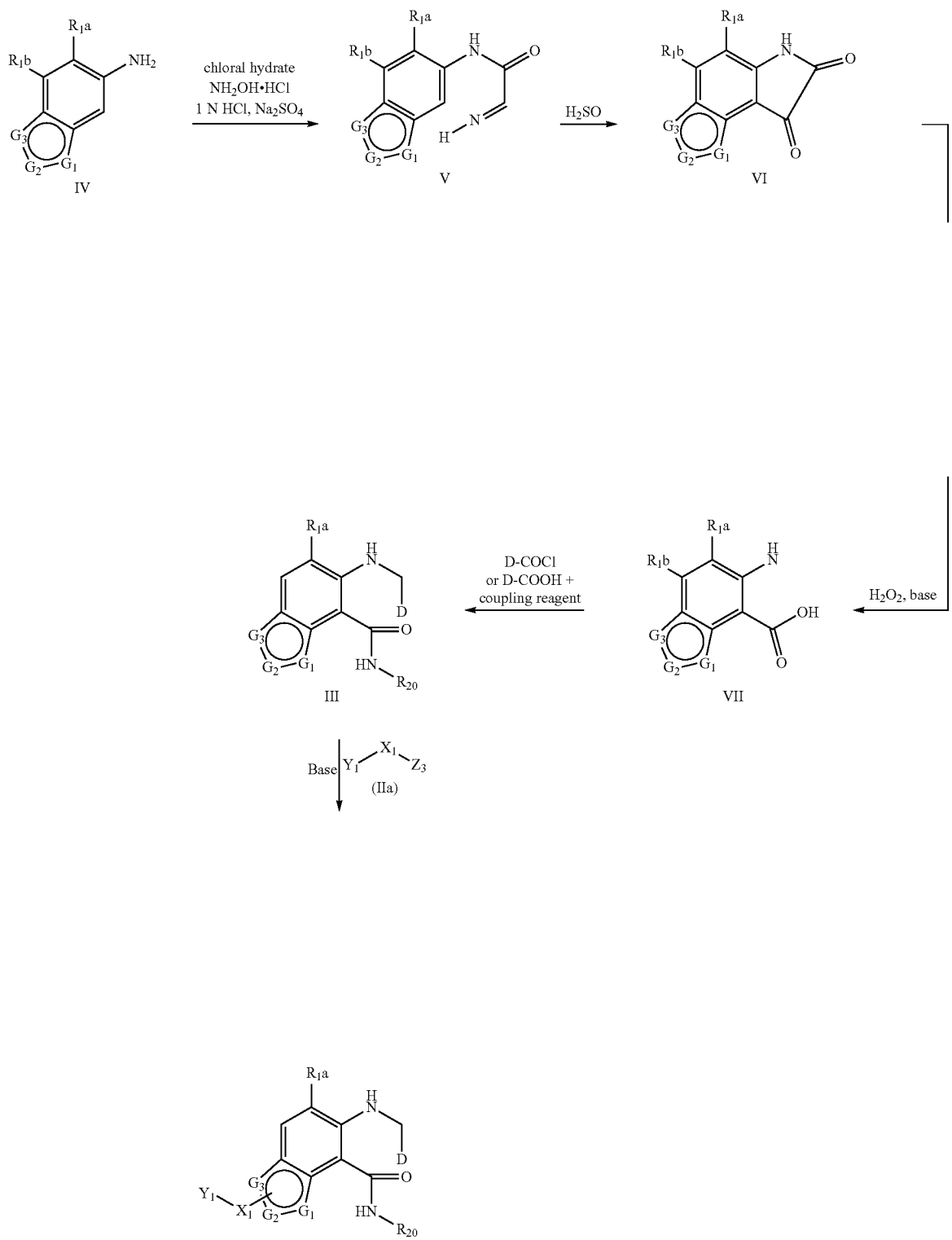
Compound of formula IV can be prepared as described in EP-A-040872. The intermediates of formulae V and VI are novel and were developed specifically for the preparation of the compounds of formula I. Accordingly, they also form part of the subject-matter of the present invention.

Alternatively, compounds of formula I can be prepared by the routes shown in Scheme 3:

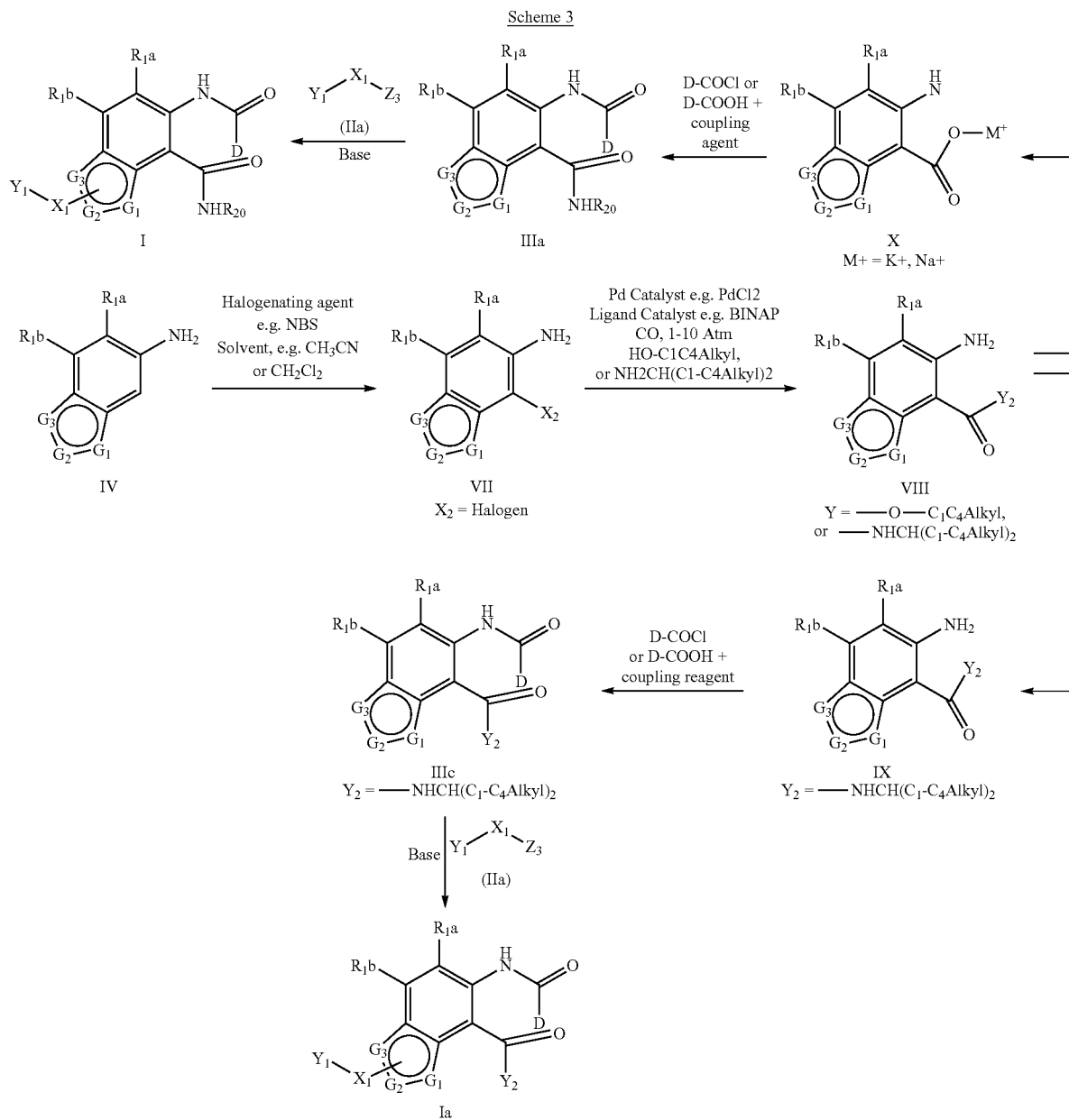

Scheme 3

In scheme 3, a compound of formula IV, wherein $G_1$ and $G_2$ are nitrogen, $G_3$ is methine, $R_{1a}$ is $C_1$-$C_6$alkyl, and $R_{1b}$ is hydrogen, is treated with a halogenating agent, such as N-halosuccinamide, for example N-bromosuccinamide in a solvent, such as acetonitrile at temperatures between −80° C. to approximately +50° C., preferably 20° C. to 25° C., to give compounds of formula VII wherein $G_1$ and $G_2$ are nitrogen, $G_3$ is CH, $R_{1a}$ is $C_1$-$C_6$alkyl, $R_{1b}$ is hydrogen and $Y_2$ is halogen. Palladium catalysed oxidative insertion into the C—$Y_2$ bond of compounds of formula VII and trapping of the intermediate palladium species with nucleophiles such as HO—$C_1$-$C_4$Alkyl, or ($C_1$-$C_4$Alkyl)$_2$CHNH$_2$) gives compounds of formula VIII. Such carbonylations and amidocarbonylations are known to a person skilled in the art (see for example *Organic Letters,* 6(13), 2097-2100; 2004 and *Angewandte Chemie, International Edition* (2007), 46(16), 2875-2878)). Compounds of formula VIII can then be converted to compounds of formula I as shown in scheme 3 by methods known to those skilled in the art, and as described in WO 2007/093402.

The reactants can be reacted in the presence of a base. Examples of suitable bases are alkali metal or alkaline earth metal hydroxides, alkali metal or alkaline earth metal hydrides, alkali metal or alkaline earth metal amides, alkali metal or alkaline earth metal alkoxides, alkali metal or alkaline earth metal acetates, alkali metal or alkaline earth metal carbonates, alkali metal or alkaline earth metal dialkylamides or alkali metal or alkaline earth metal alkylsilylamides, alkylamines, alkylenediamines, free or N-alkylated saturated or unsaturated cycloalkylamines, basic heterocycles, ammonium hydroxides and carbocyclic amines. Examples which may be mentioned are sodium hydroxide, sodium hydride, sodium amide, sodium methoxide, sodium acetate, sodium carbonate, potassium tert-butoxide, potassium hydroxide, potassium carbonate, potassium hydride, lithium diisopropylamide, potassium bis(trimethylsilyl)amide, calcium hydride, triethylamine, diisopropylethylamine, triethylenediamine, cyclohexylamine, N-cyclohexyl-N,N-dimethylamine, N,N-diethylaniline, pyridine, 4-(N,N-dimethylamino)pyridine, quinuclidine, N-methylmorpholine, benzyltrimethylammonium hydroxide and 1,8-diazabicyclo[5.4.0]undec-7-ene (DBU).

The reactants can be reacted with each other as such, i.e. without adding a solvent or diluent. In most cases, however, it is advantageous to add an inert solvent or diluent or a mixture of these. If the reaction is carried out in the presence of a base, bases which are employed in excess, such as triethylamine, pyridine, N-methylmorpholine or N,N-diethylaniline, may also act as solvents or diluents.

The reaction is advantageously carried out in a temperature range from approximately −80° C. to approximately +140° C., preferably from approximately −30° C. to approximately +100° C., in many cases in the range between ambient temperature and approximately +80° C.

A compound of formula I can be converted in a manner known per se into another compound of formula I by replacing one or more substituents of the starting compound of formula I in the customary manner by (an)other substituent(s) according to the invention.

Depending on the choice of the reaction conditions and starting materials which are suitable in each case, it is possible, for example, in one reaction step only to replace one substituent by another substituent according to the invention, or a plurality of substituents can be replaced by other substituents according to the invention in the same reaction step.

Salts of compounds of formula I can be prepared in a manner known per se. Thus, for example, acid addition salts of compounds of formula I are obtained by treatment with a suitable acid or a suitable ion exchanger reagent and salts with bases are obtained by treatment with a suitable base or with a suitable ion exchanger reagent.

Salts of compounds of formula I can be converted in the customary manner into the free compounds I, acid addition salts, for example, by treatment with a suitable basic compound or with a suitable ion exchanger reagent and salts with bases, for example, by treatment with a suitable acid or with a suitable ion exchanger reagent.

Salts of compounds of formula I can be converted in a manner known per se into other salts of compounds of formula I, acid addition salts, for example, into other acid addition salts, for example by treatment of a salt of inorganic acid such as hydrochloride with a suitable metal salt such as a sodium, barium or silver salt, of an acid, for example with silver acetate, in a suitable solvent in which an inorganic salt which forms, for example silver chloride, is insoluble and thus precipitates from the reaction mixture.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl celulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

The compounds of formula I according to the invention are preventively and/or curatively valuable active ingredients in the field of pest control, even at low rates of application, which have a very favorable biocidal spectrum and are well tolerated by warm-blooded species, fish and plants. The active ingredients according to the invention act against all or individual developmental stages of normally sensitive, but also resistant, animal pests, such as insects or representatives of the order Acarina. The insecticidal or acaricidal activity of the active ingredients according to the invention can manifest itself directly, i.e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:
from the order Acarina, for example,
*Acarus siro, Aceria sheldoni, Aculus schlechtendali, Amblyomma* spp., *Argas* spp., *Boophilus* spp., *Brevipalpus* spp., *Bryobia praetiosa, Calipitrimerus* spp., *Chorioptes* spp., *Dermanyssus gallinae, Eotetranychus carpini, Eriophyes* spp., *Hyalomma* spp., *Ixodes* spp., *Olygonychus pratensis, Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Tarsonemus* spp. and *Tetranychus* spp.;
from the order Anoplura, for example,
*Haematopinus* spp., *Linognathus* spp., *Pediculus* spp., *Pemphigus* spp. and *Phylloxera* spp.;
from the order Coleoptera, for example,
*Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemLineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp.;
from the order Diptera, for example,
*Aedes* spp., *Antherigona soccata, Bibio hortulanus, Calliphora erythrocephala, Ceratitis* spp., *Chrysomyia* spp., *Culex* spp., *Cuterebra* spp., *Dacus* spp., *Drosophila melanogaster, Fannia* spp., *Gastrophilus* spp., *Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis pomonella, Sciara* spp., *Stomoxys* spp., *Tabanus* spp., *Tannia* spp. and *Tipula* spp.;
from the order Heteroptera, for example,
*Cimex* spp., *Distantiella theobroma, Dysdercus* spp., *Euchistus* spp., *Eurygaster* spp., *Leptocorisa* spp., *Nezara* spp., *Piesma* spp., *Rhodnius* spp., *Sahibergella singularis, Scotinophara* spp. and *Triatoma* spp.;
from the order Homoptera, for example,
*Aleurothrixus floccosus, Aleyrodes brassicae, Aonidiella* spp., *Aphididae, Aphis* spp., *Aspidiotus* spp., *Bemisia tabaci, Ceroplaster* spp., *Chrysomphalus aonidium, Chrysomphalus dictyospermi, Coccus hesperidum, Empoasca* spp., *Eriosoma larigerum, Erythroneura* spp., *Gascardia* spp., *Laodelphax* spp., *Lecanium corni, Lepidosaphes* spp., *Macrosiphus* spp., *Myzus* spp., *Nephotettix* spp., *Nilaparvata* spp., *Parlatoria* spp., *Pemphigus* spp., *Planococcus* spp., *Pseudaulacaspis* spp., *Pseudococcus* spp., *Psylla* spp., *Pulvinaria aethiopica, Quadraspidiotus* spp., *Rhopalosiphum* spp., *Saissetia* spp., *Scaphoideus* spp., *Schizaphis* spp., *Sitobion* spp., *Trialeurodes vaporariorum, Trioza erytreae* and *Unaspis citri*;
from the order Hymenoptera, for example,
*Acromyrmex, Atta* spp., *Cephus* spp., *Diprion* spp., *Diprionidae, Gilpinia polytoma, Hoplocampa* spp., *Lasius* spp., *Monomorium pharaonis, Neodiprion* spp., *Solenopsis* spp. and *Vespa* spp.;
from the order Isoptera, for example,
*Reticulitermes* spp.;
from the order Lepidoptera, for example,
*Acleris* spp., *Adoxophyes* spp., *Aegeria* spp., *Agrotis* spp., *Alabama argillaceae, Amylois* spp., *Anticarsia gemmatalis, Archips* spp., *Argyrotaenia* spp., *Autographa* spp., *Busseola fusca, Cadra cautella, Carposina nipponensis, Chilo* spp., *Choristoneura* spp., *Clysia ambiguella, Cnaphalocrocis* spp., *Cnephasia* spp., *Cochylis* spp., *Coleophora* spp., *Crocidolomia binotalis, Cryptophlebia leucotreta, Cydia* spp., *Diatraea* spp., *Diparopsis castanea, Earias* spp., *Ephestia* spp., *Eucosma* spp., *Eupoecilia ambiguella, Euproctis* spp., *Euxoa* spp., *Grapholita* spp., *Hedya nubiferana, Heliothis* spp., *Hellula undalis, Hyphantria cunea, Keiferia lycopersicella, Leucoptera scitella, Lithocollethis* spp., *Lobesia botrana, Lymantria* spp., *Lyonetia* spp., *Malacosoma* spp., *Mamestra brassicae, Manduca sexta, Operophtera* spp., *Ostrinia nubilalis, Pammene* spp., *Pandemis* spp., *Panolis flammea, Pectinophora gossypiela, Phthorimaea operculella, Pieris rapae, Pieris* spp., *Plutella xylostella, Prays* spp., *Scirpophaga* spp., *Sesamia* spp., *Sparganothis* spp., *Spodoptera* spp., *Synanthedon* spp., *Thaumetopoea* spp., *Tortrix* spp., *Trichoplusia ni* and *Yponomeuta* spp.;
from the order Mallophaga, for example,
*Damalinea* spp. and *Trichodectes* spp.; from the order Orthoptera, for example,
*Blatta* spp., *Blattella* spp., *Gryllotalpa* spp., *Leucophaea maderae, Locusta* spp., *Periplaneta* spp. and *Schistocerca* spp.;
from the order Psocoptera, for example,
*Liposcelis* spp.;
from the order Siphonaptera, for example,
*Ceratophyllus* spp., *Ctenocephalides* spp. and *Xenopsylla cheopis*;
from the order Thysanoptera, for example,
*Frankliniella* spp., *Hercinothrips* spp., *Scirtothrips aurantii, Taeniothrips* spp., *Thrips palmi* and *Thrips tabaci*; and
from the order Thysanura, for example,
*Lepisma saccharina.*

The active ingredients according to the invention can be used for controlling, i.e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The active ingredients according to the invention are especially suitable for controlling *Aphis craccivora, Diabrotica balteata, Heliothis virescens, Myzus persicae, Plutella xylostella* and *Spodoptera littoralis* in cotton, vegetable, maize, rice and soya crops. The active ingredients according to the invention are further especially suitable for controlling *Mamestra* (preferably in vegetables), *Cydia pomonella* (preferably in apples), *Empoasca* (preferably in vegetables, vineyards), *Leptinotarsa* (preferably in potatos) and *Chilo supressalis* (preferably in rice).

The term "crops" is to be understood as including also crops that have been rendered tolerant to herbicides like bromoxynil or classes of herbicides (such as, for example, HPPD inhibitors, ALS inhibitors, for example primisulphuron, prosulphuron and trifloxysulphuron, EPSPS (5-enol-pyrovyl-shikimate-3-phosphate-synthase) inhibitors, GS (glutamine synthetase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady® and LibertyLink®.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Toxins that can be expressed by such transgenic plants include, for example, insecticidal proteins, for example insecticidal proteins from *Bacillus cereus* or *Bacillus popliae*; or insecticidal proteins from *Bacillus thuringiensis*, such as δ-endotoxins, e.g. CryIA(b), CryIA(c), CryIF, CryIF(a2), CryIIA(b), CryIIIA, CryIIIB(b1) or Cry9c, or vegetative insecticidal proteins (VIP), e.g. VIP1, VIP2, VIP3 or VIP3A; or insecticidal proteins of bacteria colonising nematodes, for example *Photorhabdus* spp. or *Xenorhabdus* spp., such as *Photorhabdus luminescens, Xenorhabdus nematophilus*; toxins produced by animals, such as scorpion toxins, arachnid toxins, wasp toxins and other insect-specific neurotoxins; toxins produced by fungi, such as *Streptomycetes* toxins, plant lectins, such as pea lectins, barley lectins or snowdrop lectins; agglutinins; proteinase inhibitors, such as trypsine inhibitors, serine protease inhibitors, patatin, cystatin, papain inhibitors; ribosome-inactivating proteins (RIP), such as ricin, maize-RIP, abrin, luffin, saporin or bryodin; steroid metabolism enzymes, such as 3-hydroxysteroidoxidase, ecdysteroid-UDP-glycosyl-transferase, cholesterol oxidases, ecdysone inhibitors, HMG-COA-reductase, ion channel blockers, such as blockers of sodium or calcium channels, juvenile hormone esterase, diuretic hormone receptors, stilbene synthase, bibenzyl synthase, chitinases and glucanases.

In the context of the present invention there are to be understood by δ-endotoxins, for example CryIA(b), CryIA (c), CryIF, CryIF(a2), CryIIA(b), CryIIIA, CryIIIB(b1) or Cry9c, or vegetative insecticidal proteins (VIP), for example VIP1, VIP2, VIP3 or VIP3A, expressly also hybrid toxins, truncated toxins and modified toxins. Hybrid toxins are produced recombinantly by a new combination of different domains of those proteins (see, for example, WO 02/15701). Truncated toxins, for example a truncated CryIA(b), are known. In the case of modified toxins, one or more amino acids of the naturally occurring toxin are replaced. In such amino acid replacements, preferably non-naturally present protease recognition sequences are inserted into the toxin, such as, for example, in the case of CryIIIA055, a cathepsin-D-recognition sequence is inserted into a CryIIIA toxin (see WO 03/018810).

Examples of such toxins or transgenic plants capable of synthesising such toxins are disclosed, for example, in EP-A-0 374 753, WO 93/07278, WO 95/34656, EP-A-0 427 529, EP-A-451 878 and WO 03/052073.

The processes for the preparation of such transgenic plants are generally known to the person skilled in the art and are described, for example, in the publications mentioned above. CryI-type deoxyribonucleic acids and their preparation are known, for example, from WO 95/34656, EP-A-0 367 474, EP-A-0 401 979 and WO 90/13651.

The toxin contained in the transgenic plants imparts to the plants tolerance to harmful insects. Such insects can occur in any taxonomic group of insects, but are especially commonly found in the beetles (Coleoptera), two-winged insects (Diptera) and butterflies (Lepidoptera).

Transgenic plants containing one or more genes that code for an insecticidal resistance and express one or more toxins are known and some of them are commercially available. Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB(b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard®, Agrisure® GT Advantage (GA21 glyphosate-tolerant trait), Agrisure® CB Advantage (Bt11 corn borer (CB) trait) and Protecta®.

Further examples of such transgenic crops are:

1. Bt11 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a truncated CryIA(b) toxin. Bt11 maize also transgenically expresses the enzyme PAT to achieve tolerance to the herbicide glufosinate ammonium.

2. Bt176 Maize from Syngenta Seeds SAS, Chemin de l'Hobit 27, F-31 790 St. Sauveur, France, registration number C/FR/96/05/10. Genetically modified *Zea mays* which has been rendered resistant to attack by the European corn borer (*Ostrinia nubilalis* and *Sesamia nonagrioides*) by transgenic expression of a CryIA(b) toxin. Bt176 maize also transgenically expresses the enzyme PAT to achieve tolerance to the herbicide glufosinate ammonium.

3. MIR604 Maize from Syngenta Seeds SAS, Chemin de l'Hobit 27, F-31 790 St. Sauveur, France, registration number C/FR/96/05/10. Maize which has been rendered insect-resistant by transgenic expression of a modified CryIIIA toxin. This toxin is Cry3A055 modified by insertion of a cathepsin-D-protease recognition sequence. The preparation of such transgenic maize plants is described in WO 03/018810.

4. MON 863 Maize from Monsanto Europe S.A. 270-272 Avenue de Tervuren, B-1150 Brussels, Belgium, registration number C/DE/02/9. MON 863 expresses a CryIIIB(b1) toxin and has resistance to certain Coleoptera insects.

5. IPC 531 Cotton from Monsanto Europe S.A. 270-272 Avenue de Tervuren, B-1150 Brussels, Belgium, registration number C/ES/96/02.

6. 1507 Maize from Pioneer Overseas Corporation, Avenue Tedesco, 7 B-1160 Brussels, Belgium, registration number C/NL/00/10. Genetically modified maize for the expression of the protein CryI F for achieving resistance to certain Lepidoptera insects and of the PAT protein for achieving tolerance to the herbicide glufosinate ammonium.

7. NK603×MON 810 Maize from Monsanto Europe S.A. 270-272 Avenue de Tervuren, B-1150 Brussels, Belgium, registration number C/GB/02/M3/03. Consists of conventionally bred hybrid maize varieties by crossing the genetically modified varieties NK603 and MON 810. NK603× MON 810 Maize transgenically expresses the protein CP4 EPSPS, obtained from *Agrobacterium* sp. strain CP4, which imparts tolerance to the herbicide Roundup® (contains glyphosate), and also a CryIA(b) toxin obtained from *Bacillus thuringiensis* subsp. *kurstaki* which brings about tolerance to certain Lepidoptera, include the European corn borer.

Transgenic crops of insect-resistant plants are also described in BATS (Zentrum für Biosicherheit and Nachhaltigkeit, Zentrum BATS, Clarastrasse 13, 4058 Basel, Switzerland) Report 2003, (http://bats.ch).

The term "crops" is to be understood as including also crop plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818 and EP-A-0 353 191. The methods of producing such transgenic plants are generally known to the person skilled in the art and are described, for example, in the publications mentioned above.

Antipathogenic substances which can be expressed by such transgenic plants include, for example, ion channel blockers, such as blockers for sodium and calcium channels, for example the viral KP1, KP4 or KP6 toxins; stilbene synthases; bibenzyl synthases; chitinases; glucanases; the so-called "pathogenesis-related proteins" (PRPs; see e.g. EP-A-0 392 225); antipathogenic substances produced by microorganisms, for example peptide antibiotics or heterocyclic antibiotics (see e.g. WO 95/33818) or protein or polypeptide factors involved in plant pathogen defence (so-called "plant disease resistance genes", as described in WO 03/000906).

Further areas of use of the compositions according to the invention are the protection of stored goods and storerooms and the protection of raw materials, such as wood, textiles, floor coverings or buildings, and also in the hygiene sector, especially the protection of humans, domestic animals and productive livestock against pests of the mentioned type.

In the hygiene sector, the compositions according to the invention are active against ectoparasites such as hard ticks, soft ticks, mange mites, harvest mites, flies (biting and licking), parasitic fly larvae, lice, hair lice, bird lice and fleas.

Examples of such parasites are:

Of the order Anoplurida: *Haematopinus* spp., *Linognathus* spp., *Pediculus* spp. and *Phtirus* spp., *Solenopotes* spp.

Of the order Mallophagida: *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

Of the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

Of the order Siphonapterida, for example *Pulex* spp., *Ctenocephalides* spp., *Xenopsylla* spp., *Ceratophyllus* spp.

Of the order Heteropterida, for example *Cimex* spp., *Triatoma* spp., *Rhodnius* spp., *Panstrongylus* spp.

Of the order Blattarida, for example *Blatta orientalis, Periplaneta americana, Blattelagermanica* and *Supella* spp.

Of the subclass Acaria (Acarida) and the orders Meta- and Meso-stigmata, for example *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

Of the orders Actinedida (Prostigmata) and Acaridida (Astigmata), for example *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The compositions according to the invention are also suitable for protecting against insect infestation in the case of materials such as wood, textiles, plastics, adhesives, glues, paints, paper and card, leather, floor coverings and buildings.

The compositions according to the invention can be used, for example, against the following pests: beetles such as *Hylotrupes bajulus, Chlorophorus pilosis, Anobium punctatum, Xestobium rufovillosum, Ptilinuspecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthesrugicollis, Xyleborus* spec., *Tryptodendron* spec., *Apate monachus, Bostrychus capucins, Heterobostrychus brunneus, Sinoxylon* spec. and *Dinoderus minutus*, and also hymenopterans such as *Sirex juvencus, Urocerus gigas, Urocerus gigas taignus* and *Urocerus augur*, and termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis* and *Coptotermes formosanus*, and bristletails such as *Lepisma saccharina*.

The invention therefore also relates to pesticidal compositions such as emulsifiable concentrates, suspension concentrates, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable particulate adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (un-substituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulphuric ester or of a fatty alcohol sulfate mixture prepared from natural fatty acids. This group also includes the salts of the sulphuric esters and sulfonic acids of fatty alcohol/ethylene oxide adducts. The sulfonated benzimidazole derivatives preferably contain 2 sulphonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a pnonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):
Emulsifiable Concentrates:
active ingredient: 1 to 95%, preferably 5 to 20%
surfactant: 1 to 30%, preferably 10 to 20%
solvent: 5 to 98%, preferably 70 to 85%
Dusts:
active ingredient: 0.1 to 10%, preferably 0.1 to 1%
solid carrier: 99.9 to 90%, preferably 99.9 to 99%
Suspension Concentrates:
active ingredient: 5 to 75%, preferably 10 to 50%
water: 94 to 24%, preferably 88 to 30%
surfactant: 1 to 40%, preferably 2 to 30%
Wettable Powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

Example 1

6-{[2-(3-chloro-pyridin-1-yl)-5-methoxy-2H-pyrazole-3-carbonyl]-amino}-7-isopropylcarbamoyl-5-methyl-indazole-2-carboxylic acid tert-butyl ester a) Preparation of 2-[(E)-hydroxyimino]-N-(5-methyl-1H-indazol-6-yl)-acetamide

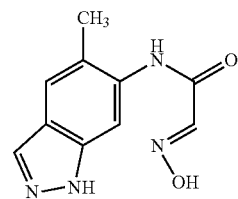 [SMILES: Cc1cc2cn[nH]c2cc1NC(=O)/C=N/O]

To a solution of sodium sulphate (8.69 g, 61.15 mmol) in water (20 ml) was added chloralhydrate (0.62 g, 3.74 mmol) at ambient temperature. To the resulting clear solution was added a solution of 5-methyl-6-aminoindazol (0.5 g, 3.4 mmol, prepared as described in Eur. Pat. Appl. EP 040872) in 1N aqueous hydrochloric acid (3.7 ml). The resulting mixture turned cloudy and hydroxylamine hydrochloride (0.75 g, 10.9 mmol) was then added. The resulting reaction mixture was heated-up gradually from ambient temperature to 80° C. When the reaction mixture has reached an internal temperature of 80° C., it was stirred for an additional 30 min at 80° C. The reaction mixture was then cooled down to ambient temperature with an ice bath. The reaction mixture was filtrated. The filtercake was washed thoroughly with water and dried at 50° C. for 15 hours to afford the desired product as a brown powder of >95% purity according to HPLC. LC/MS: 219 (M+H)$^+$.

b) Preparation of 5-methyl-1,6-dihydro-pyrrolo[2,3-g]indazole-7,8-dione

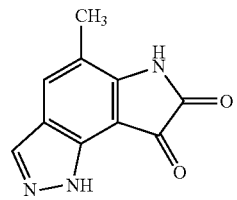

To concentrated sulphuric acid (119 ml) was added portionwise 2-[(E)-hydroxyimino]-N-(5-methyl-1H-indazol-6-yl)-acetamide (34.7 g, 146.3 mmol). The addition was strongly exothermic and the internal temperature was maintained at 70° C. with an ice bath. At the end of the addition the resulting reaction mixture was heated at 80° C. and stirred for 45 min at this temperature. According to LC-MS analysis, the reaction has then reached completion. The reaction mixture was cooled down to ambient temperature. The reaction mixture was poured onto 3.00 kg of ice. The resulting dark-brown suspension was stirred for 30 min and then filtrated. The filter cake was washed extensively with water and dried in vacuo at 55° C. The title product was obtained as a red-brown powder. LC/MS: 202 (M+H)$^+$, 224 (M+H)$^+$.

c) Preparation of
6-amino-5-methyl-1H-indazole-7-carboxylic acid

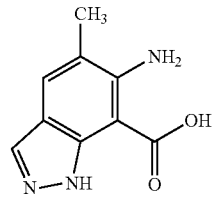

To a solution of 5-methyl-1,6-dihydro-pyrrolo[2,3-g]indazole-7,8-dione (23 g, 114.3 mmol) in 4N aqueous sodium hydroxide solution (160 ml) at ambient temperature, was added dropwise 30% aqueous hydrogen peroxide solution (27 ml) maintaining the temperature <30° C. with external cooling. The resulting reaction mixture was stirred at ambient temperature for 2 hours. According to TLC, the reaction was complete after 2 hours. The pH was adjusted to pH 3.5 by addition of concentrated hydrochloric acid. The resulting brown suspension was filtered and the filtercake washed with cold water and dried in vacuo at 50° C. to afford the desired product as brown solid. LC/MS: 192 (M+H)$^+$.

c) Preparation of 7-[2-(3-chloro-pyridin-2-yl)-5-methoxy-2H-pyrazol-3-yl]-5-methyl-1H-8-oxa-1,2,6-triaza-benz[e]inden-9-one

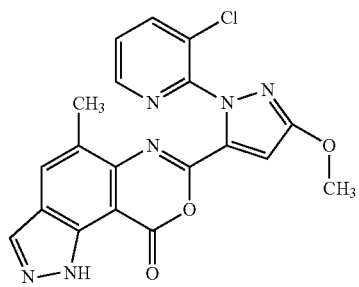 [SMILES: COc1cc(-c2nc3c(C)cc4cn[nH]c4c3c(=O)o2)n(-c2ncccc2Cl)n1]

To a solution of 2-(3-chloro-pyridin-2-yl)-5-methoxy-2H-pyrazole-3-carboxylic acid (40 g, 157 mmol) and acetonitrile (1000 mL) was added 6-amino-5-methyl-1H-indazole-7-carboxylic acid (30 g, 157 mmol). To the resulting brown suspension were added sequentially pyridine (57 mL, 706 mml) and dropwise mesylchloride (43 mL, 549 mmol). The reaction mixture was stirred for 6 h at 50° C. and 15 hours at ambient temperature. The reaction mixture was concentrated in vacuo. The residue was suspended in water and stirred for 15 min. The resulting yellow suspension was filtrated. The filtercake was washed sequentially with water and heptane/AcOEt 2:1 and dried to afford the title compound as beige powder, which was submitted to the next step without further purification. LC/MS: 409 (M+H)$^+$.

d) Preparation of 6-{([2-(3-chloro-pyridin-1-yl)-5-methoxy-2H-pyrazole-3-carbonyl]-amino}-5-methyl-1H-indazole-7-carboxylic acid isopropylamide

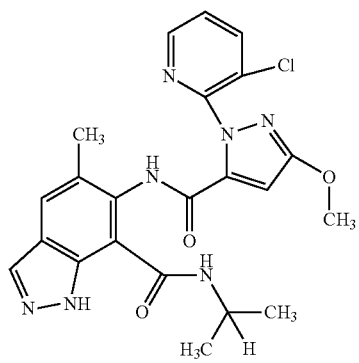 [SMILES: COc1cc(C(=O)Nc2c(C)cc3cn[nH]c3c2C(=O)NC(C)C)n(-c2ncccc2Cl)n1]

To a suspension of crude 7-[2-(3-chloro-pyridin-2-yl)-5-methoxy-2H-pyrazol-3-yl]-5-methyl-1H-8-oxa-1,2,6-triaza-benz[e]inden-9-one (64 g, 157 mmol) in acetonitrile/H$_2$O 40:1 v/v (1025 mL) was added isopropylamine (134 mL, 1572 mmol). The reaction mixture was stirred at 50° C. for 4 hours and concentrated in vacuo. Purification of the residue by flash-chromatography affords the title compound as a pale yellowish solid. LC/MS:468/470 (M+H)$^+$.

e) Preparation of 6-{[2-(3-chloro-pyridin-1-yl)-5-methoxy-2H-pyrazole-3-carbonyl]-amino}-7-isopropylcarbamoyl-5-methyl-indazole-2-carboxylic acid tert-butyl ester

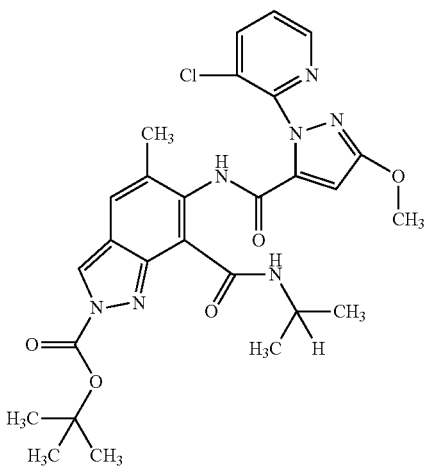 [SMILES: COc1cc(C(=O)Nc2c(C)cc3cn(C(=O)OC(C)(C)C)nc3c2C(=O)NC(C)C)n(-c2ncccc2Cl)n1]

To a solution of 6-{[2-(3-chloro-pyridin-1-yl)-5-methoxy-2H-pyrazole-3-carbonyl]-amino}-5-methyl-1H-indazole-7-carboxylic acid isopropylamide (0.5 g, 1.07 mmol) in methylenechloride (20 ml) was added BOC-anhydride (0.26 g, 1:175 mmol), and dimethyl amino pyridine (10 mg, 0.107 mmol) and the mixture stirred at ambient temperature. TLC analysis after 1 hour showed reaction completion. The reaction mixture was concentrated in vacuo and purified by flash chromatography eluting with a 1:1 mixture of ethyl acetate and hexane to give the title product as white crystals. M.p. 161-162° C.

Example 2

5-chloro-6-{[2-(3-chloro-pyridin-2-yl)-5-trifluoromethyl-2H-pyrazole-3-carbonyl]-amino}-1-methoxymethyl-1H-indazole-7-carboxylic acid isopropylamide

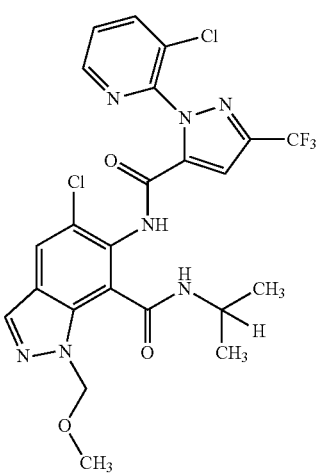 [SMILES: COCn1ncc2cc(Cl)c(NC(=O)c3cc(C(F)(F)F)nn3-c3ncccc3Cl)c(C(=O)NC(C)C)c21]

A mixture of 5-chloro-6-{[2-(3-chloro-pyridin-2-yl)-5-trifluoromethyl-2H-pyrazole-3-carbonyl]-amino}-1H-indazole-7-carboxylic acid isopropylamide (1.00 g, 1.90 mmol), KOH (310 mgs, 5.70 mmol) and t-BuOK (6.4 mg, 0.02 mmol) in THF (5 mL) was treated dropwise with chloro-methoxy-methane (0.39 mL, 5.1 mmol). The resulting reaction mixture was stirred at ambient temperature for 18 h. AcOEt and water was added. The phases were separated. The aqueous layer was extracted with AcOEt. The organic layers were washed with water, combined, dried over MgSO$_4$ and concentrated in vacuo. Purification of the residue by reverse phase HPLC affords the title product as a colorless solid. M.p. 180-182° C., LC/MS: 570/572 (M+H)$^+$, 592/594 (M+Na)$^+$.

Example 3

6-{[2-(3-chloro-pyridin-2-yl)-5-methoxy-2H-pyrazole-3-carbonyl]-amino}-2-methoxymethyl-5-methyl-2H-indazole-7-carboxylic acid isopropylamide

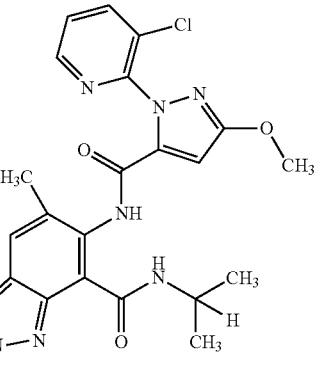

A mixture of 6-{[2-(3-chloro-pyridin-2-yl)-5-methoxy-2H-pyrazole-3-carbonyl]-amino}-5-methyl-2H-indazole-7-carboxylic acid isopropylamide (500 mg, 1.07 mmol) and diisopropylethylamine (225 µL, 1.2 mmol) in THF (10 mL) was treated dropwise with chloro-methoxy-methane (90 µL, 1.2 mmol). The resulting reaction mixture was stirred for 2 hours at ambient temperature. The reaction mixture was concentrated in vacuo. Purification of the residue by flash-chromatography (SiO$_2$, CH$_2$Cl$_2$/acetone 7:3) afforded the title compound as a colorless crystalline solid. M.p. 148° C., LC/MS:512/514 (M+H)$^+$.

Example 4

6-{[2-(3-chloro-pyridin-2-yl)-5-methoxy-2H-pyrazole-3-carbonyl]-amino}-7-isopropylcarbamoyl-5-methyl-indazole-2-carbothioic acid S-octyl ester

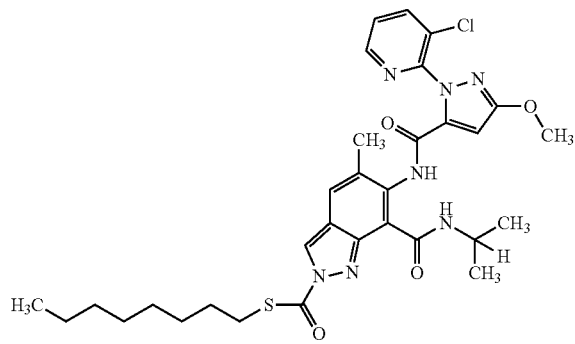 [SMILES: CCCCCCCCSC(=O)n1cc2cc(C)c(NC(=O)c3cc(OC)nn3-c3ncccc3Cl)c(C(=O)NC(C)C)c2n1]

To a suspension of 6-{[2-(3-chloro-pyridin-2-yl)-5-methoxy-2H-pyrazole-3-carbonyl]-amino}-5-methyl-2H-indazole-7-carboxylic acid isopropylamide (0.300 g, 0.64 mmol) in dichloromethane (3.0 mL) was added triethylamine (90 μL, 0.65 mmol), then S-octyl chlorothioformate (0.133 g, 0.64 mmol). The resulting homogeneous reaction mixture was stirred for 0.5 h at 20° C. The reaction mixture was then concentrated in vacuo and the residue was purified by flash-chromatography (SiO$_2$, CH$_2$Cl$_2$/ethyl acetate 9:1) affording the title compound as yellow crystals with a melting point of 98-102° C.

Example 5

6-{[2-(3-chloro-pyridin-2-yl)-5-methoxy-2H-pyrazole-3-carbonyl]-amino}-2-methanesulphonyl-5-methyl-2H-indazole-7-carboxylic acid isopropylamide

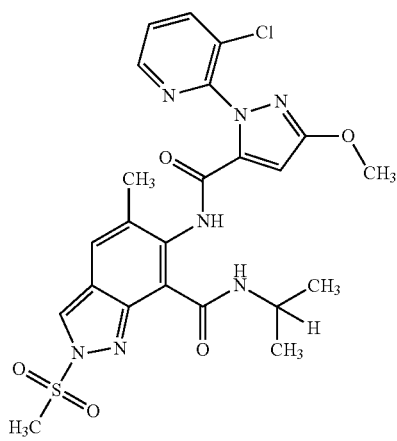 [SMILES: COc1cc(C(=O)Nc2c(C)cc3cn(S(C)(=O)=O)nc3c2C(=O)NC(C)C)n(-c2ncccc2Cl)n1]

To a suspension of 6-{[2-(3-chloro-pyridin-2-yl)-5-methoxy-2H-pyrazole-3-carbonyl]-amino}-5-methyl-2H-indazole-7-carboxylic acid isopropylamide (0.800 g, 1.71 mmol) in dichloromethane (5.0 mL) was added triethylamine (0.476 mL, 3.42 mmol), followed by methanesulphonyl chloride (0.265 mL, 3.42 mmol). The dark colored homogeneous reaction mixture was stirred for 1 h at 20° C. The reaction mixture was then concentrated in vacuo and the residue was purified by flash-chromatography (SiO$_2$, CH$_2$Cl$_2$/ethyl acetate 4:1) yielding a brown solid that was recrystallized from ethyl acetate to afford the title compound as colourless crystals with a melting range of 135-175° C. (with decomposition).

Example 6

6-{[2-(3-chloro-pyridin-2-yl)-5-methoxy-2H-pyrazole-3-carbonyl]-amino}-5-methyl2-prop-2-ynyl-2H-indazole-7-carboxylic acid isopropylamide

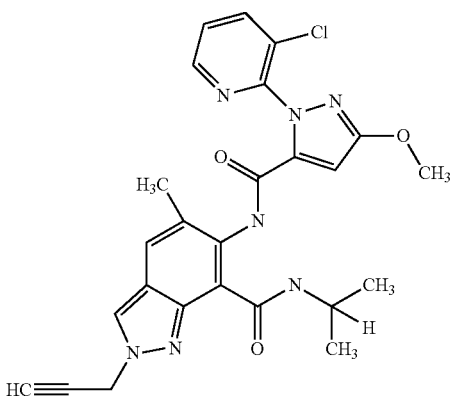 [SMILES: C#CCn1cc2cc(C)c(NC(=O)c3cc(OC)nn3-c3ncccc3Cl)c(C(=O)NC(C)C)c2n1]

A mixture of 6-{[2-(3-chloro-pyridin-2-yl)-5-methoxy-2H-pyrazole-3-carbonyl]-amino}-5-methyl-2H-indazole-7-carboxylic acid isopropylamide (500 mg, 1.07 mmol) and K$_2$CO$_3$ (196 mg, 1.6 mmol) in THF (5 mL) was stirred for 1 hour at ambient temperature, and was treated with propargylbromide (120 μL, 1.6 mmol). The resulting reaction mixture was stirred for 24 hours at 60° C. AcOEt and water was added. The phases were separated. The aqueous layer was extracted with AcOEt. The organic layers were washed with water, combined, dried over MgSO$_4$ and concentrated in vacuo. Purification of the residue by flash-chromatography (SiO$_2$, Toluene/AcOEt 7:3) afforded the title compound as a colorless crystalline solid. LC/MS: 506 (M+H)⁺, 528 (M+Na)⁺.

Example 7

6-{[2-(3-chloro-pyridin-2-yl)-5-methoxy-2H-pyrazole-3-carbonyl]-amino}-5-methyl-2-(2,2,2-trifluoro-ethyl)-2H-indazole-7-carboxylic acid isopropylamide

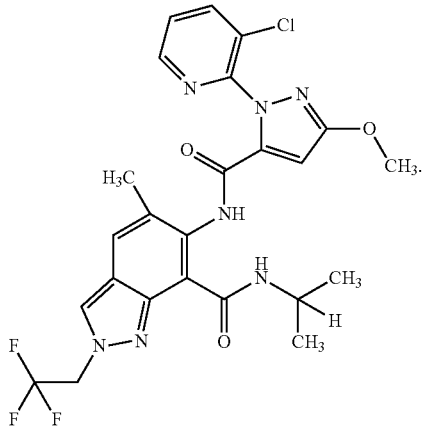 [SMILES: COc1cc(C(=O)Nc2c(C)cc3cn(CC(F)(F)F)nc3c2C(=O)NC(C)C)n(-c2ncccc2Cl)n1]

A mixture of 6-{[2-(3-chloro-pyridin-2-yl)-5-methoxy-2H-pyrazole-3-carbonyl]-amino}-5-methyl-2H-indazole-7-carboxylic acid isopropylamide (500 mg, 1.07 mmol) and NaH (60%) (67 mg, 1.6 mmol) in THF (5 mL) was stirred for 1 hour at ambient temperature, and was treated with 2,2,2-trifluoroethyl trifluoromethanesulfonate (246 mg, 1.06 mmol). The resulting reaction mixture was stirred for 4 hours at 60° C. AcOEt and water was added. The phases were separated. The aqueous layer was extracted with AcOEt. The organic layers were washed with water, combined, dried over MgSO₄ and concentrated in vacuo. Purification of the residue by flash-chromatography (SiO₂, Toluene/AcOEt 7:3) afforded the title compound as a colorless crystalline solid. M.p. 178-181° C., LC/MS: 550 (M+H)⁺, 572/574 (M+Na)⁺.

Example 8

6-{[2-(3-chloro-pyridin-2-yl)-5-methoxy-2H-pyrazole-3-carbonyl]-amino}-2-(2-methoxy-ethoxymethyl)-5-methyl-2H-indazole-7-carboxylic acid isopropylamide and 6-{[2-(3-chloro-pyridin-2-yl)-5-methoxy-2H-pyrazole-3-carbonyl]-amino}-1-(2-methoxy-ethoxymethyl)-5-methyl-1H-indazole-7-carboxylic acid isopropylamide

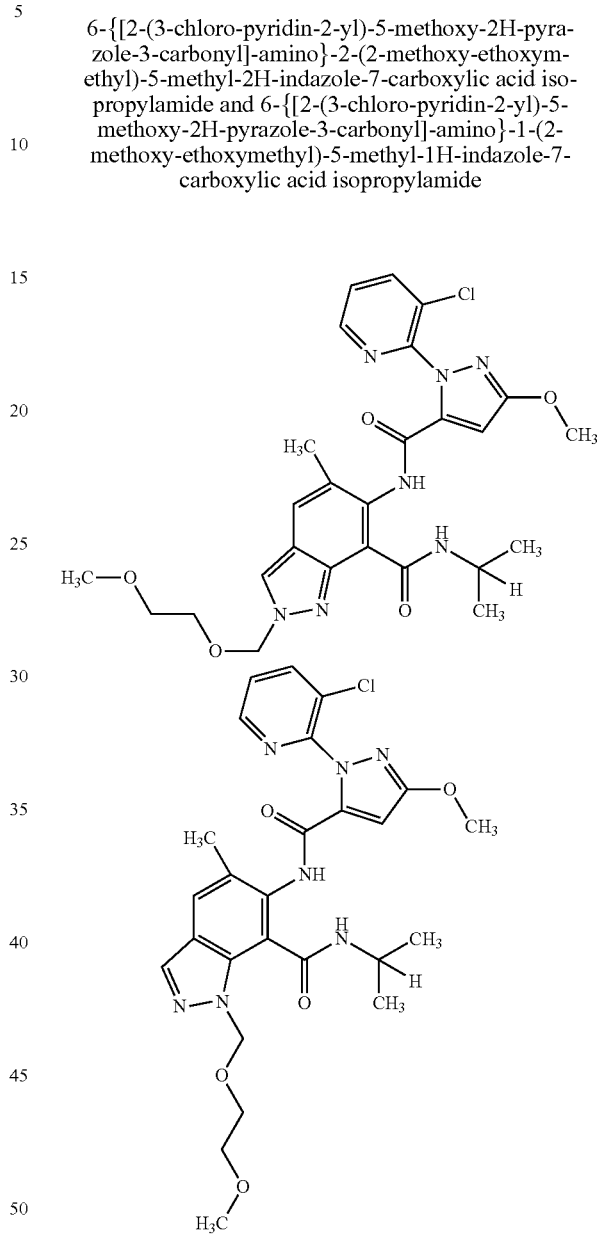

A mixture of 6-{[2-(3-chloro-pyridin-2-yl)-5-methoxy-2H-pyrazole-3-carbonyl]-amino}-5-methyl-2H-indazole-7-carboxylic acid isopropylamide (500 mg, 1.07 mmol) and diisopropylethylamine (1 mL, 5.8 mmol) in THF (5 mL) was treated dropwise with 2-methoxyethoxymethyl chloride (663 μL, 5.8 mmol). The resulting reaction mixture was stirred for 24 hours at ambient temperature. AcOEt and water was added. The phases were separated. The aqueous layer was extracted with AcOEt. The organic layers were washed with water, combined, dried over MgSO₄ and concentrated in vacuo. The two isomers were separated by reverse phase HPLC to afford P.12 (peack 1) as a colorless solid. M.p. 132-133° C., LC/MS:556/558 (M+H)⁺, 578/580 (M+Na)⁺ and P.13 (peack 2) as a colorless solid M.p. 167-168° C., LC/MS:556/558 (M+H)⁺, 578/580 (M+Na)⁺.

Example 9

6-{[2-(3-chloro-pyridin-2-yl)-5-methoxy-2H-pyrazole-3-carbonyl]-amino}-2-(4,6-difluoro-[1,3,5]triazin-2-yl)-5-methyl-2H-indazole-7-carboxylic acid isopropylamide

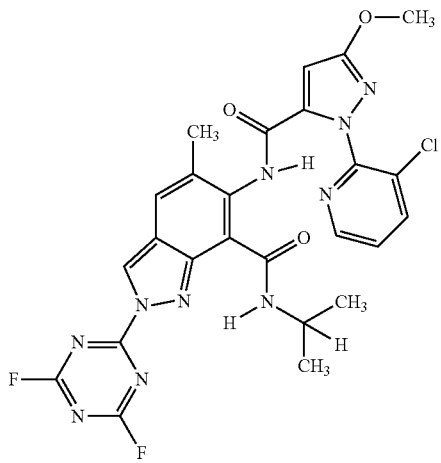 [SMILES: COc1cc(C(=O)Nc2c(C)cc3cn(-c4nc(F)nc(F)n4)nc3c2C(=O)NC(C)C)n(-c2ncccc2Cl)n1]

To a solution of 6-{[2-(3-chloro-pyridin-2-yl)-5-methoxy-2H-pyrazole-3-carbonyl]-amino}-5-methyl-2H-indazole-7-carboxylic acid isopropyl amide (0.300 g, 0.641 mmol) in chloroform (2.0 ml) was added cyanuryl fluoride (2,4,6-trifluoro-1,3,5-triazine) (0.220 g, 1.669 mmol) followed by triethylamine (0.090 ml, 0.046 mmol). The reaction mixture was stirred at 20° C. for three hours, then evaporated to dryness and submitted to high vacuum. The residue was taken up in a small amount of chloroform and separated from some less soluble material, then evaporated to give the compound showing the physical data described in the table under P.43.

Example 10

6-{[2-(3-chloro-pyridin-2-yl)-5-methoxy-2H-pyrazole-3-carbonyl]-amino}-2-(4,6-dimethoxy-[1,3,5]triazin-2-yl)-5-methyl-2H-indazole-7-carboxylic acid isopropylamide

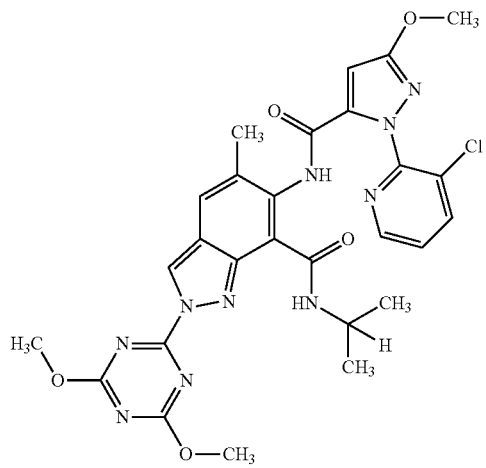 [SMILES: COc1cc(C(=O)Nc2c(C)cc3cn(-c4nc(OC)nc(OC)n4)nc3c2C(=O)NC(C)C)n(-c2ncccc2Cl)n1]

In a round bottomed flask, (6-{[2-(3-chloro-pyridin-2-yl)-5-methoxy-2H-pyrazole-3-carbonyl]-amino}-2-(4,6-difluoro-[1,3,5]triazin-2-yl)-5-methyl-2H-indazole-7-carboxylic acid isopropylamide) (234 mg, 0.401 mmol) was suspended in methanol (2 ml) containing triethylamine (0.064 ml). The resulting suspension was stirred for fourteen hours at 20° C. Water (10 ml) was then added and the mixture was extracted with dichloromethane (3×20 ml). The combined organic phases were washed with water, brine and dried over sodium sulphate before being evaporated. The residue was purified by flash column chromatography over silica gel using a gradient of ethyl acetate-cyclohexane (from 50%-50% to 75%-25%). The desired compound was isolated as a yellowwash solid showing the physical properties reported in the table (P.40).

Example 11

(6-{[2-(3-chloro-pyridin-2-yl)-5-methoxy-2H-pyrazole-3-carbonyl]-amino}-7-isopropylcarbamoyl-5-methyl-indazole-2-carbonylsulfanyl)-acetic acid ethyl ester

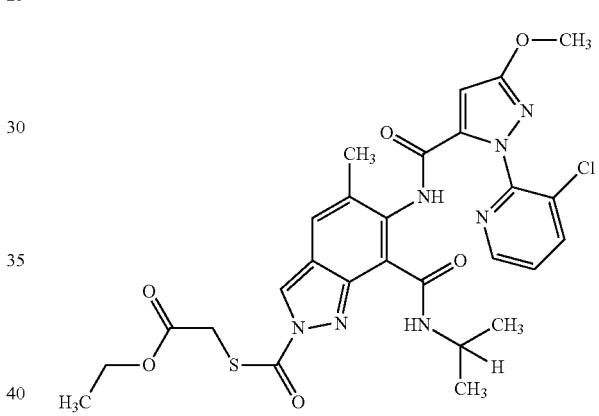

a) Preparation of (chlorocarbonylthio)-acetic acid ethyl ester

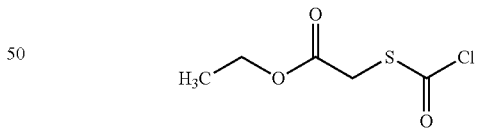

A flask equipped with a refrigerant cooled with dry ice was charged with thioglycolic acid ethyl ester (1.202 g, 10.0 mmol) and triphosgene (2.000 g, 6.7 mmol). A catalytical amount of tetrabutylammonium chloride was added and the mixture was heated to a temperature of 80° C. for fifteen hours. The exhaust gases were treated with 4N sodium hydroxide aqueous solution. The resulting light brown liquid was flushed with a stream of nitrogen, then distilled under vacuum (110° C./4 mbar) to yield the desired compound as a colorless oil. $^{1}$H-NMR (400 MHz, CDCl$_3$, reference TMS); δ (ppm): 4.22 (q, 2H), 3.76 (s, 2H), 1.30 (t, 3H). $^{13}$C-NMR (100 MHz, CDCl$_3$, reference TMS); δ (ppm): 166.63, 165.05, 62.44, 35.43, 14.02.

b) Preparation of (6-{[2-(3-chloro-pyridin-2-yl)-5-methoxy-2H-pyrazole-3-carbonyl]-amino}-7-isopropylcarbamoyl-5-methyl-indazole-2-carbonylsulfanyl)-acetic acid ethyl ester

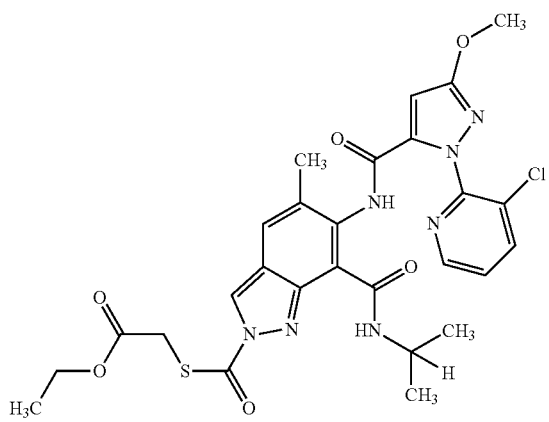 [SMILES: CCOC(=O)CSC(=O)n1cc2cc(C)c(NC(=O)c3cc(OC)nn3-c3ncccc3Cl)c(C(=O)NC(C)C)c2n1]

In a vial, 6-{[2-(3-chloro-pyridin-2-yl)-5-methoxy-2H-pyrazole-3-carbonyl]-amino}-5-methyl-2H-indazole-7-carboxylic acid isopropyl amide (0.200 g, 0.427 mmol) was suspended in chloroform (1 ml), then a solution of (chlorocarbonylthio)-acetic acid ethyl ester (0.086 g, 0.471 mmol) in chloroform (1 ml) was added, followed by triethylamine (0.065 ml). The reaction mixture became a clear solution that was stirred for 1 hour at a temperature of 20° C. The reaction mixture was concentrated and the residue was purified by flash chromatography over silica gel using a 50% ethyl acetate-50% cyclohexane mixture. The desired compound was isolated as a yellow solid showing the physical properties reported in the corresponding table (P.41.).

Example 12

6-{[2-(3-chloro-pyridin-2-yl)-5-methoxy-2H-pyrazole-3-carbonyl]-amino}-5-methyl-indazole-2,7-dicarboxylic acid 7-isopropylamide 2-(methyl-octyl-amide)

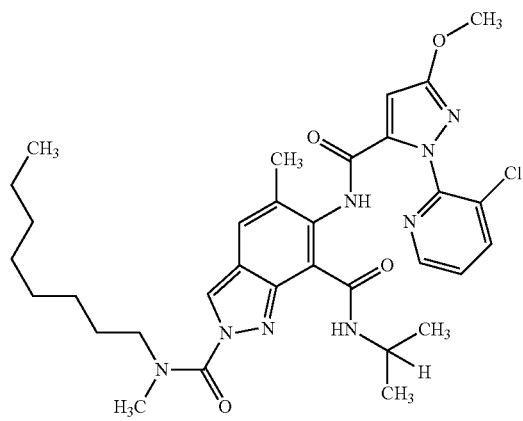 [SMILES: CCCCCCCCN(C)C(=O)n1cc2cc(C)c(NC(=O)c3cc(OC)nn3-c3ncccc3Cl)c(C(=O)NC(C)C)c2n1]

In a vial, 6-{[2-(3-chloro-pyridin-2-yl)-5-methoxy-2H-pyrazole-3-carbonyl]-amino}-5-methyl-2H-indazole-7-carboxylic acid isopropyl amide (0.150 g, 0.320 mmol) was suspended in a solution of methyl-octyl-carbamoyl chloride (0.140 g, 0.680 mmol) in chloroform (0.5 ml). triethylamine (0.090 ml) and a catalytic amount of 4-dimethylaminopyridine were added and the mixture was stirred at 20° C. for 2.5 hours. The reaction mixture was then concentrated and the residue was treated with water (20 ml) and aqueous sodium bicarbonate. After extraction with ethyl acetate (2×10 ml) the organic phases were combined, washed with brine, dried over sodium sulphate and evaporated. The residue was purified by flash chromatography over silica gel using a 50% ethyl acetate-50% cyclohexane mixture. The desired compound was isolated as a solid showing the physical properties reported in the corresponding table (P.38.).

Example 13

6-{[2-(3-chloro-pyridin-2-yl)-5-methoxy-2H-pyrazole-3-carbonyl]-amino}-2-(4-methoxy-benzyl)-5-methyl-2H-indazole-7-carboxylic acid isopropyl amide

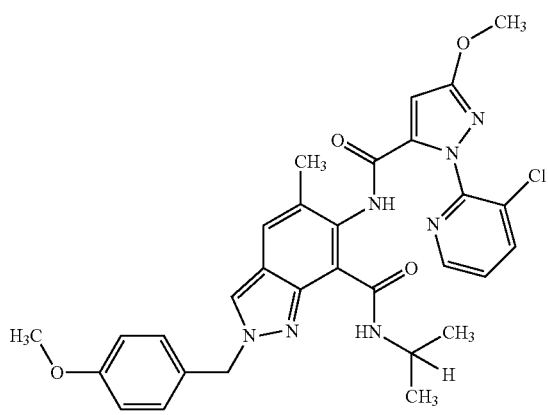 [SMILES: COc1ccc(Cn2cc3cc(C)c(NC(=O)c4cc(OC)nn4-c4ncccc4Cl)c(C(=O)NC(C)C)c3n2)cc1]

a) Preparation of 6-amino-2-(4-methoxy-benzyl)-5-methyl-2H-indazole-7-carboxylic acid

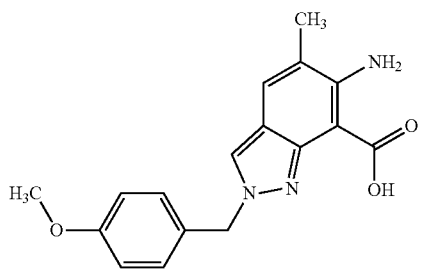 [SMILES: COc1ccc(Cn2cc3cc(C)c(N)c(C(=O)O)c3n2)cc1]

To a suspension of 6-amino-5-methyl-1H-indazole-7-carboxylic acid (0.956 g, 5 mmol) in dimethylformamide (4 ml) was added sodium hydrogenocarbonate (0.462 g, 5.5 mmol) and the resulting mixture was stirred at 40° C. for 15 minutes before 4-methoxybenzyl chloride (0.861 g, 5.5 mmol) was introduced. A catalytic amount of potassium iodide was added and the mixture was stirred for 18 hours at that temperature. After cooling down, the crude mixture was placed on top of a silica gel column and the product was purified by flash chromatography using a gradient starting from 50% ethyl acetate-50% cyclohexane to 100% ethyl acetate, then 1% acetic acid in ethyl acetate. The fractions containing the desired compound were evaporated and the residue was triturated with diethyl ether and filtered to yield light orange crystals.

$^1$H-NMR (400 MHz, CDCl$_3$, reference TMS); δ (ppm): 12.50 (s, 1H), 7.60 (s, 1H), 7.39 (s, 1H), 7.25 (d, 2H), 6.90 (d, 2H), 6.59 (s, 1H), 5.37 (s, 2H), 3.80 (s, 3H), 2.22 (s, 3H).

b) Preparation of 7-[2-(3-chloro-pyridin-2-yl)-5-methoxy-2H-pyrazol-3-yl]-2-(4-methoxy-benzyl)-5-methyl-2H-8-oxa-1,2,6-triaza-cyclopenta[a]naphthalen-9-one

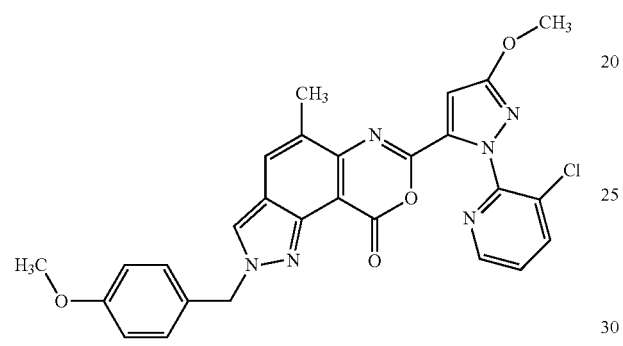

A suspension of 6-amino-2-(4-methoxy-benzyl)-5-methyl-2H-indazole-7-carboxylic acid (0.288 g, 0.925 mmol) in acetonitrile (4 ml) was stirred at 20° C. for 10 minutes before the acyl chloride prepared from 2-(3-chloro-pyridin-2-yl)-5-methoxy-2H-pyrazole-3-carboxylic acid and oxalyl chloride (0.265 g, 0.971 mmol) was added. After 45 minutes stirring, 2,6-lutidine (0.215 ml) was added, followed 10 minutes later by methanesulfonyl chloride (0.072 ml, 0.925 mmol). After 18 hours of reaction, the mixture was concentrated under vacuum and water (25 ml) was added. The product was extracted with ethyl acetate and purified by flash chromatography on silica gel using a gradient from 50% to 100% ethyl acetate in cyclohexane. The desired product was obtained as light orange crystals.

$^1$H-NMR (400 MHz, CDCl$_3$, reference TMS); δ (ppm): 8.54 (dd, 1H), 7.92 (dd, 1H), 7.73 (s, 1H), 7.69 (s, 1H), 7.42 (dd, 1H), 7.28 (d, 2H), 6.90 (d, 2H), 6.80 (s, 1H), 5.64 (s, 2H), 4.02 (s, 3H), 3.80 (s, 3H), 1.75 (s, 3H).

c) Preparation of 6-{[2-(3-chloro-pyridin-2-yl)-5-methoxy-2H-pyrazole-3-carbonyl]-amino}-2-(4-methoxy-benzyl)-5-methyl-2H-indazole-7-carboxylic acid isopropyl amide A solution of 7-[2-(3-chloro-pyridin-2-yl)-5-methoxy-2H-pyrazol-3-yl]-2-(4-methoxy-benzyl)-5-methyl-2H-8-oxa-1,2,6-triaza-cyclopenta[a]naphthalen-9-one (0.100 g, 0.189 mmol) in tetrahydrofurane (2 ml) was treated with 16 drops of isopropyl amine and stirred at 20° C. for three hours. The reaction mixture was evaporated and the crude product was purified by flash chromatography on silica gel using a mixture of 75% ethyl acetate 25% cyclohexane. The desired product showed the physical data reported in the corresponding table (P.34.).

Example 14

3-(6-{[2-(3-chloro-pyridin-2-yl)-5-methoxy-2H-pyrazole-3-carbonyl]-amino}-7-isopropylcarbamoyl-5-methyl-indazol-1-yl)-2,2-dimethyl-3-oxo-propionic acid

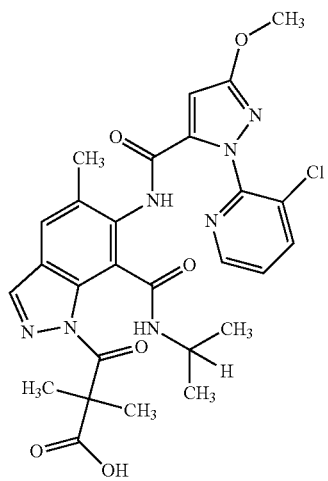 [SMILES: COc1cc(C(=O)Nc2c(C)cc3cnn(C(=O)C(C)(C)C(=O)O)c3c2C(=O)NC(C)C)n(-c2ncccc2Cl)n1]

a) Preparation of 2,2-dimethyl-propanedioyl dichloride

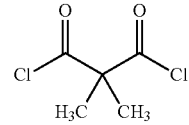

A mixture of 2,2-dimethyl-propanedioic acid (13.21 g, 0.1 mol) in dichloromethane (100 ml) and a few drops of dimethylformamide was portion wise treated with oxalyl chloride (31.73 g, 0.25 mol) under stirring at 20° C. and stirred for 14 hours. The reaction mixture was then concentrated under vacuum and the residue was dwastilled under reduced pressure (100-125° C./110 mmHg) to yield the desired compound as a light yellow liquid.

b) Preparation of 3-(6-{[2-(3-chloro-pyridin-2-yl)-5-methoxy-2H-pyrazole-3-carbonyl]-amino}-7-isopropylcarbamoyl-5-methyl-indazol-1-yl)-2,2-dimethyl-3-oxo-propionic acid A suspension of 7-[2-(3-chloro-pyridin-2-yl)-5-methoxy-2H-pyrazol-3-yl]-2-(4-methoxybenzyl)-5-methyl-2H-8-oxa-1,2,6-triaza-cyclopenta[a]naphthalen-9-one (0.234 g, 0.50 mmol) in dichloromethane (2 ml) and triethylamine (0.152 g, 1.5 mmol) was stirred at 0° C. and treated with a solution of 2,2-dimethyl-propanedioyl dichloride (0.253 g, 1.5 mmol) in dichloromethane (2 ml). The reaction mixture became homogeneous and was stirred for a few hours before being shaked with 1N sodium hydroxide solution (10 ml). The organic phase was removed and the aqueous phase was washed with dichloromethane, and then acidified to a pH of 3-4 with 1N HCl. A white precipitate formed and was extracted with dichloromethane. After drying of the organic phase and removal of the solvent, the targeted compound was isolated as a colorless solid showing the physical properties reported in the corresponding table (P.42.).

TABLE P

Physical data of compounds of formula I:

| Compound No. | Structures | Melting Point | MS/NMR |
|---|---|---|---|
| P.1. | 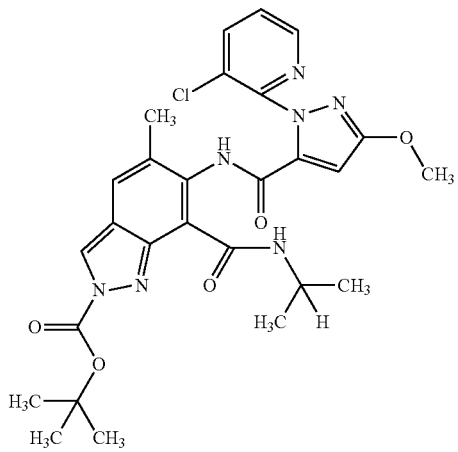<br>example 1 | 161-162° C. | $^1$H-NMR (300 MHz, CDCl$_3$, reference TMS); δ (ppm): 12.88 (s, 1 H), 9.57 (d, 1 H), 8.57 (s, 1 H), 8.47 (dd, 1 H), 7.79 (dd, 1 H), 7.54 (s, 1 H), 7.29 (dd, 1 H), 6.62 (s, 1 H), 4.29 (m, 1 H), 4.02 (s, 3 H), 2.31 (s, 3 H), 1.72 (s, 9 H), 1.47 (tt, 2 H), 1.35 ppm |
| P.2. | 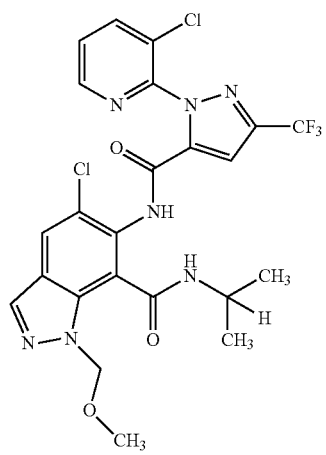<br>example 2 | 180-182° C. | LC/MS: 570/572 (M + H)$^+$<br>592/594 (M + Na)$^+$ |

TABLE P-continued
Physical data of compounds of formula I:
| Compound No. | Structures | Melting Point | MS/NMR |
|---|---|---|---|
| P.3. | 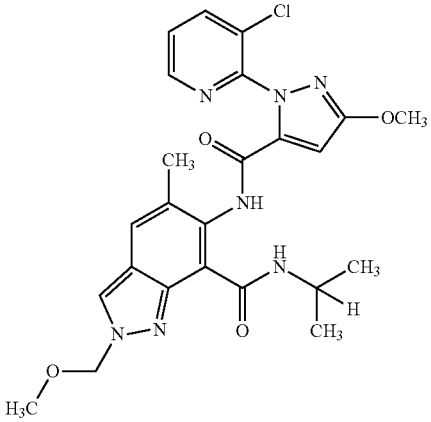<br>example 3 | 148° C. | LC/MS: 512/514 (M + H)+ |
| P.4. | 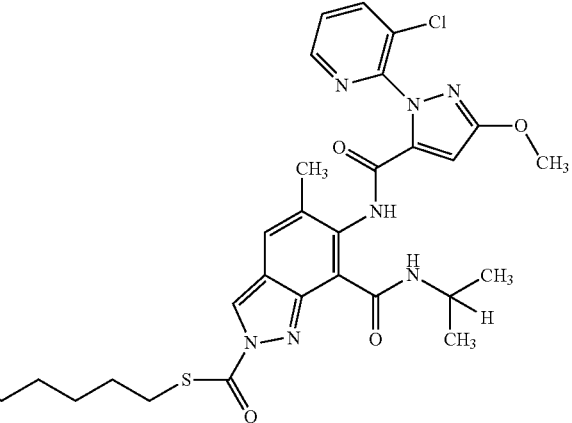<br>example 4 | 98-102° C. | 1H-NMR (300 MHz, CDCl3, reference TMS); δ (ppm): 12.85 (s, 1 H), 9.20 (d, 1 H), 8.57 (s, 1 H), 8.46 (d, 1 H), 7.79 (d, 1 H), 7.54 (s, 1 H), 7.30 (dd, 1 H), 6.62 (s, 1 H), 4.30 (m, 1 H), 4.01 (s, 3 H), 3.12 (t, 2 H), 2.30 (s, 3 H), 1.78 (tt, 2 H), 1.47 (tt, 2 H), 1.35 (d, 6 H), 1.32-1.20 (m, 8 H), 0.88 (t, 3 H) |
| P.5. | 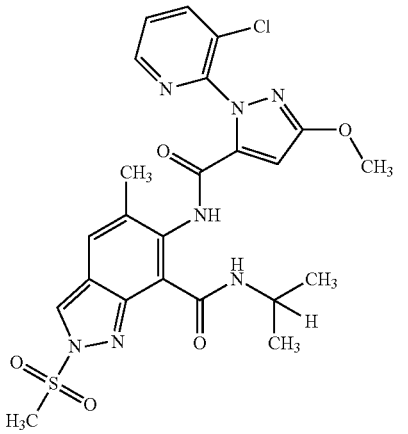<br>example 5 | 135-175° C. | 1H-NMR (400 MHz, CDCl3, reference TMS); δ (ppm): 12.72 (s, 1 H), 9.00 (d, 1 H), 8.48 (s, 1 H), 8.43 (d, 1 H), 7.78 (d, 1 H) 7.57 (s, 1 H) 7.29 (dd, 1 H) 6.60 (s, 1 H), 4.30 (m, 1 H) 4.00 (s, 3 H), 3.43 (s, 3 H), 2.32 (s, 3 H), 1.32 (d, 6 H) |

TABLE P-continued

Physical data of compounds of formula I:

| Compound No. | Structures | Melting Point | MS/NMR |
|---|---|---|---|
| P.6. | 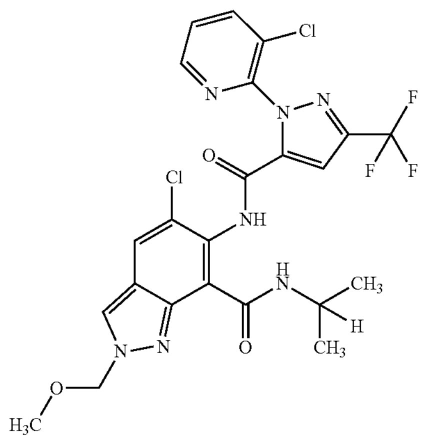 [SMILES: COCn1cc2cc(Cl)c(NC(=O)c3cc(C(F)(F)F)nn3-c3ncccc3Cl)c(C(=O)NC(C)C)c2n1] | 144-148° C. | LC/MS: 570/572 (M + H)+<br>592/594 (M + Na)+ |
| P.7. | example 6 | | LC/MS: 506 (M + H)+<br>528 (M + Na)+ |
| P.8. | 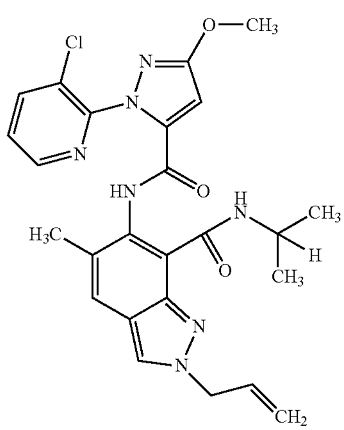 [SMILES: C=CCn1cc2cc(C)c(NC(=O)c3cc(OC)nn3-c3ncccc3Cl)c(C(=O)NC(C)C)c2n1] | 71-74° C. | LC/MS: 508/510 (M + H)+ |

TABLE P-continued

Physical data of compounds of formula I:

| Compound No. | Structures | Melting Point | MS/NMR |
|---|---|---|---|
| P.9. | 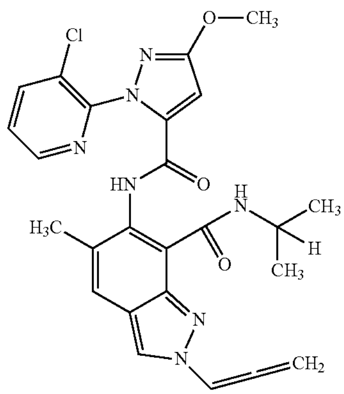 | 172-175° C. | LC/MS: 506/508 (M + H)+ <br> 528/530 (M + Na)+ |
| P.10. | example 7 | 178-181° C. | LC/MS: 550 (M + H)+ <br> 572/574 (M + Na)+ |
| P.11. | 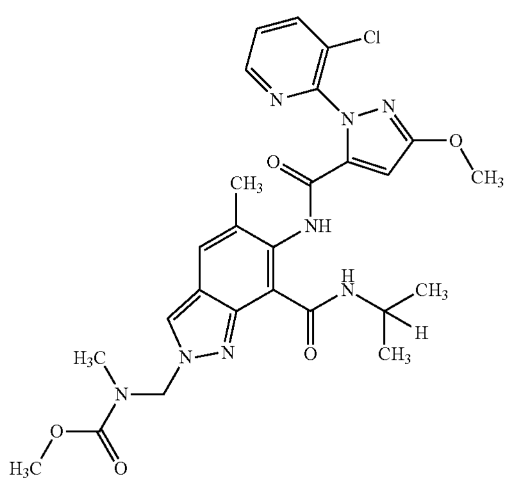 | 163-166° C. | |

TABLE P-continued

Physical data of compounds of formula I:

| Compound No. | Structures | Melting Point | MS/NMR |
|---|---|---|---|
| P.12. | example 8 | 132-133° C. | LC/MS: 556/558 (M + H)+ <br> 578/580 (M + Na)+ |
| P.13. | 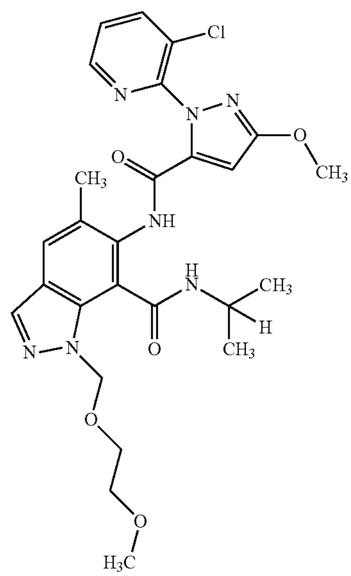 [SMILES: COCCOCn1ncc2cc(C)c(NC(=O)c3cc(OC)nn3-c3ncccc3Cl)c(C(=O)NC(C)C)c21] | 167-168° C. | LC/MS: 556/558 (M + H)+ <br> 578/580 (M + Na)+ |
| P.14. | 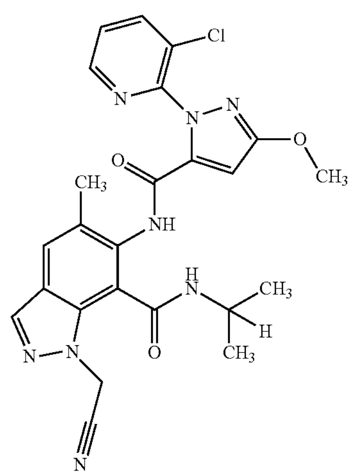 [SMILES: COc1cc(C(=O)Nc2c(C)cc3cnn(CC#N)c3c2C(=O)NC(C)C)n(-c2ncccc2Cl)n1] | 262-265° C. | LC/MS: 507 (M + H)+ <br> 529/531 (M + Na)+ |

TABLE P-continued

Physical data of compounds of formula I:

| Compound No. | Structures | Melting Point | MS/NMR |
|---|---|---|---|
| P.15. | 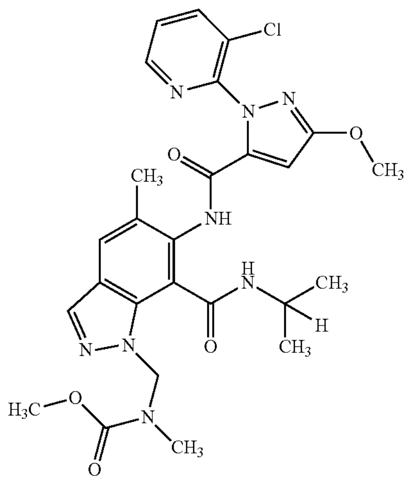 | 164-169° C. | |
| P.16. | 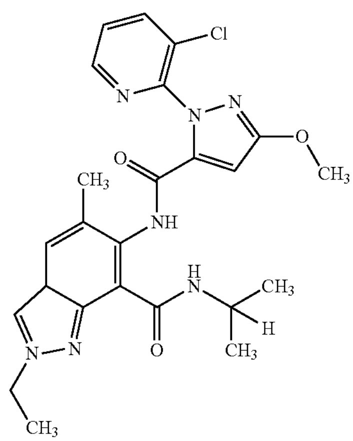 | 165-168° C. | LC/MS: 496/498 (M + H)+ <br> 518/520 (M + Na)+ |
| P.17. | 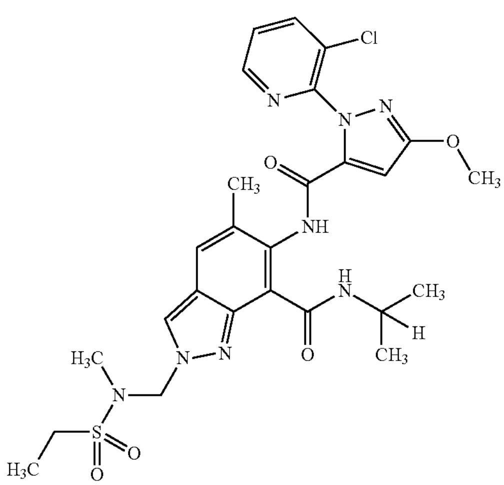 [SMILES: CCS(=O)(=O)N(C)Cn1cc2cc(C)c(NC(=O)c3cc(OC)nn3-c3ncccc3Cl)c(C(=O)NC(C)C)c2n1] | | LC/MS: 603/605 (M + H)+ |

TABLE P-continued

Physical data of compounds of formula I:

| Compound No. | Structures | Melting Point | MS/NMR |
|---|---|---|---|
| P.18. | 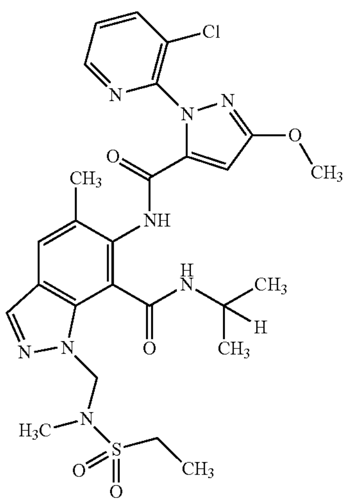 [SMILES: CCS(=O)(=O)N(C)Cn1ncc2cc(C)c(NC(=O)c3cc(OC)nn3-c3ncccc3Cl)c(C(=O)NC(C)C)c21] | | LC/MS: 603/605 (M + H)+ |
| P.19. | 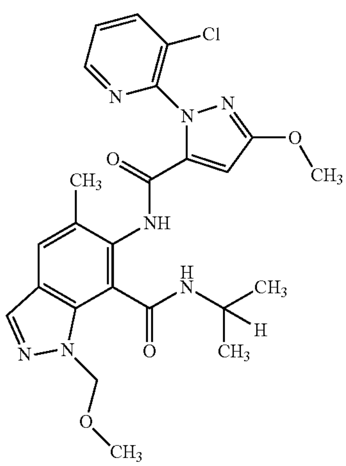 [SMILES: COCn1ncc2cc(C)c(NC(=O)c3cc(OC)nn3-c3ncccc3Cl)c(C(=O)NC(C)C)c21] | 143-146° C. | LC/MS: 512/514 (M + H)+ |
| P.20. | 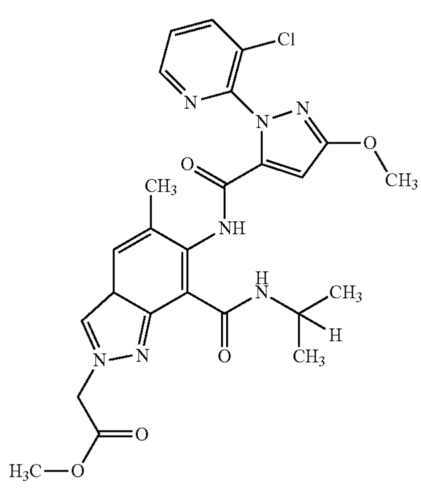 | 164-167° C. | LC/MS: 540/542 (M + H)+ |

TABLE P-continued

Physical data of compounds of formula I:

| Compound No. | Structures | Melting Point | MS/NMR |
|---|---|---|---|
| P.21. | 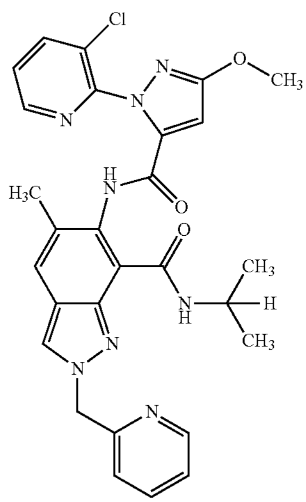 [SMILES: COc1cc(C(=O)Nc2c(C)cc3cn(Cc4ccccn4)nc3c2C(=O)NC(C)C)n(-c2ncccc2Cl)n1] | 156-160° C. | LC/MS: 559/561 (M + H)+ |
| P.23. | 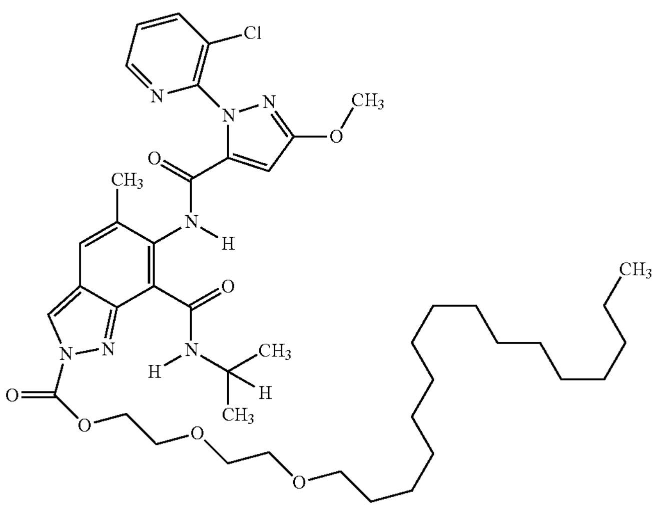 [SMILES: CCCCCCCCCCCCCCCCOCCOCCOC(=O)n1cc2cc(C)c(NC(=O)c3cc(OC)nn3-c3ncccc3Cl)c(C(=O)NC(C)C)c2n1] | gum | $^1$H-NMR (400 MHz, CDCl$_3$, reference TMS); δ (ppm): 12.90 (s, 1 H), 9.50 (d, 1 H), 8.60 (s, 1 H), 8.46 (d, 1 H), 7.80 (d, 1 H), 7.53 (s, 1 H), 7.30 (dd, 1 H), 6.62 (s, 1 H), 4.68 (t, 2 H), 4.29 (m, 1 H), 4.02 (s, 3 H), 3.91 (t, 2 H), 3.69 (t, 2 H), 3.60 (t, 2 H), 3.44 (t, 2 H), 2.30 (s, 3 H), 1.57 (m, 2 H), 1.35 (d, 6 H), 1.32-1.18 (m, 26 H), 0.87 (t, 3 H). |
| P.24. | 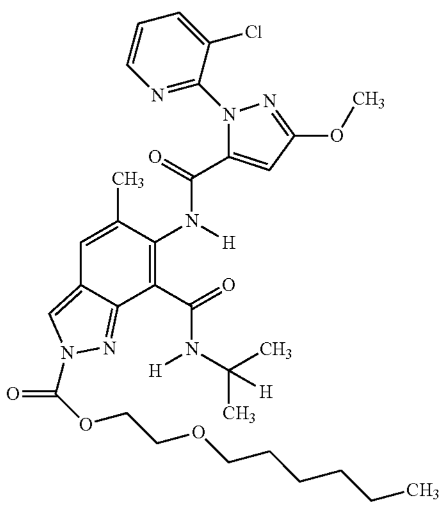 [SMILES: CCCCCCOCCOC(=O)n1cc2cc(C)c(NC(=O)c3cc(OC)nn3-c3ncccc3Cl)c(C(=O)NC(C)C)c2n1] | 96-99° C. | $^1$H-NMR (400 MHz, CDCl$_3$, reference TMS); δ (ppm): 12.88 (s, 1 H), 9.50 (d, 1 H), 8.57 (s, 1 H), 8.44 (d, 1 H), 7.78 (d, 1 H), 7.52 (s, 1 H), 7.29 (dd, 1 H), 6.61 (s, 1 H), 4.66 (m, 2 H), 4.28 (m, 1 H), 4.02 (s, 3 H), 3.82 (m, 2 H), 3.51 (t, 2 H), 2.30 (s, 3 H), 1.58 (m, 2 H), 1.35 (d, 6 H), 1.32-1.20 (m, 6 H), 0.86 (t, 3 H). |

TABLE P-continued

Physical data of compounds of formula I:

| Compound No. | Structures | Melting Point | MS/NMR |
|---|---|---|---|
| P.25. | 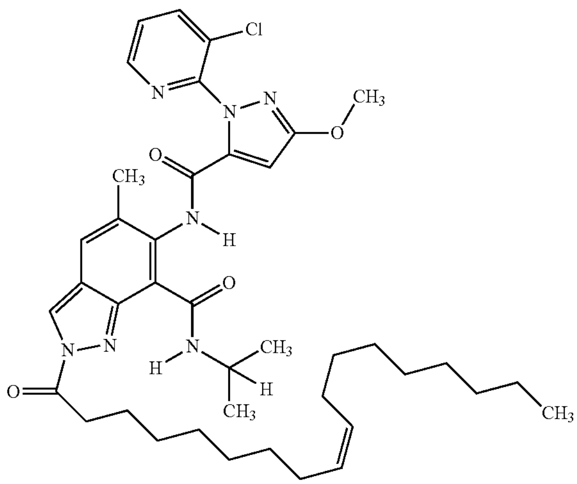 [SMILES: CCCCCCCC/C=C\CCCCCCCC(=O)n1cc2cc(C)c(NC(=O)c3cc(OC)nn3-c3ncccc3Cl)c(C(=O)NC(C)C)c2n1] | Gum | ¹H-NMR (400 MHz, CDCl₃, reference TMS); δ (ppm): 12.74 (s, 1 H), 9.24 (d, 1 H), 8.64 (s, 1 H), 8.44 (d, 1 H), 7.80 (d, 1 H), 7.53 (s, 1 H), 7.29 (dd, 1 H), 6.61 (s, 1 H), 5.40-5.30 (m, 2 H), 4.30 (m, 1 H), 4.02 (s, 3 H), 3.28 (t, 2 H), 2.31 (s, 3 H), 2.07-1.96 (m, 4 H), 1.87 (quint, 2 H), 1.58 (m, 2 H), 1.50-1.40 (m, 2 H), 1.35 (d, 6 H), 1.32-1.20 (m, 16 H), 0.87 (t, 3 H). |
| P.26. | 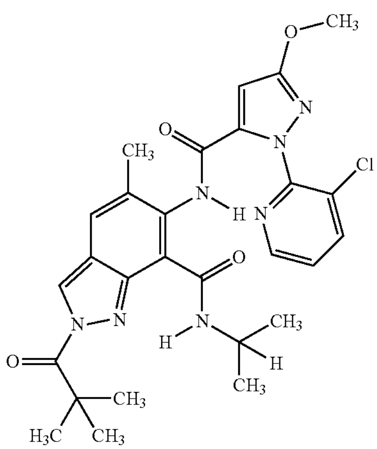 [SMILES: COc1cc(C(=O)Nc2c(C)cc3cn(C(=O)C(C)(C)C)nc3c2C(=O)NC(C)C)n(-c2ncccc2Cl)n1] | 199-202° C. | ¹H-NMR (400 MHz, CDCl₃, reference TMS); δ (ppm): 12.75 (s, 1 H), 9.11 (d, 1 H), 8.68 (s, 1 H), 8.46 (dd, 1 H), 7.79 (dd, 1 H), 7.55 (s, 1 H), 7.28 (dd, 1 H), 6.61 (s, 1 H), 4.40-4.30 (m, 1 H), 4.02 (s, 3 H), 2.30 (s, 3 H), 1.63 (s, 9 H), 1.31 (d, 6 H). |
| P.27. | 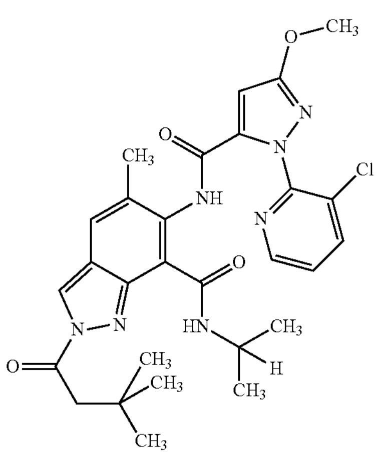 [SMILES: COc1cc(C(=O)Nc2c(C)cc3cn(C(=O)CC(C)(C)C)nc3c2C(=O)NC(C)C)n(-c2ncccc2Cl)n1] | 190-191° C. | ¹H-NMR (400 MHz, CDCl₃, reference TMS); δ (ppm): 12.76 (s, 1 H), 9.27 (d, 1 H), 8.67 (s, 1 H), 8.47 (dd, 1 H), 7.79 (dd, 1 H), 7.57 (s, 1 H), 7.29 (dd, 1 H), 6.60 (s, 1 H), 4.37-4.29 (m, 1 H), 4.01 (s, 3 H), 3.22 (s, 2 H), 2.29 (s, 3 H), 1.35 (d, 6 H), 1.13 (s, 9 H). |

TABLE P-continued

Physical data of compounds of formula I:

| Compound No. | Structures | Melting Point | MS/NMR |
|---|---|---|---|
| P.28. | 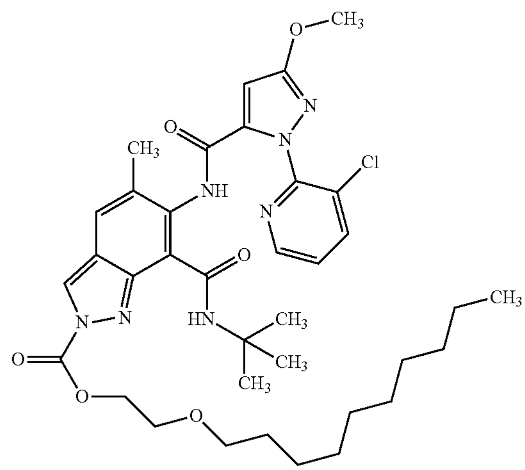 [SMILES: CCCCCCCCCCOCCOC(=O)n1cc2cc(C)c(NC(=O)c3cc(OC)nn3-c3ncccc3Cl)c(C(=O)NC(C)(C)C)c2n1] | 92-95° C. | ¹H-NMR (400 MHz, CDCl$_3$, reference TMS); δ (ppm): 12.89 (s, 1 H), 9.50 (d, 1 H), 8.58 (s, 1 H), 8.47 (d, 1 H), 7.80 (d, 1 H), 7.52 (s, 1 H), 7.29 (dd, 1 H), 6.62 (s, 1 H), 4.68-4.62 (m, 2 H), 4.28 (m, 1 H), 4.01 (s, 3 H), 3.84-3.80 (m, 2 H), 3.50 (t, 2 H), 2.31 (s, 3 H), 1.63-1.55 (m, 2 H), 1.36 (d, 6 H), 1.31-1.20 (m, 14 H), 0.87 (t, 3 H). |
| P.29. | 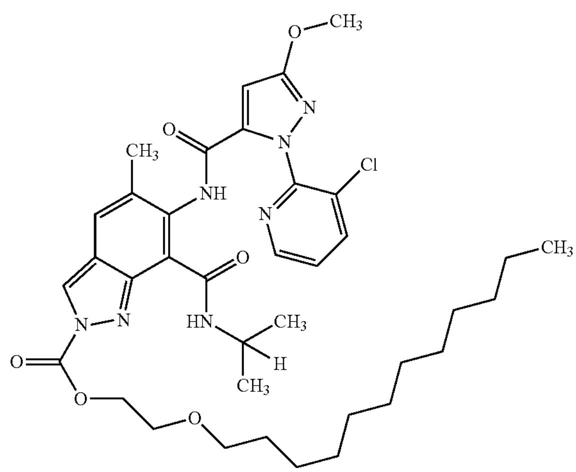 [SMILES: CCCCCCCCCCCCOCCOC(=O)n1cc2cc(C)c(NC(=O)c3cc(OC)nn3-c3ncccc3Cl)c(C(=O)NC(C)C)c2n1] | 89-94° C. | ¹H-NMR (400 MHz, CDCl$_3$, reference TMS); δ (ppm): 12.89 (s, 1 H), 9.51 (d, 1 H), 8.57 (s, 1 H), 8.47 (d, 1 H), 7.79 (d, 1 H), 7.53 (s, 1 H), 7.29 (dd, 1 H), 6.61 (s, 1 H), 4.70-4.63 (m, 2 H), 4.29 (m, 1 H), 4.01 (s, 3 H), 3.83-3.78 (m, 2 H), 3.50 (t, 2 H), 2.30 (s, 3 H), 1.63-1.54 (m, 2 H), 1.36 (d, 6 H), 1.31-1.20 (m, 18 H), 0.87 (t, 3 H). |
| P.30. | 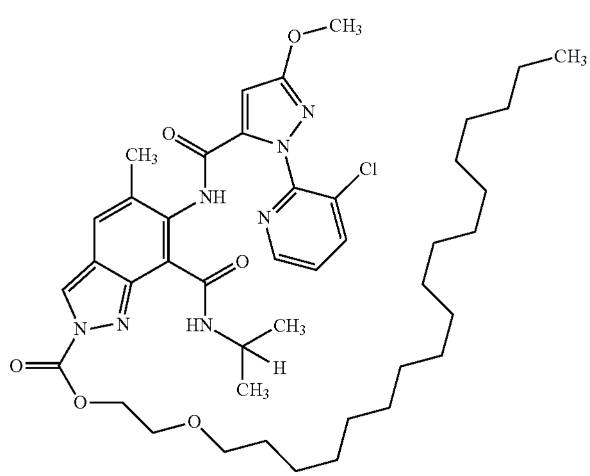 [SMILES: CCCCCCCCCCCCCCCCCCOCCOC(=O)n1cc2cc(C)c(NC(=O)c3cc(OC)nn3-c3ncccc3Cl)c(C(=O)NC(C)C)c2n1] | 89-94° C. | ¹H-NMR (400 MHz, CDCl$_3$, reference TMS); δ (ppm): 12.90 (s, 1 H), 9.50 (d, 1 H), 8.57 (s, 1 H), 8.46 (d, 1 H), 7.78 (d, 1 H), 7.53 (s, 1 H), 7.30 (dd, 1 H), 6.61 (s, 1 H), 4.68-4.62 (m, 2 H), 4.28 (m, 1 H), 4.01 (s, 3 H), 3.83-3.78 (m, 2 H), 3.50 (t, 2 H), 2.30 (s, 3 H), 1.63-1.53 (m, 2 H), 1.36 (d, 6 H), 1.31-1.16 (m, 30 H), 0.87 (t, 3 H). |

TABLE P-continued

Physical data of compounds of formula I:

| Compound No. | Structures | Melting Point | MS/NMR |
|---|---|---|---|
| P.31. | 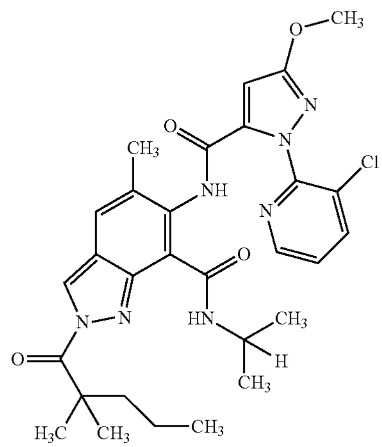 [SMILES: CCCC(C)(C)C(=O)n1cc2cc(C)c(NC(=O)c3cc(OC)nn3-c3ncccc3Cl)c(C(=O)NC(C)C)c2n1] | 162-166° C. | $^1$H-NMR (400 MHz, CDCl$_3$, reference TMS); δ (ppm): 12.77 (s, 1 H), 9.13 (d, 1 H), 8.68 (s, 1 H), 8.47 (dd, 1 H), 7.79 (dd, 1 H), 7.56 (s, 1 H), 7.30 (dd, 1 H), 6.62 (s, 1 H), 4.42-432 (m, 1 H), 4.01 (s, 3 H), 2.30 (s, 3 H), 2.14-2.07 (m, 2 H), 1.57 (s, 6 H), 1.33 (d, 6 H), 1.27-1.14 (m, 2 H), 0.84 (t, 3 H). |
| P.32. | 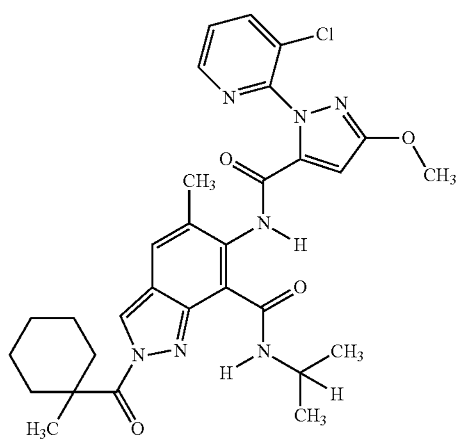 [SMILES: COc1cc(C(=O)Nc2c(C)cc3cn(C(=O)C4(C)CCCCC4)nc3c2C(=O)NC(C)C)n(-c2ncccc2Cl)n1] | 172-175° C. | $^1$H-NMR (400 MHz, CDCl$_3$, reference TMS); δ (ppm): 12.77 (s, 1 H), 9.14 (d, 1 H), 8.68 (s, 1 H), 8.46 (dd, 1 H), 7.78 (dd, 1 H), 7.56 (s, 1 H), 7.29 (dd, 1 H), 6.61 (s, 1 H), 4.40-430 (m, 1 H), 4.01 (s, 3 H), 2.55-2.45 (broad, 2 H), 2.30 (s, 3 H), 1.80-1.40 (m, 11 H), 1.30 (d, 6 H). |
| P.33. | 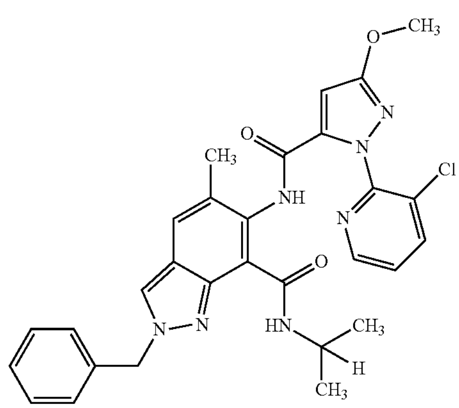 [SMILES: COc1cc(C(=O)Nc2c(C)cc3cn(Cc4ccccc4)nc3c2C(=O)NC(C)C)n(-c2ncccc2Cl)n1] | 192-196° C. | $^1$H-NMR (400 MHz, CDCl$_3$, reference TMS); δ (ppm): 12.60 (s, 1 H), 9.49 (s, 1 H), 8.43 (dd, 1 H), 7.82 (s, 1 H), 7.75 (dd, 1 H), 7.51 (s, 1 H), 7.40-7.32 (m, 3 H), 7.31-7.22 (m, 3 H), 6.60 (s, 1 H), 5.51 (s, 2 H), 4.33-4.22 (m, 1 H), 4.00 (s, 3 H), 2.27 (s, 3 H), 1.28 (d, 6 H). |

TABLE P-continued

Physical data of compounds of formula I:

| Compound No. | Structures | Melting Point | MS/NMR |
|---|---|---|---|
| P.34. | 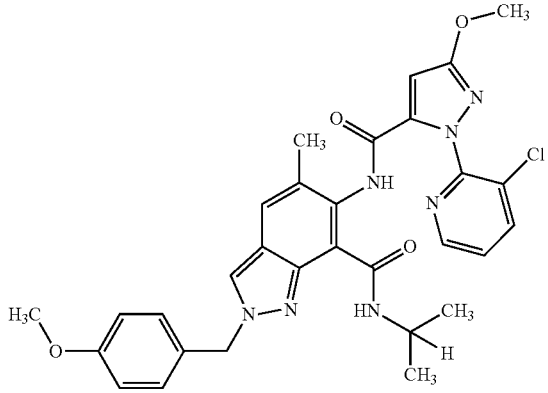  Example 13 | 170-172° C. | ¹H-NMR (400 MHz, CDCl₃, reference TMS); δ (ppm): 12.60 (s, 1 H), 9.50 (s, 1 H), 8.44 (dd, 1 H), 7.79 (s, 1 H), 7.75 (dd, 1 H), 7.50 (s, 1 H), 7.28-7.22 (m, 3 H), 6.90 (d, 2 H), 6.59 (s, 1 H), 5.45 (s, 2 H), 4.33-4.22 (m, 1 H), 4.00 (s, 3 H), 3.80 (s, 3 H), 2.27 (s, 3 H), 1.30 (d, 6 H). |
| P.35. | 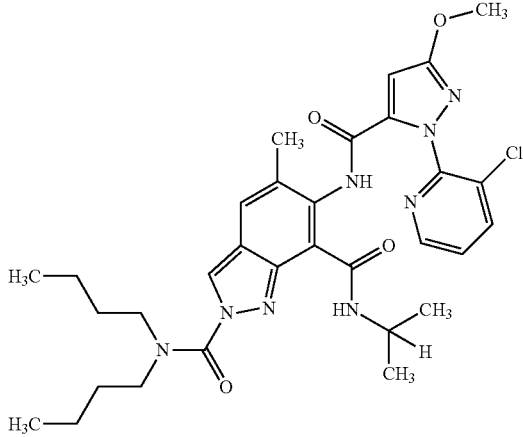 [SMILES: CCCCN(CCCC)C(=O)n1cc2cc(C)c(NC(=O)c3cc(OC)nn3-c3ncccc3Cl)c(C(=O)NC(C)C)c2n1] | 160-170° C. | ¹H-NMR (400 MHz, CDCl₃, reference TMS); δ (ppm): 12.63 (s, 1 H), 9.12 (broad d, 1 H), 8.47 (dd, 1 H), 8.40 (s, 1 H), 7.79 (dd, 1 H), 7.60 (s, 1 H), 7.30 (dd, 1 H), 6.60 (s, 1 H), 4.37-4.23 (m, 1 H), 4.00 (s, 3 H), 3.58 (broad t, 4 H), 2.30 (s, 3 H), 1.80-0.70 (broad m (including d at 1.30 ppm), 20 H). |
| P.36. | 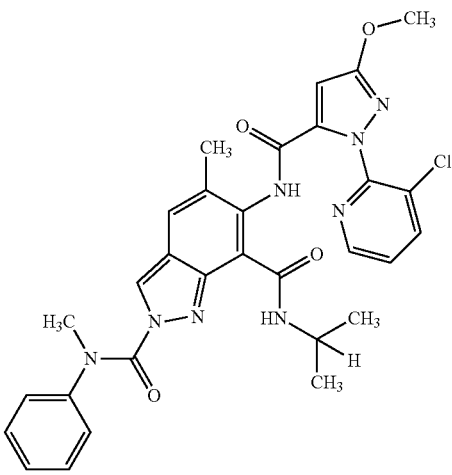 [SMILES: COc1cc(C(=O)Nc2c(C)cc3cn(C(=O)N(C)c4ccccc4)nc3c2C(=O)NC(C)C)n(-c2ncccc2Cl)n1] | 227-232° C. | ¹H-NMR (400 MHz, CDCl₃, reference TMS); δ (ppm): 12.75 (s, 1 H), 8.47-8.40 (m, 3 H), 7.79 (dd, 1 H), 7.52 (s, 1 H), 7.30-7.13 (m, 5 H), 6.98 (d, 1 H), 6.56 (s, 1 H), 4.22-4.08 (m, 1 H), 4.00 (s, 3 H), 3.62 (s, 2 H), 2.26 (s, 3 H), 1.22 (d, 6 H). |

TABLE P-continued

Physical data of compounds of formula I:

| Compound No. | Structures | Melting Point | MS/NMR |
|---|---|---|---|
| P.37. | (structure) | Gum | $^1$H-NMR (400 MHz, CDCl$_3$, reference TMS); δ (ppm): 12.70 (s, 1 H), 9.15 (broad d, 1 H), 8.50 (broad s, 1 H), 8.47 (dd, 1 H), 7.79 (dd, 1 H), 7.58 (s, 1 H), 7.28 (dd, 1 H), 6.61 (s, 1 H), 4.37-4.27 (m, 1 H), 4.01 (s, 3 H), 3.60 (broad s, 2 H), 3.27 (broad s, 3 H), 2.31 (s, 3 H), 1.30 (d, 6 H), 1.70 (broad s, 2 H), 1.28-1.18 (broad s, 30 H), 0.87 (t, 3 H). |
| P.38. | (structure) example 12 | 66-70° C. | $^1$H-NMR (400 MHz, CDCl$_3$, reference TMS); (ppm): 12.70 (s, 1 H), 9.15 (broad d, 1 H), 8.50 (broad s, 1 H), 8.47 (dd, 1 H), 7.79 (dd, 1 H), 7.59 (s, 1 H), 7.28 (dd, 1 H), 6.60 (s, 1 H), 4.37-4.27 (m, 1 H), 4.00 (s, 3 H), 3.61 (broad s, 2 H), 3.27 (broad s, 3 H), 2.31 (s, 3 H), 1.70 (broad m, 2 H), 1.50-1.10 (broad m, 16 H), 0.87 (broad t, 3 H). |
| P.39. | (structure) | 216° C. (decomposition) | $^1$H-NMR (400 MHz, CDCl$_3$, reference TMS); δ (ppm): 12.95 (s, 1 H), 9.55 (d, 1 H), 8.95 (s, 1 H), 8.47 (dd, 1 H), 7.80 (dd, 1 H), 7.53 (s, 1 H), 7.29 (dd, 1 H), 6.61 (s, 1 H), 4.38-4.25 (m, 1 H), 4.01 (s, 3 H), 2.31 (s, 3 H), 1.37 (d, 6 H). |

TABLE P-continued

Physical data of compounds of formula I:

| Compound No. | Structures | Melting Point | MS/NMR |
|---|---|---|---|
| P.40. | example 10 | 226-230° C. | $^1$H-NMR (400 MHz, CDCl$_3$, reference TMS); δ (ppm): 12.90 (s, 1 H), 9.70 (d, 1 H), 9.01 (s, 1 H), 8.47 (dd, 1 H), 7.78 (dd, 1 H), 7.56 (s, 1 H), 7.29 (dd, 1 H), 6.61 (s, 1 H), 4.38-4.27 (m, 1 H), 4.18 (s, 6 H), 4.02 (s, 3 H), 2.31 (s, 3 H), 1.37 (d, 6 H). |
| P.41. | Example 11 | 85-86° C. | $^1$H-NMR (400 MHz, CDCl$_3$, ref. TMS); δ (ppm): 12.82 (s, 1 H), 9.08 (d, 1 H), 8.57 (s, 1 H), 8.46 (dd, 1 H), 7.79 (dd, 1 H), 7.54 (s, 1 H), 7.30 (dd, 1 H), 6.60 (s, 1 H), 4.33-4.22 (m, 3 H), 4.01 (s, 3 H), 3.90 (s, 2 H), 2.30 (s, 3 H), 1.38-1.28 (m, 9 H). |
| P.42. | Example 14 |  | $^1$H-NMR (400 MHz, DMSO-d6, ref. TMS); δ (ppm): 12.60 (broad s, 1 H), 10.20 (s, 1 H), 8.46-8.38 (m, 2 H), 8.09 (broad d, 1 H), 7.80-7.63 (m, 2 H), 7.52 (dd, 1 H), 6.79 (s, 1 H), 4.10-3.95 (m, 1 H), 3.97 (s, 3 H), 2.22 (broad s, 3 H), 1.53-1.40 (broad s, 6 H), 1.03 (d, 6 H). |

TABLE P-continued

Physical data of compounds of formula I:

| Compound No. | Structures | Melting Point | MS/NMR |
|---|---|---|---|
| P.43. | 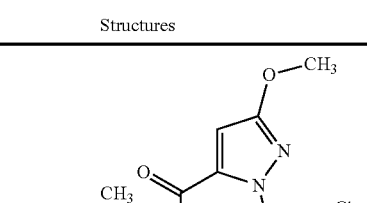<br>Example 9 | | $^1$H-NMR (500 MHz, CDCl$_3$, reference TMS); δ (ppm): 13.00 (s, 1 H), 9.44 (d, 1 H), 8.96 (s, 1 H), 8.47 (dd, 1 H), 7.78 (dd, 1 H), 7.54 (s, 1 H), 7.29 (dd, 1 H), 6.61 (s, 1 H), 4.38-4.27 (m, 1 H), 4.02 (s, 3 H), 2.31 (s, 3 H), 1.37 (d, 6 H). |

The compounds according to the following tables can be prepared analogously. The examples which follow are intended to illustrate the invention and show preferred compounds of formula I.

TABLE A

Compounds of formula Ib:

| Line | R$_1$a | R$_{100}$ | R$_{20}$ |
|---|---|---|---|
| A.1.1 | CH$_3$ | CF$_3$ | H |
| A.1.2 | CH$_3$ | CF$_3$ | CH$_3$ |
| A.1.3 | CH$_3$ | CF$_3$ | CH$_2$CH$_3$ |
| A.1.4 | CH$_3$ | CF$_3$ | CH(CH$_3$)CH$_3$ |
| A.1.5 | CH$_3$ | CF$_3$ | C(CH$_3$)(CH$_3$)CH$_3$ |
| A.1.6 | CH$_3$ | CF$_3$ | (cyclopropylmethyl) |
| A.1.7 | CH$_3$ | CF$_3$ | (bicyclopropyl) |
| A.1.8 | CH$_3$ | CF$_3$ | (bicyclopropyl isomer) |
| A.1.9 | CH$_3$ | CF$_3$ | (cyclopropyl-cyclobutyl spiro) |
| A.1.10 | CH$_3$ | CF$_3$ | CH(CH$_3$)$_2$CH$_2$SCH$_3$ |
| A.1.11 | CH$_3$ | CF$_3$ | CH(CH$_3$)$_2$CH$_2$S(O)CH$_3$ |
| A.1.12 | CH$_3$ | CF$_3$ | CH(CH$_3$)$_2$CH$_2$S(O)$_2$CH$_3$ |
| A.1.13 | CH$_3$ | OCH$_2$CF$_3$ | H |
| A.1.14 | CH$_3$ | OCH$_2$CF$_3$ | CH$_3$ |

TABLE A-continued

Compounds of formula Ib:

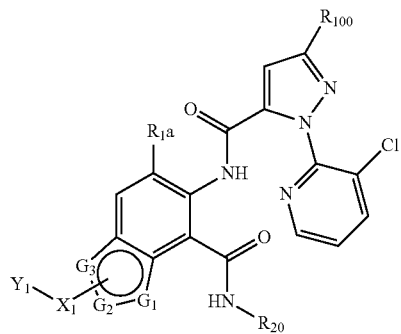

(Ib)

| Line | $R_{1a}$ | $R_{100}$ | $R_{20}$ |
|---|---|---|---|
| A.1.15 | $CH_3$ | $OCH_2CF_3$ | $CH_2CH_3$ |
| A.1.16 | $CH_3$ | $OCH_2CF_3$ | $CH(CH_3)CH_3$ |
| A.1.17 | $CH_3$ | $OCH_2CF_3$ | $C(CH_3)(CH_3)CH_3$ |
| A.1.18 | $CH_3$ | $OCH_2CF_3$ | |
| A.1.19 | $CH_3$ | $OCH_2CF_3$ | |
| A.1.20 | $CH_3$ | $OCH_2CF_3$ | |
| A.1.21 | $CH_3$ | $OCH_2CF_3$ | |
| A.1.22 | $CH_3$ | $OCH_2CF_3$ | $CH(CH_3)_2CH_2SCH_3$ |
| A.1.23 | $CH_3$ | $OCH_2CF_3$ | $CH(CH_3)_2CH_2S(O)CH_3$ |
| A.1.24 | $CH_3$ | $OCH_2CF_3$ | $CH(CH_3)_2CH_2S(O)_2CH_3$ |
| A.1.25 | $CH_3$ | Br | H |
| A.1.26 | $CH_3$ | Br | $CH_3$ |
| A.1.27 | $CH_3$ | Br | $CH_2CH_3$ |
| A.1.28 | $CH_3$ | Br | $CH(CH_3)CH_3$ |
| A.1.29 | $CH_3$ | Br | $C(CH_3)(CH_3)CH_3$ |
| A.1.30 | $CH_3$ | Br | |
| A.1.31 | $CH_3$ | Br | |
| A.1.32 | $CH_3$ | Br | |
| A.1.33 | $CH_3$ | Br | |

TABLE A-continued

Compounds of formula Ib:

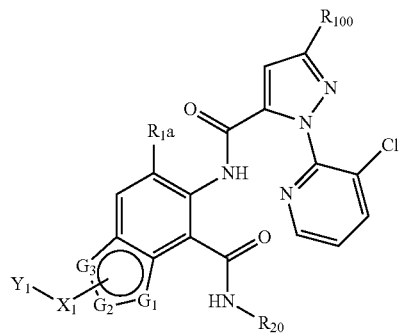

(Ib)

| Line | $R_{1a}$ | $R_{100}$ | $R_{20}$ |
|---|---|---|---|
| A.1.34 | $CH_3$ | Br | $CH(CH_3)_2CH_2SCH_3$ |
| A.1.35 | $CH_3$ | Br | $CH(CH_3)_2CH_2S(O)CH_3$ |
| A.1.36 | $CH_3$ | Br | $CH(CH_3)_2CH_2S(O)_2CH_3$ |
| A.1.37 | $CH_3$ | Cl | H |
| A.1.38 | $CH_3$ | Cl | $CH_3$ |
| A.1.39 | $CH_3$ | Cl | $CH_2CH_3$ |
| A.1.40 | $CH_3$ | Cl | $CH(CH_3)CH_3$ |
| A.1.41 | $CH_3$ | Cl | $C(CH_3)(CH_3)CH_3$ |
| A.1.42 | $CH_3$ | Cl | |
| A.1.43 | $CH_3$ | Cl | |
| A.1.44 | $CH_3$ | Cl | |
| A.1.45 | $CH_3$ | Cl | |
| A.1.46 | $CH_3$ | Cl | $CH(CH_3)_2CH_2SCH_3$ |
| A.1.47 | $CH_3$ | Cl | $CH(CH_3)_2CH_2S(O)CH_3$ |
| A.1.48 | $CH_3$ | Cl | $CH(CH_3)_2CH_2S(O)_2CH_3$ |
| A.1.49 | $CH_3$ | $CF_2H$ | H |
| A.1.50 | $CH_3$ | $CF_2H$ | $CH_3$ |
| A.1.51 | $CH_3$ | $CF_2H$ | $CH_2CH_3$ |
| A.1.52 | $CH_3$ | $CF_2H$ | $CH(CH_3)CH_3$ |
| A.1.53 | $CH_3$ | $CF_2H$ | $C(CH_3)(CH_3)CH_3$ |
| A.1.54 | $CH_3$ | $CF_2H$ | |
| A.1.55 | $CH_3$ | $CF_2H$ | |
| A.1.56 | $CH_3$ | $CF_2H$ | |

TABLE A-continued

Compounds of formula Ib:

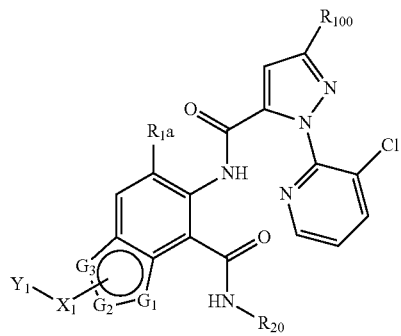
(Ib)

| Line | R₁a | R₁₀₀ | R₂₀ |
|---|---|---|---|
| A.1.57 | CH₃ | CF₂H | |
| A.1.58 | CH₃ | CF₂H | CH(CH₃)₂CH₂SCH₃ |
| A.1.59 | CH₃ | CF₂H | CH(CH₃)₂CH₂S(O)CH₃ |
| A.1.60 | CH₃ | CF₂H | CH(CH₃)₂CH₂S(O)₂CH₃ |
| A.1.61 | CH₃ | OCF₃ | H |
| A.1.62 | CH₃ | OCF₃ | CH₃ |
| A.1.63 | CH₃ | OCF₃ | CH₂CH₃ |
| A.1.64 | CH₃ | OCF₃ | CH(CH₃)CH₃ |
| A.1.65 | CH₃ | OCF₃ | C(CH₃)(CH₃)CH₃ |
| A.1.66 | CH₃ | OCF₃ | |
| A.1.67 | CH₃ | OCF₃ | |
| A.1.68 | CH₃ | OCF₃ | |
| A.1.69 | CH₃ | OCF₃ | |
| A.1.70 | CH₃ | OCF₃ | CH(CH₃)₂CH₂SCH₃ |
| A.1.71 | CH₃ | OCF₃ | CH(CH₃)₂CH₂S(O)CH₃ |
| A.1.72 | CH₃ | OCF₃ | CH(CH₃)₂CH₂S(O)₂CH₃ |
| A.1.73 | Cl | CF₃ | H |
| A.1.74 | Cl | CF₃ | CH₃ |
| A.1.75 | Cl | CF₃ | CH₂CH₃ |
| A.1.76 | Cl | CF₃ | CH(CH₃)CH₃ |
| A.1.77 | Cl | CF₃ | C(CH₃)(CH₃)CH₃ |
| A.1.78 | Cl | CF₃ | |
| A.1.79 | Cl | CF₃ | |

TABLE A-continued

Compounds of formula Ib:

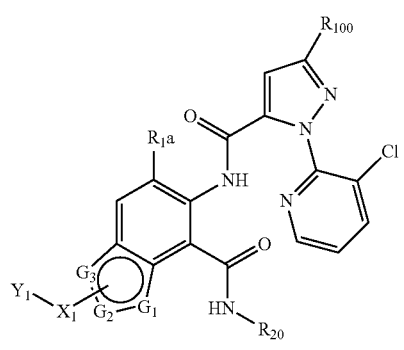
(Ib)

| Line | R₁a | R₁₀₀ | R₂₀ |
|---|---|---|---|
| A.1.80 | Cl | CF₃ | |
| A.1.81 | Cl | CF₃ | |
| A.1.82 | Cl | CF₃ | CH(CH₃)₂CH₂SCH₃ |
| A.1.83 | Cl | CF₃ | CH(CH₃)₂CH₂S(O)CH₃ |
| A.1.84 | Cl | CF₃ | CH(CH₃)₂CH₂S(O)₂CH₃ |
| A.1.85 | Cl | OCH₂CF₃ | H |
| A.1.86 | Cl | OCH₂CF₃ | CH₃ |
| A.1.87 | Cl | OCH₂CF₃ | CH₂CH₃ |
| A.1.88 | Cl | OCH₂CF₃ | CH(CH₃)CH₃ |
| A.1.89 | Cl | OCH₂CF₃ | C(CH₃)(CH₃)CH₃ |
| A.1.90 | Cl | OCH₂CF₃ | |
| A.1.91 | Cl | OCH₂CF₃ | |
| A.1.92 | Cl | OCH₂CF₃ | |
| A.1.93 | Cl | OCH₂CF₃ | |
| A.1.94 | Cl | OCH₂CF₃ | CH(CH₃)₂CH₂SCH₃ |
| A.1.95 | Cl | OCH₂CF₃ | CH(CH₃)₂CH₂S(O)CH₃ |
| A.1.96 | Cl | OCH₂CF₃ | CH(CH₃)₂CH₂S(O)₂CH₃ |
| A.1.97 | Cl | Br | H |
| A.1.98 | Cl | Br | CH₃ |
| A.1.99 | Cl | Br | CH₂CH₃ |
| A.1.100 | Cl | Br | CH(CH₃)CH₃ |
| A.1.101 | Cl | Br | C(CH₃)(CH₃)CH₃ |
| A.1.102 | Cl | Br | |

TABLE A-continued

Compounds of formula Ib:

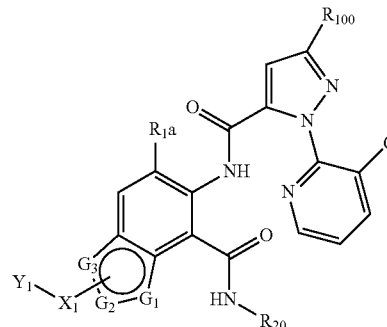
(Ib)

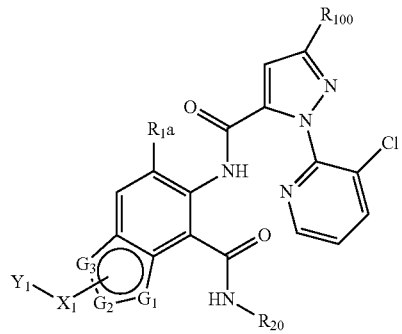
(Ib)

| Line | R₁a | R₁₀₀ | R₂₀ |
|---|---|---|---|
| A.1.103 | Cl | Br |  |
| A.1.104 | Cl | Br | 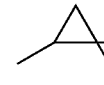 |
| A.1.105 | Cl | Br |  |
| A.1.106 | Cl | Br | CH(CH₃)₂CH₂SCH₃ |
| A.1.107 | Cl | Br | CH(CH₃)₂CH₂S(O)CH₃ |
| A.1.108 | Cl | Br | CH(CH₃)₂CH₂S(O)₂CH₃ |
| A.1.109 | Cl | Cl | H |
| A.1.110 | Cl | Cl | CH₃ |
| A.1.111 | Cl | Cl | CH₂CH₃ |
| A.1.112 | Cl | Cl | CH(CH₃)CH₃ |
| A.1.113 | Cl | Cl | C(CH₃)(CH₃)CH₃ |
| A.1.114 | Cl | Cl |  |
| A.1.115 | Cl | Cl |  |
| A.1.116 | Cl | Cl | 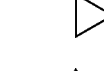 |
| A.1.117 | Cl | Cl | 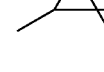 |
| A.1.118 | Cl | Cl | CH(CH₃)₂CH₂SCH₃ |
| A.1.119 | Cl | Cl | CH(CH₃)₂CH₂S(O)CH₃ |
| A.1.120 | Cl | Cl | CH(CH₃)₂CH₂S(O)₂CH₃ |
| A.1.121 | Cl | CF₂H | H |
| A.1.122 | Cl | CF₂H | CH₃ |
| A.1.123 | Cl | CF₂H | CH₂CH₃ |
| A.1.124 | Cl | CF₂H | CH(CH₃)CH₃ |
| A.1.125 | Cl | CF₂H | C(CH₃)(CH₃)CH₃ |
| A.1.126 | Cl | CF₂H |  |
| A.1.127 | Cl | CF₂H |  |
| A.1.128 | Cl | CF₂H |  |
| A.1.129 | Cl | CF₂H |  |
| A.1.130 | Cl | CF₂H | CH(CH₃)₂CH₂SCH₃ |
| A.1.131 | Cl | CF₂H | CH(CH₃)₂CH₂S(O)CH₃ |
| A.1.132 | Cl | CF₂H | CH(CH₃)₂CH₂S(O)₂CH₃ |
| A.1.133 | Cl | OCF₃ | H |
| A.1.134 | Cl | OCF₃ | CH₃ |
| A.1.135 | Cl | OCF₃ | CH₂CH₃ |
| A.1.136 | Cl | OCF₃ | CH(CH₃)CH₃ |
| A.1.137 | Cl | OCF₃ | C(CH₃)(CH₃)CH₃ |
| A.1.138 | Cl | OCF₃ |  |
| A.1.139 | Cl | OCF₃ |  |
| A.1.140 | Cl | OCF₃ |  |
| A.1.141 | Cl | OCF₃ |  |
| A.1.142 | Cl | OCF₃ | CH(CH₃)₂CH₂SCH₃ |
| A.1.143 | Cl | OCF₃ | CH(CH₃)₂CH₂S(O)CH₃ |
| A.1.144 | Cl | OCF₃ | CH(CH₃)₂CH₂S(O)₂CH₃ |
| A.1.145 | Br | CF₃ | H |

TABLE A-continued

Compounds of formula Ib:

| Line | R₁a | R₁₀₀ | R₂₀ |
|------|-----|------|-----|
| A.1.146 | Br | CF₃ | CH₃ |
| A.1.147 | Br | CF₃ | CH₂CH₃ |
| A.1.148 | Br | CF₃ | CH(CH₃)CH₃ |
| A.1.149 | Br | CF₃ | C(CH₃)(CH₃)CH₃ |
| A.1.150 | Br | CF₃ | (cyclopropyl) |
| A.1.151 | Br | CF₃ | (bicyclopropyl) |
| A.1.152 | Br | CF₃ | (spiro tricycle) |
| A.1.153 | Br | CF₃ | (cyclopropyl-cyclobutyl) |
| A.1.154 | Br | CF₃ | CH(CH₃)₂CH₂SCH₃ |
| A.1.155 | Br | CF₃ | CH(CH₃)₂CH₂S(O)CH₃ |
| A.1.156 | Br | CF₃ | CH(CH₃)₂CH₂S(O)₂CH₃ |
| A.1.157 | Br | OCH₂CF₃ | H |
| A.1.158 | Br | OCH₂CF₃ | CH₃ |
| A.1.159 | Br | OCH₂CF₃ | CH₂CH₃ |
| A.1.160 | Br | OCH₂CF₃ | CH(CH₃)CH₃ |
| A.1.161 | Br | OCH₂CF₃ | C(CH₃)(CH₃)CH₃ |
| A.1.162 | Br | OCH₂CF₃ | (cyclopropyl) |
| A.1.163 | Br | OCH₂CF₃ | (bicyclopropyl) |
| A.1.164 | Br | OCH₂CF₃ | (spiro tricycle) |
| A.1.165 | Br | OCH₂CF₃ | (cyclopropyl-cyclobutyl) |
| A.1.166 | Br | OCH₂CF₃ | CH(CH₃)₂CH₂SCH₃ |
| A.1.167 | Br | OCH₂CF₃ | CH(CH₃)₂CH₂S(O)CH₃ |
| A.1.168 | Br | OCH₂CF₃ | CH(CH₃)₂CH₂S(O)₂CH₃ |
| A.1.169 | Br | Br | H |
| A.1.170 | Br | Br | CH₃ |
| A.1.171 | Br | Br | CH₂CH₃ |
| A.1.172 | Br | Br | CH(CH₃)CH₃ |
| A.1.173 | Br | Br | C(CH₃)(CH₃)CH₃ |
| A.1.174 | Br | Br | (cyclopropyl) |
| A.1.175 | Br | Br | (bicyclopropyl) |
| A.1.176 | Br | Br | (spiro tricycle) |
| A.1.177 | Br | Br | (cyclopropyl-cyclobutyl) |
| A.1.178 | Br | Br | CH(CH₃)₂CH₂SCH₃ |
| A.1.179 | Br | Br | CH(CH₃)₂CH₂S(O)CH₃ |
| A.1.180 | Br | Br | CH(CH₃)₂CH₂S(O)₂CH₃ |
| A.1.181 | Br | Cl | H |
| A.1.182 | Br | Cl | CH₃ |
| A.1.183 | Br | Cl | CH₂CH₃ |
| A.1.184 | Br | Cl | CH(CH₃)CH₃ |
| A.1.185 | Br | Cl | C(CH₃)(CH₃)CH₃ |
| A.1.186 | Br | Cl | (cyclopropyl) |
| A.1.187 | Br | Cl | (bicyclopropyl) |
| A.1.188 | Br | Cl | (cyclopropyl-cyclobutyl) |

TABLE A-continued

Compounds of formula Ib:

(Ib)

| Line | R₁a | R₁₀₀ | R₂₀ |
|---|---|---|---|
| A.1.189 | Br | Cl | (spiro[2.3]hexyl group) |
| A.1.190 | Br | Cl | CH(CH₃)₂CH₂SCH₃ |
| A.1.191 | Br | Cl | CH(CH₃)₂CH₂S(O)CH₃ |
| A.1.192 | Br | Cl | CH(CH₃)₂CH₂S(O)₂CH₃ |
| A.1.193 | Br | CF₂H | H |
| A.1.194 | Br | CF₂H | CH₃ |
| A.1.195 | Br | CF₂H | CH₂CH₃ |
| A.1.196 | Br | CF₂H | CH(CH₃)CH₃ |
| A.1.197 | Br | CF₂H | C(CH₃)(CH₃)CH₃ |
| A.1.198 | Br | CF₂H | (cyclopropylmethyl) |
| A.1.199 | Br | CF₂H | (bicyclopropyl) |
| A.1.200 | Br | CF₂H | (spiropentyl) |
| A.1.201 | Br | CF₂H | (spiro[2.3]hexyl) |
| A.1.202 | Br | CF₂H | CH(CH₃)₂CH₂SCH₃ |
| A.1.203 | Br | CF₂H | CH(CH₃)₂CH₂S(O)CH₃ |
| A.1.204 | Br | CF₂H | CH(CH₃)₂CH₂S(O)₂CH₃ |
| A.1.205 | Br | OCF₃ | H |
| A.1.206 | Br | OCF₃ | CH₃ |
| A.1.207 | Br | OCF₃ | CH₂CH₃ |
| A.1.208 | Br | OCF₃ | CH(CH₃)CH₃ |
| A.1.209 | Br | OCF₃ | C(CH₃)(CH₃)CH₃ |
| A.1.210 | Br | OCF₃ | (cyclopropylmethyl) |
| A.1.211 | Br | OCF₃ | (bicyclopropyl) |
| A.1.212 | Br | OCF₃ | (spiropentyl) |
| A.1.213 | Br | OCF₃ | (spiro[2.3]hexyl) |
| A.1.214 | Br | OCF₃ | CH(CH₃)₂CH₂SCH₃ |
| A.1.215 | Br | OCF₃ | CH(CH₃)₂CH₂S(O)CH₃ |
| A.1.216 | Br | OCF₃ | CH(CH₃)₂CH₂S(O)₂CH₃ |
| A.1.217 | CH₃ | OCHF₂ | H |
| A.1.218 | CH₃ | OCHF₂ | CH₃ |
| A.1.219 | CH₃ | OCHF₂ | CH₂CH₃ |
| A.1.220 | CH₃ | OCHF₂ | CH(CH₃)CH₃ |
| A.1.221 | CH₃ | OCHF₂ | C(CH₃)(CH₃)CH₃ |
| A.1.222 | CH₃ | OCHF₂ | (cyclopropylmethyl) |
| A.1.223 | CH₃ | OCHF₂ | (bicyclopropyl) |
| A.1.224 | CH₃ | OCHF₂ | (spiropentyl) |
| A.1.225 | CH₃ | OCHF₂ | (spiro[2.3]hexyl) |
| A.1.226 | CH₃ | OCHF₂ | CH(CH₃)₂CH₂SCH₃ |
| A.1.227 | CH₃ | OCHF₂ | CH(CH₃)₂CH₂S(O)CH₃ |
| A.1.228 | CH₃ | OCHF₂ | CH(CH₃)₂CH₂S(O)₂CH₃ |
| A.1.229 | Cl | OCHF₂ | H |
| A.1.230 | Cl | OCHF₂ | CH₃ |
| A.1.231 | Cl | OCHF₂ | CH₂CH₃ |
| A.1.232 | Cl | OCHF₂ | CH(CH₃)CH₃ |
| A.1.233 | Cl | OCHF₂ | C(CH₃)(CH₃)CH₃ |
| A.1.234 | Cl | OCHF₂ | (cyclopropylmethyl) |

TABLE A-continued

Compounds of formula Ib:

(Ib)

| Line | R1a | R100 | R20 |
|---|---|---|---|
| A.1.235 | Cl | OCHF2 | (bicyclopropyl) |
| A.1.236 | Cl | OCHF2 | (spiropentyl) |
| A.1.237 | Cl | OCHF2 | (spiro[2.3]hexyl) |
| A.1.238 | Cl | OCHF2 | CH(CH3)2CH2SCH3 |
| A.1.239 | Cl | OCHF2 | CH(CH3)2CH2S(O)CH3 |
| A.1.240 | Cl | OCHF2 | CH(CH3)2CH2S(O)2CH3 |
| A.1.241 | Br | OCHF2 | H |
| A.1.242 | Br | OCHF2 | CH3 |
| A.1.243 | Br | OCHF2 | CH2CH3 |
| A.1.244 | Br | OCHF2 | CH(CH3)CH3 |
| A.1.245 | Br | OCHF2 | C(CH3)(CH3)CH3 |
| A.1.246 | Br | OCHF2 | (cyclopropylmethyl) |
| A.1.247 | Br | OCHF2 | (bicyclopropyl) |
| A.1.248 | Br | OCHF2 | (spiropentyl) |
| A.1.249 | Br | OCHF2 | (spiro[2.3]hexyl) |
| A.1.250 | Br | OCHF2 | CH(CH3)2CH2SCH3 |
| A.1.251 | Br | OCHF2 | CH(CH3)2CH2S(O)CH3 |
| A.1.252 | Br | OCHF2 | CH(CH3)2CH2S(O)2CH3 |
| A.1.253 | I | CF3 | H |
| A.1.254 | I | CF3 | CH3 |
| A.1.255 | I | CF3 | CH2CH3 |
| A.1.256 | I | CF3 | CH(CH3)CH3 |
| A.1.257 | I | CF3 | C(CH3)(CH3)CH3 |
| A.1.258 | I | CF3 | (cyclopropylmethyl) |
| A.1.259 | I | CF3 | (bicyclopropyl) |
| A.1.260 | I | CF3 | (spiropentyl) |
| A.1.261 | I | CF3 | (spiro[2.3]hexyl) |
| A.1.262 | I | CF3 | CH(CH3)2CH2SCH3 |
| A.1.263 | I | CF3 | CH(CH3)2CH2S(O)CH3 |
| A.1.264 | I | CF3 | CH(CH3)2CH2S(O)2CH3 |
| A.1.265 | I | OCH2CF3 | H |
| A.1.266 | I | OCH2CF3 | CH3 |
| A.1.267 | I | OCH2CF3 | CH2CH3 |
| A.1.268 | I | OCH2CF3 | CH(CH3)CH3 |
| A.1.269 | I | OCH2CF3 | C(CH3)(CH3)CH3 |
| A.1.270 | I | OCH2CF3 | (cyclopropylmethyl) |
| A.1.271 | I | OCH2CF3 | (bicyclopropyl) |
| A.1.272 | I | OCH2CF3 | (spiropentyl) |
| A.1.273 | I | OCH2CF3 | (spiro[2.3]hexyl) |
| A.1.274 | I | OCH2CF3 | CH(CH3)2CH2SCH3 |
| A.1.275 | I | OCH2CF3 | CH(CH3)2CH2S(O)CH3 |
| A.1.276 | I | OCH2CF3 | CH(CH3)2CH2S(O)2CH |
| A.1.277 | I | Br | H |
| A.1.278 | I | Br | CH3 |
| A.1.279 | I | Br | CH2CH3 |
| A.1.280 | I | Br | CH(CH3)CH3 |

TABLE A-continued

Compounds of formula Ib:

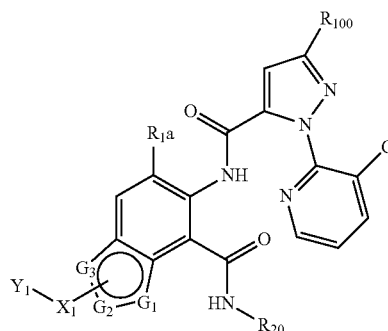

(Ib)

| Line | R₁a | R₁₀₀ | R₂₀ |
|---|---|---|---|
| A.1.281 | I | Br | C(CH₃)(CH₃)CH₃ |
| A.1.282 | I | Br | △ |
| A.1.283 | I | Br | △-△ |
| A.1.284 | I | Br | △-▽ |
| A.1.285 | I | Br | △-□ |
| A.1.286 | I | Br | CH(CH₃)₂CH₂SCH₃ |
| A.1.287 | I | Br | CH(CH₃)₂CH₂S(O)CH₃ |
| A.1.288 | I | Br | CH(CH₃)₂CH₂S(O)₂CH₃ |
| A.1.289 | I | Cl | H |
| A.1.290 | I | Cl | CH₃ |
| A.1.291 | I | Cl | CH₂CH₃ |
| A.1.292 | I | Cl | CH(CH₃)CH₃ |
| A.1.293 | I | Cl | C(CH₃)(CH₃)CH₃ |
| A.1.294 | I | Cl | △ |
| A.1.295 | I | Cl | △-△ |
| A.1.296 | I | Cl | △-▽ |
| A.1.297 | I | Cl | △-□ |
| A.1.298 | I | Cl | CH(CH₃)₂CH₂SCH₃ |
| A.1.299 | I | Cl | CH(CH₃)₂CH₂S(O)CH₃ |

TABLE A-continued

Compounds of formula Ib:

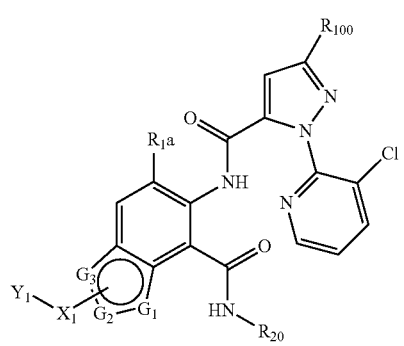

(Ib)

| Line | R₁a | R₁₀₀ | R₂₀ |
|---|---|---|---|
| A.1.300 | I | Cl | CH(CH₃)₂CH₂S(O)₂CH₃ |
| A.1.301 | I | CF₂H | H |
| A.1.302 | I | CF₂H | CH₃ |
| A.1.303 | I | CF₂H | CH₂CH₃ |
| A.1.304 | I | CF₂H | CH(CH₃)CH₃ |
| A.1.305 | I | CF₂H | C(CH₃)(CH₃)CH₃ |
| A.1.306 | I | CF₂H | △ |
| A.1.307 | I | CF₂H | △-△ |
| A.1.308 | I | CF₂H | △-▽ |
| A.1.309 | I | CF₂H | △-□ |
| A.1.310 | I | CF₂H | CH(CH₃)₂CH₂SCH₃ |
| A.1.311 | I | CF₂H | CH(CH₃)₂CH₂S(O)CH₃ |
| A.1.312 | I | CF₂H | CH(CH₃)₂CH₂S(O)₂CH₃ |
| A.1.313 | I | OCF₃ | H |
| A.1.314 | I | OCF₃ | CH₃ |
| A.1.315 | I | OCF₃ | CH₂CH₃ |
| A.1.316 | I | OCF₃ | CH(CH₃)CH₃ |
| A.1.317 | I | OCF₃ | C(CH₃)(CH₃)CH₃ |
| A.1.318 | I | OCF₃ | △ |
| A.1.319 | I | OCF₃ | △-△ |
| A.1.320 | I | OCF₃ | △-▽ |

TABLE A-continued

Compounds of formula Ib:

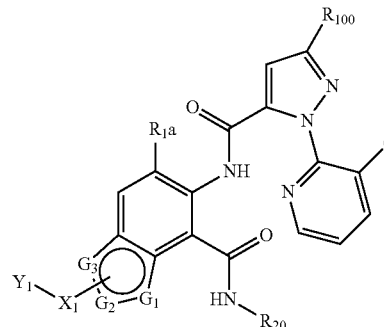
(Ib)

| Line | R₁a | R₁₀₀ | R₂₀ |
|---|---|---|---|
| A.1.321 | I | OCF₃ |  |
| A.1.322 | I | OCF₃ | CH(CH₃)₂CH₂SCH₃ |
| A.1.323 | I | OCF₃ | CH(CH₃)₂CH₂S(O)CH₃ |
| A.1.324 | I | OCF₃ | CH(CH₃)₂CH₂S(O)₂CH₃ |
| A.1.325 | I | OCHF₂ | H |
| A.1.326 | I | OCHF₂ | CH₃ |
| A.1.327 | I | OCHF₂ | CH₂CH₃ |
| A.1.328 | I | OCHF₂ | CH(CH₃)CH₃ |
| A.1.329 | I | OCHF₂ | C(CH₃)(CH₃)CH₃ |
| A.1.330 | I | OCHF₂ |  |
| A.1.331 | I | OCHF₂ |  |
| A.1.332 | I | OCHF₂ |  |
| A.1.333 | I | OCHF₂ |  |
| A.1.334 | I | OCHF₂ | CH(CH₃)₂CH₂SCH₃ |
| A.1.335 | I | OCHF₂ | CH(CH₃)₂CH₂S(O)CH₃ |
| A.1.336 | I | OCHF₂ | CH(CH₃)₂CH₂S(O)₂CH₃ |
| A.1.337 | H | CF₃ | H |
| A.1.338 | H | CF₃ | CH₃ |
| A.1.339 | H | CF₃ | CH₂CH₃ |
| A.1.340 | H | CF₃ | CH(CH₃)CH₃ |
| A.1.341 | H | CF₃ | C(CH₃)(CH₃)CH₃ |
| A.1.342 | H | CF₃ |  |
| A.1.343 | H | CF₃ |  |

TABLE A-continued

Compounds of formula Ib:

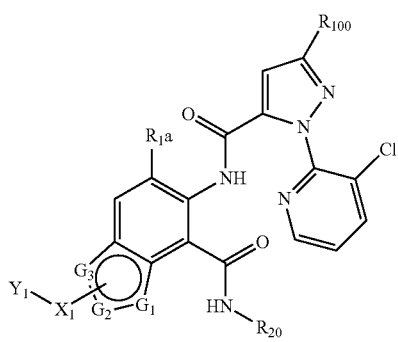
(Ib)

| Line | R₁a | R₁₀₀ | R₂₀ |
|---|---|---|---|
| A.1.344 | H | CF₃ |  |
| A.1.345 | H | CF₃ |  |
| A.1.346 | H | CF₃ | CH(CH₃)₂CH₂SCH₃ |
| A.1.347 | H | CF₃ | CH(CH₃)₂CH₂S(O)CH₃ |
| A.1.348 | H | CF₃ | CH(CH₃)₂CH₂S(O)₂CH₃ |
| A.1.349 | H | OCH₂CF₃ | H |
| A.1.350 | H | OCH₂CF₃ | CH₃ |
| A.1.351 | H | OCH₂CF₃ | CH₂CH₃ |
| A.1.352 | H | OCH₂CF₃ | CH(CH₃)CH₃ |
| A.1.353 | H | OCH₂CF₃ | C(CH₃)(CH₃)CH₃ |
| A.1.354 | H | OCH₂CF₃ |  |
| A.1.355 | H | OCH₂CF₃ |  |
| A.1.356 | H | OCH₂CF₃ |  |
| A.1.357 | H | OCH₂CF₃ |  |
| A.1.358 | H | OCH₂CF₃ | CH(CH₃)₂CH₂SCH₃ |
| A.1.359 | H | OCH₂CF₃ | CH(CH₃)₂CH₂S(O)CH₃ |
| A.1.360 | H | OCH₂CF₃ | CH(CH₃)₂CH₂S(O)₂CH₃ |
| A.1.361 | H | Br | H |
| A.1.362 | H | Br | CH₃ |
| A.1.363 | H | Br | CH₂CH₃ |
| A.1.364 | H | Br | CH(CH₃)CH₃ |
| A.1.365 | H | Br | C(CH₃)(CH₃)CH₃ |
| A.1.366 | H | Br |  |

TABLE A-continued

Compounds of formula Ib:

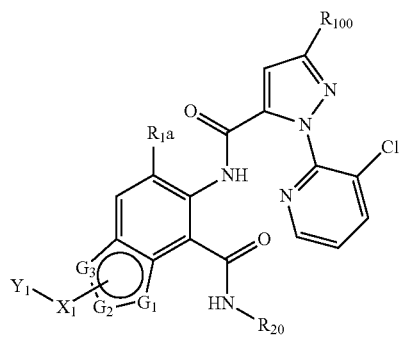

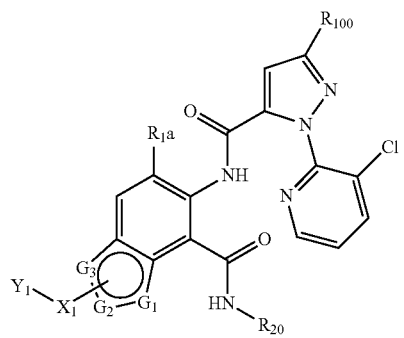

| Line | R₁a | R₁₀₀ | R₂₀ |
|---|---|---|---|
| A.1.367 | H | Br | (cyclopropyl-cyclopropyl spiro) |
| A.1.368 | H | Br | (bicyclic) |
| A.1.369 | H | Br | (cyclopropyl-cyclobutyl spiro) |
| A.1.370 | H | Br | CH(CH₃)₂CH₂SCH₃ |
| A.1.371 | H | Br | CH(CH₃)₂CH₂S(O)CH₃ |
| A.1.372 | H | Br | CH(CH₃)₂CH₂S(O)₂CH₃ |
| A.1.373 | H | Cl | H |
| A.1.374 | H | Cl | CH₃ |
| A.1.375 | H | Cl | CH₂CH₃ |
| A.1.376 | H | Cl | CH(CH₃)CH₃ |
| A.1.377 | H | Cl | C(CH₃)(CH₃)CH₃ |
| A.1.378 | H | Cl | (cyclopropyl) |
| A.1.379 | H | Cl | (cyclopropyl-cyclopropyl spiro) |
| A.1.380 | H | Cl | (bicyclic) |
| A.1.381 | H | Cl | (cyclopropyl-cyclobutyl spiro) |
| A.1.382 | H | Cl | CH(CH₃)₂CH₂SCH₃ |
| A.1.383 | H | Cl | CH(CH₃)₂CH₂S(O)CH₃ |
| A.1.384 | H | Cl | CH(CH₃)₂CH₂S(O)₂CH₃ |
| A.1.385 | H | CF₂H | H |
| A.1.386 | H | CF₂H | CH₃ |
| A.1.387 | H | CF₂H | CH₂CH₃ |
| A.1.388 | H | CF₂H | CH(CH₃)CH₃ |
| A.1.389 | H | CF₂H | C(CH₃)(CH₃)CH₃ |
| A.1.390 | H | CF₂H | (cyclopropyl) |
| A.1.391 | H | CF₂H | (cyclopropyl-cyclopropyl spiro) |
| A.1.392 | H | CF₂H | (bicyclic) |
| A.1.393 | H | CF₂H | (cyclopropyl-cyclobutyl spiro) |
| A.1.394 | H | CF₂H | CH(CH₃)₂CH₂SCH₃ |
| A.1.395 | H | CF₂H | CH(CH₃)₂CH₂S(O)CH₃ |
| A.1.396 | H | CF₂H | CH(CH₃)₂CH₂S(O)₂CH₃ |
| A.1.397 | H | OCF₃ | H |
| A.1.398 | H | OCF₃ | CH₃ |
| A.1.399 | H | OCF₃ | CH₂CH₃ |
| A.1.400 | H | OCF₃ | CH(CH₃)CH₃ |
| A.1.401 | H | OCF₃ | C(CH₃)(CH₃)CH₃ |
| A.1.402 | H | OCF₃ | (cyclopropyl) |
| A.1.403 | H | OCF₃ | (cyclopropyl-cyclopropyl spiro) |
| A.1.404 | H | OCF₃ | (bicyclic) |
| A.1.405 | H | OCF₃ | (cyclopropyl-cyclobutyl spiro) |
| A.1.406 | H | OCF₃ | CH(CH₃)₂CH₂SCH₃ |
| A.1.407 | H | OCF₃ | CH(CH₃)₂CH₂S(O)CH₃ |
| A.1.408 | H | OCF₃ | CH(CH₃)₂CH₂S(O)₂CH₃ |
| A.1.409 | H | OCHF₂ | H |

TABLE A-continued

Compounds of formula Ib:

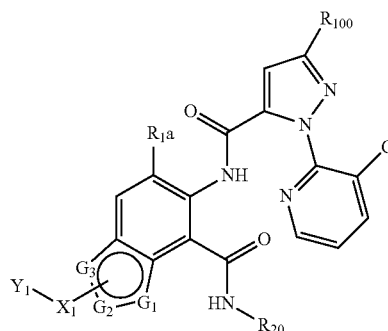

(Ib)

| Line | R₁a | R₁₀₀ | R₂₀ |
|---|---|---|---|
| A.1.410 | H | OCHF₂ | CH₃ |
| A.1.411 | H | OCHF₂ | CH₂CH₃ |
| A.1.412 | H | OCHF₂ | CH(CH₃)CH₃ |
| A.1.413 | H | OCHF₂ | C(CH₃)(CH₃)CH₃ |
| A.1.414 | H | OCHF₂ | 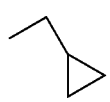 |
| A.1.415 | H | OCHF₂ |  |
| A.1.416 | H | OCHF₂ |  |
| A.1.417 | H | OCHF₂ |  |
| A.1.418 | H | OCHF₂ | CH(CH₃)₂CH₂SCH₃ |
| A.1.419 | H | OCHF₂ | CH(CH₃)₂CH₂S(O)CH₃ |
| A.1.420 | H | OCHF₂ | CH(CH₃)₂CH₂S(O)₂CH₃ |
| A.1.421 | CH₃ | OCH₃ | H |
| A.1.422 | CH₃ | OCH₃ | CH₃ |
| A.1.423 | CH₃ | OCH₃ | CH₂CH₃ |
| A.1.424 | CH₃ | OCH₃ | CH(CH₃)CH₃ |
| A.1.425 | CH₃ | OCH₃ | C(CH₃)(CH₃)CH₃ |
| A.1.426 | CH₃ | OCH₃ | |
| A.1.427 | CH₃ | OCH₃ | |
| A.1.428 | CH₃ | OCH₃ | |
| A.1.429 | CH₃ | OCH₃ | |
| A.1.430 | CH₃ | OCH₃ | CH(CH₃)₂CH₂SCH₃ |
| A.1.431 | CH₃ | OCH₃ | CH(CH₃)₂CH₂S(O)CH₃ |
| A.1.432 | CH₃ | OCH₃ | CH(CH₃)₂CH₂S(O)₂CH₃ |
| A.1.433 | Cl | OCH₃ | H |
| A.1.434 | Cl | OCH₃ | CH₃ |
| A.1.435 | Cl | OCH₃ | CH₂CH₃ |
| A.1.436 | Cl | OCH₃ | CH(CH₃)CH₃ |
| A.1.437 | Cl | OCH₃ | C(CH₃)(CH₃)CH₃ |
| A.1.438 | Cl | OCH₃ | |
| A.1.439 | Cl | OCH₃ |  |
| A.1.440 | Cl | OCH₃ | 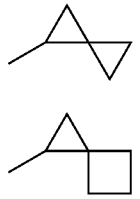 |
| A.1.441 | Cl | OCH₃ |  |
| A.1.442 | Cl | OCH₃ | CH(CH₃)₂CH₂SCH₃ |
| A.1.443 | Cl | OCH₃ | CH(CH₃)₂CH₂S(O)CH₃ |
| A.1.444 | Cl | OCH₃ | CH(CH₃)₂CH₂S(O)₂CH₃ |
| A.1.445 | Br | OCH₃ | H |
| A.1.446 | Br | OCH₃ | CH₃ |
| A.1.447 | Br | OCH₃ | CH₂CH₃ |
| A.1.448 | Br | OCH₃ | CH(CH₃)CH₃ |
| A.1.449 | Br | OCH₃ | C(CH₃)(CH₃)CH₃ |
| A.1.450 | Br | OCH₃ | |
| A.1.451 | Br | OCH₃ | |
| A.1.452 | Br | OCH₃ | |
| A.1.453 | Br | OCH₃ | |
| A.1.454 | Br | OCH₃ | CH(CH₃)₂CH₂SCH₃ |
| A.1.455 | Br | OCH₃ | CH(CH₃)₂CH₂S(O)CH₃ |
| A.1.456 | Br | OCH₃ | CH(CH₃)₂CH₂S(O)₂CH₃ |
| A.1.457 | I | OCH₃ | H |
| A.1.458 | I | OCH₃ | CH₃ |
| A.1.459 | I | OCH₃ | CH₂CH₃ |
| A.1.460 | I | OCH₃ | CH(CH₃)CH₃ |
| A.1.461 | I | OCH₃ | C(CH₃)(CH₃)CH₃ |
| A.1.462 | I | OCH₃ | |

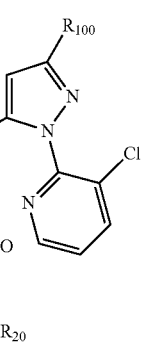

TABLE A-continued

Compounds of formula Ib:

(Ib)

| Line | $R_1a$ | $R_{100}$ | $R_{20}$ |
|---|---|---|---|
| A.1.463 | I | $OCH_3$ | (1,1'-bicyclopropyl-methyl) |
| A.1.464 | I | $OCH_3$ | (spiropentyl-methyl) |
| A.1.465 | I | $OCH_3$ | (cyclopropyl-cyclobutyl-methyl) |
| A.1.466 | I | $OCH_3$ | $CH(CH_3)_2CH_2SCH_3$ |
| A.1.467 | I | $OCH_3$ | $CH(CH_3)_2CH_2S(O)CH_3$ |
| A.1.468 | I | $OCH_3$ | $CH(CH_3)_2CH_2S(O)_2CH_3$ |
| A.1.469 | H | $OCH_3$ | H |
| A.1.470 | H | $OCH_3$ | $CH_3$ |
| A.1.471 | H | $OCH_3$ | $CH_2CH_3$ |
| A.1.472 | H | $OCH_3$ | $CH(CH_3)CH_3$ |
| A.1.473 | H | $OCH_3$ | $C(CH_3)(CH_3)CH_3$ |
| A.1.474 | H | $OCH_3$ | (1,1'-bicyclopropyl-methyl) |
| A.1.475 | H | $OCH_3$ | (spiropentyl-methyl) |
| A.1.476 | H | $OCH_3$ | (cyclopropyl-cyclobutyl-methyl) |
| A.1.477 | H | $OCH_3$ | (cyclopropyl-cyclobutyl-methyl) |
| A.1.478 | H | $OCH_3$ | $CH(CH_3)_2CH_2SCH_3$ |
| A.1.479 | H | $OCH_3$ | $CH(CH_3)_2CH_2S(O)CH_3$ |
| A.1.480 | H | $OCH_3$ | $CH(CH_3)_2CH_2S(O)_2CH_3$ |

In the following tables, "Me" represents the methyl group.

TABLE 1

This table discloses the 480 compounds T1.1.1 to T1.1.480 of formula

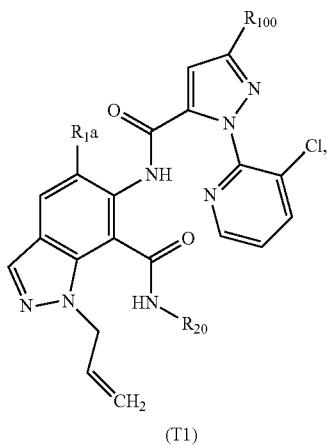

(T1)

in which, for each of these 480 specific compounds, each of the of the variables $R_1a$, $R_{20}$ and
$R_{100}$ has the specific meaning given in the corresponding line, appropriately selected from TABLE 1-continued the 480 lines A.1.1 to A.1.480 of the Table A. For example, the specific compound T1.1.23 is the compound of formula T1, in which each of the of the variables $R_1a$, $R_{20}$ and $R_{100}$ has the specific meaning given in the line A.1.23 of the Table A. According to the same system, also all of the other 480 specific compounds disclosed in the Table 1 as well as all of the specific compounds disclosed in Tables 2 to 121 are specified analogously.

TABLE 2

This table discloses the 480 compounds T2.1.1 to T2.1.480 of formula

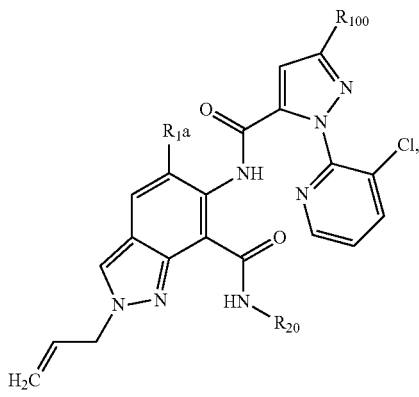

(T2)

in which, for each of these 480 specific compounds,
each of the variables $R_{1a}$, $R_{20}$ and $R_{100}$ has the
specific meaning given in the corresponding line, appropriately
selected from the 480 lines A.1.1 to A.1.480 of the Table A.

TABLE 3

This table discloses the 480 compounds T3.1.1 to T3.1.480 of formula

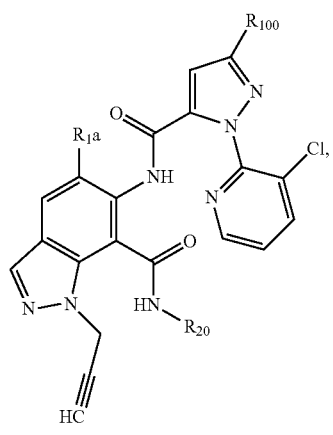

(T3)

in which, for each of these 480 specific compounds,
each of the variables $R_{1a}$, $R_{20}$ and $R_{100}$ has the
specific meaning given in the corresponding line, appropriately
selected from the 480 lines A.1.1 to A.1.480 of the Table A.

TABLE 4

This table discloses the 480 compounds T4.1.1 to T4.1.480 of formula

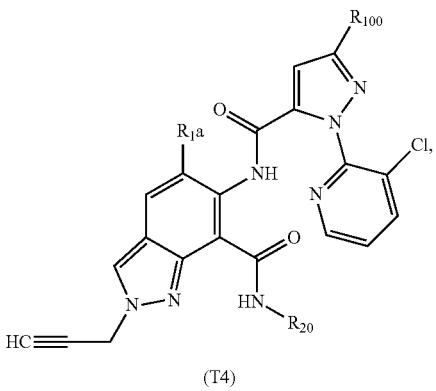

(T4)

in which, for each of these 480 specific compounds,
each of the variables $R_{1a}$, $R_{20}$ and $R_{100}$ has the
specific meaning given in the corresponding line, appropriately
selected from the 480 lines A.1.1 to A.1.480 of the Table A.

TABLE 5

This table discloses the 480 compounds T5.1.1 to T5.1.480 of formula

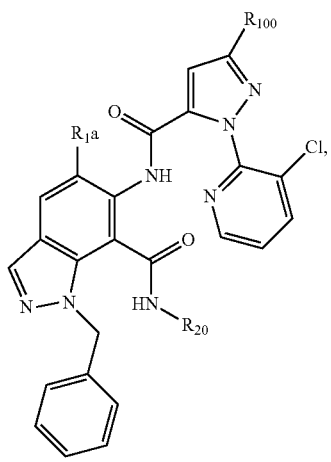

(T5)

in which, for each of these 480 specific compounds,
each of the variables $R_{1a}$, $R_{20}$ and $R_{100}$ has the
specific meaning given in the corresponding line, appropriately
selected from the 480 lines A.1.1 to A.1.480 of the Table A.

TABLE 6

This table discloses the 480 compounds T6.1.1 to T6.1.480 of formula

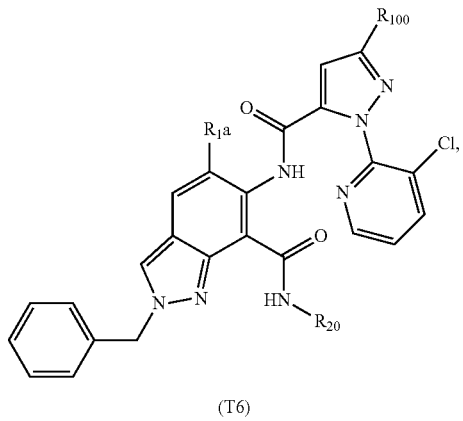

(T6)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 7

This table discloses the 480 compounds T7.1.1 to T7.1.480 of formula

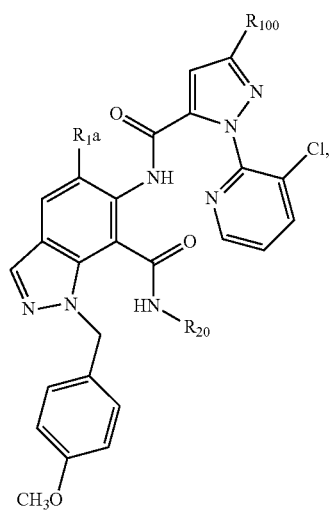

(T7)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 8

This table discloses the 480 compounds T8.1.1 to T8.1.480 of formula

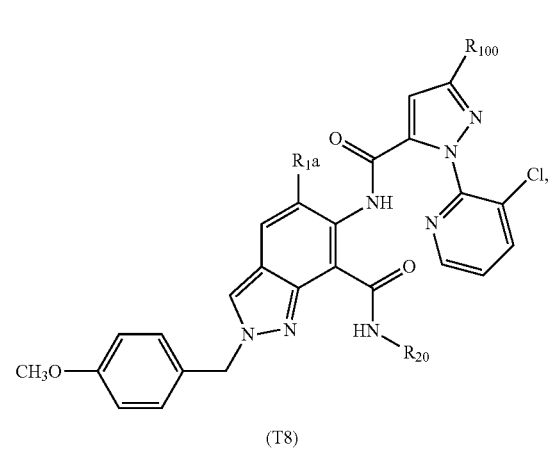

(T8)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 9

This table discloses the 480 compounds T9.1.1 to T9.1.480 of formula

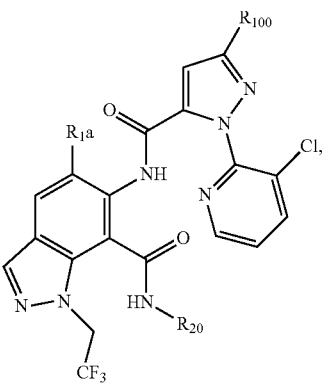

(T9)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 10

This table discloses the 480 compounds T10.1.1 to T10.1.480 of formula

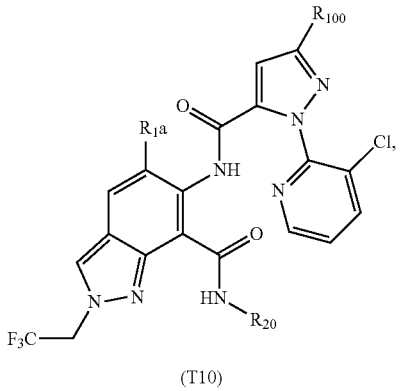

(T10)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 11

This table discloses the 480 compounds T11.1.1 to T11.1.480 of formula

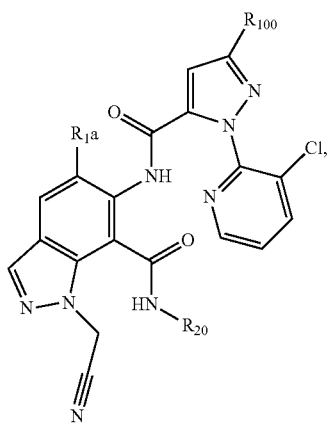

(T11)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 12

This table discloses the 480 compounds T12.1.1 to T12.1.480 of formula

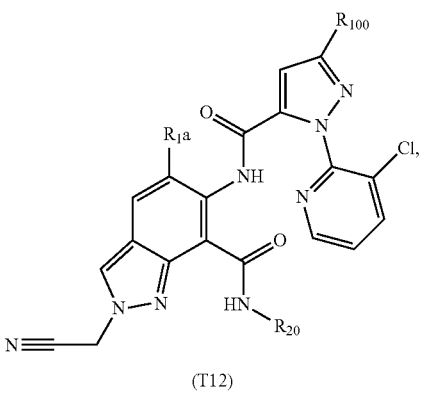

(T12)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 13

This table discloses the 480 compounds T13.1.1 to T13.1.480 of formula

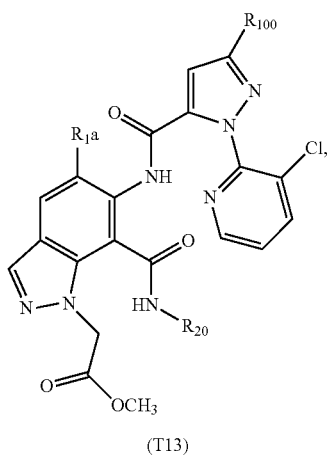

(T13)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 14

This table discloses the 480 compounds T14.1.1 to T14.1.480 of formula

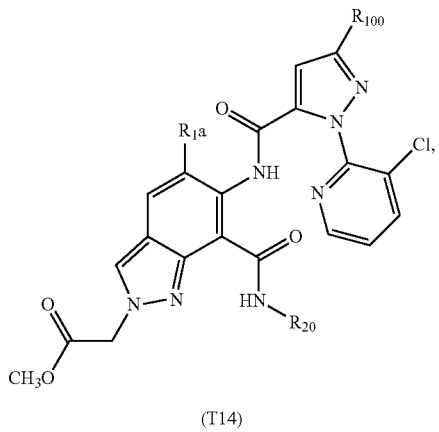

(T14)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 15

This table discloses the 480 compounds T15.1.1 to T15.1.480 of formula

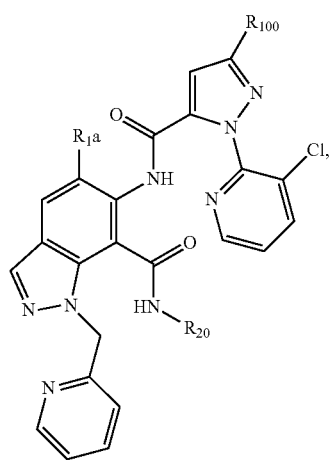

(T15)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 16

This table discloses the 480 compounds T16.1.1 to T16.1.480 of formula

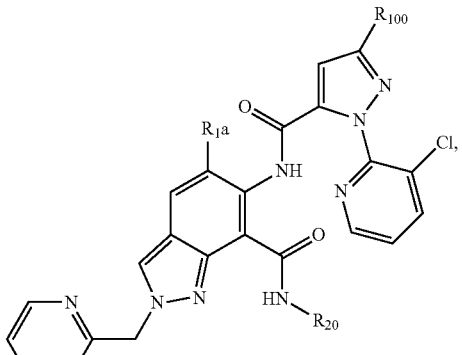

(T16)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 17

This table discloses the 480 compounds T17.1.1 to T17.1.480 of formula

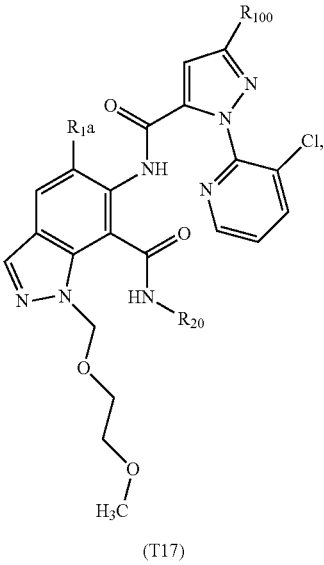

(T17)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 18

This table discloses the 480 compounds T18.1.1 to T18.1.480 of formula

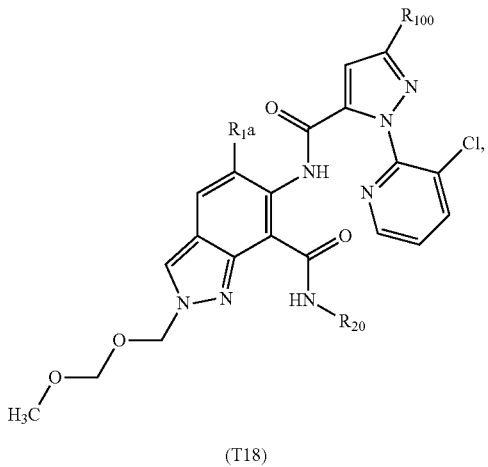

(T18)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 19

This table discloses the 480 compounds T19.1.1 to T19.1.480 of formula

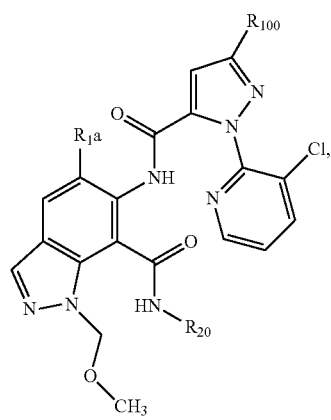

(T19)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 20

This table discloses the 480 compounds T20.1.1 to T20.1.480 of formula

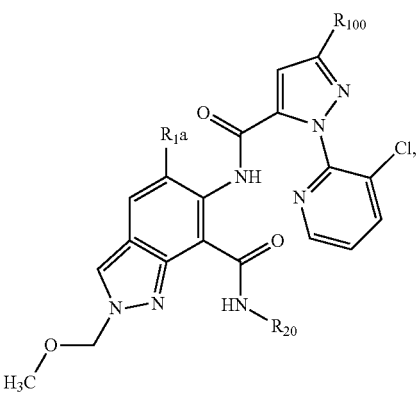

(T20)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 21

This table discloses the 480 compounds T21.1.1 to T21.1.480 of formula

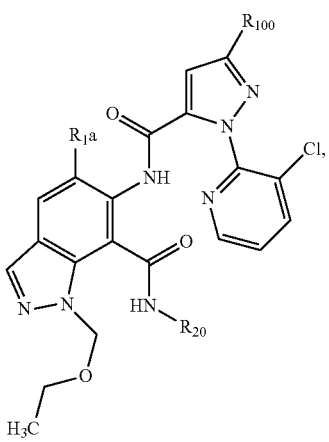

(T21)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 22

This table discloses the 480 compounds T22.1.1 to T22.1.480 of formula

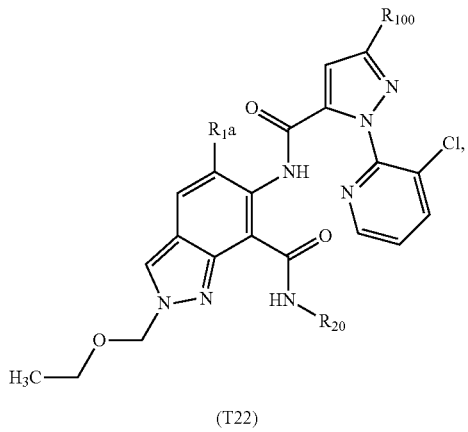

(T22)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 23

This table discloses the 480 compounds T23.1.1 to T23.1.480 of formula

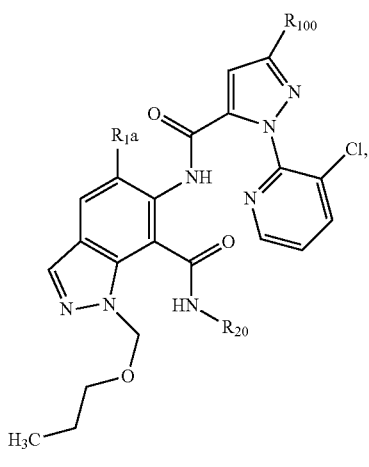

(T23)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 24

This table discloses the 480 compounds T24.1.1 to T24.1.480 of formula

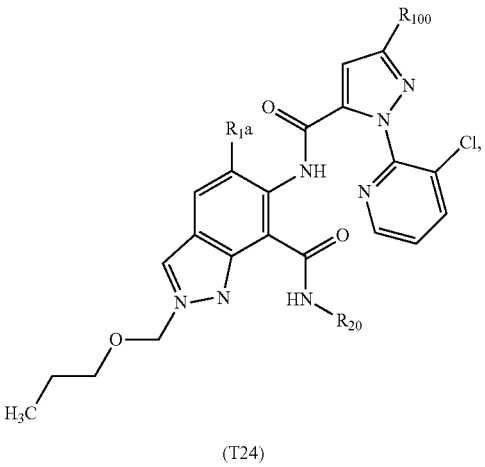

(T24)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 25

This table discloses the 480 compounds T25.1.1 to T25.1.480 of formula

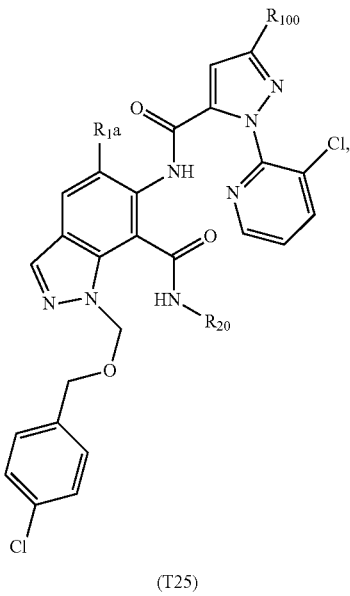

(T25)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 26

This table discloses the 480 compounds T26.1.1 to T26.1.480 of formula

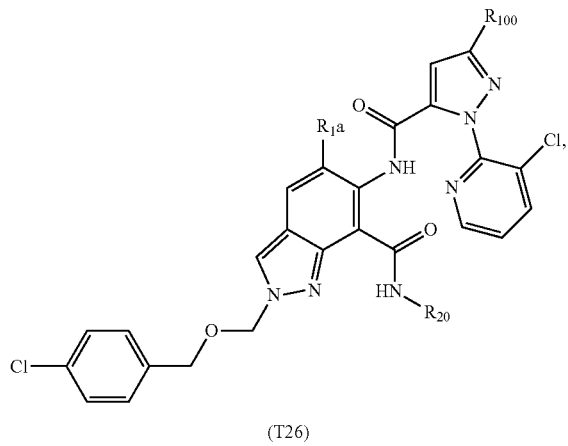

(T26)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 27

This table discloses the 480 compounds T27.1.1 to T27.1.480 of formula

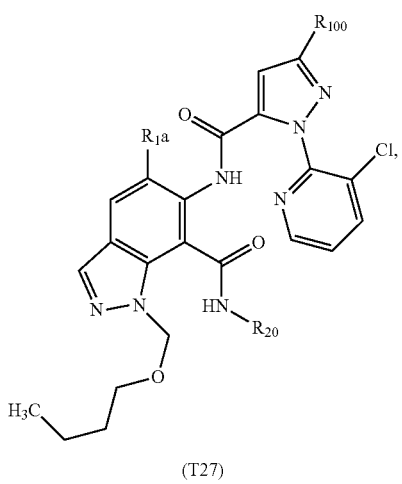

(T27)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 28

This table discloses the 480 compounds T28.1.1 to T28.1.480 of formula

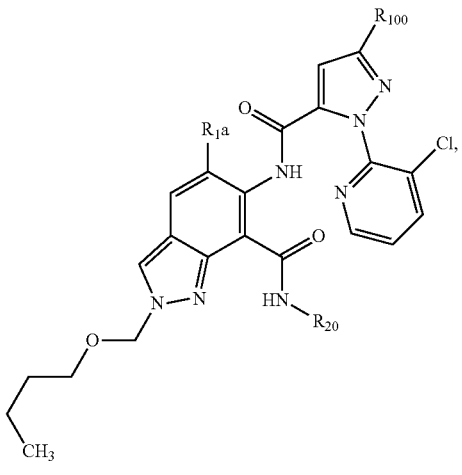

(T28)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 29

This table discloses the 480 compounds T29.1.1 to T29.1.480 of formula

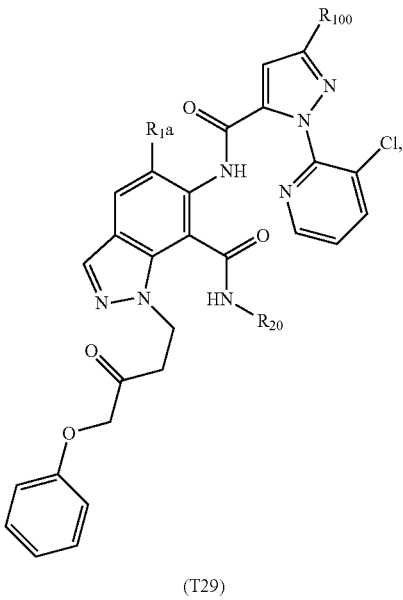

(T29)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 30

This table discloses the 480 compounds T30.1.1 to T30.1.480 of formula

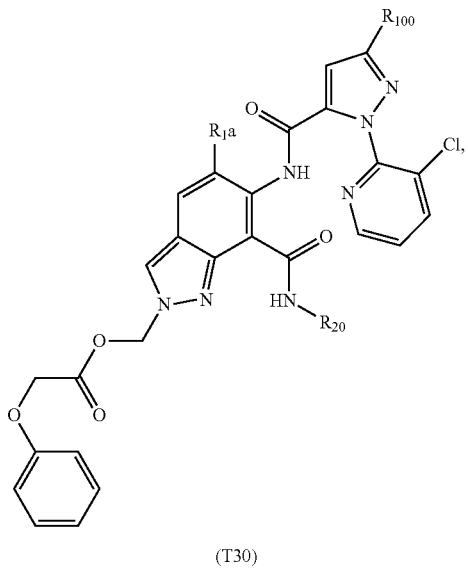

(T30)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 31

This table discloses the 480 compounds T31.1.1 to T31.1.480 of formula

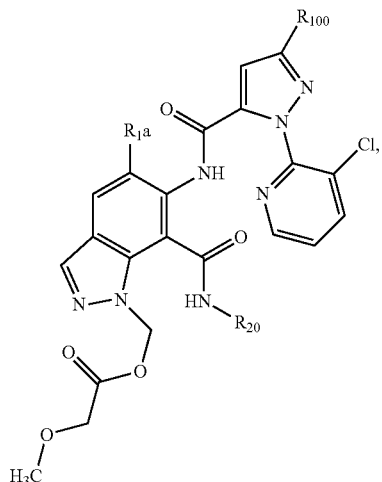

(T31)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 32

This table discloses the 480 compounds T32.1.1 to T32.1.480 of formula

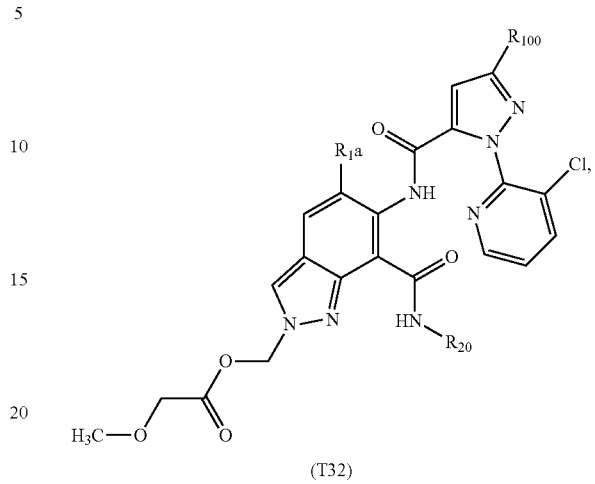

(T32)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 33

This table discloses the 480 compounds T33.1.1 to T33.1.480 of formula

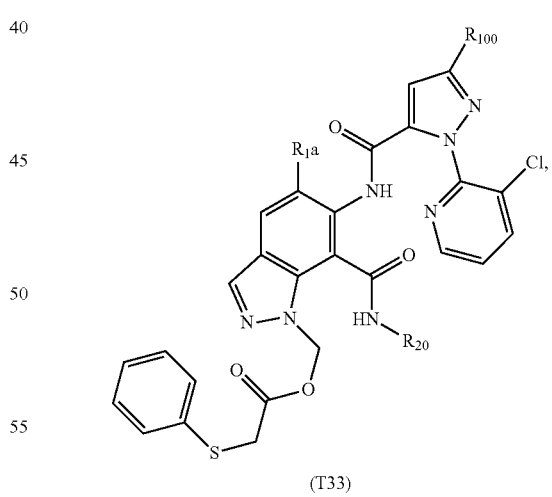

(T33)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 34

This table discloses the 480 compounds T34.1.1 to T34.1.480 of formula

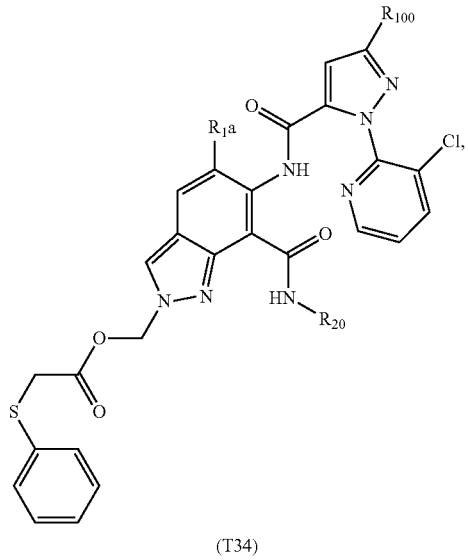

(T34)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 35

This table discloses the 480 compounds T35.1.1 to T35.1.480 of formula

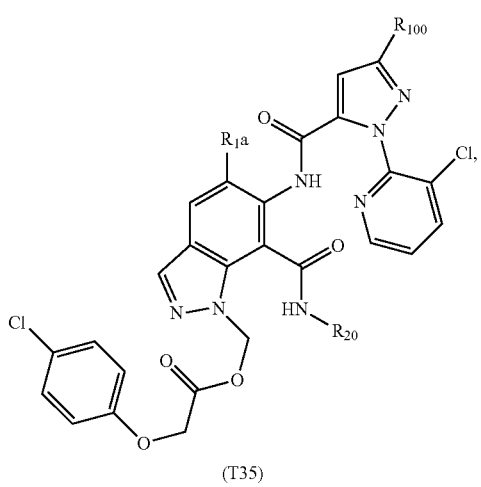

(T35)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 36

This table discloses the 480 compounds T36.1.1 to T36.1.480 of formula

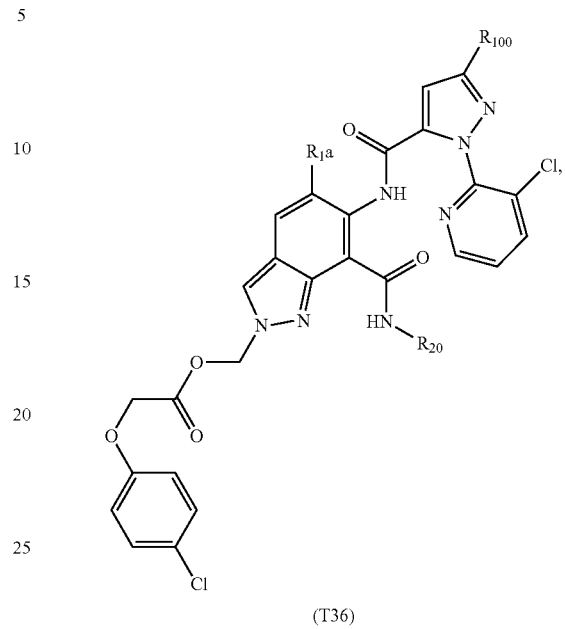

(T36)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 37

This table discloses the 480 compounds T37.1.1 to T37.1.480 of formula

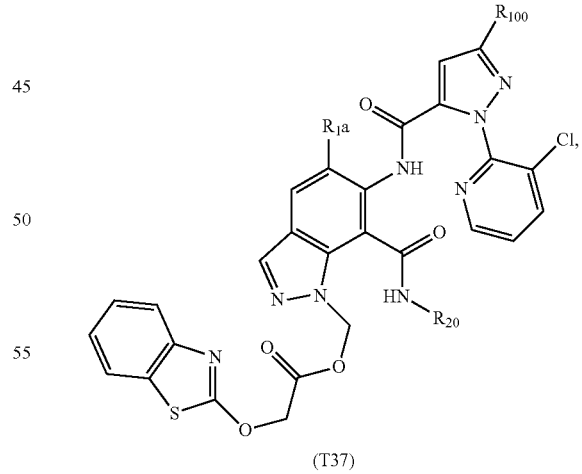

(T37)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 38

This table discloses the 480 compounds T38.1.1 to T38.1.480 of formula

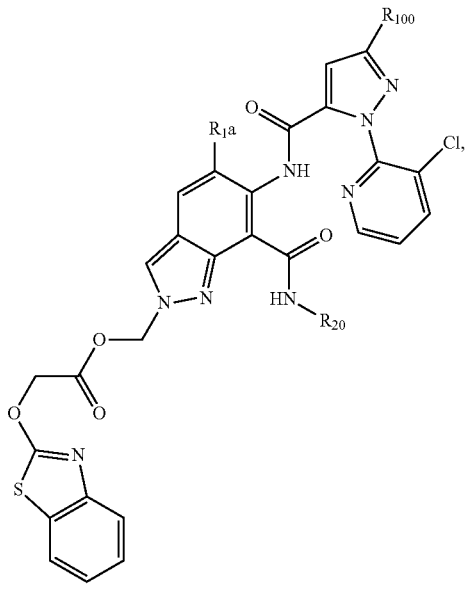

(T38)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 39

This table discloses the 480 compounds T39.1.1 to T39.1.480 of formula

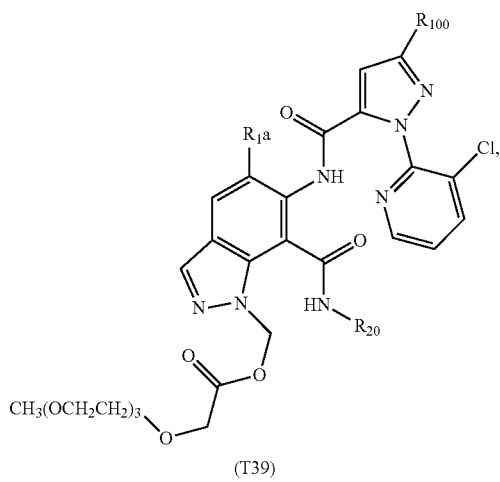

(T39)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 40

This table discloses the 480 compounds T40.1.1 to T40.1.480 of formula

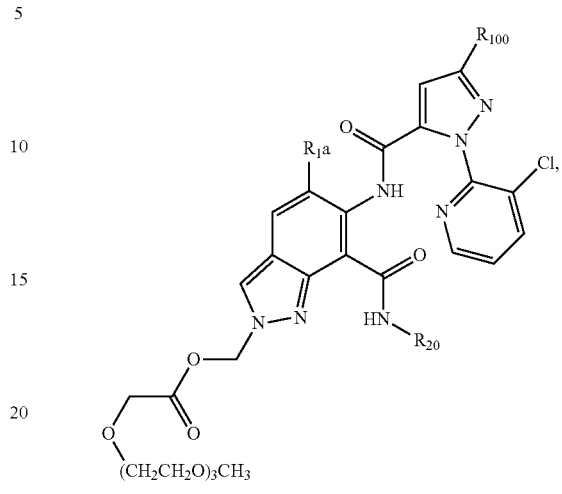

(T40)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 41

This table discloses the 480 compounds T41.1.1 to T41.1.480 of formula

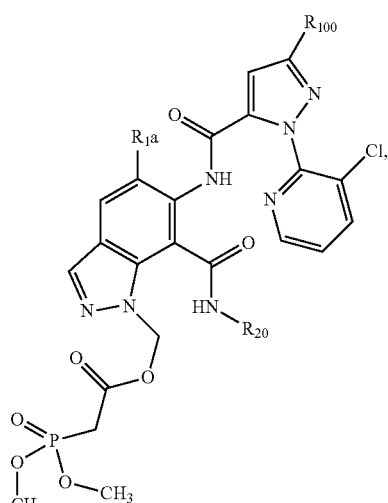

(T41)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 42

This table discloses the 480 compounds T42.1.1 to T42.1.480 of formula

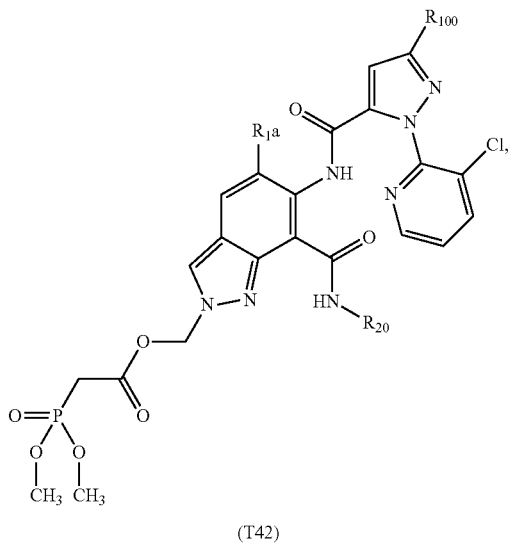

(T42)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 43

This table discloses the 480 compounds T43.1.1 to T43.1.480 of formula

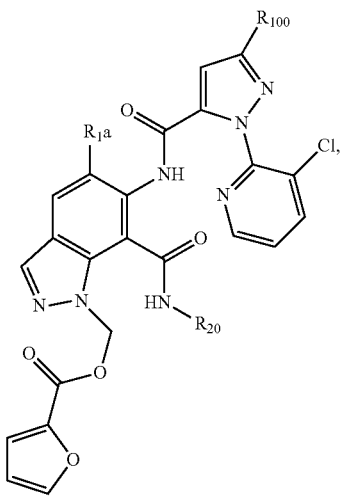

(T43)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 44

This table discloses the 480 compounds T44.1.1 to T44.1.480 of formula

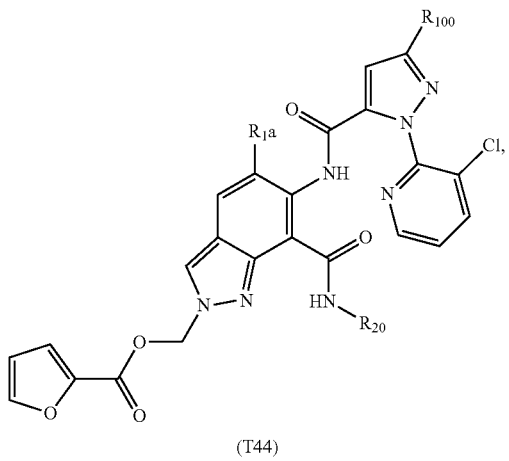

(T44)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 45

This table discloses the 480 compounds T45.1.1 to T45.1.480 of formula

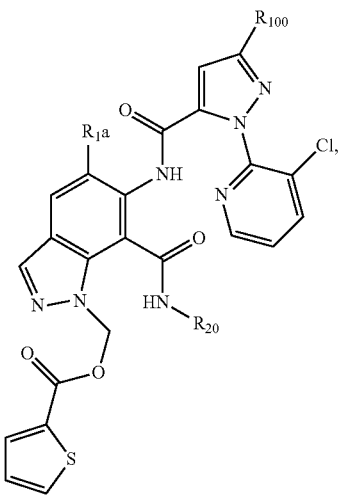

(T45)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 46

This table discloses the 480 compounds T46.1.1 to T46.1.480 of formula

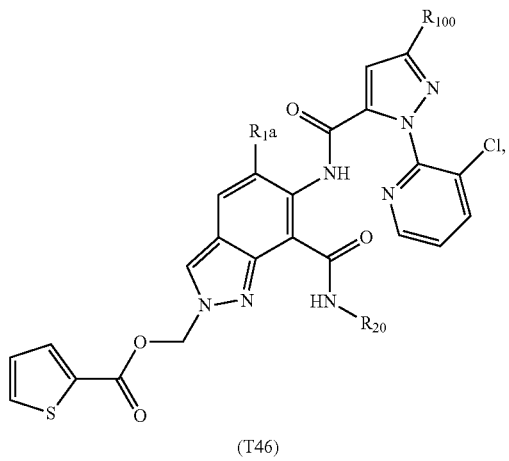

(T46)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 47

This table discloses the 480 compounds T47.1.1 to T47.1.480 of formula

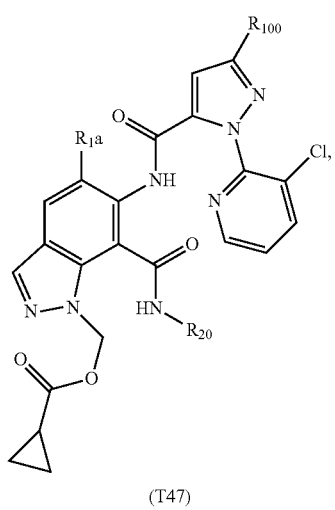

(T47)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 48

This table discloses the 480 compounds T48.1.1 to T48.1.480 of formula

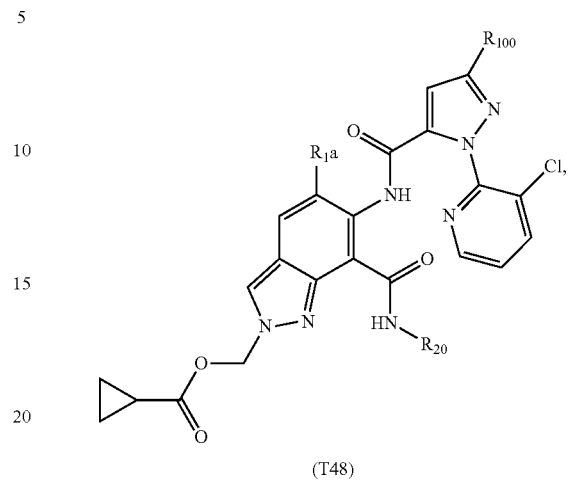

(T48)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 49

This table discloses the 480 compounds T49.1.1 to T49.1.480 of formula (T49)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 50

This table discloses the 480 compounds T50.1.1 to T50.1.480 of formula

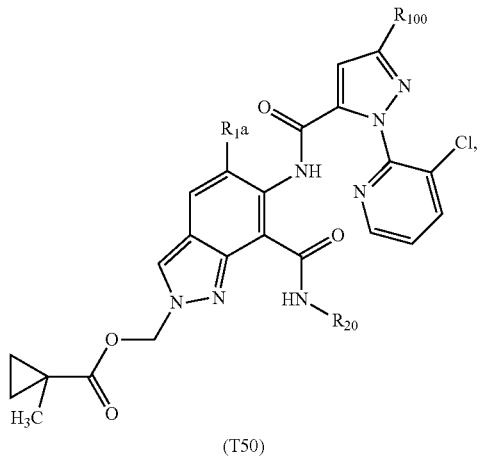

(T50)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 51

This table discloses the 480 compounds T51.1.1 to T51.1.480 of formula

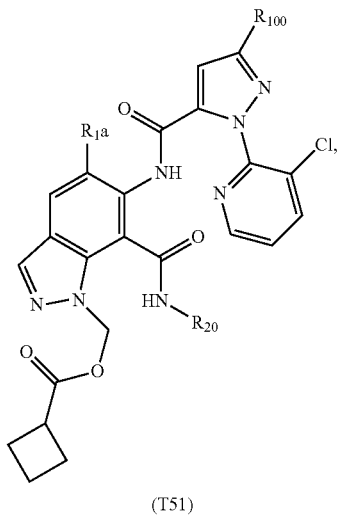

(T51)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 52

This table discloses the 480 compounds T52.1.1 to T52.1.480 of formula

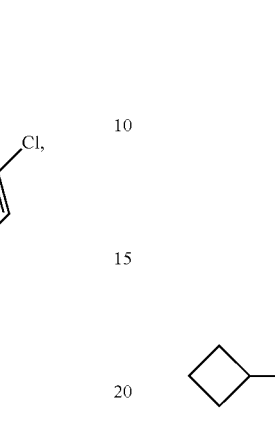

(T52)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 53

This table discloses the 480 compounds T53.1.1 to T53.1.480 of formula

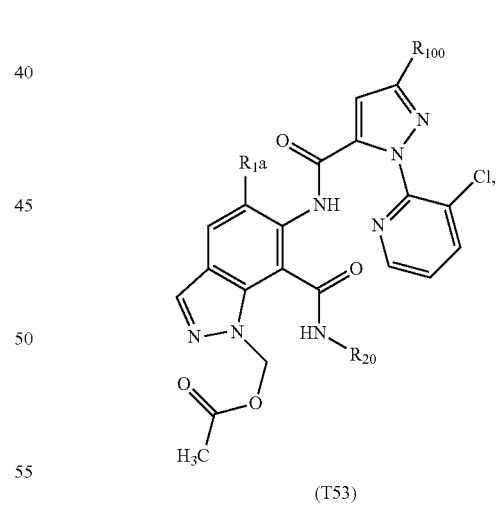

(T53)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 54

This table discloses the 480 compounds T54.1.1 to T54.1.480 of formula

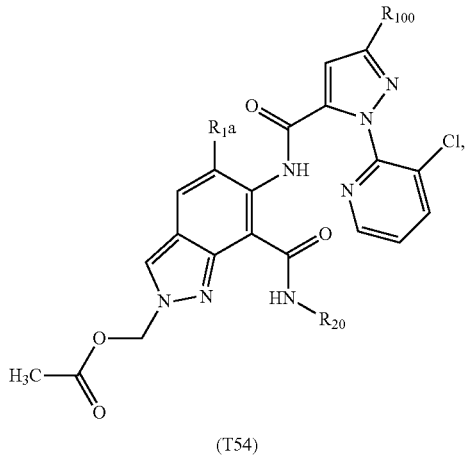

(T54)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 55

This table discloses the 480 compounds T55.1.1 to T55.1.480 of formula

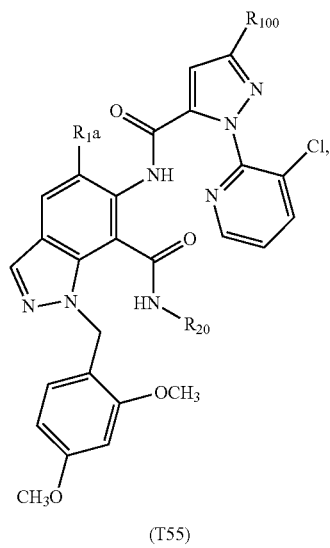

(T55)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 56

This table discloses the 480 compounds T56.1.1 to T56.1.480 of formula

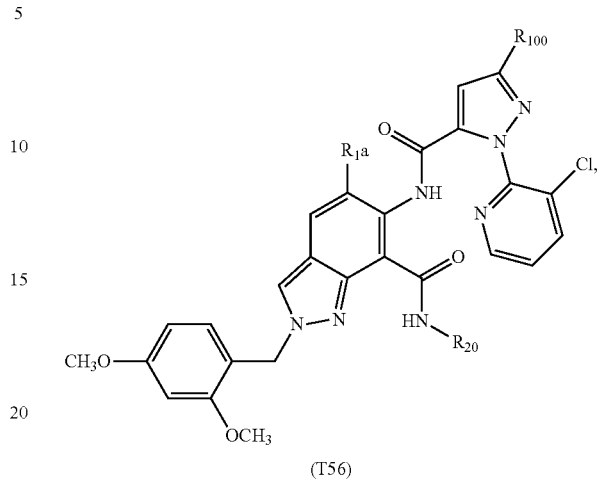

(T56)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 57

This table discloses the 480 compounds T57.1.1 to T57.1.480 of formula

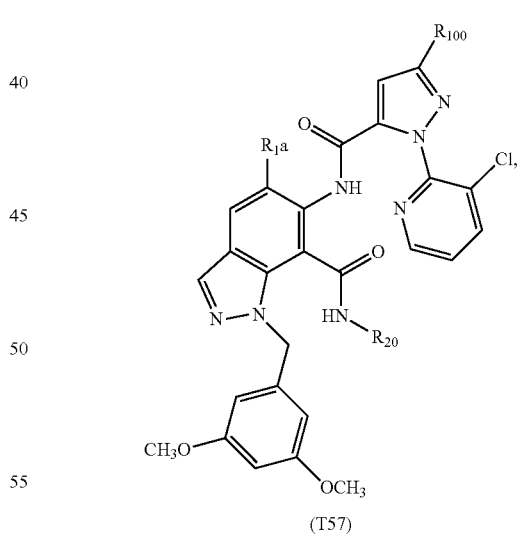

(T57)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 58

This table discloses the 480 compounds T58.1.1 to T58.1.480 of formula

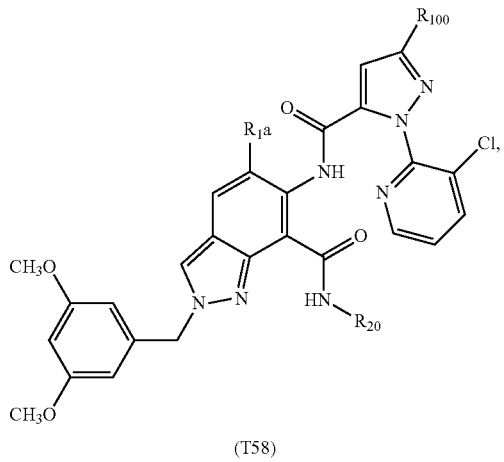

(T58)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 59

This table discloses the 480 compounds T59.1.1 to T59.1.480 of formula

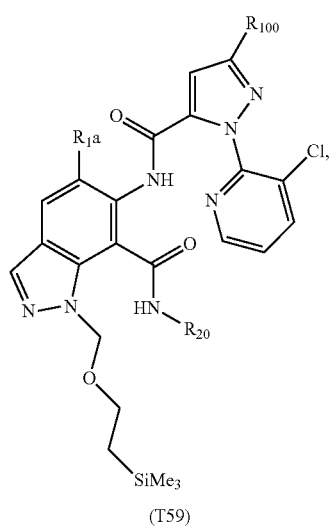

(T59)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 60

This table discloses the 480 compounds T60.1.1 to T60.1.480 of formula

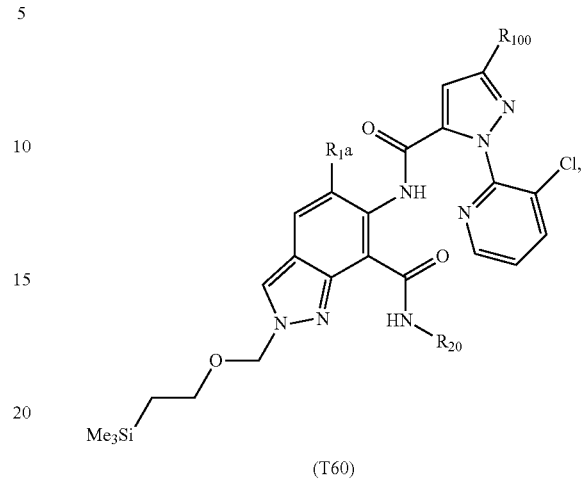

(T60)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 61

This table discloses the 480 compounds T61.1.1 to T61.1.480 of formula

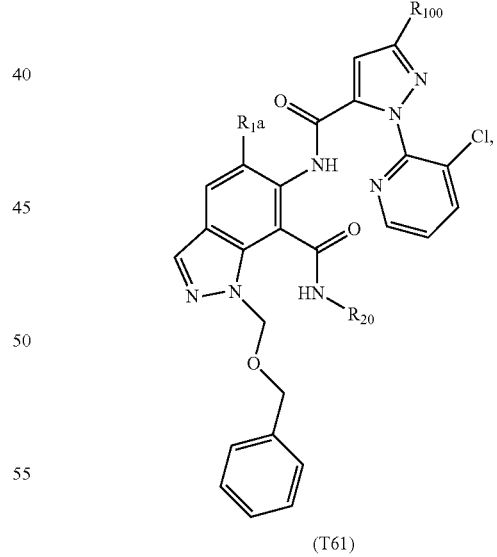

(T61)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 62

This table discloses the 480 compounds T62.1.1 to T62.1.480 of formula

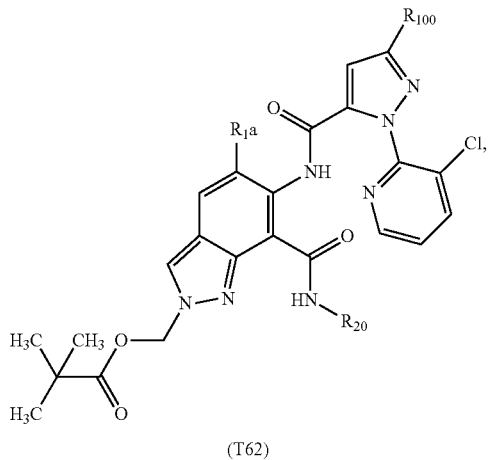

(T62)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 63

This table discloses the 480 compounds T63.1.1 to T63.1.480 of formula

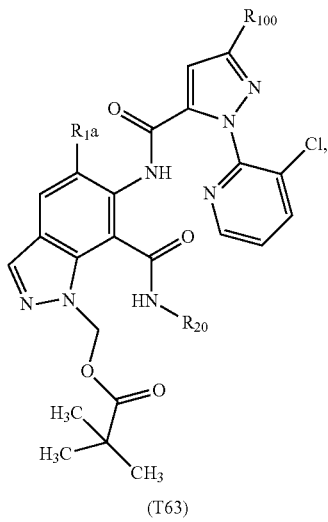

(T63)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 64

This table discloses the 480 compounds T64.1.1 to T64.1.480 of formula

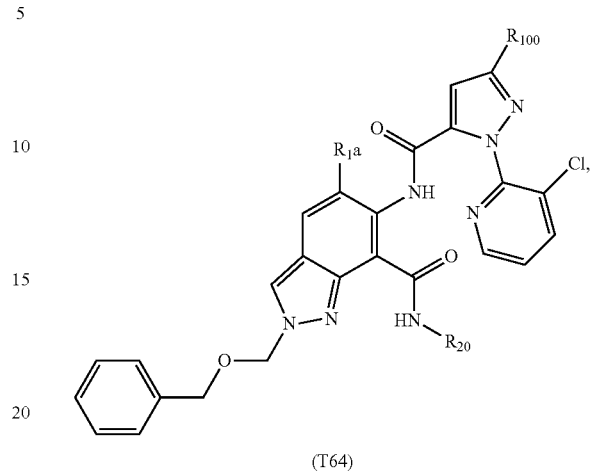

(T64)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 65

This table discloses the 480 compounds T65.1.1 to T65.1.480 of formula

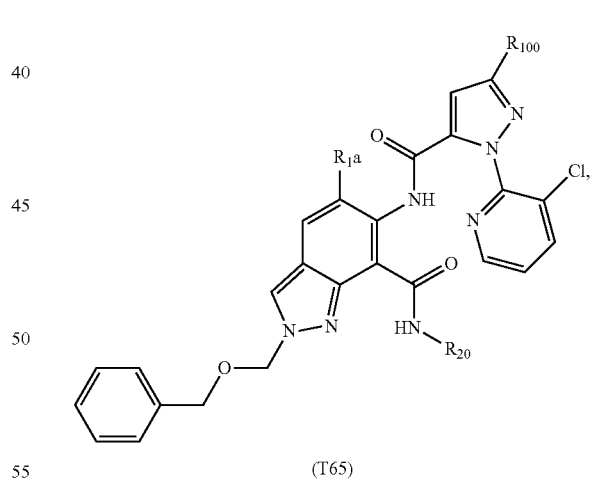

(T65)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 66

This table discloses the 480 compounds T66.1.1 to T66.1.480 of formula

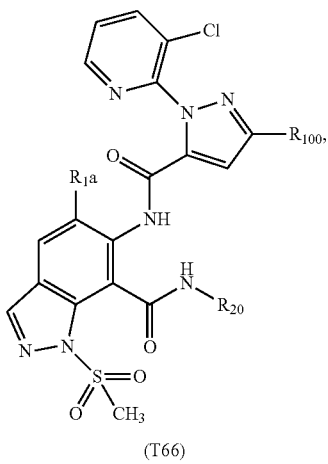

(T66)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 67

This table discloses the 480 compounds T67.1.1 to T67.1.480 of formula

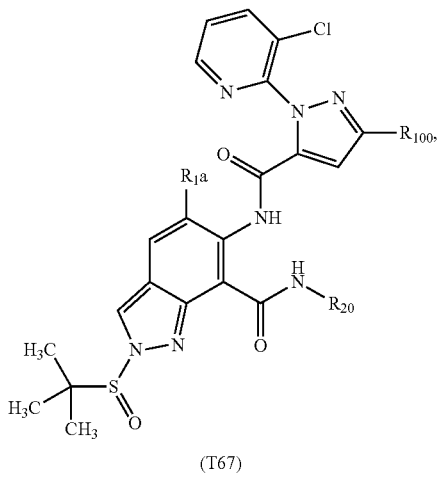

(T67)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 68

This table discloses the 480 compounds T68.1.1 to T68.1.480 of formula

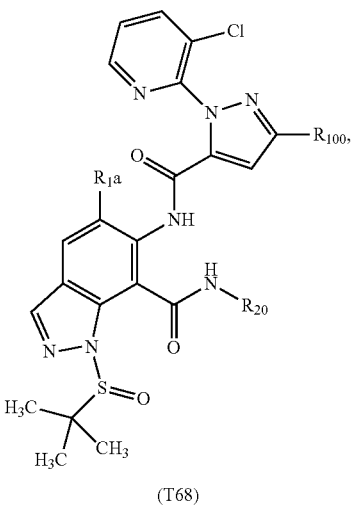

(T68)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 69

This table discloses the 480 compounds T69.1.1 to T69.1.480 of formula

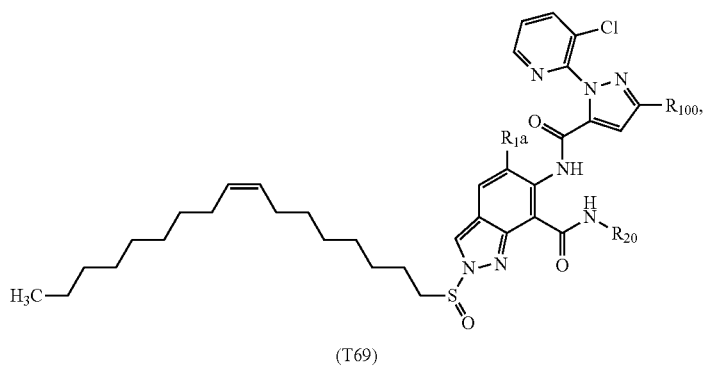

(T69)

TABLE 69-continued in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 70

This table discloses the 480 compounds T70.1.1 to T70.1.480 of formula

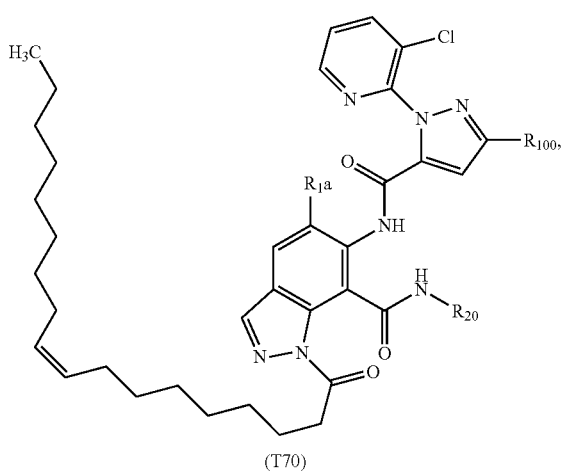

(T70)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 71

This table discloses the 480 compounds T71.1.1 to T71.1.480 of formula

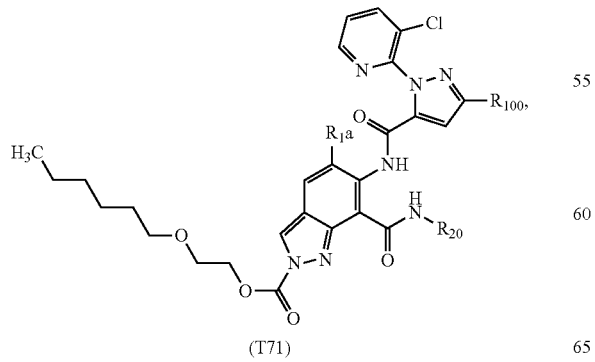

(T71)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 72

This table discloses the 480 compounds T72.1.1 to T72.1.480 of formula

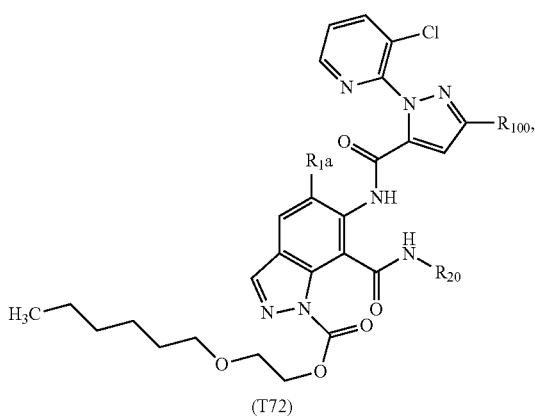

(T72)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 73

This table discloses the 480 compounds T73.1.1 to T73.1.480 of formula

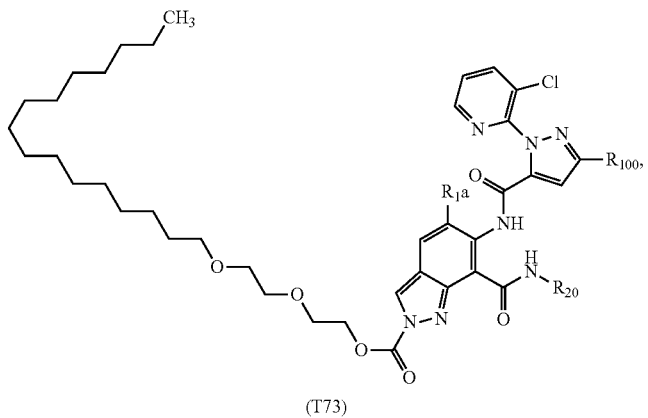

(T73)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 74

This table discloses the 480 compounds T74.1.1 to T74.1.480 of formula

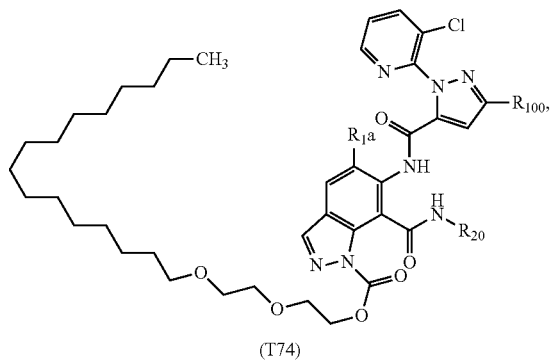

(T74)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 75

This table discloses the 480 compounds T75.1.1 to T75.1.480 of formula

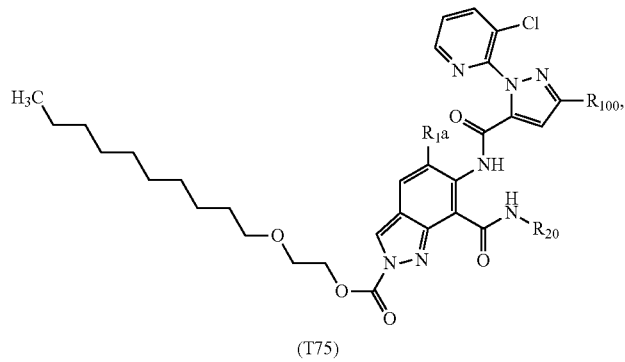

(T75)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 76

This table discloses the 480 compounds T76.1.1 to T76.1.480 of formula

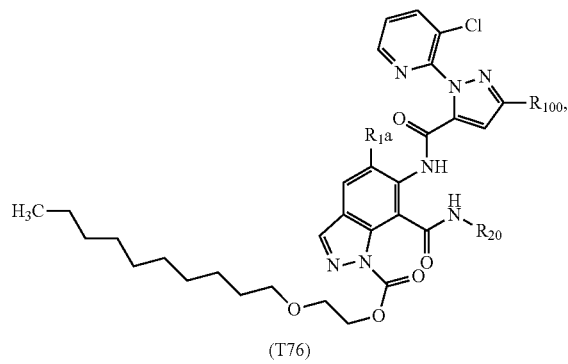

(T76)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 77

This table discloses the 480 compounds T77.1.1 to T77.1.480 of formula

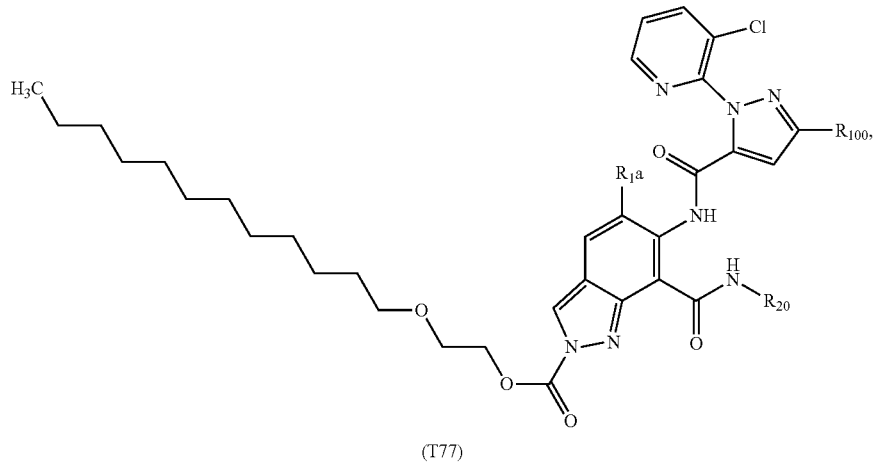

(T77)

TABLE 77-continued in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 78

This table discloses the 480 compounds T78.1.1 to T78.1.480 of formula

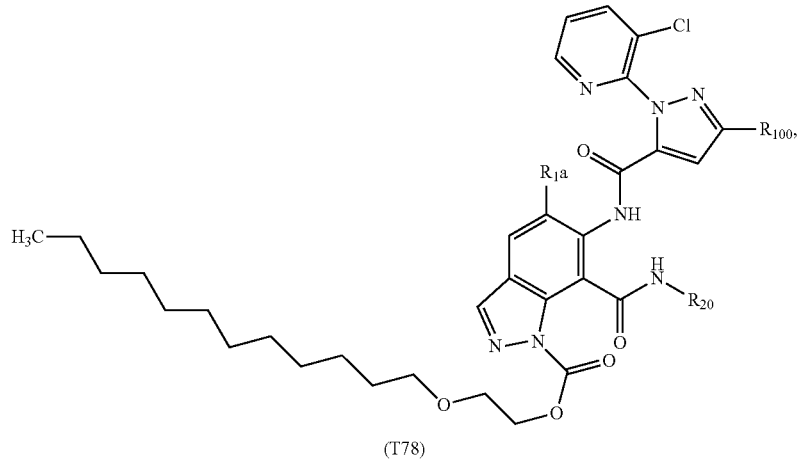

(T78)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 79

This table discloses the 480 compounds T79.1.1 to T79.1.480 of formula

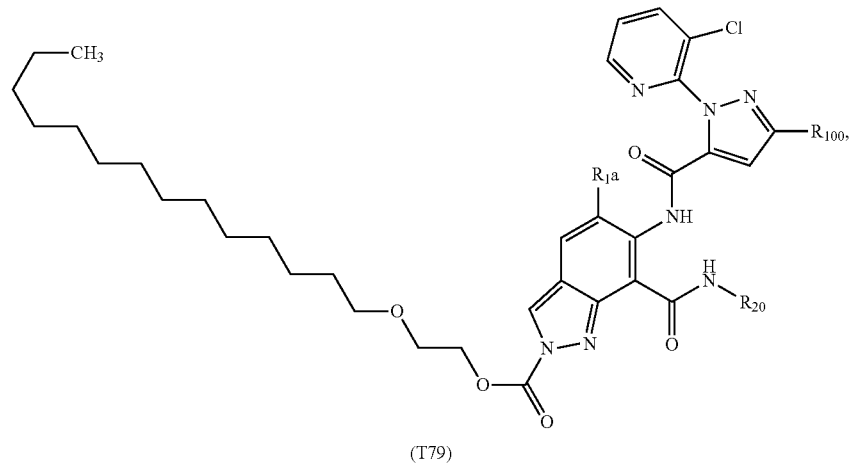

(T79)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 80

This table discloses the 480 compounds T80.1.1 to T80.1.480 of formula

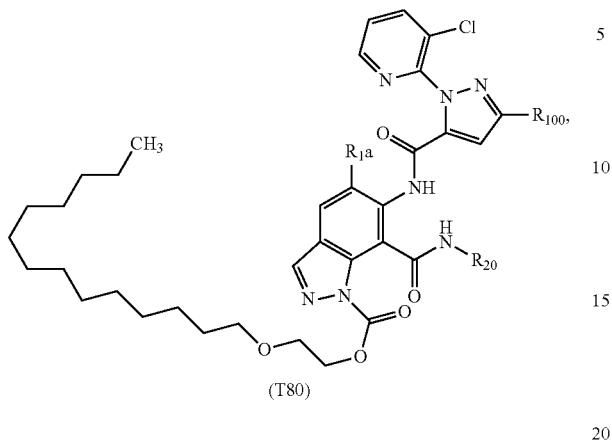

(T80)

in which, for each of these 480 specific compounds,
each of the variables $R_{1a}$, $R_{20}$ and $R_{100}$
has the specific meaning given in the corresponding line, appropriately
selected from the 480 lines A.1.1 to A.1.480 of the Table A.

TABLE 81

This table discloses the 480 compounds T81.1.1 to T81.1.480 of formula

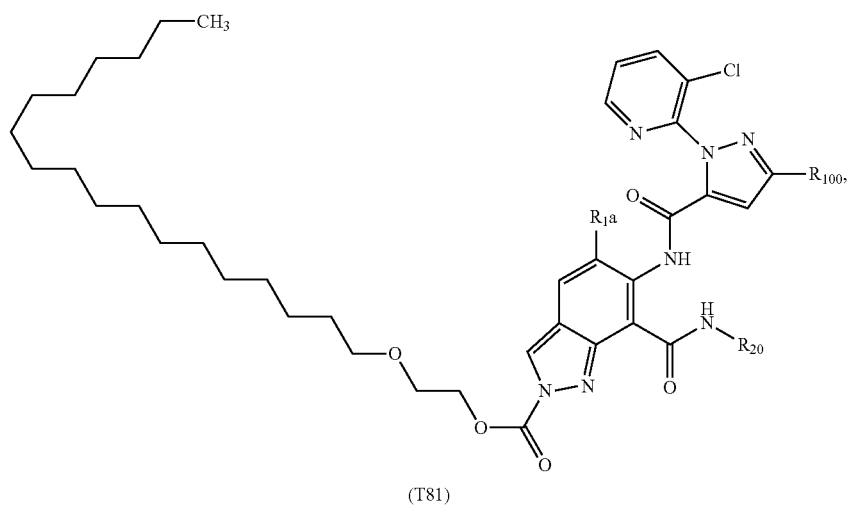

(T81)

in which, for each of these 480 specific compounds, each of the variables $R_{1a}$, $R_{20}$ and $R_{100}$
has the specific meaning given in the corresponding line, appropriately selected from the
480 lines A.1.1 to A.1.480 of the Table A.

TABLE 82

This table discloses the 480 compounds T82.1.1 to T82.1.480 of formula

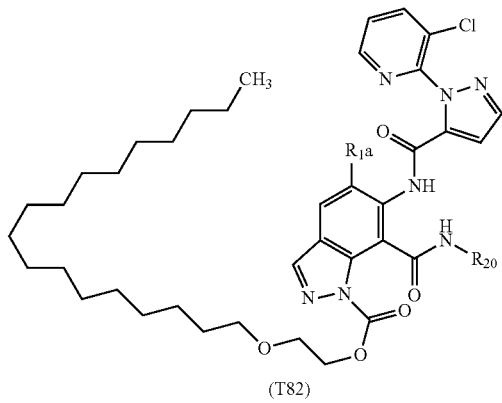

(T82)

in which, for each of these 480 specific compounds,
each of the variables $R_{1a}$, $R_{20}$ and $R_{100}$
has the specific meaning given in the corresponding line, appropriately
selected from the 480 lines A.1.1 to A.1.480 of the Table A.

TABLE 83

This table discloses the 480 compounds T83.1.1 to T83.1.480 of formula

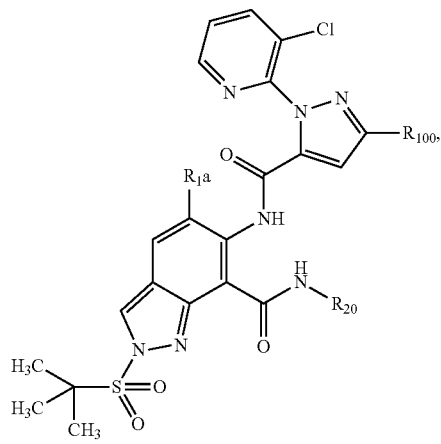

(T83)

in which, for each of these 480 specific compounds,
each of the variables $R_{1a}$, $R_{20}$ and $R_{100}$
has the specific meaning given in the corresponding line,
appropriately selected from the 480 lines A.1.1 to A.1.480 of the Table A.

TABLE 84

This table discloses the 480 compounds T84.1.1 to T84.1.480 of formula

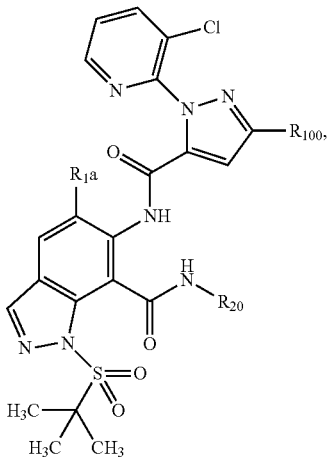

(T84)

in which, for each of these 480 specific compounds,
each of the variables $R_{1a}$, $R_{20}$ and $R_{100}$ has the specific
meaning given in the corresponding line, appropriately
selected from the 480 lines A.1.1 to A.1.480 of the Table A.

TABLE 85

This table discloses the 480 compounds T85.1.1 to T85.1.480 of formula

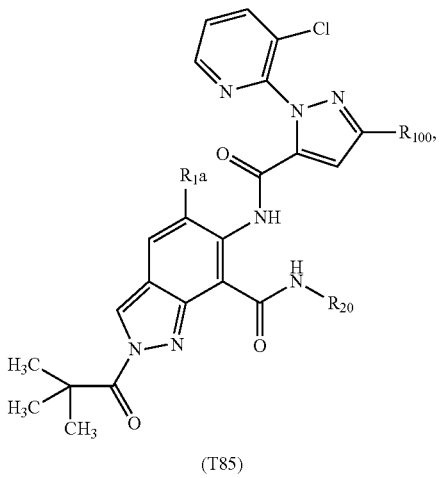

(T85)

in which, for each of these 480 specific compounds,
each of the variables $R_{1a}$, $R_{20}$ and $R_{100}$ has the specific meaning given
in the corresponding line, appropriately selected from the
480 lines A.1.1 to A.1.480 of the Table A.

TABLE 86

This table discloses the 480 compounds T86.1.1 to T86.1.480 of formula

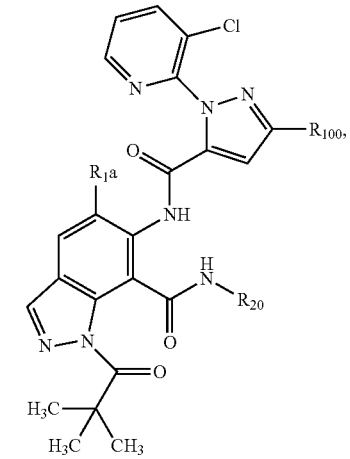

(T86)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 87

This table discloses the 480 compounds T87.1.1 to T87.1.480 of formula

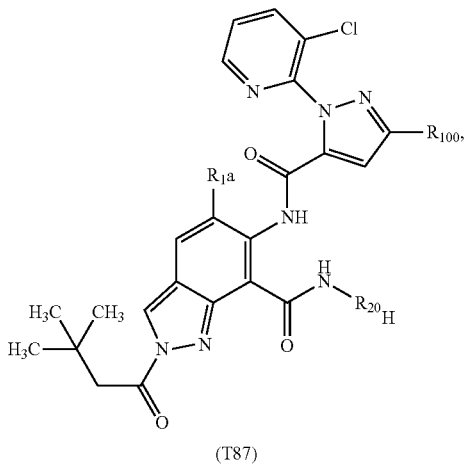

(T87)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 88

This table discloses the 480 compounds T88.1.1 to T88.1.480 of formula

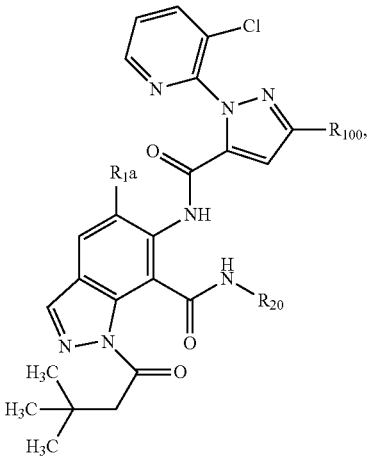

(T88)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 89

This table discloses the 480 compounds T89.1.1 to T89.1.480 of formula

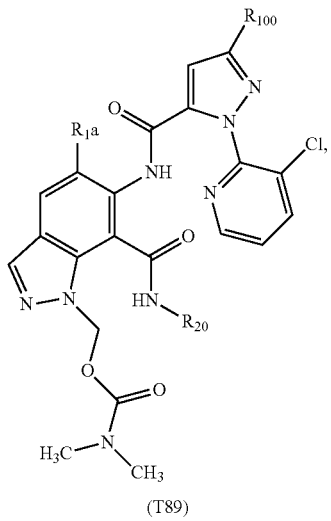

(T89)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 90

This table discloses the 480 compounds T90.1.1 to T90.1.480 of formula

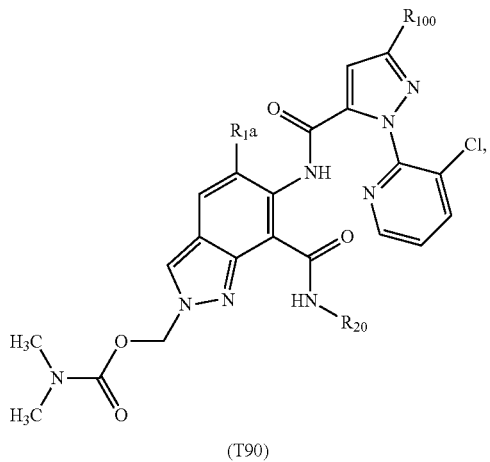

(T90)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 91

This table discloses the 480 compounds T91.1.1 to T91.1.480 of formula

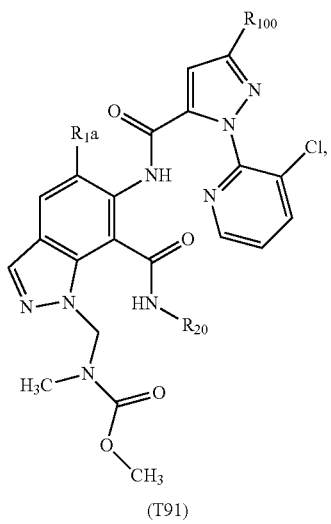

(T91)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 92

This table discloses the 480 compounds T92.1.1 to T92.1.480 of formula

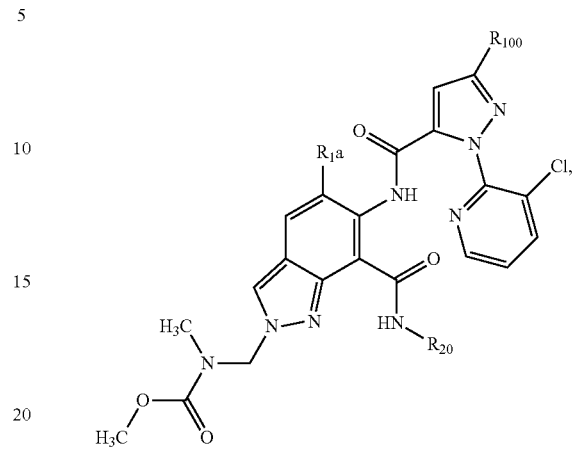

(T92)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 93

This table discloses the 480 compounds T93.1.1 to T93.1.480 of formula

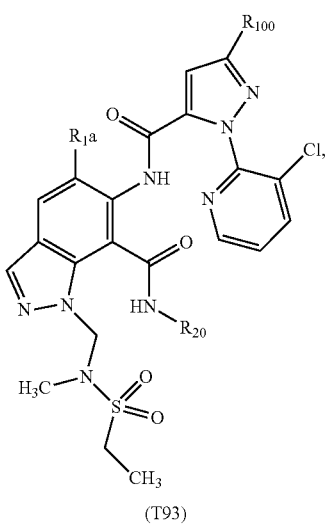

(T93)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 94

This table discloses the 480 compounds T94.1.1 to T94.1.480 of formula

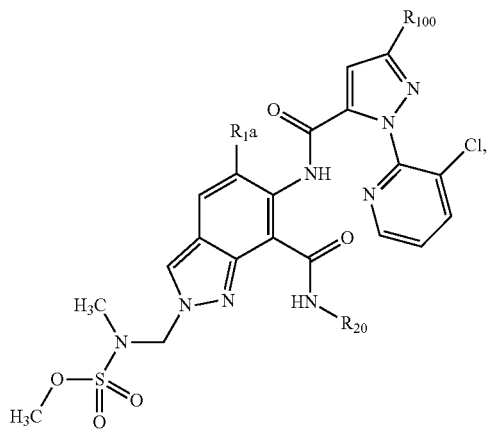

(T94)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 95

This table discloses the 480 compounds T95.1.1 to T95.1.480 of formula

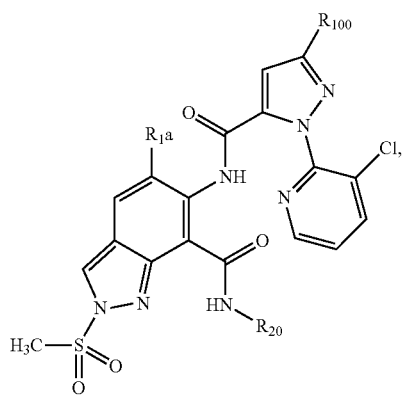

(T95)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 96

This table discloses the 480 compounds T96.1.1 to T96.1.480 of formula

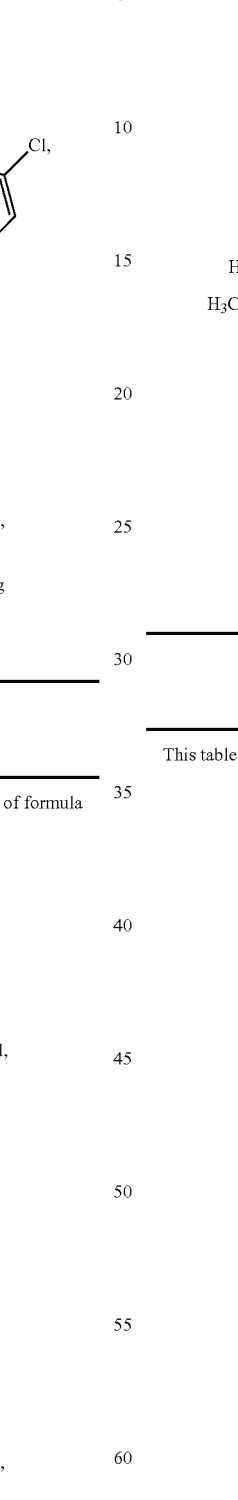

(T96)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 97

This table discloses the 480 compounds T97.1.1 to T97.1.480 of formula

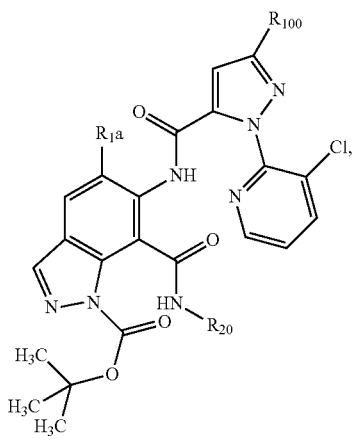

(T97)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 98

This table discloses the 480 compounds T98.1.1 to T98.1.480 of formula

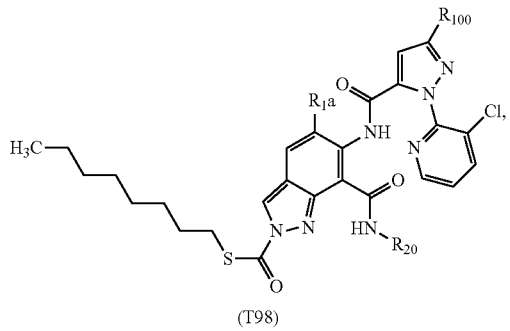

(T98)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 99

This table discloses the 480 compounds T99.1.1 to T99.1.480 of formula

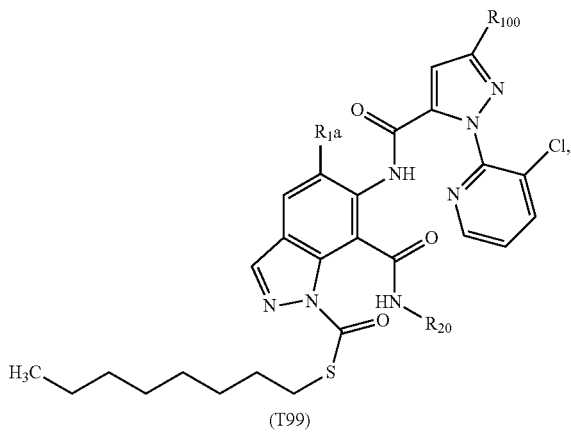

(T99)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 100

This table discloses the 480 compounds T100.1.1 to T100.1.480 of formula

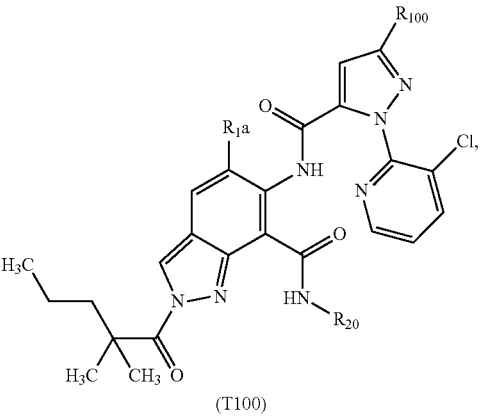

(T100)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 101

This table discloses the 480 compounds T101.1.1 to T101.1.480 of formula

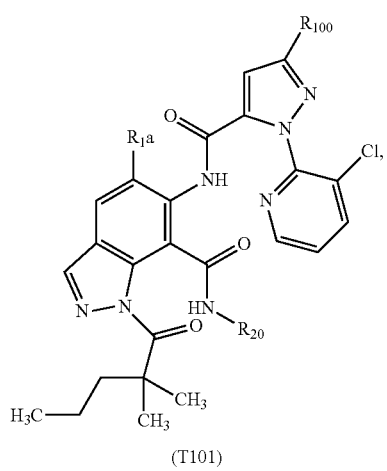

(T101)

in which, for each of these 480 specific compounds,
each of the variables $R_{1a}$, $R_{20}$ and $R_{100}$
has the specific meaning given in the corresponding
line, appropriately selected from the
480 lines A.1.1 to A.1.480 of the Table A.

TABLE 102

This table discloses the 480 compounds T102.1.1 to T102.1.480 of formula

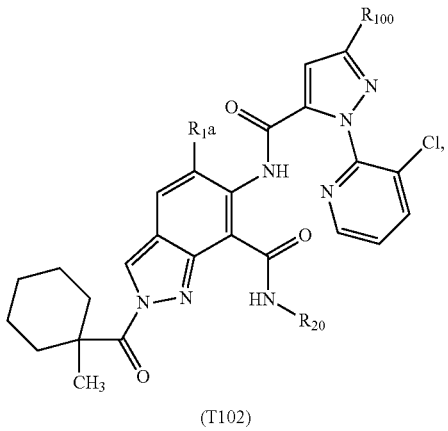

(T102)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 103

This table discloses the 480 compounds T103.1.1 to T103.1.480 of formula

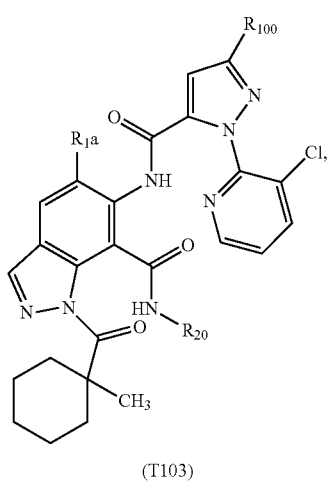

(T103)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 104

This table discloses the 480 compounds T104.1.1 to T104.1.480 of formula

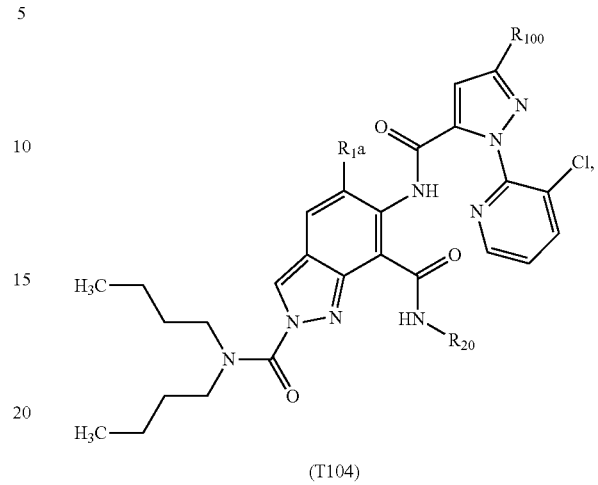

(T104)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 105

This table discloses the 480 compounds T105.1.1 to T105.1.480 of formula

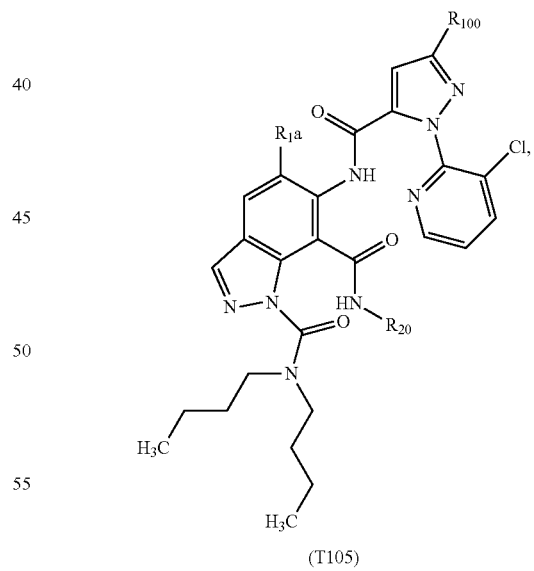

(T105)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 106

This table discloses the 480 compounds T106.1.1 to T106.1.480 of formula

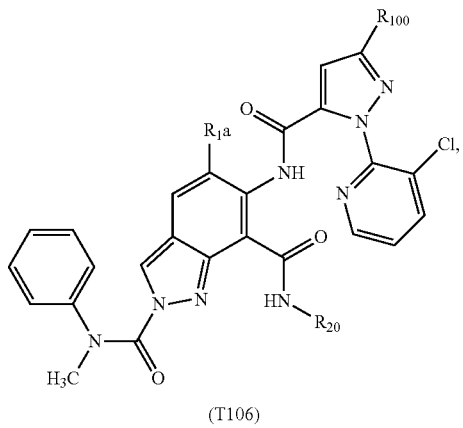

(T106)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 107

This table discloses the 480 compounds T107.1.1 to T107.1.480 of formula

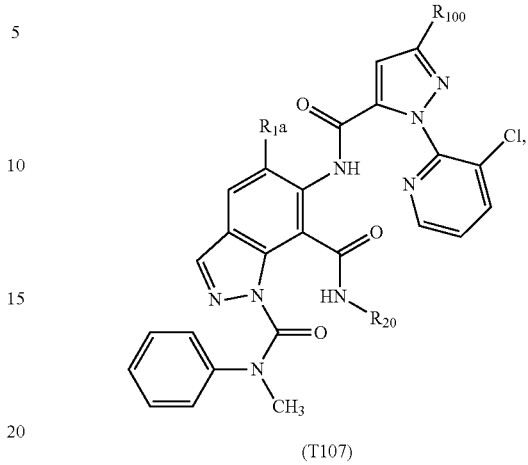

(T107)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 108

This table discloses the 480 compounds T108.1.1 to T108.1.480 of formula

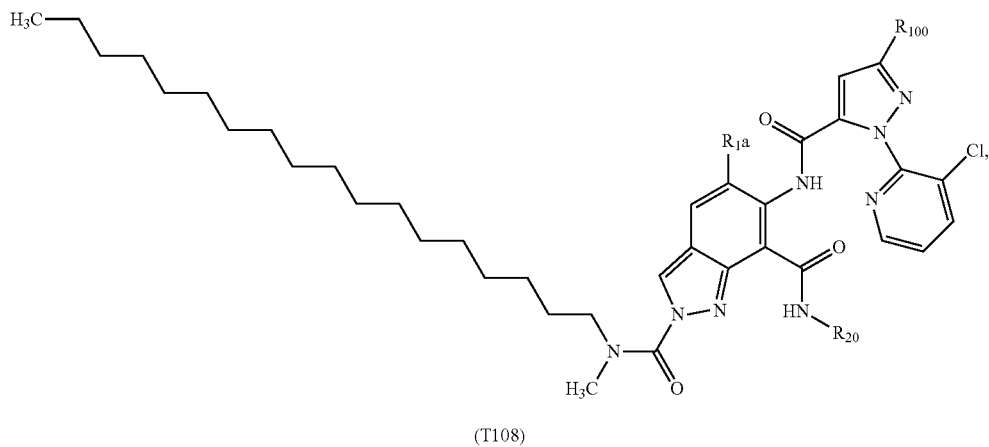

(T108)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 109

This table discloses the 480 compounds T109.1.1 to T109.1.480 of formula

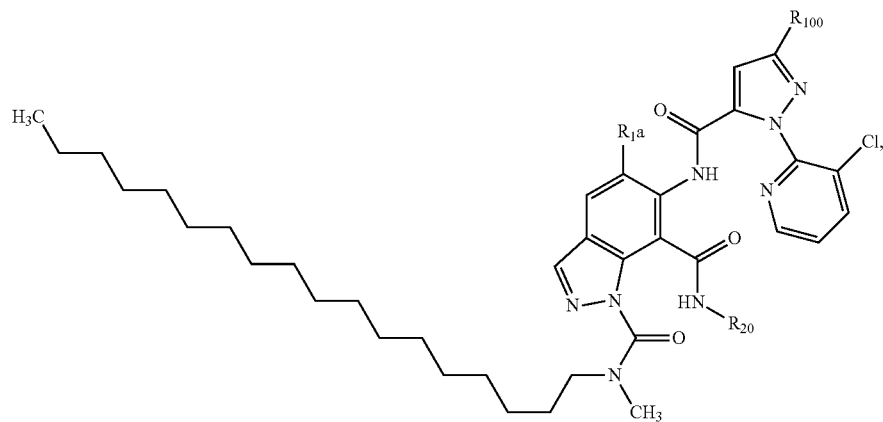

(T109)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 110

This table discloses the 480 compounds T110.1.1 to T110.1.480 of formula

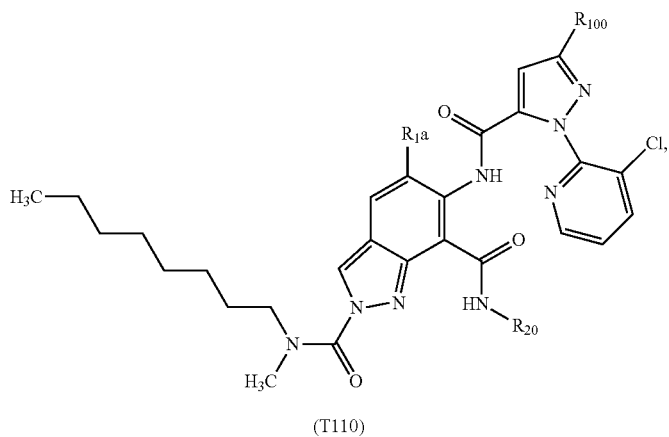

(T110)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 111

This table discloses the 480 compounds T111.1.1 to T111.1.480 of formula

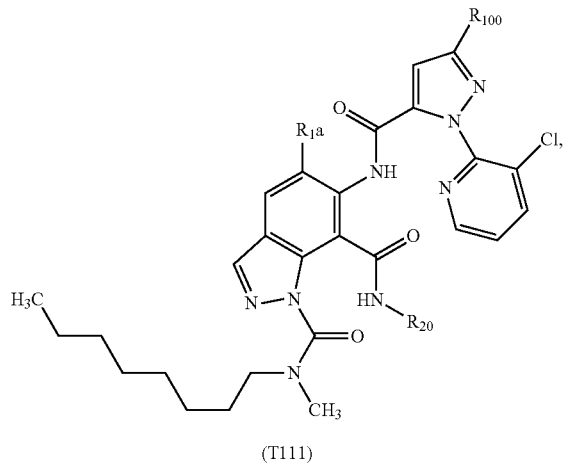

(T111)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 112

This table discloses the 480 compounds T112.1.1 to T112.1.480 of formula

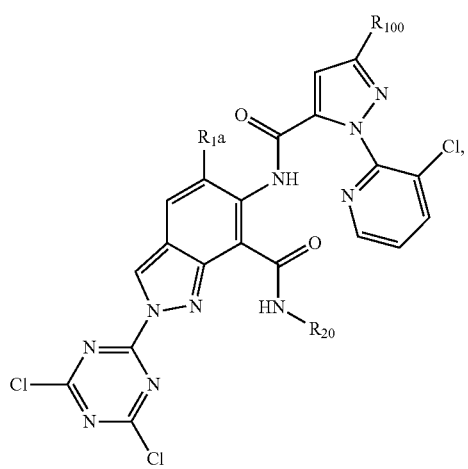

(T112)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 113

This table discloses the 480 compounds T113.1.1 to T113.1.480 of formula

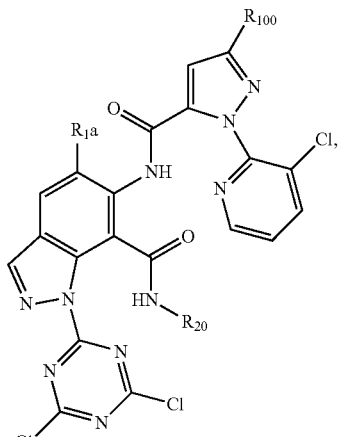

(T113)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 114

This table discloses the 480 compounds T114.1.1 to T114.1.480 of formula

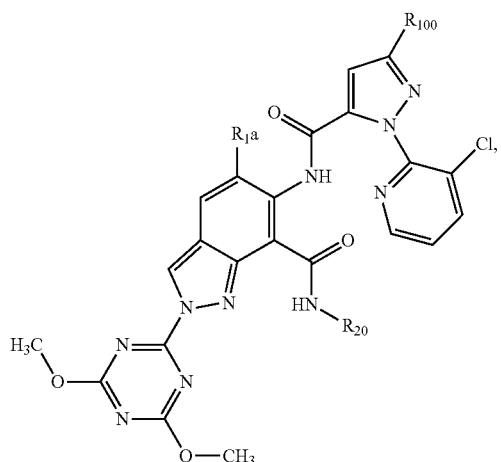

(T114)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 115

This table discloses the 480 compounds T115.1.1 to T115.1.480 of formula

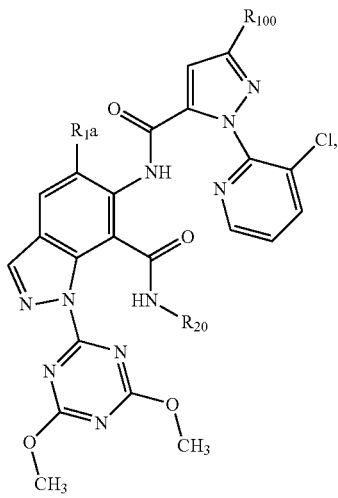

(T115)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 116

This table discloses the 480 compounds T116.1.1 to T116.1.480 of formula

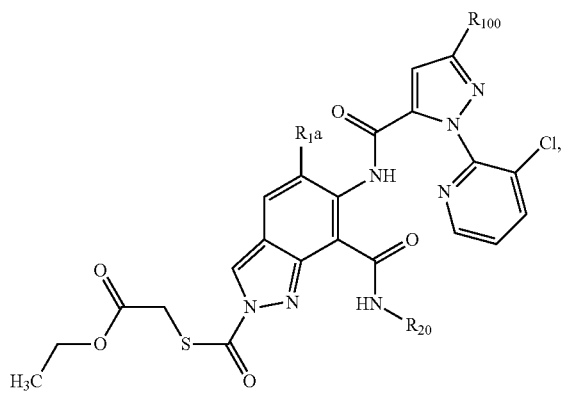

(T116)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 117

This table discloses the 480 compounds T117.1.1 to T117.1.480 of formula

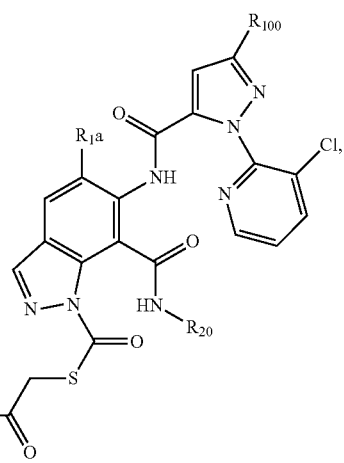

(T117)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 118

This table discloses the 480 compounds T118.1.1 to T118.1.480 of formula

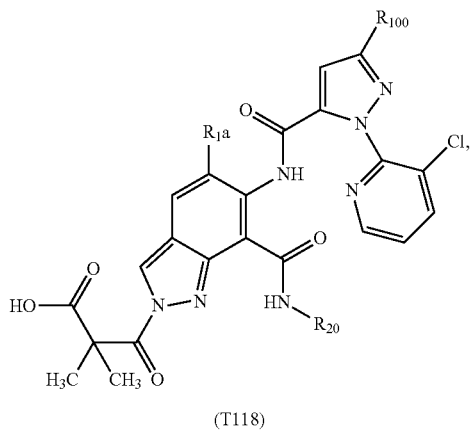

(T118)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 119

This table discloses the 480 compounds T119.1.1 to T119.1.480 of formula

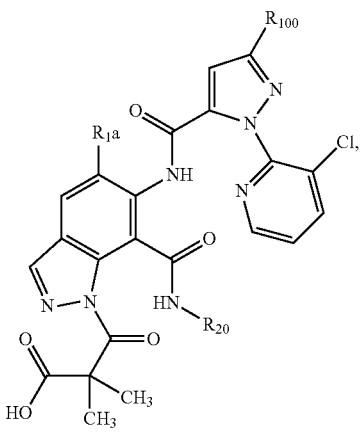

(T119)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 120

This table discloses the 480 compounds T120.1.1 to T120.1.480 of formula

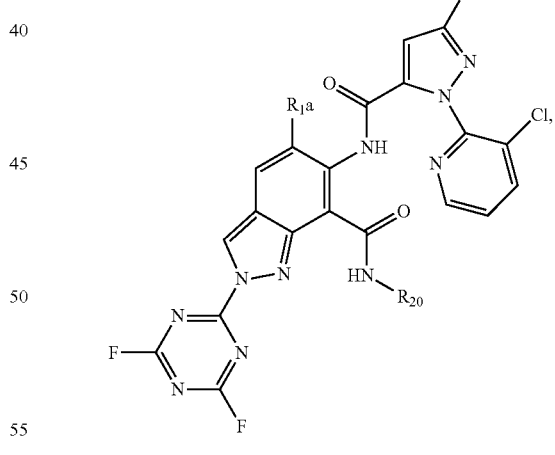

(T120)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

TABLE 121

This table discloses the 480 compounds T121.1.1 to T121.1.480 of formula

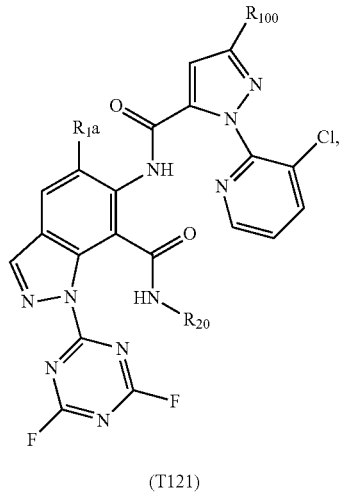

(T121)

in which, for each of these 480 specific compounds, each of the variables $R_{1a}$, $R_{20}$ and $R_{100}$ has the specific meaning given in the corresponding line, appropriately selected from the 480 lines A.1.1 to A.1.480 of the Table A.

FORMULATION EXAMPLES

%=Percent by Weight

| Example F1: Emulsion concentrates | | | |
|---|---|---|---|
| | a) | b) | c) |
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

| Example F2: Solutions | | | | |
|---|---|---|---|---|
| | a) | b) | c) | d) |
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

| Example F3: Granules | | | | |
|---|---|---|---|---|
| | a) | b) | c) | d) |
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

| Example F4: Dusts | | |
|---|---|---|
| | a) | b) |
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

| Example F5: Wettable powders | | | |
|---|---|---|---|
| | a) | b) | c) |
| Active ingredient | 25% | 50% | 75% |
| Sodium lignosulfonate | 5% | 5% | — |
| Sodium lauryl sulfate | 3% | — | 5% |
| Sodium diisobutylnaphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

| Example F6: Extruder granules | |
|---|---|
| Active ingredient | 10% |
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

| Example F7: Coated granules | |
|---|---|
| Active ingredient | 3% |
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

| Example F8: Suspension concentrate | |
|---|---|
| Active ingredient | 40% |
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32% |

The finely ground active ingredient is mixed intimately with the additives. Suspensions of any desired concentration can be prepared from the thus resulting suspension concentrate by dilution with water.

The activity of the compositions according to the invention can be broadened considerably, and adapted to prevailing circumstances, by adding other insecticidally, acaricidally and/or fungicidally active ingredients. The mixtures of the compounds of formula I with other insecticidally, acaricidally and/or fungicidally active ingredients may also have further surprising advantages which can also be described, in a wider sense, as synergistic activity. For example, better tolerance by plants, reduced phytotoxicity, insects can be controlled in their different development stages or better behaviour during their production, for example during grinding or mixing, during their storage or during their use.

Suitable additions to active ingredients here are, for example, representatives of the following classes of active ingredients: organophosphorus compounds, nitrophenol derivatives, thioureas, juvenile hormones, formamidines, benzophenone derivatives, ureas, pyrrole derivatives, carbamates, pyrethroids, chlorinated hydrocarbons, acylureas, pyridylmethyleneamino derivatives, macrolides, neonicotinoids and *Bacillus thuringiensis* preparations.

The following mixtures of the compounds of formula I with active ingredients are preferred (the abbreviation "TX" means "one compound selected from the group consisting of the compounds of formulae T1 to T121 described in Tables 1 to 121 of the present invention"):

an adjuvant selected from the group of substances consisting of petroleum oils (alternative name) (628)+TX, an acaricide selected from the group of substances consisting of 1,1-bis(4-chlorophenyl)-2-ethoxyethanol (IUPAC name) (910)+TX, 2,4-dichlorophenyl benzenesulfonate (IUPAC/Chemical Abstracts name) (1059)+TX, 2-fluoro-N-methyl-N-1-naphthylacetamide (IUPAC name) (1295)+TX, 4-chlorophenyl phenyl sulfone (IUPAC name) (981)+TX, abamectin (1)+TX, acequinocyl (3)+TX, acetoprole [CCN]+TX, acrinathrin (9)+TX, aldicarb (16)+TX, aldoxycarb (863)+TX, alpha-cypermethrin (202)+TX, amidithion (870)+TX, amidoflumet [CCN]+TX, amidothioate (872)+TX, amiton (875)+TX, amiton hydrogen oxalate (875)+TX, amitraz (24)+TX, aramite (881)+TX, arsenous oxide (882)+TX, AVI 382 (compound code)+TX, AZ 60541 (compound code)+TX, azinphos-ethyl (44)+TX, azinphos-methyl (45)+TX, azobenzene (IUPAC name) (888)+TX, azocyclotin (46)+TX, azothoate (889)+TX, benomyl (62)+TX, benoxafos (alternative name) [CCN]+TX, benzoximate (71)+TX, benzyl benzoate (IUPAC name) [CCN]+TX, bifenazate (74)+TX, bifenthrin (76)+TX, binapacryl (907)+TX, brofenvalerate (alternative name)+TX, bromocyclen (918)+TX, bromophos (920)+TX, bromophos-ethyl (921)+TX, bromopropylate (94)+TX, buprofezin (99)+TX, buto-carboxim (103)+TX, butoxycarboxim (104)+TX, butylpyridaben (alternative name)+TX, calcium polysulfide (IUPAC name) (111)+TX, camphechlor (941)+TX, carbanolate (943)+TX, carbaryl (115)+TX, carbofuran (118)+TX, carbophenothion (947)+TX, CGA 50'439 (development code) (125)+TX, chinomethionat (126)+TX, chlorbenside (959)+TX, chlordimeform (964)+TX, chlordimeform hydrochloride (964)+TX, chlorfenapyr (130)+TX, chlorfenethol (968)+TX, chlorfenson (970)+TX, chlorfensulphide (971)+TX, chlorfenvinphos (131)+TX, chlorobenzilate (975)+TX, chloromebuform (977)+TX, chloromethiuron (978)+TX, chloropropylate (983)+TX, chlorpyrifos (145)+TX, chlorpyrifos-methyl (146)+TX, chlorthiophos (994)+TX, cinerin I (696)+TX, cinerin II (696)+TX, cinerins (696)+TX, clofentezine (158)+TX, closantel (alternative name) [CCN]+TX, coumaphos (174)+TX, crotamiton (alternative name) [CCN]+TX, crotoxyphos (1010)+TX, cufraneb (1013)+TX, cyanthoate (1020)+TX, cyflumetofen (CAS Reg. No.: 400882-07-7)+TX, cyhalothrin (196)+TX, cyhexatin (199)+TX, cypermethrin (201)+TX, DCPM (1032)+TX, DDT (219)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-5-methyl (224)+TX, demeton-S-methylsulphon (1039)+TX, diafenthiuron (226)+TX, dialifos (1042)+TX, diazinon (227)+TX, dichlofluanid (230)+TX, dichlorvos (236)+TX, diclrophos (alternative name)+TX, dicofol (242)+TX, dicrotophos (243)+TX, dienochlor (1071)+TX, dimefox (1081)+TX, dimethoate (262)+TX, dinactin (alternative name) (653)+TX, dinex (1089)+TX, dinex-diclexine (1089)+TX, dinobuton (269)+TX, dinocap (270)+TX, dinocap-4 [CCN]+TX, dinocap-6 [CCN]+TX, dinocton (1090)+TX, dinopenton (1092)+TX, dinosulfon (1097)+TX, dinoterbon (1098)+TX, dioxathion (1102)+TX, diphenyl sulfone (IUPAC name) (1103)+TX, disulfuram (alternative name) [CCN]+TX, disulfoton (278)+TX, DNOC (282)+TX, dofenapyn (1113)+TX, doramectin (alternative name) [CCN]+TX, endosulfan (294)+TX, endothion (1121)+TX, EPN (297)+TX, eprinomectin (alternative name) [CCN]+TX, ethion (309)+TX, ethoate-methyl (1134)+TX, etoxazole (320)+TX, etrimfos (1142)+TX, fenazaflor (1147)+TX, fenazaquin (328)+TX, fenbutatin oxide (330)+TX, fenothiocarb (337)+TX, fenpropathrin (342)+TX, fenpyrad (alternative name)+TX, fenpyroximate (345)+TX, fenson 0157)+TX, fentrifanil (1161)+TX, fenvalerate (349)+TX, fipronil (354)+TX, fluacrypyrim (360)+TX, fluazuron (1166)+TX, flubenzimine (1167)+TX, flucycloxuron (366)+TX, flucythrinate (367)+TX, fluenetil (1169)+TX, flufenoxuron (370)+TX, flumethrin (372)+TX, fluorbenside (1174)+TX, fluvalinate (1184)+TX, FMC 1137 (development code) (1185)+TX, formetanate (405)+TX, formetanate hydrochloride (405)+TX, formothion (1192)+TX, formparanate (1193)+TX, gamma-HCH (430)+TX, glyodin (1205)+TX, halfenprox (424)+TX, heptenophos (432)+TX, hexadecyl cyclopropanecarboxylate (IUPAC/Chemical Abstracts name) (1216)+TX, hexythiazox (441)+TX, iodomethane (IUPAC name) (542)+TX, isocarbophos (alternative name) (473)+TX, isopropyl O-(methoxyaminothiophosphoryl)salicylate (IUPAC name) (473)+TX, ivermectin (alternative name) [CCN]+TX, jasmolin I (696)+TX, jasmolin II (696)+

TX, jodfenphos (1248)+TX, lindane (430)+TX, lufenuron (490)+TX, malathion (492)+TX, malonoben (1254)+TX, mecarbam (502)+TX, mephosfolan (1261)+TX, mesulfen (alternative name) [CCN]+TX, methacrifos (1266)+TX, methamidophos (527)+TX, methidathion (529)+TX, methiocarb (530)+TX, methomyl (531)+TX, methyl bromide (537)+TX, metolcarb (550)+TX, mevinphos (556)+TX, mexacarbate (1290)+TX, milbemectin (557)+TX, milbemycin oxime (alternative name) [CCN]+TX, mipafox (1293)+TX, monocrotophos (561)+TX, morphothion (1300)+TX, moxidectin (alternative name) [CCN]+TX, naled (567)+TX, NC-184 (compound code)+TX, NC-512 (compound code)+TX, nifluridide (1309)+TX, nikkomycins (alternative name) [CCN]+TX, nitrilacarb (1313)+TX, nitrilacarb 1:1 zinc chloride complex (1313)+TX, NNI-0101 (compound code)+TX, NNI-0250 (compound code)+TX, omethoate (594)+TX, oxamyl (602)+TX, oxydeprofos (1324)+TX, oxydisulfoton (1325)+TX, pp'-DDT (219)+TX, parathion (615)+TX, permethrin (626)+TX, petroleum oils (alternative name) (628)+TX, phenkapton (1330)+TX, phenthoate (631)+TX, phorate (636)+TX, phosalone (637)+TX, phosfolan (1338)+TX, phosmet (638)+TX, phosphamidon (639)+TX, phoxim (642)+TX, pirimiphos-methyl (652)+TX, polychlorotérpenes (traditional name) (1347)+TX, polynactins (alternative name) (653)+TX, proclonol (1350)+TX, profenofos (662)+TX, promacyl (1354)+TX, propargite (671)+TX, propetamphos (673)+TX, propoxur (678)+TX, prothidathion (1360)+TX, prothoate (1362)+TX, pyrethrin I (696)+TX, pyrethrin II (696)+TX, pyrethrins (696)+TX, pyridaben (699)+TX, pyridaphenthion (701)+TX, pyrimidifen (706)+TX, pyrimitate (1370)+TX, quinalphos (711)+TX, quintiofos (1381)+TX, R-1492 (development code) (1382)+TX, RA-17 (development code) (1383)+TX, rotenone (722)+TX, schradan (1389)+TX, sebufos (alternative name)+TX, selamectin (alternative name) [CCN]+TX, SI-0009 (compound code)+TX, sophamide (1402)+TX, spirodiclofen (738)+TX, spiromesifen (739)+TX, SSI-121 (development code) (1404)+TX, sulfiram (alternative name) [CCN]+TX, sulfluramid (750)+TX, sulfotep (753)+TX, sulphur (754)+TX, SZI-121 (development code) (757)+TX, tau-fluvalinate (398)+TX, tebufenpyrad (763)+TX, TEPP (1417)+TX, terbam (alternative name)+TX, tetrachlorvinphos (777)+TX, tetradifon (786)+TX, tetranactin (alternative name) (653)+TX, tetrasul (1425)+TX, thiafenox (alternative name)+TX, thiocarboxime (1431)+TX, thiofanox (800)+TX, thiometon (801)+TX, thioquinox (1436)+TX, thuringiensin (alternative name) [CCN]+TX, triamiphos (1441)+TX, triarathene (1443)+TX, triazophos (820)+TX, triazuron (alternative name)+TX, trichlorfon (824)+TX, trifenofos (1455)+TX, trinactin (alternative name) (653)+TX, vamidothion (847)+TX, vaniliprole [CCN] and YI-5302 (compound code)+TX, an algicide selected from the group of substances consisting of bethoxazin [CCN]+TX, copper dioctanoate (IUPAC name) (170)+TX, copper sulfate (172)+TX, cybutryne [CCN]+TX, dichlone (1052)+TX, dichlorophen (232)+TX, endothal (295)+TX, fentin (347)+TX, hydrated lime [CCN]+TX, nabam (566)+TX, quinoclamine (714)+TX, quinonamid (1379)+TX, simazine (730)+TX, triphenyltin acetate (IUPAC name) (347) and triphenyltin hydroxide (IUPAC name) (347)+TX, an anthelmintic selected from the group of substances consisting of abamectin (1)+TX, crufomate (1011)+TX, doramectin (alternative name) [CCN]+TX, emamectin (291)+TX, emamectin benzoate (291)+TX, eprinomectin (alternative name) [CCN]+TX, ivermectin (alternative name) [CCN]+TX, milbemycin oxime (alternative name) [CCN]+TX, moxidectin (alternative name) [CCN]+TX, piperazine [CCN]+TX, selamectin (alternative name) [CCN]+TX, spinosad (737) and thiophanate (1435)+TX, an avicide selected from the group of substances consisting of chloralose (127)+TX, endrin (1122)+TX, fenthion (346)+TX, pyridin-4-amine (IUPAC name) (23) and strychnine (745)+TX, a bactericide selected from the group of substances consisting of 1-hydroxy-1H-pyridine-2-thione (IUPAC name) (1222)+TX, 4-(quinoxalin-2-ylamino)benzenesulfonamide (IUPAC name) (748)+TX, 8-hydroxyquinoline sulfate (446)+TX, bronopol (97)+TX, copper dioctanoate (IUPAC name) (170)+TX, copper hydroxide (IUPAC name) (169)+TX, cresol [CCN]+TX, dichlorophen (232)+TX, dipyrithione (1105)+TX, dodicin (1112)+TX, fenaminosulf (1144)+TX, formaldehyde (404)+TX, hydrargaphen (alternative name) [CCN]+TX, kasugamycin (483)+TX, kasugamycin hydrochloride hydrate (483)+TX, nickel bis(dimethyldithiocarbamate) (IUPAC name) (1308)+TX, nitrapyrin (580)+TX, octhilinone (590)+TX, oxolinic acid (606)+TX, oxytetracycline (611)+TX, potassium hydroxyquinoline sulfate (446)+TX, probenazole (658)+TX, streptomycin (744)+TX, streptomycin sesquisulfate (744)+TX, tecloftalam (766)+TX, and thiomersal (alternative name) [CCN]+TX, a biological agent selected from the group of substances consisting of *Adoxophyes orana* GV (alternative name) (12)+TX, *Agrobacterium radiobacter* (alternative name) (13)+TX, *Amblyseius* spp. (alternative name) (19)+TX, *Anagrapha falcifera* NPV (alternative name) (28)+TX, *Anagrus atomus* (alternative name) (29)+TX, *Aphelinus abdominalis* (alternative name) (33)+TX, *Aphidius colemani* (alternative name) (34)+TX, *Aphidoletes aphidimyza* (alternative name) (35)+TX, *Autographa californica* NPV (alternative name) (38)+TX, *Bacillus firmus* (alternative name) (48)+TX, *Bacillus sphaericus* Neide (scientific name) (49)+TX, *Bacillus thuringiensis* Berliner (scientific name) (51)+TX, *Bacillus thuringiensis* subsp. *aizawai* (scientific name) (51)+TX, *Bacillus thuringiensis* subsp. *israelensis* (scientific name) (51)+TX, *Bacillus thuringiensis* subsp. *japonensis* (scientific name) (51)+TX, *Bacillus thuringiensis* subsp. *kurstaki* (scientific name) (51)+TX, *Bacillus thuringiensis* subsp. *tenebrionis* (scientific name) (51)+TX, *Beauveria bassiana* (alternative name) (53)+TX, *Beauveria brongniartii* (alternative name) (54)+TX, *Chrysoperla camea* (alternative name) (151)+TX, *Cryptolaemus montrouzieri* (alternative name) (178)+TX, *Cydia pomonella* GV (alternative name) (191)+TX, *Dacnusa sibirica* (alternative name) (212)+TX, *Diglyphus isaea* (alternative name) (254)+TX, *Encarsia formosa* (scientific name) (293)+TX, *Eretmocerus eremicus* (alternative name) (300)+TX, *Helicoverpa zea* NPV (alternative name) (431)+TX, *Heterorhabditis bacteriophora* and *H. megidis* (alternative name) (433)+TX, *Hippodamia convergens* (alternative name) (442)+TX, *Leptomastix dactylopii* (alternative name) (488)+TX, *Macrolophus caliginosus* (alternative name) (491)+TX, *Mamestra brassicae* NPV (alternative name) (494)+TX, *Metaphycus helvolus* (alternative name) (522)+TX, *Metarhizium anisopliae* var. *acridum* (scientific name) (523)+TX, *Metarhizium anisopliae* var. *anisopliae* (scientific name) (523)+TX, *Neodiprion sertifer* NPV and *N. lecontei* NPV (alternative name) (575)+TX, *Orius* spp. (alternative name) (596)+TX, *Paecilomyces fumosoroseus* (alternative name) (613)+TX, *Phytoseiulus persimilis* (alternative name) (644)+TX, *Spodoptera exigua* multicapsid nuclear polyhedrosis virus (scientific name) (741)+TX, *Steinernema bibionis* (alternative name) (742)+TX, *Steinemema carpocapsae* (alternative name) (742)+TX, *Steinemema feltiae* (alternative name) (742)+TX, *Steinemema glaseri* (alternative name) (742)+TX, *Steinemema riobrave* (alternative name) (742)+TX, *Steinemema riobravis* (alternative name) (742)+TX, *Steinemema scapterisci* (alternative name) (742)+TX, *Steinernema* spp. (alternative name) (742)+TX, *Trichogramma* spp. (alternative name) (826)+TX, *Typhlodromus occidentalis* (alternative name) (844) and *Verticillium lecanii* (alternative name) (848)+TX, a soil sterilant selected from the group of substances consisting of iodomethane (IUPAC name) (542) and methyl bromide (537)+TX, a chemosterilant selected from the group of substances consisting of apholate [CCN]+TX, bisazir (alternative name) [CCN]+TX, busulfan (alternative name) [CCN]+TX, diflubenzuron (250)+TX, dimatif (alternative name) [CCN]+TX, hemel [CCN]+TX, hempa [CCN]+TX, metepa [CCN]+TX, methiotepa [CCN]+TX, methyl apholate [CCN]+TX, morzid [CCN]+TX, penfluoron (alternative name) [CCN]+TX, tepa [CCN]+TX, thiohempa (alternative name) [CCN]+TX, thiotepa (alternative name) [CCN]+TX, tretamine (alternative name) [CCN] and uredepa (alternative name) [CCN]+TX, an insect pheromone selected from the group of substances consisting of (E)-dec-5-en-1-yl acetate with (E)-dec-5-en-1-ol (IUPAC name) (222)+TX, (E)-tridec-4-en-1-yl acetate (IUPAC name) (829)+TX, (E)-6-methylhept-2-en-4-ol (IUPAC name) (541)+TX, (E,Z)-tetradeca-4,10-dien-1-yl acetate (IUPAC name) (779)+TX, (Z)-dodec-7-en-1-yl acetate (IUPAC name) (285)+TX, (Z)-hexadec-11-enal (IUPAC name) (436)+TX, (Z)hexadec-11-en-1-ylacetate (IUPAC name) (437)+TX, (Z)-hexadec-13-en-11-yn-1-yl acetate (IUPAC name) (438)+TX, (Z)-icos-13-en-10-one (IUPAC name) (448)+TX, (Z)tetradec-7-en-1-yl (IUPAC name) (782)+TX, (Z)-tetradec-9-en-1-ol (IUPAC name) (783)+TX, (Z)-tetradec-9-en-1-yl acetate (IUPAC name) (784)+TX, (7E,9Z)-dodeca-7,9-dien-1-yl acetate (IUPAC name) (283)+TX, (9Z,11E)-tetradeca-9,11-dien-1-ylacetate (IUPAC name) (780)+TX, (9Z,12E)-tetradeca-9,12-dien-1-yl acetate (IUPAC name) (781)+TX, 14-methyloctadec-1-ene (IUPAC name) (545)+TX, 4-methylnonan-5-ol with 4-methylnonan-5-one (IUPAC name) (544)+TX, alpha-multistriatin (alternative name) [CCN]+TX, brevicomin (alternative name) [CCN]+TX, codlelure (alternative name) [CCN]+TX, codlemone (alternative name) (167)+TX, cuelure (alternative name) (179)+TX, disparlure (277)+TX, dodec-8-en-1-yl acetate (IUPAC name) (286)+TX, dodec-9-en-1-yl acetate (IUPAC name) (287)+TX, dodeca-8+TX, 10-dien-1-yl acetate (IUPAC name) (284)+TX, dominicalure (alternative name) [CCN]+TX, ethyl 4-methyloctanoate (IUPAC name) (317)+TX, eugenol (alternative name) [CCN]+TX, frontalin (alternative name) [CCN]+TX, gossyplure (alternative name) (420)+TX, grandlure (421)+TX, grandlure I (alternative name) (421)+TX, grandlure II (alternative name) (421)+TX, grandlure III (alternative name) (421)+TX, grandlure IV (alternative name) (421)+TX, hexylure [CCN]+TX, ipsdienol (alternative name) [CCN]+TX, ipsenol (alternative name) [CCN]+TX, japonilure (alternative name) (481)+TX, lineatin (alternative name) [CCN]+TX, litlure (alternative name) [CCN]+TX, looplure (alternative name) [CCN]+TX, medlure [CCN]+TX, megatomoic acid (alternative name) [CCN]+TX, methyl eugenol (alternative name) (540)+TX, muscalure (563)+TX, octadeca-2,13-dien-1-yl acetate (IUPAC name) (588)+TX, octadeca-3,13-dien-1-yl acetate (IUPAC name) (589)+TX, orfralure (alternative name) [CCN]+TX, oryctalure (alternative name) (317)+TX, ostramone (alternative name) [CCN]+TX, siglure [CCN]+TX, sordidin (alternative name) (736)+TX, sulcatol (alternative name) [CCN]+TX, tetradec-11-en-1-yl acetate (IUPAC name) (785)+TX, trimedlure (839)+TX, trimedlure A (alternative name) (839)+TX, trimedlure $B_1$ (alternative name) (839)+TX, trimedlure $B_2$ (alternative name) (839)+TX, trimedlure C (alternative name) (839) and trunc-call (alternative name) [CCN]+TX, an insect repellent selected from the group of substances consisting of 2-(octylthio)ethanol (IUPAC name) (591)+TX, butopyronoxyl (933)+TX, butoxy(polypropylene glycol) (936)+TX, dibutyl adipate (IUPAC name) (1046)+TX, dibutyl phthalate (1047)+TX, dibutyl succinate (IUPAC name) (1048)+TX, diethyltoluamide [CCN]+TX, dimethyl carbate [CCN]+TX, dimethyl phthalate [CCN]+TX, ethyl hexanediol (1137)+TX, hexamide [CCN]+TX, methoquin-butyl (1276)+TX, methylneodecanamide [CCN]+TX, oxamate [CCN] and picaridin [CCN]+TX, an insecticide selected from the group of substances consisting of 1-dichloro-1-nitroethane (IUPAC/Chemical Abstracts name) (1058)+TX, 1,1-dichloro-2,2-bis(4-ethylphenyl)ethane (IUPAC name) (1056), +TX, 1,2-dichloropropane (IUPAC/Chemical Abstracts name) (1062)+TX, 1,2-dichloropropane with 1,3-dichloropropene (IUPAC name) (1063)+TX, 1-bromo-2-chloroethane (IUPAC/Chemical Abstracts name) (916)+TX, 2,2,2-trichloro-1-(3,4-dichlorophenyl)ethyl acetate (IUPAC name) (1451)+TX, 2,2-dichlorovinyl 2-ethylsulphinylethyl methyl phosphate (IUPAC name) (1066)+TX, 2-(1,3-dithiolan-2-yl)phenyl dimethylcarbamate (IUPAC/Chemical Abstracts name) (1109)+TX, 2-(2-butoxyethoxy)ethyl thiocyanate (IUPAC/Chemical Abstracts name) (935)+TX, 2-(4,5-dimethyl-1,3-dioxolan-2-yl)phenyl methylcarbamate (IUPAC/Chemical Abstracts name) (1084)+TX, 2-(4-chloro-3,5-xylyloxy)ethanol (IUPAC name) (986)+TX, 2-chlorovinyl diethyl phosphate (IUPAC name) (984)+TX, 2-imidazolidone (IUPAC name) (1225)+TX, 2-isovalerylindan-1,3-dione (IUPAC name) (1246)+TX, 2-methyl(prop-2-ynyl) aminophenyl methylcarbamate (IUPAC name) (1284)+TX, 2-thiocyanatoethyl laurate (IUPAC name) (1433)+TX, 3-bromo-1-chloroprop-1-ene (IUPAC name) (917)+TX, 3-methyl-1-phenylpyrazol-5-yl dimethylcarbamate (IUPAC name) (1283)+TX, 4-methyl(prop-2-ynyl)amino-3,5-xylyl methylcarbamate (IUPAC name) (1285)+TX, 5,5-dimethyl-3-oxocyclohex-1-enyl dimethylcarbamate (IUPAC name) (1085)+TX, abamectin (1)+TX, acephate (2)+TX, acetamiprid (4)+TX, acethion (alternative name) [CCN]+TX, acetoprole [CCN]+TX, acrinathrin (9)+TX, acrylonitrile (IUPAC name) (861)+TX, alanycarb (15)+TX, aldicarb (16)+TX, aldoxycarb (863)+TX, aldrin (864)+TX, allethrin (17)+TX, allosamidin (alternative name) [CCN]+TX, allyxycarb (866)+TX, alpha-cypermethrin (202)+TX, alpha-ecdysone (alternative name) [CCN]+TX, aluminium phosphide (640)+TX, amidithion (870)+TX, amidothioate (872)+TX, aminocarb (873)+TX, amiton (875)+TX, amiton hydrogen oxalate (875)+TX, amitraz (24)+TX, anabasine (877)+TX, athidathion (883)+TX, AVI 382 (compound code)+TX, AZ 60541 (compound code)+TX, azadirachtin (alternative name) (41)+TX, azamethiphos (42)+TX, azinphos-ethyl (44)+TX, azinphos-methyl (45)+TX, azothoate (889)+TX, *Bacillus thuringiensis* delta endotoxins (alternative name) (52)+TX, barium hexafluorosilicate (alternative name) [CCN]+TX, barium polysulfide (IUPAC/Chemical Abstracts name) (892)+TX, barthrin [CCN]+TX, Bayer 22/190 (development code) (893)+TX, Bayer 22408 (development code) (894)+TX, bendiocarb (58)+TX, benfuracarb (60)+TX, bensultap (66)+TX, beta-cyfluthrin (194)+TX, betacypermethrin (203)+TX, bifenthrin (76)+TX, bioallethrin (78)+TX, bioallethrin Scyclopentenyl isomer (alternative name) (79)+TX, bioethanomethrin [CCN]+TX, biopermethrin (908)+TX, bioresmethrin (80)+TX, bis(2-chloroethyl) ether (IUPAC name) (909)+TX, bistrifluoron (83)+TX, borax (86)+TX, brofenvalerate (alternative name)+TX, bromfenvinfos (914)+TX, bromocyclen (918)+TX, bromo-DDT (alternative name) [CCN]+TX, bromophos (920)+TX, bromophos-ethyl (921)+TX, bufencarb (924)+TX, buprofezin (99)+TX, butacarb (926)+TX, butathiofos (927)+TX, butocarboxim (103)+TX, butonate (932)+TX, butoxycarboxim (104)+TX, butylpyridaben (alternative name)+TX, cadusafos (109)+TX, calcium arsenate [CCN]+TX, calcium cyanide (444)+TX, calcium polysulfide (IUPAC name) (111)+TX, camphechlor (941)+TX, carbanolate (943)+TX, carbaryl (115)+TX, carbofuran (118)+TX, carbon disulfide (IUPAC/Chemical Abstracts name) (945)+TX, carbon tetrachloride (IUPAC name) (946)+TX, carbophenothion (947)+TX, carbosulfan (119)+TX, cartap (123)+TX, cartap hydrochloride (123)+TX, cevadine (alternative name) (725)+TX, chlorbicyclen (960)+TX, chlordane (128)+TX, chlordecone (963)+TX, chlordimeform (964)+TX, chlordimeform hydrochloride (964)+TX, chlorethoxyfos (129)+TX, chlorfenapyr (130)+TX, chlorfenvinphos (131)+TX, chlorfluazuron (132)+TX, chlormephos (136)+TX, chloroform [CCN]+TX, chloropicrin (141)+TX, chlorphoxim (989)+TX, chlorprazophos (990)+TX, chlorpyrifos (145)+TX, chlorpyrifos-methyl (146)+TX, chlorthiophos (994)+TX, chromafenozide (150)+TX, cinerin I (696)+TX, cinerin II (696)+TX, cinerins (696)+TX, cis-resmethrin (alternative name)+TX, cismethrin (80)+TX, clocythrin (alternative name)+TX, cloethocarb (999)+TX, closantel (alternative name) [CCN]+TX, clothianidin (165)+TX, copper acetoarsenite [CCN]+TX, copper arsenate [CCN]+TX, copper oleate [CCN]+TX, coumaphos (174)+TX, coumithoate (1006)+TX, crotamiton (alternative name) [CCN]+TX, crotoxyphos (1010)+TX, crufomate (1011)+TX, cryolite (alternative name) (177)+TX, CS 708 (development code) (1012)+TX, cyanofenphos (1019)+TX, cyanophos (184)+TX, cyanthoate (1020)+TX, cyclethrin [CCN]+TX, cycloprothrin (188)+TX, cyfluthrin (193)+TX, cyhalothrin (196)+TX, cypermethrin (201)+TX, cyphenothrin (206)+TX, cyromazine (209)+TX, cythioate (alternative name) [CCN]+TX, d-limonene (alternative name) [CCN]+TX, d-tetramethrin (alternative name) (788)+TX, DAEP (1031)+TX, dazomet (216)+TX, DDT (219)+TX, decarbofuran (1034)+TX, deltamethrin (223)+TX, demephion (1037)+TX, demephion-O (1037)+TX, demephion-S (1037)+TX, demeton (1038)+TX, demeton-methyl (224)+TX, demeton-O (1038)+TX, demeton-O-methyl (224)+TX, demeton-S (1038)+TX, demeton-5-methyl (224)+TX, demeton-5-methylsulphon (1039)+TX, diafenthiuron (226)+TX, dialifos (1042)+TX, diamidafos (1044)+TX, diazinon (227)+TX, dicapthon (1050)+TX, dichlofenthion (1051)+TX, dichlorvos (236)+TX, dicliphos (alternative name)+TX, dicresyl (alternative name) [CCN]+TX, dicrotophos (243)+TX, dicyclanil (244)+TX, dieldrin (1070)+TX, diethyl 5-methylpyrazol-3-yl phosphate (IUPAC name) (1076)+TX, diflubenzuron (250)+TX, dilor (alternative name) [CCN]+TX, dimefluthrin [CCN]+TX, dimefox (1081)+TX, dimetan (1085)+TX, dimethoate (262)+TX, dimethrin (1083)+TX, dimethylvinphos (265)+TX, dimetilan (1086)+TX, dinex (1089)+TX, dinex-diclexine (1089)+TX, dinoprop (1093)+TX, dinosam (1094)+TX, dinoseb (1095)+TX, dinotefuran (271)+TX, diofenolan (1099)+TX, dioxabenzofos (1100)+TX, dioxacarb (1101)+TX, dioxathion (1102)+TX, disulfoton (278)+TX, dithicrofos (1108)+TX, DNOC (282)+TX, doramectin (alternative name) [CCN]+TX, DSP (1115)+TX, ecdysterone (alternative name) [CCN]+TX, EI 1642 (development code) (1118)+TX, emamectin (291)+TX, emamectin benzoate (291)+TX, EMPC (1120)+TX, empenthrin (292)+TX, endosulfan (294)+TX, endothion (1121)+TX, endrin (1122)+TX, EPBP (1123)+TX, EPN (297)+TX, epofenonane (1124)+TX, eprinomectin (alternative name) [CCN]+TX, esfenvalerate (302)+TX, etaphos (alternative name) [CCN]+TX, ethiofencarb (308)+TX, ethion (309)+TX, ethiprole (310)+TX, ethoate-methyl (1134)+TX, ethoprophos (312)+TX, ethyl formate (IUPAC name) [CCN]+TX, ethyl-DDD (alternative name) (1056)+TX, ethylene dibromide (316)+TX, ethylene dichloride (chemical name) (1136)+TX, ethylene oxide [CCN]+TX, etofenprox (319)+TX, etrimfos (1142)+TX, EXD (1143)+TX, famphur (323)+TX, fenamiphos (326)+TX, fenazaflor (1147)+TX, fenchlorphos (1148)+TX, fenethacarb (1149)+TX, fenfluthrin (1150)+TX, fenitrothion (335)+TX, fenobucarb (336)+TX, fenoxacrim (1153)+TX, fenoxycarb (340)+TX, fenpirithrin (1155)+TX, fenpropathrin (342)+TX, fenpyrad (alternative name)+TX, fensulfothion (1158)+TX, fenthion (346)+TX, fenthion-ethyl [CCN]+TX, fenvalerate (349)+TX, fipronil (354)+TX, flonicamid (358)+TX, flubendiamide (CAS. Reg. No.: 272451-65-7)+TX, flucofuron (1168)+TX, flucycloxuron (366)+TX, flucythrinate (367)+TX, fluenetil (1169)+TX, flufenerim [CCN]+TX, flufenoxuron (370)+TX, flufenprox (1171)+TX, flumethrin (372)+TX, fluvalinate (1184)+TX, FMC 1137 (development code) (1185)+TX, fonofos (1191)+TX, formetanate (405)+TX, formetanate hydrochloride (405)+TX, formothion (1192)+TX, formparanate (1193)+TX, fosmethilan (1194)+TX, fospirate (1195)+TX, fosthiazate (408)+TX, fosthietan (1196)+TX, furathiocarb (412)+TX, furethrin (1200)+TX, gamma-cyhalothrin (197)+TX, gamma-HCH (430)+TX, guazatine (422)+TX, guazatine acetates (422)+TX, GY-81 (development code) (423)+TX, halfenprox (424)+TX, halofenozide (425)+TX, HCH (430)+TX, HEOD (1070)+TX, heptachlor (1211)+TX, heptenophos (432)+TX, heterophos [CCN]+TX, hexaflumuron (439)+TX, HHDN (864)+TX, hydramethylnon (443)+TX, hydrogen cyanide (444)+TX, hydroprene (445)+TX, hyquincarb (1223)+TX, imidacloprid (458)+TX, imiprothrin (460)+TX, indoxacarb (465)+TX, iodomethane (IUPAC name) (542)+TX, IPSP (1229)+TX, isazofos (1231)+TX, isobenzan (1232)+TX, isocarbophos (alternative name) (473)+TX, isodrin (1235)+TX, isofenphos (1236)+TX, isolane (1237)+TX, isoprocarb (472)+TX, isopropyl O-(methoxyaminothiophosphoryl)salicylate (IUPAC name) (473)+TX, isoprothiolane (474)+TX, isothioate (1244)+TX, isoxathion (480)+TX, ivermectin (alternative name) [CCN]+TX, jasmolin I (696)+TX, jasmolin II (696)+TX, jodfenphos (1248)+TX, juvenile hormone I (alternative name) [CCN]+TX, juvenile hormone II (alternative name) [CCN]+TX, juvenile hormone III (alternative name) [CCN]+TX, kelevan (1249)+TX, kinoprene (484)+TX, lambda-cyhalothrin (198)+TX, lead arsenate [CCN]+TX, lepimectin (CCN)+TX, leptophos (1250)+TX, lindane (430)+TX, lirimfos (1251)+TX, lufenuron (490)+TX, lythidathion (1253)+TX, m-cumenyl methylcarbamate (IUPAC name) (1014)+TX, magnesium phosphide (IUPAC name) (640)+TX, malathion (492)+TX, malonoben (1254)+TX, mazidox (1255)+TX, mecarbam (502)+TX, mecarphon (1258)+TX, menazon (1260)+TX, mephosfolan (1261)+TX, mercurous chloride (513)+TX, mesulfenfos (1263)+TX, metaflumizone (CCN)+TX, metam (519)+TX, metam-potassium (alternative name) (519)+TX, metam-sodium (519)+TX, methacrifos (1266)+TX, methamidophos (527)+TX, methanesuiphonyl fluoride (IUPAC/Chemical Abstracts name) (1268)+TX, methidathion (529)+TX, methiocarb (530)+TX, methocrotophos (1273)+TX, methomyl (531)+TX, methoprene (532)+TX, methoquin-butyl (1276)+TX, methothrin (alternative name) (533)+TX, methoxychlor (534)+TX, methoxyfenozide (535)+TX, methyl bromide (537)+TX, methyl isothiocyanate (543)+TX, methylchloroform (alternative name) [CCN]+TX, methylene chloride [CCN]+TX, metofluthrin [CCN]+TX, metolcarb (550)+TX, metoxadiazone (1288)+TX, mevinphos (556)+TX, mexacarbate (1290)+TX, milbemectin (557)+TX, milbemycin oxime (alternative name) [CCN]+TX, mipafox (1293)+TX, mirex (1294)+TX, monocrotophos (561)+TX, morphothion (1300)+TX, moxidectin (alternative name) [CCN]+TX, naftalofos (alternative name) [CCN]+TX, naled (567)+TX, naphthalene (IUPAC/Chemical Abstracts name) (1303)+TX, NC-170 (development code) (1306)+TX, NC-184 (compound code)+TX, nicotine (578)+TX, nicotine sulfate (578)+TX, niflurdide (1309)+TX, nitenpyram (579)+TX, nithiazine (1311)+TX, nitrilacarb (1313)+TX, nitrilacarb 1:1 zinc chloride complex (1313)+TX, NNI-0101 (compound code)+TX, NNI-0250 (compound code)+TX, nornicotine (traditional name) (1319)+TX, novaluron (585)+TX, noviflumuron (586)+TX, O-5-dichloro-4-iodophenyl O-ethyl ethylphosphonothioate (IUPAC name) (1057)+TX, O,O-diethyl O-4-methyl-2-oxo-2H-chromen-7-yl phosphorothioate (IUPAC name) (1074)+TX, O,O-diethyl O-6-methyl-2-propylpyrimidin-4-yl phosphorothioate (IUPAC name) (1075)+TX, O,O,O', O'-tetrapropyl dithiopyrophosphate (IUPAC name) (1424)+TX, oleic acid (IUPAC name) (593)+TX, omethoate (594)+TX, oxamyl (602)+TX, oxydemeton-methyl (609)+TX, oxydeprofos (1324)+TX, oxydisulfoton (1325)+TX, pp'-DDT (219)+TX, para-dichlorobenzene [CCN]+TX, parathion (615)+TX, parathion-methyl (616)+TX, penfluoron (alternative name) [CCN]+TX, pentachlorophenol (623)+TX, pentachlorophenyl laurate (IUPAC name) (623)+TX, permethrin (626)+TX, petroleum oils (alternative name) (628)+TX, PH 60-38 (development code) (1328)+TX, phenkapton (1330)+TX, phenothrin (630)+TX, phenthoate (631)+TX, phorate (636)+TX, phosalone (637)+TX, phosfolan (1338)+TX, phosmet (638)+TX, phosnichlor (1339)+TX, phosphamidon (639)+TX, phosphine (IUPAC name) (640)+TX, phoxim (642)+TX, phoxim-methyl (1340)+TX, pirimetaphos (1344)+TX, pirimicarb (651)+TX, pirimiphos-ethyl (1345)+TX, pirimiphos-methyl (652)+TX, polychlorodicyclopentadiene isomers (IUPAC name) (1346)+TX, polychloroterpenes (traditional name) (1347)+TX, potassium arsenite [CCN]+TX, potassium thiocyanate [CCN]+TX, prallethrin (655)+TX, precocene I (alternative name) [CCN]+TX, precocene II (alternative name) [CCN]+TX, precocene III (alternative name) [CCN]+TX, primidophos (1349)+TX, profenofos (662)+TX, profluthrin [CCN]+TX, promacyl (1354)+TX, promecarb (1355)+TX, propaphos (1356)+TX, propetamphos (673)+TX, propoxur (678)+TX, prothidathion (1360)+TX, prothiofos (686)+TX, prothoate (1362)+TX, protrifenbute [CCN]+TX, pymetrozine (688)+TX, pyraclofos (689)+TX, pyrazophos (693)+TX, pyresmethrin (1367)+TX, pyrethrin I (696)+TX, pyrethrin II (696)+TX, pyrethrins (696)+TX, pyridaben (699)+TX, pyridalyl (700)+TX, pyridaphenthion (701)+TX, pyrimidifen (706)+TX, pyrimitate (1370)+TX, pyriproxyfen (708)+TX, quassia (alternative name) [CCN]+TX, quinalphos (711)+TX, quinalphosmethyl (1376)+TX, quinothion (1380)+TX, quintiofos (1381)+TX, R-1492 (development code) (1382)+TX, rafoxanide (alternative name) [CCN]+TX, resmethrin (719)+TX, rotenone (722)+TX, RU 15525 (development code) (723)+TX, RU 25475 (development code) (1386)+TX, ryania (alternative name) (1387)+TX, ryanodine (traditional name) (1387)+TX, sabadilla (alternative name) (725)+TX, schradan (1389)+TX, sebufos (alternative name)+TX, selamectin (alternative name) [CCN]+TX, SI-0009 (compound code)+TX, SI-0205 (compound code)+TX, SI-0404 (compound code)+TX, SI-0405 (compound code)+TX, silafluofen (728)+TX, SN 72129 (development code) (1397)+TX, sodium arsenite [CCN]+TX, sodium cyanide (444)+TX, sodium fluoride (IUPAC/Chemical Abstracts name) (1399)+TX, sodium hexafluorosilicate (1400)+TX, sodium pentachlorophenoxide (623)+TX, sodium selenate (IUPAC name) (1401)+TX, sodium thiocyanate [CCN]+TX, sophamide (1402)+TX, spinosad (737)+TX, spiromesifen (739)+TX, spirotetrmat (CCN)+TX, sulcofuron (746)+TX, sulcofuronsodium (746)+TX, sulfluramid (750)+TX, sulfotep (753)+TX, sulphuryl fluoride (756)+TX, sulprofos (1408)+TX, tar oils (alternative name) (758)+TX, tau-fluvalinate (398)+TX, tazimcarb (1412)+TX, TDE (1414)+TX, tebufenozide (762)+TX, tebufenpyrad (763)+TX, tebupirimfos (764)+TX, teflubenzuron (768)+TX, tefluthrin (769)+TX, temephos (770)+TX, TEPP (1417)+TX, terallethrin (1418)+TX, terbam (alternative name)+TX, terbufos (773)+TX, tetrachloroethane [CCN]+TX, tetrachlorvinphos (777)+TX, tetramethrin (787)+TX, theta-cypermethrin (204)+TX, thiacloprid (791)+TX, thiafenox (alternative name)+TX, thiamethoxam (792)+TX, thicrofos (1428)+TX, thiocarboxime (1431)+TX, thiocyclam (798)+TX, thiocyclam hydrogen oxalate (798)+TX, thiodicarb (799)+TX, thiofanox (800)+TX, thiometon (801)+TX, thionazin (1434)+TX, thiosultap (803)+TX, thiosultap-sodium (803)+TX, thuringiensin (alternative name) [CCN]+TX, tolfenpyrad (809)+TX, tralomethrin (812)+TX, transfluthrin (813)+TX, transpermethrin (1440)+TX, triamiphos (1441)+TX, triazamate (818)+TX, triazophos (820)+TX, triazuron (alternative name)+TX, trichlorfon (824)+TX, trichlormetaphos-3 (alternative name) [CCN]+TX, trichloronat (1452)+TX, trifenofos (1455)+TX, triflumuron (835)+TX, trimethacarb (840)+TX, triprene (1459)+TX, vamidothion (847)+TX, vaniliprole [CCN]+TX, veratridine (alternative name) (725)+TX, veratrine (alternative name) (725)+TX, XMC (853)+TX, xylylcarb (854)+TX, YI-5302 (compound code)+TX, zeta-cypermethrin (205)+TX, zetamethrin (alternative name)+TX, zinc phosphide (640)+TX, zolaprofos (1469) and ZXI 8901 (development code) (858)+TX, a molluscicide selected from the group of substances consisting of bis(tributyltin) oxide (IUPAC name) (913)+TX, bromoacetamide [CCN]+TX, calcium arsenate [CCN]+TX, cloethocarb (999)+TX, copper acetoarsenite [CCN]+TX, copper sulfate (172)+TX, fentin (347)+TX, ferric phosphate (IUPAC name) (352)+TX, metaldehyde (518)+TX, methiocarb (530)+TX, niclosamide (576)+TX, niclosamide-olamine (576)+TX, pentachlorophenol (623)+TX, sodium pentachlorophenoxide (623)+TX, tazimcarb (1412)+TX, thiodicarb (799)+TX, tributyltin oxide (913)+TX, trifenmorph (1454)+TX, trimethacarb (840)+TX, triphenyltin acetate (IUPAC name) (347) and triphenyltin hydroxide (IUPAC name) (347)+TX, a nematicide selected from the group of substances consisting of AKD-3088 (compound code)+TX, 1,2-dibromo-3-chloropropane (IUPAC/Chemical Abstracts name) (1045)+TX, 1,2-dichloropropane (IUPAC/Chemical Abstracts name) (1062)+TX, 1,2-dichloropropane with 1,3-dichloropropene (IUPAC name) (1063)+TX, 1,3-dichloropropene (233)+TX, 3,4-dichlorotetrahydrothiophene 1,1-dioxide (IUPAC/Chemical Abstracts name) (1065)+TX, 3-(4-chlorophenyl)-5-methylrhodanine (IUPAC name) (980)+TX, 5-methyl-6-thioxo-1,3,5-thiadiazinan-3-ylacetic acid (IUPAC name) (1286)+TX, 6-isopentenylaminopurine (alternative name) (210)+TX, abamectin (1)+TX, acetoprole [CCN]+TX, alanycarb (15)+TX, aldicarb (16)+TX, aldoxycarb (863)+TX, AZ 60541 (compound code)+TX, benclothiaz [CCN]+TX, benomyl (62)+TX, butylpyridaben (alternative name)+TX, cadusafos (109)+TX, carbofuran (118)+TX, carbon disulfide (945)+TX, carbosulfan (119)+TX, chloropicrin (141)+TX, chlorpyrifos (145)+TX, cloethocarb (999)+TX, cytokinins (alternative name) (210)+TX, dazomet (216)+TX, DBCP (1045)+TX, DCIP (218)+TX, diamidafos (1044)+TX, dichlofenthion (1051)+TX, dicliphos (alternative name)+TX, dimethoate (262)+TX, doramectin (alternative name) [CCN]+TX, emamectin (291)+TX, emamectin benzoate (291)+TX, eprinomectin (alternative name) [CCN]+TX, ethoprophos (312)+TX, ethylene dibromide (316)+TX, fenamiphos (326)+TX, fenpyrad (alternative name)+TX, fensulfothion (1158)+TX, fosthiazate (408)+TX, fosthietan (1196)+TX, furfural (alternative name) [CCN]+TX, GY-81 (development code) (423)+TX, heterophos [CCN]+TX, iodomethane (IUPAC name) (542)+TX, isamidofos (1230)+TX, isazofos (1231)+TX, ivermectin (alternative name) (210)+TX, kinetin (alternative name) (210)+TX, mecarphon (1258)+TX, metam (519)+TX, metam-potassium (alternative name) (519)+TX, metam-sodium (519)+TX, methyl bromide (537)+TX, methyl isothiocyanate (543)+TX, milbemycin oxime (alternative name) [CCN]+TX, moxidectin (alternative name) [CCN]+TX, *Myrothecium verrucaria* composition (alternative name) (565)+TX, NC-184 (compound code)+TX, oxamyl (602)+TX, phorate (636)+TX, phosphamidon (639)+TX, phosphocarb [CCN]+TX, sebufos (alternative name)+TX, selamectin (alternative name) [CCN]+TX, spinosad (737)+TX, terbam (alternative name)+TX, terbufos (773)+TX, tetrachlorothiophene (IUPAC/Chemical Abstracts name) (1422)+TX, thiafenox (alternative name)+TX, thionazin (1434)+TX, triazophos (820)+TX, triazuron (alternative name)+TX, xylenols [CCN]+TX, YI-5302 (compound code) and zeatin (alternative name) (210)+TX, a nitrification inhibitor selected from the group of substances consisting of potassium ethylxanthate [CCN] and nitrapyrin (580)+TX, a plant activator selected from the group of substances consisting of acibenzolar (6)+TX, acibenzolar-5-methyl (6)+TX, probenazole (658) and *Reynoutria sachalinensis* extract (alternative name) (720)+TX, a rodenticide selected from the group of substances consisting of 2-isovalerylindan-1,3-dione (IUPAC name) (1246)+TX, 4-(quinoxalin-2-ylamino)benzenesulfonamide (IUPAC name) (748)+TX, alpha-chlorohydrin [CCN]+TX, aluminium phosphide (640)+TX, antu (880)+TX, arsenous oxide (882)+TX, barium carbonate (891)+TX, bisthiosemi (912)+TX, brodifacoum (89)+TX, bromadiolone (91)+TX, bromethalin (92)+TX, calcium cyanide (444)+TX, chloralose (127)+TX, chlorophacinone (140)+TX, cholecalciferol (alternative name) (850)+TX, coumachlor (1004)+TX, coumafuryl (1005)+TX, coumatetralyl (175)+TX, crimidine (1009)+TX, difenacoum (246)+TX, difethialone (249)+TX, diphacinone (273)+TX, ergocalciferol (301)+TX, flocoumafen (357)+TX, fluoroacetamide (379)+TX, flupropadine (1183)+TX, flupropadine hydrochloride (1183)+TX, gamma-HCH (430)+TX, HCH (430)+TX, hydrogen cyanide (444)+TX, iodomethane (IUPAC name) (542)+TX, lindane (430)+TX, magnesium phosphide (IUPAC name) (640)+TX, methyl bromide (537)+TX, norbormide (1318)+TX, phosacetim (1336)+TX, phosphine (IUPAC name) (640)+TX, phosphorus [CCN]+TX, pindone (1341)+TX, potassium arsenite [CCN]+TX, pyrinuron (1371)+TX, scilliroside (1390)+TX, sodium arsenite [CCN]+TX, sodium cyanide (444)+TX, sodium fluoroacetate (735)+TX, strychnine (745)+TX, thallium sulfate [CCN]+TX, warfarin (851) and zinc phosphide (640)+TX, a synergist selected from the group of substances consisting of 2-(2-butoxyethoxy)ethyl piperonylate (IUPAC name) (934)+TX, 5-(1,3-benzodioxol-5-yl)-3-hexylcyclohex-2-enone (IUPAC name) (903)+TX, farnesol with nerolidol (alternative name) (324)+TX, MB-599 (development code) (498)+TX, MGK 264 (development code) (296)+TX, piperonyl butoxide (649)+TX, piprotal (1343)+TX, propyl isomer (1358)+TX, S421 (development code) (724)+TX, sesamex (1393)+TX, sesasmolin (1394) and sulfoxide (1406)+TX, an animal repellent selected from the group of substances consisting of anthraquinone (32)+TX, chloralose (127)+TX, copper naphthenate [CCN]+TX, copper oxychloride (171)+TX, diazinon (227)+TX, dicyclopentadiene (chemical name) (1069)+TX, guazatine (422)+TX, guazatine acetates (422)+TX, methiocarb (530)+TX, pyridin-4-amine (IUPAC name) (23)+TX, thiram (804)+TX, trimethacarb (840)+TX, zinc naphthenate [CCN] and ziram (856)+TX, a virucide selected from the group of substances consisting of imanin (alternative name) [CCN] and ribavirin (alternative name) [CCN]+TX, a wound protectant selected from the group of substances consisting of mercuric oxide (512)+TX, octhilinone (590) and thiophanate-methyl (802)+TX, an insecticide selected from the group consisting of the compound of formula A-1

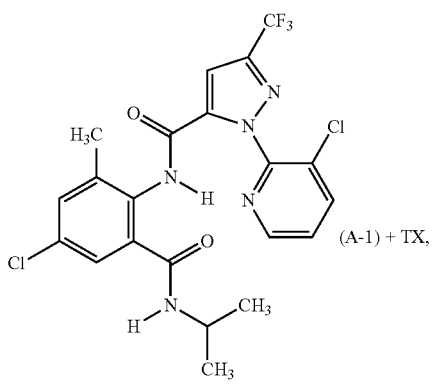

the formula A-2

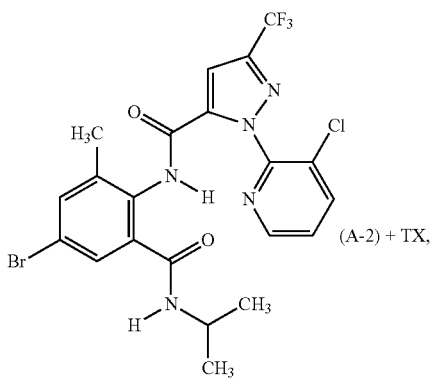

the formula A-3

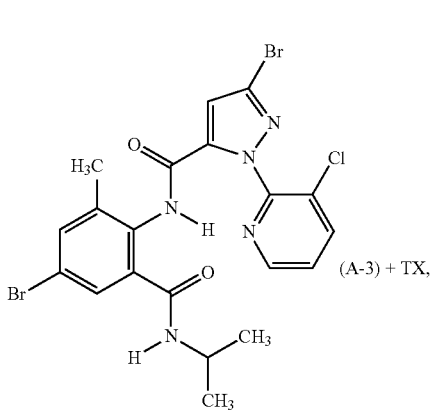

the formula A-4

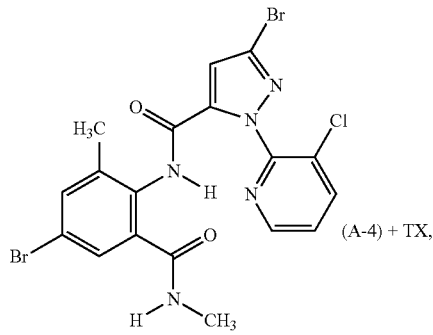

the formula A-5

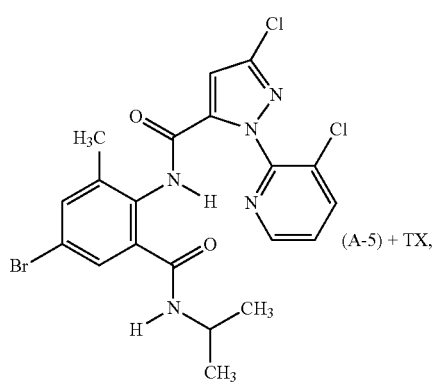

the formula A-6

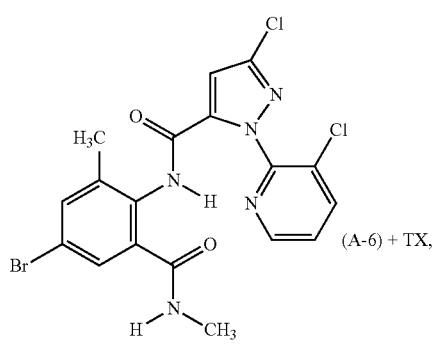

the formula A-7

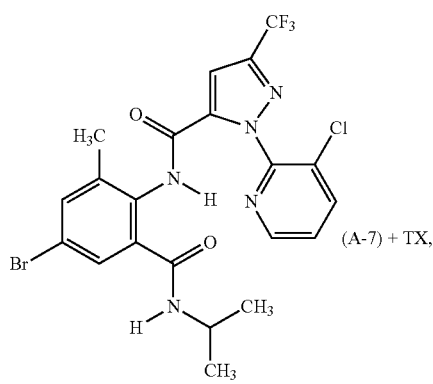

the formula A-8
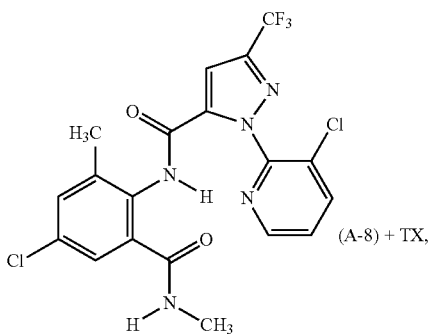
(A-8) + TX,
the formula A-9
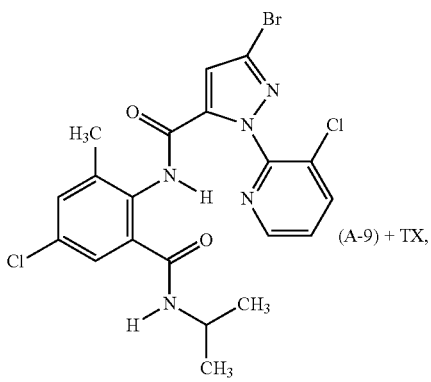
(A-9) + TX,
the formula A-10
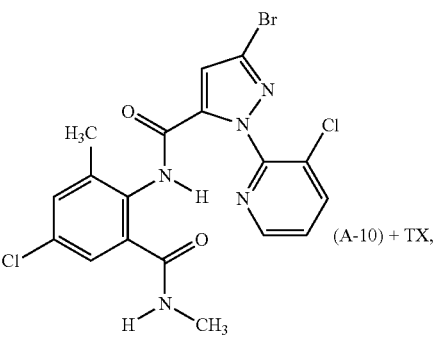
(A-10) + TX,
the formula A-11
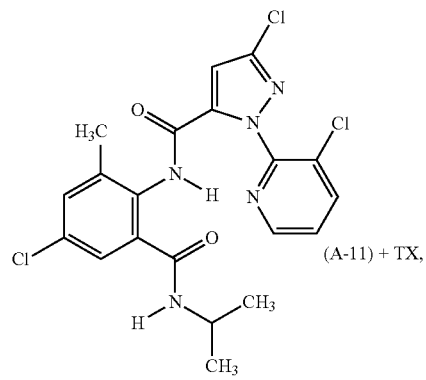
(A-11) + TX,
the formula A-12
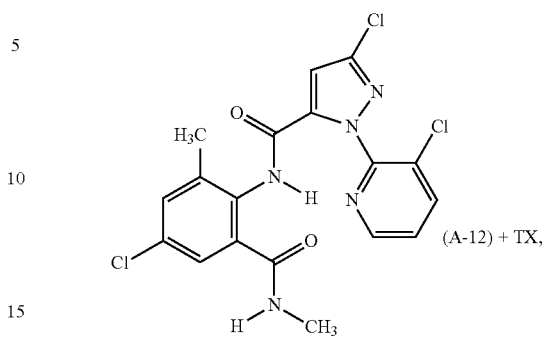
(A-12) + TX,
the formula A-13
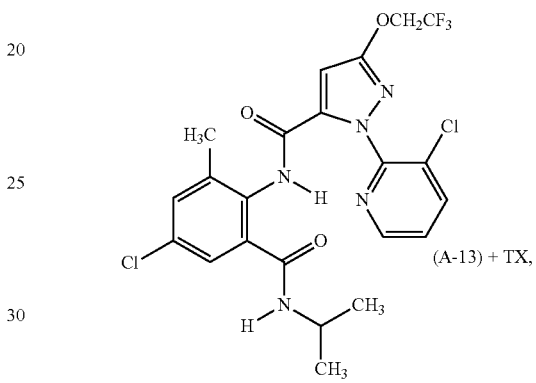
(A-13) + TX,
the formula A-14
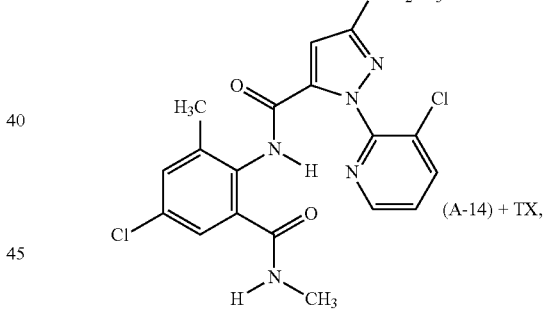
(A-14) + TX,
the formula A-15
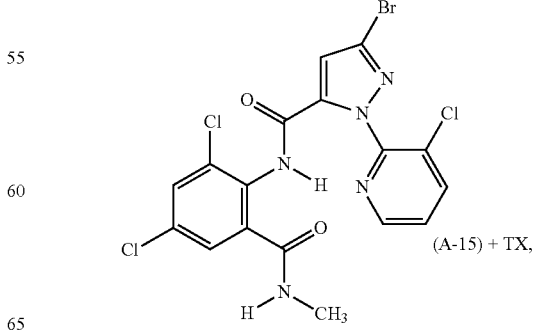
(A-15) + TX, -continued
the formula A-16
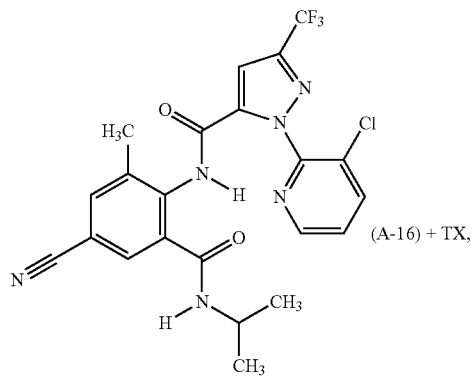
(A-16) + TX,
the formula A-17
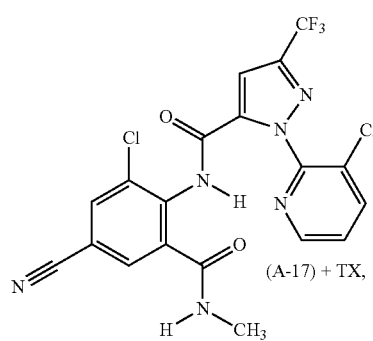
(A-17) + TX,
the formula A-18
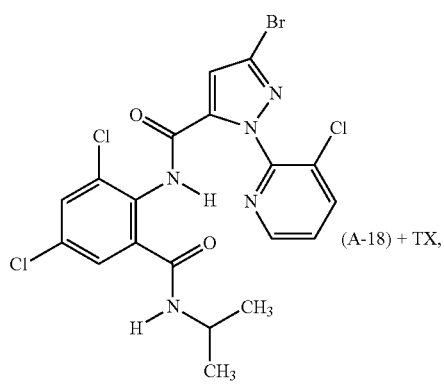
(A-18) + TX,
the formula A-19
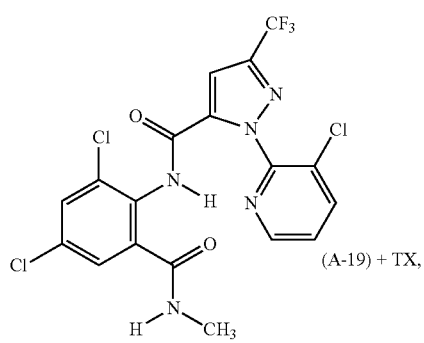
(A-19) + TX,
-continued
the formula A-20
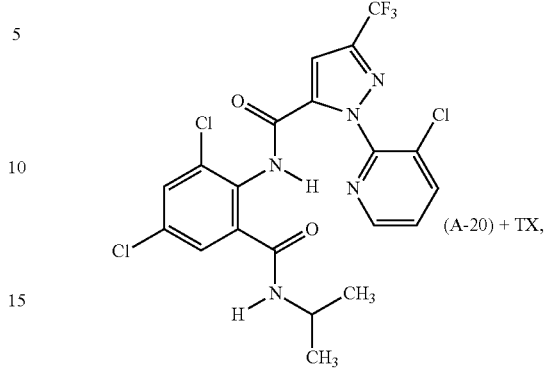
(A-20) + TX,
the formula A-21
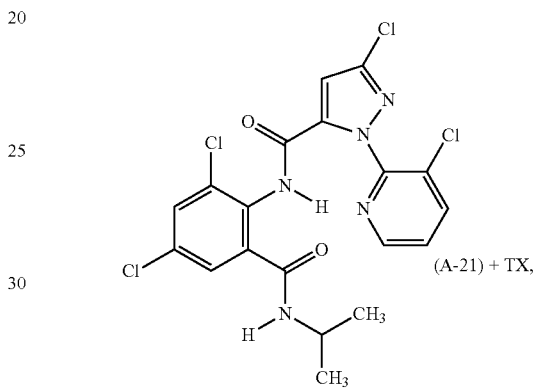
(A-21) + TX,
the formula A-22
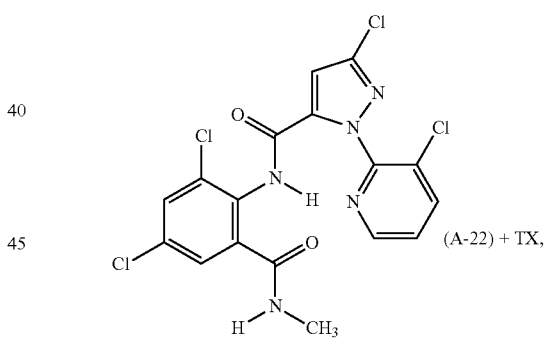
(A-22) + TX,
the formula A-23
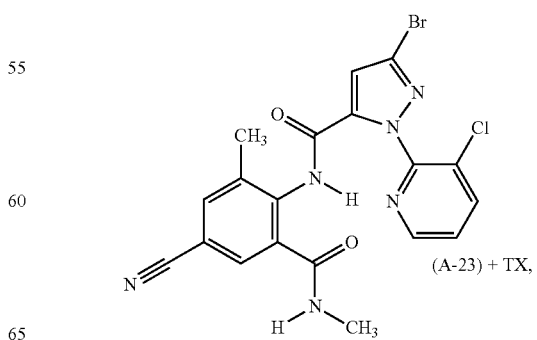
(A-23) + TX, -continued the formula A-24

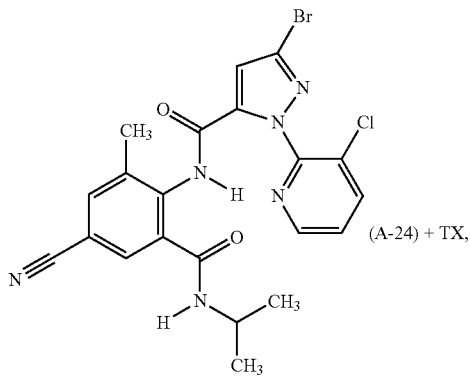

(A-24) + TX, the formula A-25

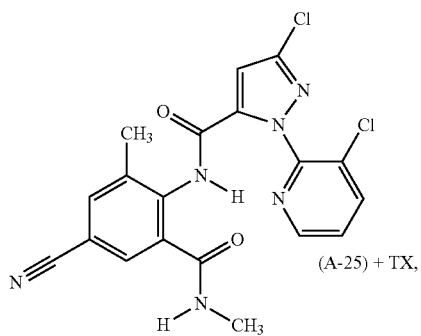

(A-25) + TX, the formula A-26

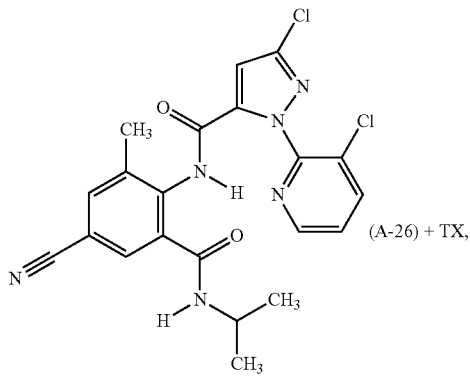

(A-26) + TX, and biologically active compounds selected from the group consisting of azaconazole (60207-31-0]+TX, bitertanol [70585-36-3]+TX, bromuconazole [116255-48-2]+TX, cyproconazole [94361-06-5]+TX, difenoconazole [119446-68-3]+TX, diniconazole [83657-24-3]+TX, epoxiconazole [106325-08-0]+TX, fenbuconazole [114369-43-6]+TX, fluquinconazole [136426-54-5]+TX, flusilazole [85509-19-9]+TX, flutriafol [76674-21-0]+TX, hexaconazole [79983-71-4]+TX, imazalil [35554-44-0]+TX, imibenconazole [86598-92-7]+TX, ipconazole [125225-28-7]+TX, metconazole [125116-23-6]+TX, myclobutanil [88671-89-0]+TX, pefurazoate [101903-30-4]+TX, penconazole [66246-88-6]+TX, prothioconazole [178928-70-6]+TX, pyrifenox [88283-41-4]+TX, prochloraz [67747-09-5]+TX, propiconazole [60207-90-1]+TX, simeconazole [149508-90-7]+TX, tebuconazole [107534-96-3]+TX, tetraconazole [112281-77-3]+TX, triadimefon [43121-43-3]+TX, triadimenol [55219-65-3]+TX, triflumizole [99387-89-0]+TX, triticonazole [131983-72-7]+TX, ancymidol [12771-68-5]+TX, fenarimol [60168-88-9]+TX, nuarimol [63284-71-9]+TX, bupirimate [41483-43-6]+TX, dimethirimol [5221-53-4]+TX, ethirimol [23947-60-6]+TX, dodemorph [1593-77-7]+TX, fenpropidine [67306-00-7]+TX, fenpropimorph [67564-91-4]+TX, spiroxamine [118134-30-8]+TX, tridemorph [81412-43-3]+TX, cyprodinil [121552-61-2]+TX, mepanipyrim [110235-47-7]+TX, pyrimethanil [53112-28-0]+TX, fenpiclonil [74738-17-3]+TX, fludioxonil [131341-86-1]+TX, benalaxyl [71626-11-4]+TX, furalaxyl [57646-30-7]+TX, metalaxyl [57837-19-1]+TX, R-metalaxyl [70630-17-0]+TX, ofurace [58810-48-3]+TX, oxadixyl [77732-09-3]+TX, benomyl [17804-35-2]+TX, carbendazim [10605-21-7]+TX, debacarb [62732-91-6]+TX, fuberidazole [3878-19-1]+TX, thiabendazole [148-79-8]+TX, chlozolinate [84332-86-5]+TX, dichlozoline [24201-58-9]+TX, iprodione [36734-19-7]+TX, myclozoline [54864-61-8]+TX, procymidone [32809-16-8]+TX, vinclozoline [50471-44-8]+TX, boscalid [188425-85-6]+TX, carboxin [5234-68-4]+TX, fenfuram [24691-80-3]+TX, flutolanil [66332-96-5]+TX, mepronil [55814-41-0]+TX, oxycarboxin [5259-88-1]+TX, penthiopyrad [183675-82-3]+TX, thifluzamide [130000-40-7]+TX, guazatine [108173-90-6]+TX, dodine [2439-10-3] [112-65-2] (free base)+TX, iminoctadine [13516-27-3]+TX, azoxystrobin [131860-33-8]+TX, dimoxystrobin [149961-52-4]+TX, enestroburin {Proc. BCPC, Int. Congr., Glasgow, 2003, 1, 93}+TX, fluoxastrobin [361377-29-9]+TX, kresoxim-methyl [143390-89-0]+TX, metominostrobin [133408-50-1]+TX, trifloxystrobin [141517-21-7]+TX, orysastrobin [248593-16-0]+TX, picoxystrobin [117428-22-5]+TX, pyraclostrobin [175013-18-0]+TX, ferbam [14484-64-1]+TX, mancozeb [8018-01-7]+TX, maneb [12427-38-2]+TX, metiram [9006-42-2]+TX, propineb [12071-83-9]+TX, thiram [137-26-8]+TX, zineb [12122-67-7]+TX, ziram [137-30-4]+TX, captafol [2425-06-1]+TX, captan [133-06-2]+TX, dichlofluanid [1085-98-9]+TX, fluoroimide [41205-21-4]+TX, folpet [133-07-3]+TX, tolylfluanid [731-27-1]+TX, bordeaux mixture [8011-63-0]+TX, copperhydroxid [20427-59-2]+TX, copperoxychlorid [1332-40-7]+TX, coppersulfat [7758-98-7]+TX, copperoxid [1317-39-1]+TX, mancopper [53988-93-5]+TX, oxine-copper [10380-28-6]+TX, dinocap [131-72-6]+TX, nitrothal-isopropyl [10552-74-6]+TX, edifenphos [17109-49-8]+TX, iprobenphos [26087-47-8]+TX, isoprothiolane [50512-35-1]+TX, phosdiphen [36519-00-3]+TX, pyrazophos [13457-18-6]+TX, tolclofos-methyl [57018-04-9]+TX, acibenzolar S-methyl [135158-54-2]+TX, anilazine [101-05-3]+TX, benthiavalicarb [413615-35-7]+TX, blasticidin-S [2079-00-7]+TX, chinomethionat [2439-01-2]+TX, chloroneb [2675-77-6]+TX, chlorothalonil [1897-45-6]+TX, cyflufenamid [180409-60-3]+TX, cymoxanil [57966-95-7]+TX, dichlone [117-80-6]+TX, diclocymet [139920-32-4]+TX, diclomezine [62865-36-5]+TX, dicloran [99-30-9]+TX, diethofencarb [87130-20-9]+TX, dimethomorph [110488-70-5]+TX, SYP-LI90 (Flumorph) [211867-47-9]+TX, dithianon [3347-22-6]+TX, ethaboxam [162650-77-3]+TX, etridiazole [2593-15-9]+TX, famoxadone [131807-57-3]+TX, fenamidone [161326-34-7]+TX, fenoxanil [115852-48-7]+TX, fentin [668-34-8]+TX, ferimzone [89269-64-7]+TX, fluazinam [79622-59-6]+TX, fluopicolide [239110-15-7]+TX, flusulfamide [106917-52-6]+TX, fenhexamid [126833-17-8]+TX, fosetyl-aluminium [39148-24-8]+TX, hymexazol [10004-44-1]+TX, iprovalicarb [140923-17-7]+TX, IKF-916 (Cyazofamid) [120116-88-3]+TX, kasugamycin [6980-18-3]+TX, methasulfocarb [66952-49-6]+TX, metrafenone [220899-03-6]+TX, pencycuron [66063-05-6]+TX, phthalide [27355-22-2]+TX, polyoxins [11113-80-7]+TX, probenazole [27605-76-1]+TX, propamocarb [25606-41-1]+TX, proquinazid

[189278-12-4]+TX, pyroquilon [57369-32-1]+TX, quinoxyfen [124495-18-7]+TX, quintozene [82-68-8]+TX, sulphur [7704-34-9]+TX, tiadinil [223580-51-6]+TX, triazoxide [72459-58-6]+TX, tricyclazole [41814-78-2]+TX, triforine [26644-46-2]+TX, validamycin [37248-47-8]+TX, zoxamide (RH7281) [156052-68-5]+TX, mandipropamid [374726-62-2]+TX, the compound of formula F-1

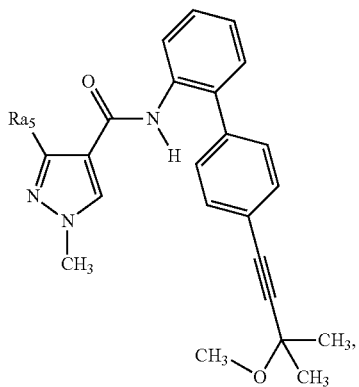

(F-1)

wherein $Ra_5$ is trifluoromethyl or difluoromethyl (WO2004/058723)+TX,
the compound of formula F-2

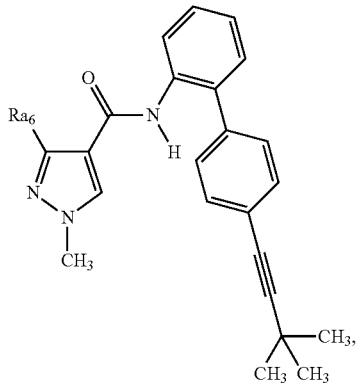

(F-2)

wherein $Ra_6$ is trifluoromethyl or difluoromethyl (WO2004/058723)+TX,
the racemic compound of formula F-3 (syn)

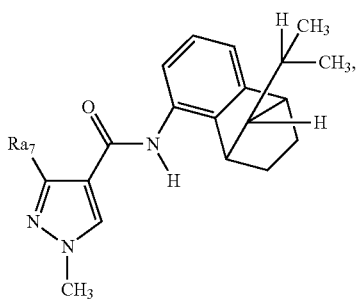

(F-3)

wherein $Ra_7$ is trifluoromethyl or difluoromethyl (WO2004/035589)+TX, the racemic mixture of formula F-4 (anti)

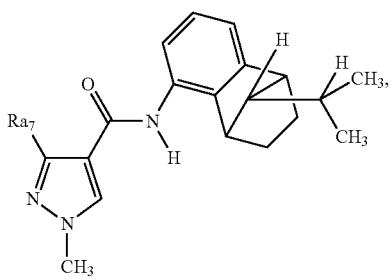

(F-4)

wherein $Ra_z$ is trifluoromethyl or difluoromethyl (WO2004/035589)+TX, the compound of formula F-5

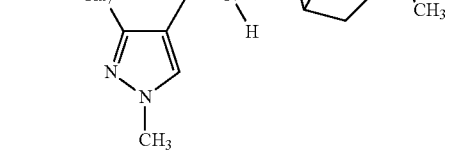

(F-5)

which is an epimeric mixture of racemic compounds of formulae F-3 (syn) and F-4 (anti), wherein the ratio from racemic compounds of formula F-3 (syn) to racemic compounds of formula F-4 (anti) is from 1000:1 to 1:1000 and wherein $Ra_7$ is trifluoromethyl or difluoromethyl (WO2004/035589)+TX, the compound of formula F-6

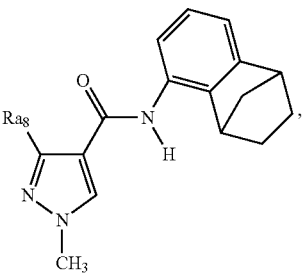

(F-6)

wherein $Ra_8$ is trifluoromethyl or difluoromethyl (WO2004/035589)+TX, the racemic compound of formula F-7 (trans)

(F-7)

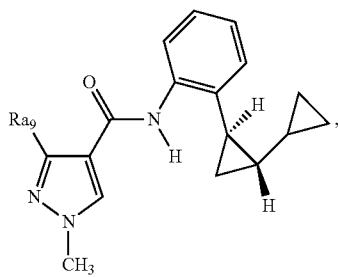

wherein Ra₉ is trifluoromethyl or difluoromethyl (WO03/074491)+TX, the racemic compound of formula F-8 (cis)

(F-8)

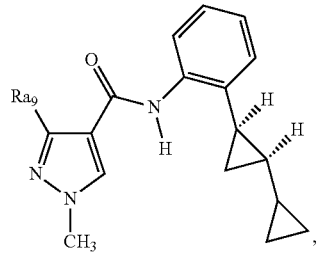

wherein Ra₉ is trifluoromethyl or difluoromethyl (WO03/074491)+TX, the compound of formula F-9

(F-9)

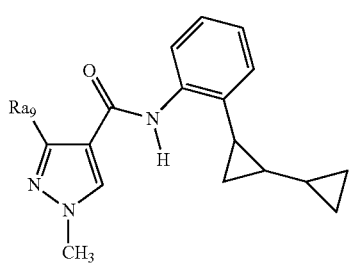

which is a mixture of the racemic compounds of formulae F-7 (trans) and F-8 (cis), wherein the ratio of the racemic compound of formula F-7 (trans) to the racemic compound of formula F-8 (cis) is 2:1 to 100:1; and wherein Ra₉ is trifluoromethyl or difluoromethyl (WO03/074491)+TX, the compound of formula F-10

(F-10)

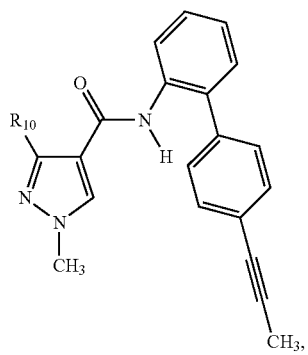

wherein R₁₃ is trifluoromethyl or difluoromethyl (WO2004/058723)+TX, the racemic compound of formula F-11 (trans)

(F-11)

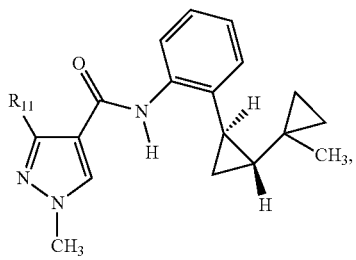

wherein R₁₁ is trifluoromethyl or difluoromethyl (WO03/074491)+TX, the racemic compound of formula F-12 (cis)

(F-12)

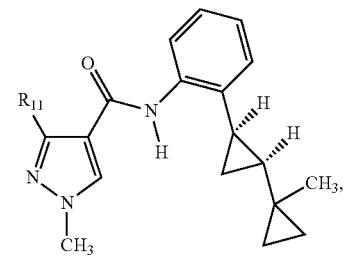

wherein R₁₁ is trifluoromethyl or difluoromethyl (WO03/074491)+TX, the compound of formula F-13

(F-13)

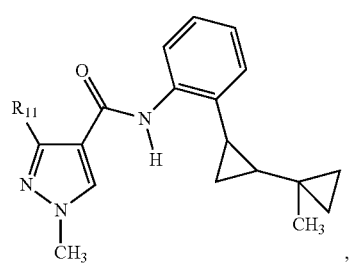

which is a racemic mixture of formulae F-11 (trans) and F-12 (cis), and wherein $R_{11}$ is trifluoromethyl or difluoromethyl (WO 03/074491)+TX,
the compound of formula F-14

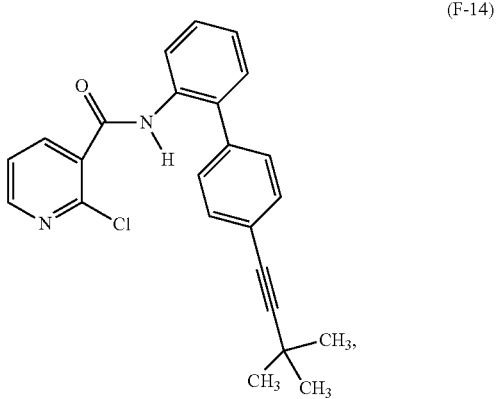 [SMILES: CC(C)(C)C#Cc1ccc(-c2ccccc2NC(=O)c2cccnc2Cl)cc1]

(F-14)

(WO2004/058723)+TX, and the compound of formula F-15

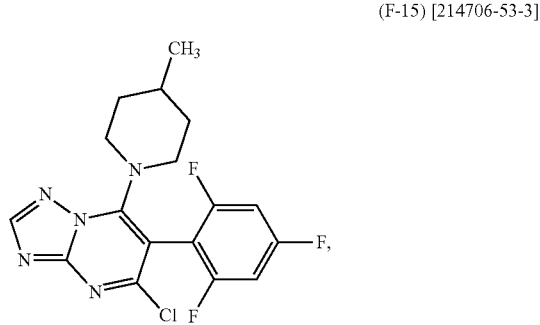 [SMILES: CC1CCN(c2c(-c3c(F)cc(F)cc3F)c(Cl)nc3ncnn23)CC1]

(F-15) [214706-53-3]

+TX.

The references in brackets behind the active ingredients, e.g. (3878-19-11 refer to the Chemical Abstracts Registry number. The compounds of formulae A-1 to A-26 are described in WO 03/015518 or in WO 04/067528. The above described mixing partners are known. Where the active ingredients are included in "The Pesticide Manual" [The Pesticide Manual—A World Compendium; Thirteenth Edition; Editor: C. D. S. TomLin; The British Crop Protection Council], they are described therein under the entry number given in round brackets hereinabove for the particular compound; for example, the compound "abamectin" is described under entry number (1). Where "[CCN]" is added hereinabove to the particular compound, the compound in question is included in the "Compendium of Pesticide Common Names", which is accessible on the internet [A. Wood; *Compendium of Pesticide Common Names*, Copyright 1995-2004]; for example, the compound "acetoprole" is described under the internet address http://www.alanwood.net/pesticides/acetoprole.htmL.

Most of the active ingredients described above are referred to hereinabove by a so-called "common name", the relevant "ISO common name" or another "common name" being used in individual cases. If the designation is not a "common name", the nature of the designation used instead is given in round brackets for the particular compound; in that case, the IUPAC name, the IUPAC/Chemical Abstracts name, a "chemical name", a "traditional name", a "compound name" or a "development code" is used or, if neither one of those designations nor a "common name" is used, an "alternative name" is employed. "CAS Reg. No" means the Chemical Abstracts Registry Number.

The active ingredient mixture of the compounds of formula I selected from tables T1 to T121 with active ingredients described above comprises a compound selected from tables T1 to T121 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

The mixtures comprising a compound of formula I selected from tables T1 to T121 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from tables T1 to T121 and the active ingredients as described above is not essential for working the present invention.

The compositions can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compositions according to the invention are also suitable for the protection of plant propagation material, for example seeds, such as fruit, tubers or kernels, or nursery plants, against pests of the abovementioned type. The propagation material can be treated with the compositions prior to planting, for example seed can be treated prior to sowing. Alternatively, the compositions can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention.

BIOLOGICAL EXAMPLES

%=Percent by Weight, Unless Otherwise Specified

Example B1

Activity Against Spodoptera littoralis (Egyptian Cotton Leafworm)

(Larvicide, Feeding/Residual Contact Activity, Preventive)

Cotton leaf discs were placed on agar in a 24-well microtiter plate and sprayed with test solutions. After drying, the leaf discs were infested with 5 $L_1$ larvae. The samples were checked for mortality, repellent effect, feeding behaviour, and growth regulation 3 days after treatment.

In this test, compounds P.2, P.3, P.6, P.7, P.8, P.9, P.10, P.11, P.12, P.13, P.14, P.15, P.16, P.17, P.18, P.19, P.23, P.24, P.25, P.26, P.27, P.28, P.29, P.30, P.31, P.32, P.33 and P.34 showed an activity of over 80% at a concentration of 400 ppm.

Example B2

Activity Against Heliothis virescens (Tobacco Budworm)

(Ovo-Larvicide, Feeding/Contact Activity, Curative)

Eggs (0-24 h old) were placed in 24-well microtiter plate on artificial diet and treated with test solutions by pipetting. After an incubation period of 4 days, samples were checked for egg mortality, larval mortality, and growth regulation.

In this test, compounds P.2, P.3, P.6, P.7, P.8, P.9, P.10, P.11, P.12, P.13, P.14, P.15, P.16, P.17, P.18, P.19, P.20, P.23, P.24, P.25, P.26, P.27, P.28, P.29, P.30, P.31, P.32, P.33, P. 34, P.35 and P.36 showed an activity of over 80% at a concentration of 400 ppm.

Example B3

Plutella xylostella (Diamond Back Moth)

(Larvicide, Feeding/Residual Contact Activity, Preventive)

24-well microtiter plate (MTP) with artificial diet was treated with test solutions by pipetting. After drying, the MTP's were infested with larvae (L2) (10-15 per well). After an incubation period of 5 days, samples were checked for larval mortality, antifeedant and growth regulation.

In this test, compounds P.2, P.3, P.6, P.7, P.8, P.9, P.10, P.11, P.12, P.13, P.14, P.15, P.16, P.17, P.18, P.19, P.20, P.23, P.24, P.25, P.26, P.27, P.28, P.29, P.30, P.31, P.32, P.33, P.34, P.35 and P.36 showed an activity of over 80% at a concentration of 400 ppm.

Example B4

Diabrotica balteata (Corn Root Worm)

(Larvicide, Feeding/Residual Contact Activity, Preventive)

24-well microtiter plate (MTP) with artificial diet was treated with test solutions by pipetting. After drying, the MTP's were infested with larvae (L2) (6-10 per well). After an incubation period of 5 days, samples were checked for larval mortality, antifeedant and growth regulation.

In this test, compounds P.2, P.6, P.7, P.8, P.9, P.11, P.15, P.16, P.19, P.23, P.24, P.26, P.27, P.29, P.30, P.31, P.32 and P.33 showed an activity of over 80% at a concentration of 400 ppm.

Example B5

Activity Against Myzus persicae (Green Peach Aphid)

(Mixed Population, Feeding/Residual Contact Activity, Preventive)

Sunflower leaf discs were placed on agar in a 24-well microtiter plate and sprayed with test solutions. After drying, the leaf discs were infested with an aphid population of mixed ages. After an incubation period of 6 days, samples were checked for mortality and special effects (e.g. phytotoxicity). In this test, compounds P.2, P.3, P.6, P.7, P.8, P.9, P.10, P.11, P.12, P.13, P.14, P.15, P.16, P.17, P.18, P.19, P.23, P.24, P.25, P.26, P.27, P.28, P.29, P.30, P.31, P.32, P.33 and P.34 showed an activity of over 80% at a concentration of 400 ppm.

Example B6

Activity Against Myzus persicae (Green Peach Aphid)

(Mixed Population, Systemic/Feeding Activity, Curative)

Roots of pea seedlings, infested with an aphid population of mixed ages, were placed directly in the test solutions. 6 days after introduction, samples were checked for mortality and special effects on the plant. In this test, compounds P.2, P.3, P.6, P.7, P.8, P.9, P.11, P.12, P.13, P.14, P.15, P.16 P.17, P.18, P.19, P.24, P.26, P.27, P.28, P.29, P.30, P.31, P.32, P.34 and P.36 showed an activity of over 80% at a concentration of 400 ppm.

Example B7

Activity Against Thrips tabaci (Onion Thrips)

(Mixed Population, Feeding/Residual Contact Activity, Preventive)

Sunflower leaf discs were placed on agar in a 24-well microtiter plate and sprayed with test solutions. After drying, the leaf discs were infested with a thrips population of mixed ages. After an incubation period of 6 days, samples were checked for mortality and special effects (e.g. phytotoxicity).

In this test, compounds P.2, P.3, P.6, P.7, P.8, P.9, P.10, P.11, P.12, P.13, P.14, P.15, P.16, P.19, P.23, P.25, P.27, P.31, P.32, P.33, P.34, P.35, P.36 showed an activity of over 80% at a concentration of 400 ppm.

Example B8

Activity Against *Nilaparvata lugens* (Brown Rice Planthopper)

(Larvicide, Feeding/Contact)

Rice seedlings were treated with the diluted test solutions in a spray chamber. After drying, they were infested with 20 $N_3$ nymphs (2 replicates). 6-12 days after the treatment samples were checked for mortality, growth regulation, and effects on the $F_1$ generation.

In this test, compounds P.2, P.12, P.19, P.23, P.26, P.29, P.31 showed an activity of over 80% at a concentration of 400 ppm.

What is claimed is:
1. A compound of formula $Ic_a$ or $Ic_b$

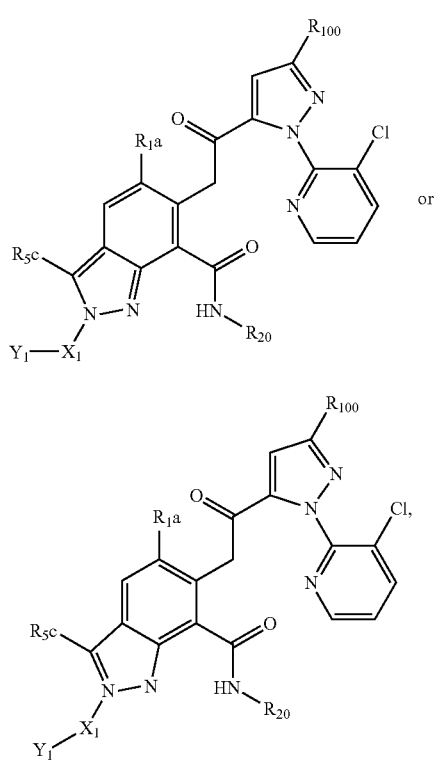

wherein
$R_{5c}$ is hydrogen, $C_1$-$C_4$alkyl, $C_2$-$C_4$alkynyl, halogen or cyano;
$R_{20}$ is hydrogen, $C_1$-$C_6$alkyl, $C_1$-$C_6$alkylthio-$C_1$-$C_6$alkyl, $C_1$-$C_6$alkylsulphonyl-$C_1$-$C_6$alkyl, $C_1$-$C_6$alkylsulphinyl-$C_1$-$C_6$alkyl, thiethan-3-yl, thiethan-3-yl substituted by $C_1$-$C_4$alkyl,
$R_{100}$ is halogen, $C_1$-$C_6$alkyl, $C_1$-$C_6$haloalkyl, $C_1$-$C_6$alkoxy or $C_1$-$C_6$haloalkoxy;
$X_1$ is oxygen, —C(O)—, —(CO)O—, thio, sulphinyl, sulphonyl, —$SO_2NR_{5d}$, —C(S)—, (P(=O) O($R_{5a}$)—, —C(O)S—, —C(S)O—, —C(S)$NR_{5f}$—, —(CO)$NR_{5g}$—, or a direct bond;

$Y_1$ is $C_1$-$C_{30}$alkyl, $C_3$-$C_{30}$alkenyl or $C_3$-$C_{30}$alkynyl which may be interrupted one, two, three, four or five times by atoms or group of atoms independently selected from the group consisting of oxygen, sulphur, suphinyl, sulphonyl, —C(O)—, —OC(O)— and —$NR_{5h}$—, with the proviso that the interrupting atoms are separated from each other by at least one methylene group; and which may be mono- or polysubstituted by substituents selected from the group consisting of halogen, hydroxyl, amino, formyl, nitro, cyano, mercapto, carbamoyl, $C_3$-$C_6$-trialkylsilyl, $C_1$-$C_6$alkoxy, $C_1$-$C_6$alkoxycarbonyl, $C_2$-$C_6$alkenyl, $C_2$-$C_6$haloalkenyl, $C_2$-$C_6$alkynyl, $C_2$-$C_6$haloalkynyl, $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkoxy-$C_1$-$C_6$alkoxy-$C_1$-$C_6$alkoxy, $C_1$-$C_6$alkylthio-$C_1$-$C_6$alkoxy, $C_1$-$C_6$alkylsulphinyl-$C_1$-$C_6$alkoxy, $C_1$-$C_6$alkylsulphonyl-$C_1$-$C_6$alkoxy, $C_1$-$C_6$alkoxycarbonyl-$C_1$-$C_6$alkoxy, $C_1$-$C_6$alkoxycarbonyl, $C_1$-$C_6$alkylcarbonyl, —P(O)(O$C_1$-$C_4$alkyl)$_2$, $C_1$-$C_6$alkylthio, $C_1$-$C_6$alkylsulphinyl, $C_1$-$C_6$alkylsulphonyl, $C_1$-$C_6$haloalkylthio, $C_1$-$C_6$haloalkylsulphinyl, $C_1$-$C_6$haloalkylsulphonyl, oxiranyl, which for its part may be substituted by $C_1$-$C_6$alkyl; and by a five- to ten-membered monocyclic or fused bicyclic ring system which may be aromatic, partially saturated or fully saturated and may contain 1 to 4 heteroatoms selected from the group consisting of nitrogen, oxygen and sulphur, and wherein each ring system may not contain more than 2 oxygen atoms and not more than 2 sulphur atoms, and wherein the ring system itself can be substituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulphinyl, $C_1$-$C_6$alkylsulphonyl, di($C_1$-$C_4$alkyl)aminosulphonyl, di($C_1$-$C_4$alkyl)amino, halogen, cyano, nitro and phenyl, and wherein the substituents on the nitrogen in the heterocyclic ring are different from halogen;
or $Y_1$ is a five- to ten-membered monocyclic or fused bicyclic ring system which may be aromatic, partially saturated or fully saturated and may contain 1 to 4 heteroatoms selected from the group consisting of nitrogen, oxygen and sulphur, and where each ring system may not contain more than 2 oxygen atoms and not more than 2 sulphur atoms, and where the ring system itself can be mono- or polysubstituted by substituents selected from the group consisting of $C_1$-$C_6$alkyl, $C_1$-$C_6$haloalkyl, $C_1$-$C_6$alkoxy, $C_1$-$C_6$haloalkoxy, $C_1$-$C_6$alkylthio, $C_1$-$C_6$alkylsulphinyl, $C_1$-$C_6$alkylsulphonyl, di($C_1$-$C_4$alkyl)aminosulphonyl, di($C_1$-$C_4$alkyl)amino, halogen, cyano, nitro and phenyl, and where the substituents on the nitrogen in the heterocyclic ring are different from halogen;
or the group $X_1$—$Y_1$ together is formyl or cyano;
each of $R_{1a}$, $R_{5c}$, $R_{5d}$, $R_{5e}$, $R_{5f}$, $R_{5g}$, and $R_{5h}$ which may be the same or different, represents hydrogen, halogen, nitro, cyano, hydroxy, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulphinyl, $C_1$-$C_4$haloalkylsulphonyl, $C_1$-$C_4$alkylsulphinyl, $C_1$-$C_4$alkylsulphonyl, $C_1$-$C_4$alkylsulphonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, $C_3$-$C_6$-trialkylsilyl, phenyl, benzyl or phenoxy; or represents phenyl, benzyl or phenoxy mono-, di- or trisubstituted by substituents selected from the group consisting of halogen, cyano, nitro, halogen, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$haloalkoxy, $C_1$-$C_4$alkylthio, $C_1$-$C_4$haloalkylthio, $C_1$-$C_4$alkylsulphinyl, $C_1$-$C_4$alkylsulphonyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy and $C_3$-$C_6$-trialkylsilyl;

or agronomically acceptable salts/enantiomers/tautomers/N-oxides thereof.

2. A compound of formula I according to claim 1, wherein $Y_1$ is $C_1$-$C_{20}$ alkyl, $C_3$-$C_{20}$ alkenyl or $C_3$-$C_{20}$ alkynyl which may be interrupted one, two or three times by oxygen, with the proviso that the interrupting atoms are separated from each other by at least one methylene group; and which $Y_1$ may be mono- or polysubstituted by substituents selected from halogen, cyano, $C_3$-$C_6$cycloalkyl, pyridyl, phenyl and triazinyl, wherein said $C_3$-$C_6$cycloalkyl, pyridyl, phenyl and triazinyl may be substituted by $C_1$-$C_6$alkoxy or halogen.

3. A compound of formula I according to claim 1, wherein $X_1$ is —C(O), —C(O)O—, thio, sulfonyl, —C(O)S—, C(O)NR$_{5g}$ or a direct bond, and R$_{5g}$ is as defined under formula I in claim 1.

4. A pesticidal composition, which comprises at least one compound of formula Ic$_a$ or Ic$_b$ according to claim 1 or, where appropriate, a tautomer thereof, in each case in free form or in agrochemically utilizable salt form, as active ingredient.

5. A composition according to claim 4 for controlling insects of the order Acarina.

6. A method for controlling pests, which comprises applying a composition according to claim 4 to the pests or their environment.

7. A method according to claim 6 for the protection of plant propagation material from the attack by pests, which comprises treating the propagation material or the site, where the propagation material is planted.

8. Plant propagation material treated in accordance with the method described in claim 7.

* * * * *